(12) United States Patent
Komori et al.

(10) Patent No.: US 9,481,893 B2
(45) Date of Patent: Nov. 1, 2016

(54) DNA CAPABLE OF INDUCING OSTEOBLAST-SPECIFIC EXPRESSION

(75) Inventors: Toshihisa Komori, Nagasaki (JP);
Shinichi Izumi, Nagasaki (JP);
Toshihiro Miyazaki, Nagasaki (JP);
Satoshi Rokutanda, Nagasaki (JP);
Hisato Komori, Nagasaki (JP);
Wenguang Liu, Jilin Province (CN)

(73) Assignee: Nagasaki University, Nagasaki (JP)

( * ) Notice: Subject to any disclaimer, the term of this patent is extended or adjusted under 35 U.S.C. 154(b) by 77 days.

(21) Appl. No.: 13/389,204

(22) PCT Filed: Aug. 6, 2010

(86) PCT No.: PCT/JP2010/063411
§ 371 (c)(1),
(2), (4) Date: Apr. 5, 2012

(87) PCT Pub. No.: WO2011/016561
PCT Pub. Date: Feb. 10, 2011

(65) Prior Publication Data
US 2012/0183972 A1    Jul. 19, 2012

(30) Foreign Application Priority Data
Aug. 6, 2009   (JP) .................................. 2009-183366

(51) Int. Cl.
*C12N 15/85* (2006.01)
*C12N 15/63* (2006.01)
*G01N 33/50* (2006.01)

(52) U.S. Cl.
CPC .............. *C12N 15/85* (2013.01); *C12N 15/63* (2013.01); *C12N 15/8509* (2013.01); *G01N 33/5044* (2013.01); *G01N 33/5073* (2013.01); *A01K 2267/0393* (2013.01); *C12N 2830/008* (2013.01)

(58) Field of Classification Search
None
See application file for complete search history.

(56) References Cited

U.S. PATENT DOCUMENTS 7,741,113 B2   6/2010  Strong et al.
2006/0134663 A1*  6/2006  Harkin et al. ................... 435/6
2006/0242725 A1  10/2006  Strong et al.
2007/0028314 A1*  2/2007  Komori et al. ................. 800/18
2008/0008996 A1*  1/2008  Byrum ............................ 435/6

OTHER PUBLICATIONS

Makita et al. Gene 413 (2008) 8-17.*
Lowe et al. Nucleic Acids Research, vol. 18, No. 7, p. 1757-1761, 1990.*
Mefford et al. Copy number variation analysis in sigle-suture craniosynostosis: Multiple rare variants including RUNX2 duplication in two cousins with metopic craniosynostosis. American Journal of Medical Genetics: Part A, vol. 152a, pp. 2203-2210, Aug. 3, 2010.*
La Starza et al. Genomic gain at 6p21: a new cryptic molecular rearrangement in secondary myelodysplastic syndrome and actue myeloid leukemia. Leukemia, vol. 20, pp. 958-964, 2006.*
Cartharius et al. MatInspector and beyond: promoter analysis based on transcription factor binding sites. Bioinformatics, vol. 21, No. 13, pp. 2933-2942, 2005.*
Alam et al. Chapter 6: Reporter genes for monitoring gene expression in mammalian cells. In Gene Transfer and Expression in Mammalian Cells. Ed. S.C. Makrides. Elsevier Science B.V., 2003, pp. 291-308.*
Enomoto et al., *J. Biol. Chem.*, 275(12): 8695-8702 (Mar. 24, 2000).
Fujiwara et al., *Biochim. & Biophys. Acta*, 1446: 265-272 (1999).
Kamekura et al., *Arthritis & Rheumatism*, 54(8): 2462-2470 (Aug. 2006).
Kanatani et al., *Developmental Biol.*, 296: 48-61 (Apr. 4, 2006).
Komori et al., *Curr. Opinion Genet. & Dev.*, 8: 494-499 (1998).
Lengner et al., *Mech. Dev.*, 114: 167-170 (2002).
Liu et al., *J. Cell. Biol.*, 155(1): 157-166 (Oct. 1, 2001).
Strong et al., *J. Bone & Min. Research*, 22(suppl. 1): S80, Abstract 1288 (Sep. 16-19, 2007).
Thirunavukkarusu et al., *BioTechniques*, 28(3):506-510 (Mar. 2000).
Ueta et al., *J. Cell Biol.*, 153(1): 87-100 (Apr. 2, 2001).
Zambotti et al., *J. of Biol. Chem.*, 277(44): 41497-41506 (Nov. 1, 2002).
Japanese Patent Office, International Search Report in International Patent Application No. PCT/JP2010/063411 (Oct. 5, 2010).
Harada et al., *J. Biol. Chem.*, 274(11): 6972-6978 (1999).
Zheng et al., *J. Bone & Min. Research*, 24(6): 1002-1032 (2009).

* cited by examiner

*Primary Examiner* — Jennifer Dunston
(74) *Attorney, Agent, or Firm* — Leydig, Voit & Mayer, Ltd.

(57) ABSTRACT

The invention provides nucleotide sequences that function as enhancers and induce osteoblast-specific expression, expression vectors comprising such an enhancer, a promoter, and a gene containing a coding region, as well as screening methods utilizing such expression vectors.

6 Claims, 26 Drawing Sheets

FIG. 1
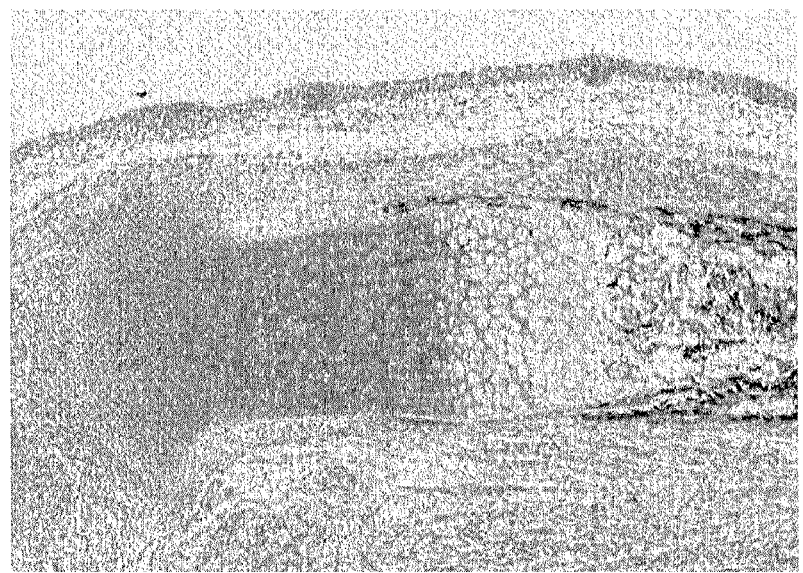

| | | | | | | |
|---|---|---|---|---|---|---|
| aggcccccag | cagactacga | caggcacaag | gcttactcga | acttgattte | tcacctacta | -103 |
| tgtacagtca | catccatcct | atttccgcca | ccgtctcgcc | tccaccccct | cgatttccta | -43 |
| ctcctcgccc | cccatttcca | ccctcctccc | cctcccagg | ccaattcgat | aacttgtggc | 18 |
| tattgtgatg | cgtattcctg | tagatccgag | caccagccgg | cgcttcagcc | ccccctccag | 78 |
| cagcctgcag | cccggcaaga | tgagcgacgt | gagcccggtg | gtggctgc | | 126 |

FIG. 7

```
   1 TTAGCATTTGCTTGTTGGGAAGAGATGAGAAAATAAGATGCGTTTATCAGATCTTCCAAT   60
  61 TGCGCACCAGAAATACTTTCAAAGTACCTATGTTGTAATTTCATTTTTAAAAAATTCTTT  120
 121 TCAATTGGGGGGGAGGGTGAATAAGTAATTACAAAGAATGGCTGCCTTTAGATAGAGGTT  180
 181 TATCATGTAATTATAATAATGATCATTTAAAAGGATCCAAAATGTCTCCACTAGTTTAAA  240
 241 GGGCTAGGCAGAGTTATTTTTAAAATCAAACGTATGTGCTTTTTCTGTTTATGTCTTTGG  300
 301 AAAGAACATTCTGTATAATGAAAAACATGACCAAATTTTTCACAGTACATCACTATAAAA  360
 361 CCCTGTAATTGACTTTTGGGGTTGGTTTACTCTATATCTATTTTTGACCTCGTAGAAAAC  420
 421 AGCAATGATGTGGTGAAAGGCCCAAAATTTAAGTCTCATTGCAGGATAAGACTCCATCCT  480
 481 GATTAGTATAGAAGTATCATATTTGTGCTGGGAAATGTGCCCATTCTAGTAGAGAAAACT  540
 541 TTAGTGCATAGGAACCACCTCTTTTCTAATCAAGCCATGTAAAAACTAGTAACTCTGGTG  600
 601 TCTAGTCTGGGCCTTGGATGGAATGTGGATGTTGTTTACACCGATCCCCTCCATTAAAGG  660
 661 CAGCATAATGTTGGTCTTCAAAACTGATGTTGGAAATGACAGGTTCATTGCAGTTAATCT  720
 721 GATGGAAAGTAACAATGTATGTCACAGGTAAATTATAAATTAACCTTTAAACATATAAAT  780
 781 TATCATTAGATAGTTCTTTTTCTCTTGTGTTAACACAGATTAAATAAAGAACTTAATCTC  840
 841 CTTCTAAAAGCTTTGAATTCCGTTACTAAGGAACAAACTAATATGTTATTCCTAACAAAA  900
 901 AGCACTGTTCTTCATCGAAGTCTAAAATACCTCTGAATGGGTACTCCTGCTTTCACCAGT  960
 961 AAAATTTACATACTACCAAGTAAAATAAACTTATGTTACATGGTATAAAAATCAGCCCTG 1020
1021 TAACACCTACCACAGATTTATCTCCTGTGAGTTGACTCAATCATTCCTTCTTTTCAGTAA 1080
1081 ATAAACTACATTCTACGCAGGGAACTGCAGGAAAGTTTTTCAGAGGCCAAGTCAAAGAAT 1140
1141 ATGTTTCACATGGAAACTTCCAAATTGACAGCCTGCCCATTTTTGGTAGGTATTAAAGGG 1200
1201 TCCTCAGCACTTTATGAATTAGTTGTGGTTTACCTAAATAATCATGGCCAAAGCTGCCAC 1260
1261 CGTCACTGCATTC 1273
```

DNA CAPABLE OF INDUCING OSTEOBLAST-SPECIFIC EXPRESSION

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 260,375 bytes ASCII (Text) file named 709816ReplacementSequenceListing created Feb. 9, 2016.

TECHNICAL FIELD

The present invention relates to an enhancer capable of inducing osteoblast-specific expression and a utilization thereof. Specifically, the present invention relates to the enhancer, a vector having the enhancer, a transduced cell having the vector, a transgenic non-human animal incorporating the vector, a method of regulating gene expression efficiency comprising enhancing the expression efficiency for a specified gene in an osteoblast-specific fashion under the control of the enhancer, a method of screening for a compound that influences osteoblast activity by utilizing the enhancer, and the like.

BACKGROUND ART

Runx2, a gene expressed in an osteoblast-specific fashion, is a transcriptional factor responsible for the determination of differentiation from undifferentiated mesenchymal cells into the osteoblast series and the maturity of chondrocytes. The expression of Runx2 in osteoblasts is high in immature stages and decreases with the maturity of osteoblasts. It has been reported that Runx2 promotes osteoblast differentiation in the initial stage and suppresses late-phase differentiation and final differentiation into osteocytes (non-patent documents 1 and 2). Runx2 is also expressed in prehypertrophic chondrocytes and hypertrophic chondrocytes, possessing both the action of promoting the differentiation and maturity of immature chondrocytes and the action of inhibiting the formation of permanent chondrocytes (non-patent documents 3-5). Also, an analysis using animals with a modified Runx2 gene is ongoing.

Runx2 occurs in an isoform starting with exon 1 (type II Runx2) and another isoform starting with exon 2 (type I Runx2), which undergo transcriptional regulation by a distal promoter and a proximal promoter, respectively (non-patent document 6). Both isoforms are expressed in osteoblasts and chondrocytes (non-patent document 3). Thereof, absolutely no report is available on the proximal promoter; with regard to the distal promoter, however, a transcriptional regulatory region 1.5 kb upstream of the exon 1 has been reported using cultured cells (non-patent document 7). Also available is a report of transgenic mice generated using a transcriptional regulatory region 3 kb upstream of the exon 1, but they exhibit an expression pattern totally different from the physiological expression pattern for Runx2 (non-patent document 8).

There are 2.3 kb and 3.2 kb type I collagen promoters that have been used so far as promoters (DNAs) to allow expression by osteoblasts. With the 3.2 kb type I collagen promoter, expression induction is possible from the early stage of osteoblast differentiation; the expression is highly induced in dental odontoblasts, tendons, and fascia, and weakly induced in subcutaneous fibroblasts. The 2.3 kb type I collagen promoter is unable to induce the expression in the early stage of osteoblast differentiation. The same also strongly induces the expression in dental odontoblasts as well as in osteoblasts, and weakly induces the expression in subcutaneous fibroblasts. Also, the expression induction potential in cultured cells is extremely low. Besides, a 1.3 kb osteocalcin promoter is available, but this is not so commonly used for induction of gene expression in osteoblasts because the expression induction level in living organisms is rather low. Also, the expression thereof is restricted to mature osteoblasts. Therefore, it has been impossible to express a gene comprising a coding region in time of need in a required amount in an osteoblast-specific fashion.

DOCUMENT LIST

Non-patent Documents non-patent document 1: J. Cell Biol. 155: 157-166, 2001
non-patent document 2: Dev. Biol. 296: 48-61, 2006
non-patent document 3: J. Biol. Chem. 275: 8695-8702, 2000
non-patent document 4: J. Cell Biol. 153: 87-100, 2001
non-patent document 5: Arthritis Rheum. 54: 2462-2470, 2006
non-patent document 6: Curr. Opin. in Genet. Dev. 8: 494-499, 1998
non-patent document 7: Biochim. Biophys. Acta 1446: 265-272, 1999
non-patent document 8: Mech Dev 114: 167-170, 2002

SUMMARY OF THE INVENTION

Problems to be Solved by the Invention

The present invention aims to provide an enhancer capable of inducing osteoblast specific expression and use thereof.

Means of Solving the Problems

The present inventors have found during the process of closely investigating two promoters of Runx2 (distal and proximal promoters) that about 1.3 kb region in Runx2 gene has a function as an enhancer, and further confirmed the transcription of osteoblast specific gene can be activated by binding the region with a promoter, which resulted in the completion of the present invention.

That is, the present invention relates to the following.
[1] An enhancer consisting of the following DNA (a), (b) or (c):
(a) a DNA consisting of the base sequence shown by SEQ ID NO: 1
(b) a DNA consisting of the base sequence shown by SEQ ID NO: 1 wherein one or more bases are deleted, substituted or added, which has a function of osteoblast-specifically enhancing the gene expression efficiency
(c) a DNA consisting of a base sequence capable of hybridizing under stringent conditions to a base sequence complementary to the base sequence shown by SEQ ID NO: 1, which has a function of osteoblast-specifically enhancing the gene expression efficiency.
[2] An enhancer consisting of the following DNA (a), (b) or (c):
(a) a DNA consisting of the 92878th-94145th base sequence of SEQ ID NO: 2
(b) a DNA consisting of the 92878th-94145th base sequence of SEQ ID NO: 2, wherein one or more bases are deleted, substituted or added, which has a function of osteoblast-specifically enhancing the gene expression efficiency (c) a DNA consisting of a base sequence capable of hybridizing under stringent conditions to a base sequence complementary to the 92878th-94145th base sequence of SEQ ID NO: 2, which has a function of osteoblast-specifically enhancing the gene expression efficiency.

[3] An enhancer consisting of the following DNA (a), (b) or (c):
(a) a DNA consisting of the base sequence shown by SEQ ID NO: 3
(b) a DNA consisting of the base sequence shown by SEQ ID NO: 3 wherein one or more bases are deleted, substituted or added, which has a function of osteoblast-specifically enhancing the gene expression efficiency
(c) a DNA consisting of a base sequence capable of hybridizing under stringent conditions to a base sequence complementary to the base sequence shown by SEQ ID NO: 3, which has a function of osteoblast-specifically enhancing the gene expression efficiency.

[4] An enhancer consisting of the following DNA (a), (b) or (c):
(a) a DNA consisting of the base sequence shown by SEQ ID NO: 4
(b) a DNA consisting of the base sequence shown by SEQ ID NO: 4 wherein one or more bases are deleted, substituted or added, which has a function of osteoblast-specifically enhancing the gene expression efficiency
(c) a DNA consisting of a base sequence capable of hybridizing under stringent conditions to a base sequence complementary to the base sequence shown by SEQ ID NO: 4, which has a function of osteoblast-specifically enhancing the gene expression efficiency.

[5] An enhancer consisting of the following DNA (a), (b) or (c):
(a) a DNA consisting of the base sequence shown by SEQ ID NO: 5
(b) a DNA consisting of the base sequence shown by SEQ ID NO: 5 wherein one or more bases are deleted, substituted or added, which has a function of osteoblast-specifically enhancing the gene expression efficiency
(c) a DNA consisting of a base sequence capable of hybridizing under stringent conditions to a base sequence complementary to the base sequence shown by SEQ ID NO: 5, which has a function of osteoblast-specifically enhancing the gene expression efficiency.

[6] A vector comprising the enhancer of any of the above-mentioned [1] to [5].

[7] The vector of the above-mentioned [6], further comprising a promoter.

[8] An expression vector comprising the enhancer of any of the above-mentioned [1] to [5], a promoter and a gene containing a coding region.

[9] The expression vector of the above-mentioned [8], wherein the gene containing a coding region is a reporter gene and/or a gene encoding a protein for treatment of a target disease.

[10] The vector of any of the above-mentioned [7]-[9], wherein the promoter is a minimal promoter.

[11] The vector of the above-mentioned [10], wherein the minimal promoter is one kind selected from the group consisting of HSP68 minimal promoter, CMV minimal promoter, SV40 minimal promoter and minimal promoter of PGL4 vector (minP).

[12] A transduced cell comprising the vector of any of the above-mentioned [6] to [11].

[13] A transgenic non-human animal incorporating the vector of is any of the above-mentioned [6] to [11].

[14] A gene expression agent comprising an expression vector comprising the enhancer of any of the above-mentioned [1] to [5], a promoter and a gene containing a coding region as an active ingredient, which is capable of expressing the gene osteoblast-specifically.

[15] A gene therapy agent comprising the gene expression agent of the above-mentioned [14] as an active ingredient, which is for a disease treatable by osteoblast-specific expression of the gene.

[16] The gene therapy agent of the above-mentioned [15], wherein the disease is at least one kind selected from the group consisting of osteoporosis, bone fracture, bone defect, periodontal disease, osteosarcoma, chondrosarcoma, cyst and benign tumor developed in the bone, bone metastasis of cancer, infiltration of cancer into the bone, alveolar bone resorption due to loss of teeth, fibrodysplasia ossificans progressiva, arteriosclerosis, ossification of spine ligament and osteoarthritis.

[17] The gene therapy agent of the above-mentioned [15], which is used for bone regeneration, distraction osteogenesis and/or suppression of osteophyte formation.

[18] A method of confirming differentiation of a pluripotent stem cell into an osteoblast, comprising the following steps:
(a) a step of introducing an expression vector comprising the enhancer of any of the above-mentioned [1]-[5], a promoter and a reporter gene into a pluripotent stem cell,
(b) a step of inducing differentiation of the aforementioned pluripotent stem cell, and
(c) a step of determining whether or not the above-mentioned pluripotent stem cell has differentiated into an osteoblast by measuring the expression of the reporter gene.

[19] A method of screening for a compound that influences the differentiation of a pluripotent stem cell into an osteoblast, comprising the following steps:
(a) a step of introducing an expression vector comprising the enhancer of any of the above-mentioned [1]-[5], a promoter and a reporter gene into a pluripotent stem cell,
(b) a step of inducing differentiation of the aforementioned pluripotent stem cell in the presence or absence of a test substance,
(c) a step of measuring the expression level of the reporter gene in the pluripotent stem cell differentiation induced in the presence of a test substance and comparing the level with that in a pluripotent stem cell differentiation induced in the absence of a test substance, and
(d) a step of screening for a compound that influences the differentiation of the pluripotent stem cell into an osteoblast, based on the aforementioned comparison results.

[20] A method of screening for a compound that influences the activities of an osteoblast, comprising the following steps:
(a) a step of introducing an expression vector comprising the enhancer of any of the above-mentioned [1]-[5], a promoter and a reporter gene into a cultured osteoblast,
(b) a step of contacting or not contacting the aforementioned cultured osteoblast with a test substance,
(c) a step of measuring the expression level and/or activity of the reporter gene in the cultured osteoblast contacted with the aforementioned test substance and comparing the level and/or activity with those/that in a cultured osteoblast not contacted with the test substance, and (d) a step of screening for a compound that influences the activity of the osteoblast, based on the aforementioned comparison results.

[21] A method of screening for a compound that influences the activities of an osteoblast, comprising the following steps:
(a) a step of preparing a transgenic non-human animal by introducing an expression vector comprising the enhancer of any of the above-mentioned [1]-[5], a promoter and a reporter gene,
(b) a step of administering or not administering a test substance to the aforementioned transgenic non-human animal,
(c) a step of measuring the expression level and/or activity of the reporter gene in the transgenic non-human animal administered with the aforementioned test substance and comparing the level and/or activity with those/that in a transgenic non-human animal not administered with the test substance, and
(d) a step of screening for a compound that influences the activity of the osteoblast, based on the aforementioned comparison results.

Effect of the Invention

By using the enhancer of the present invention, osteoblast-specific expression of a specified gene can be induced. This induction enables a wide variety of gene therapies (prevention and treatment of bone fractures, osteogenesis imperfecta, bone calcification and the like). Furthermore, by using the enhancer of the present invention, it is possible to screen for a compound that influences an osteoblast activity (for example, differentiation of osteoblasts), specifically enabling the provision of an osteogenesis promoter, an osteogenesis suppressant and the like.

BRIEF DESCRIPTION OF THE DRAWINGS

FIG. 1, upper panel, is a picture of a transgenic founder on embryonic day 16.5 by fluorescent stereoscopic microscope. GFP is detected in the skeleton. FIG. 1, lower panel, is an immunohistologically stained image of GFP taken using a femur section. GFP is detected in osteoblasts in bone marrow and bone collar, and preosteoblasts around proliferating chondrocytes and hypertrophic chondrocytes.

Figure 6A:
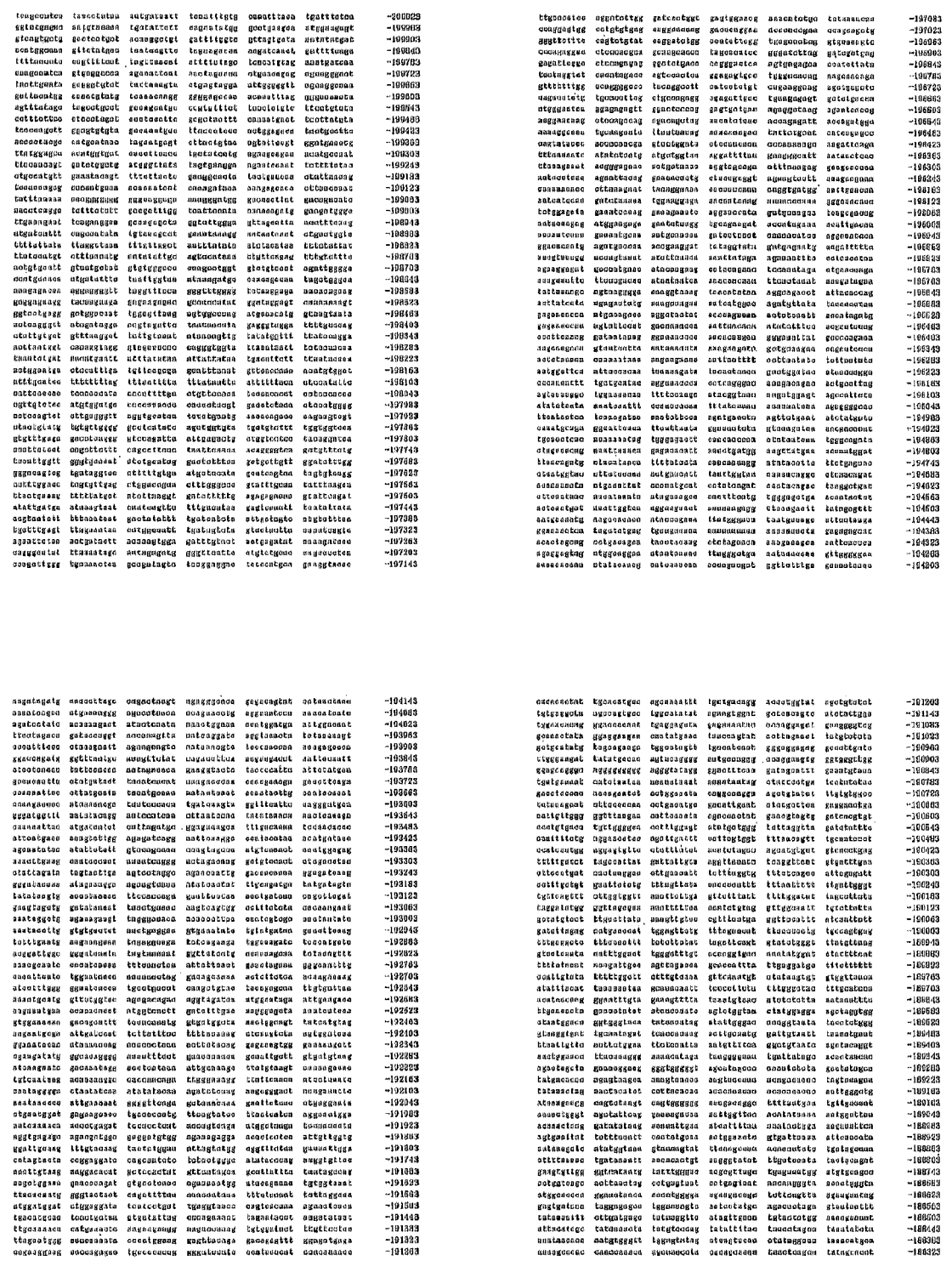
Figure 6B:
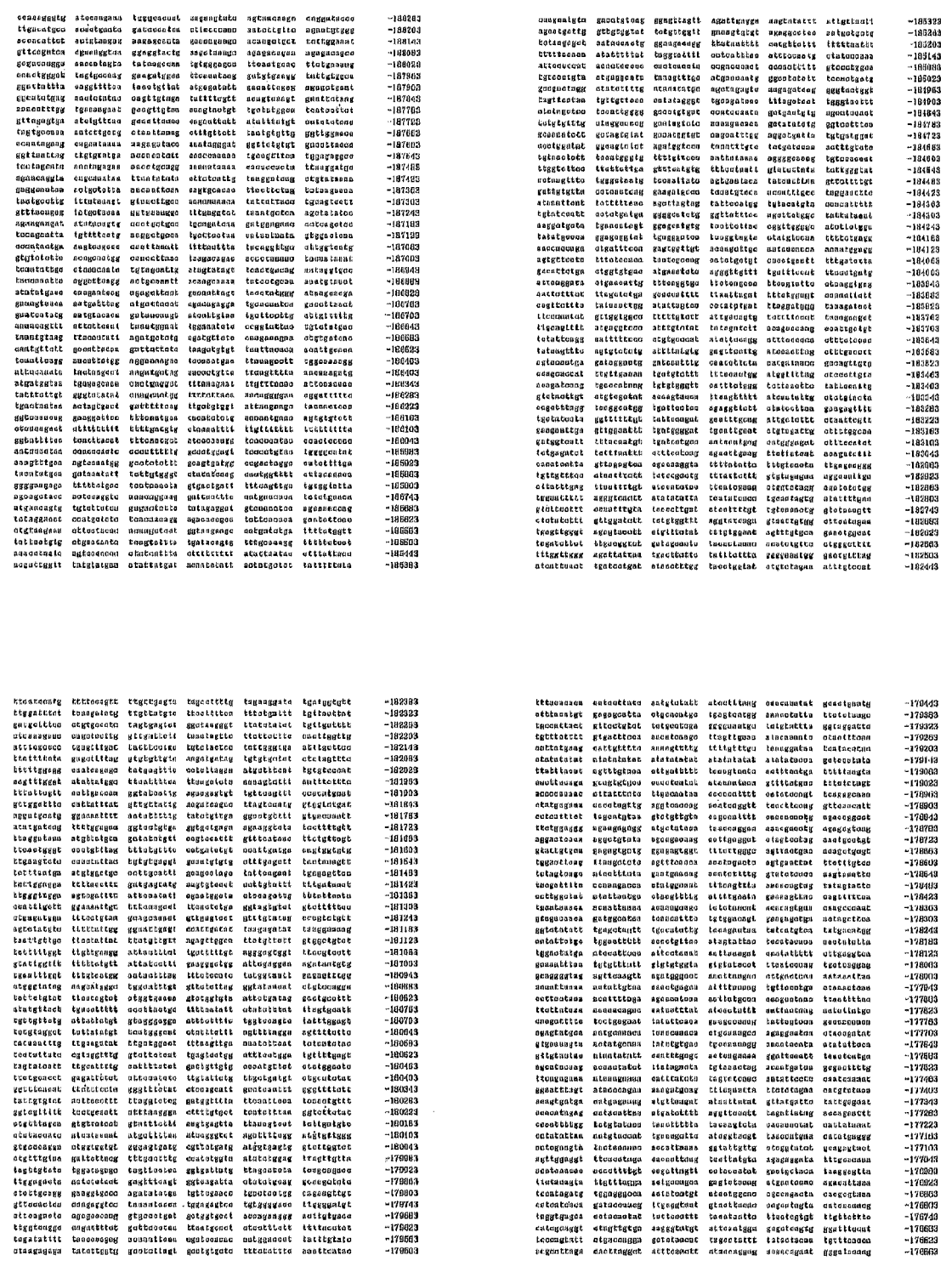
Figure 6C:
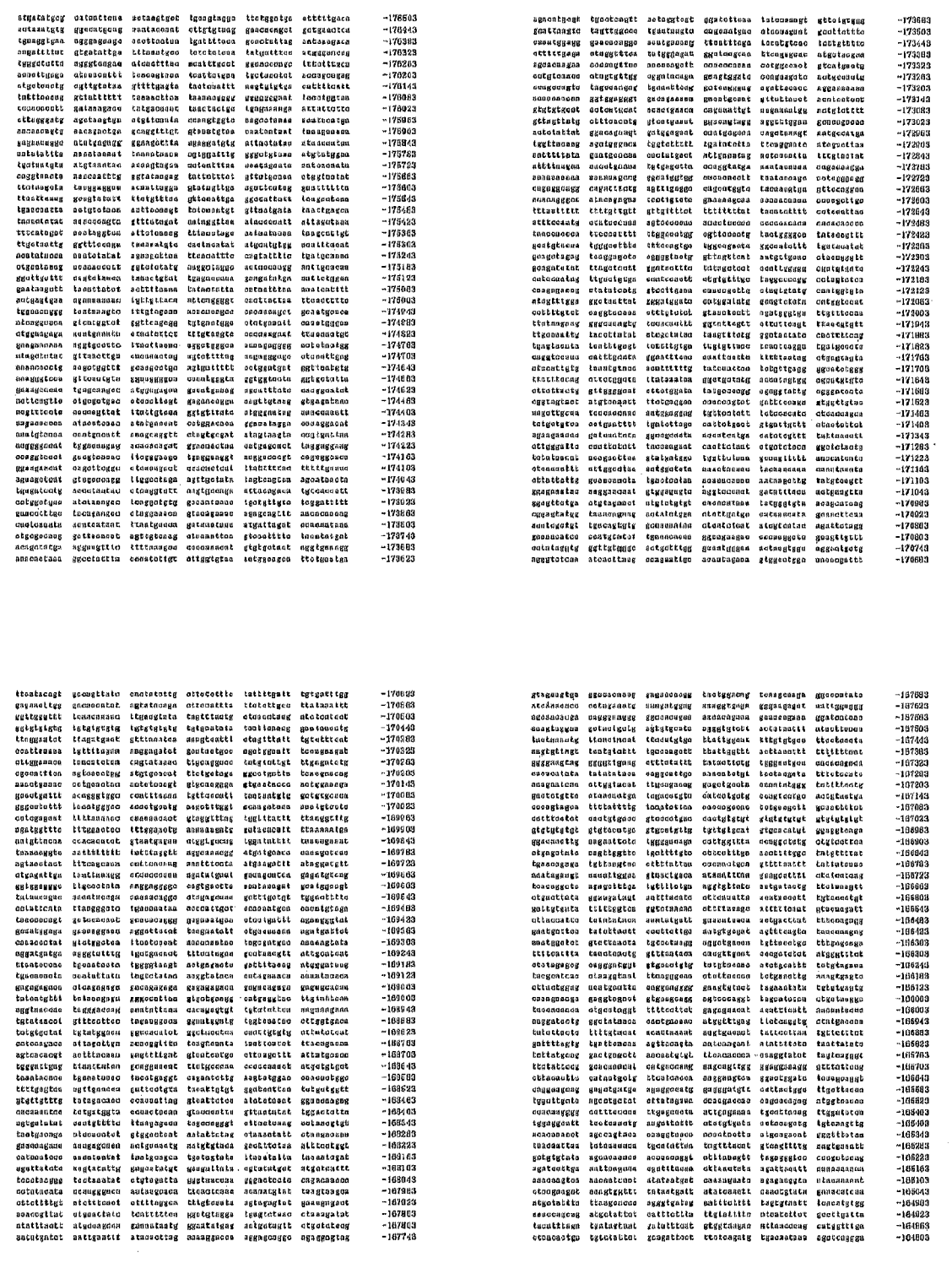
Figure 6E:
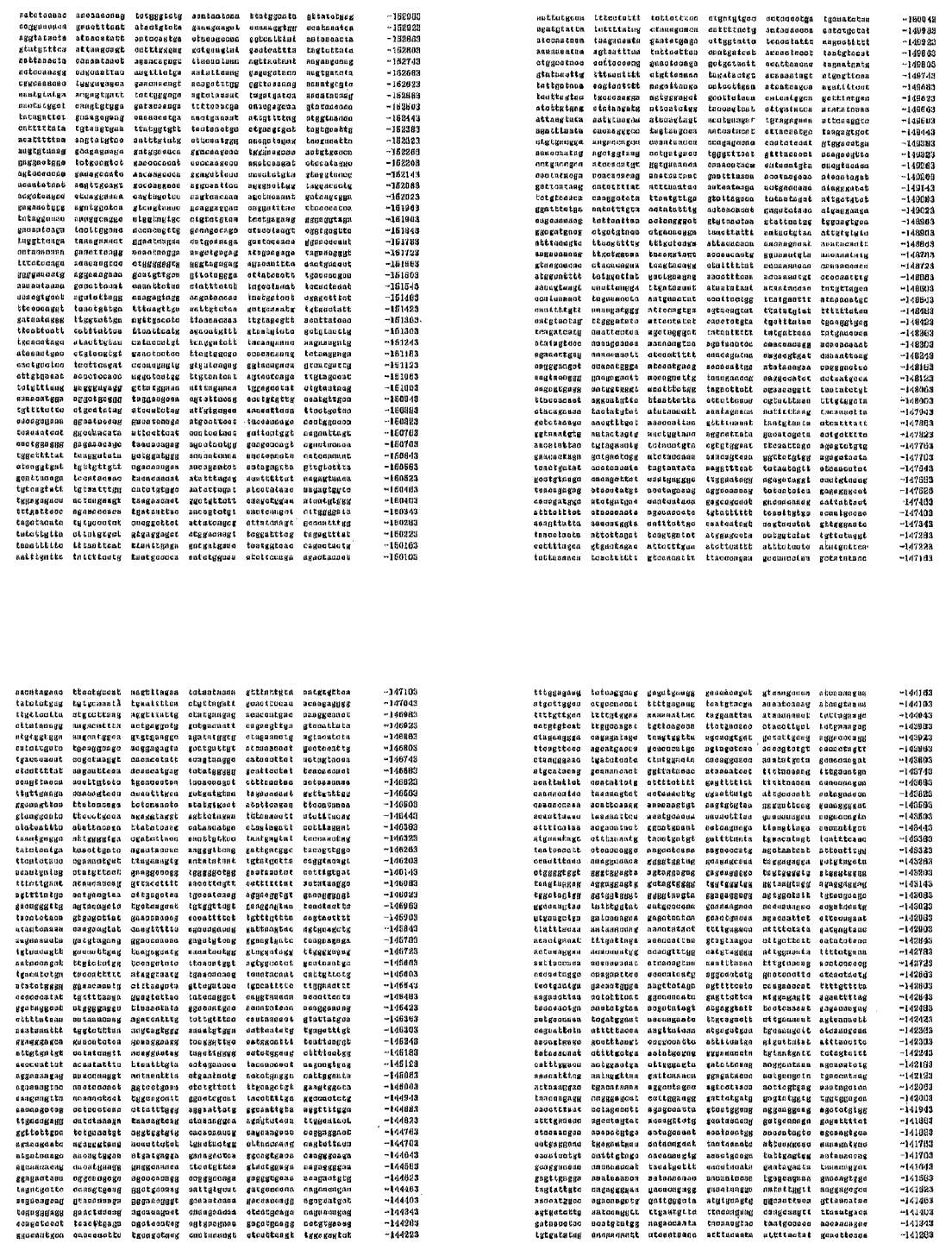
Figure 6F:
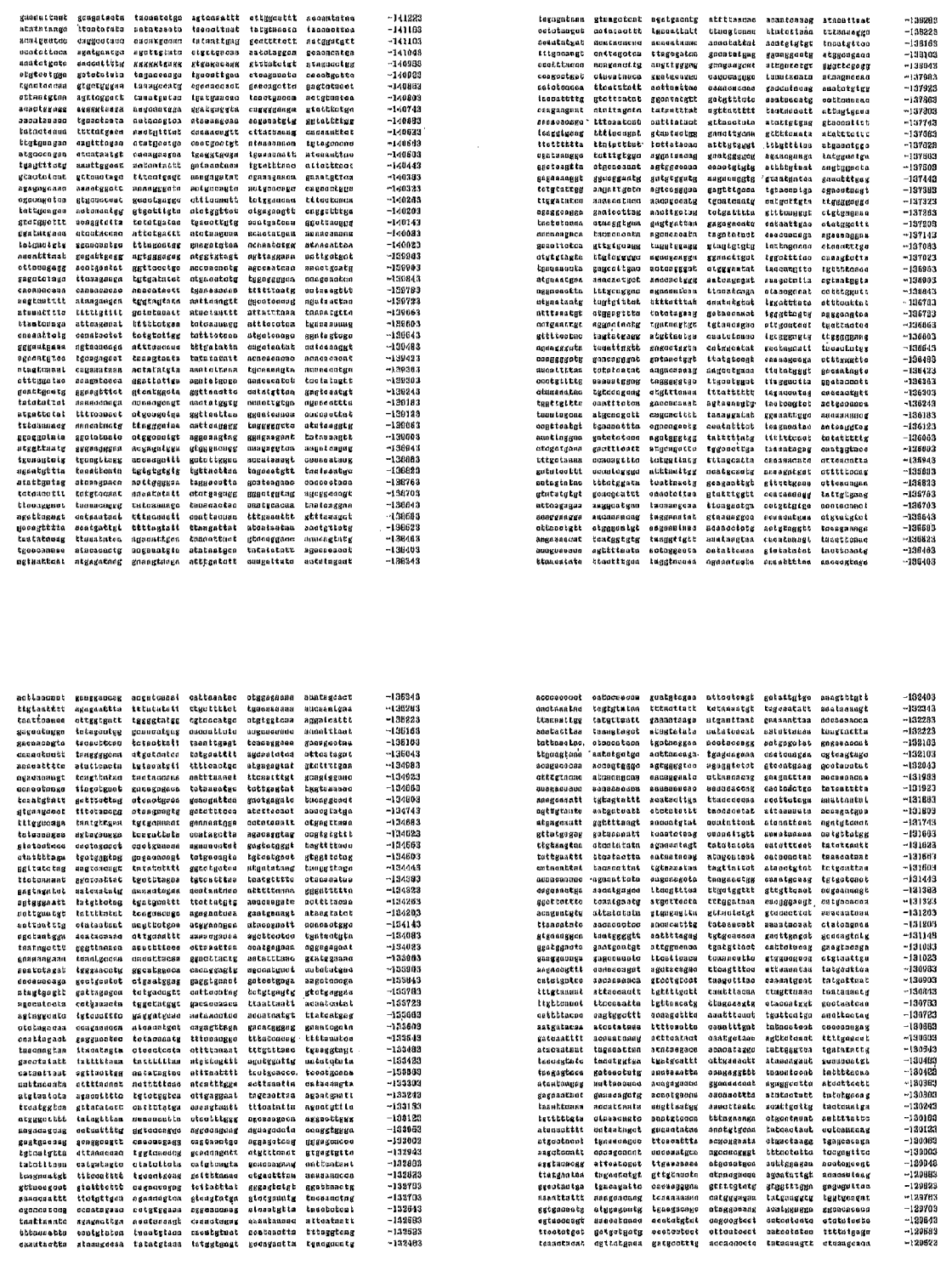
Figure 6H:
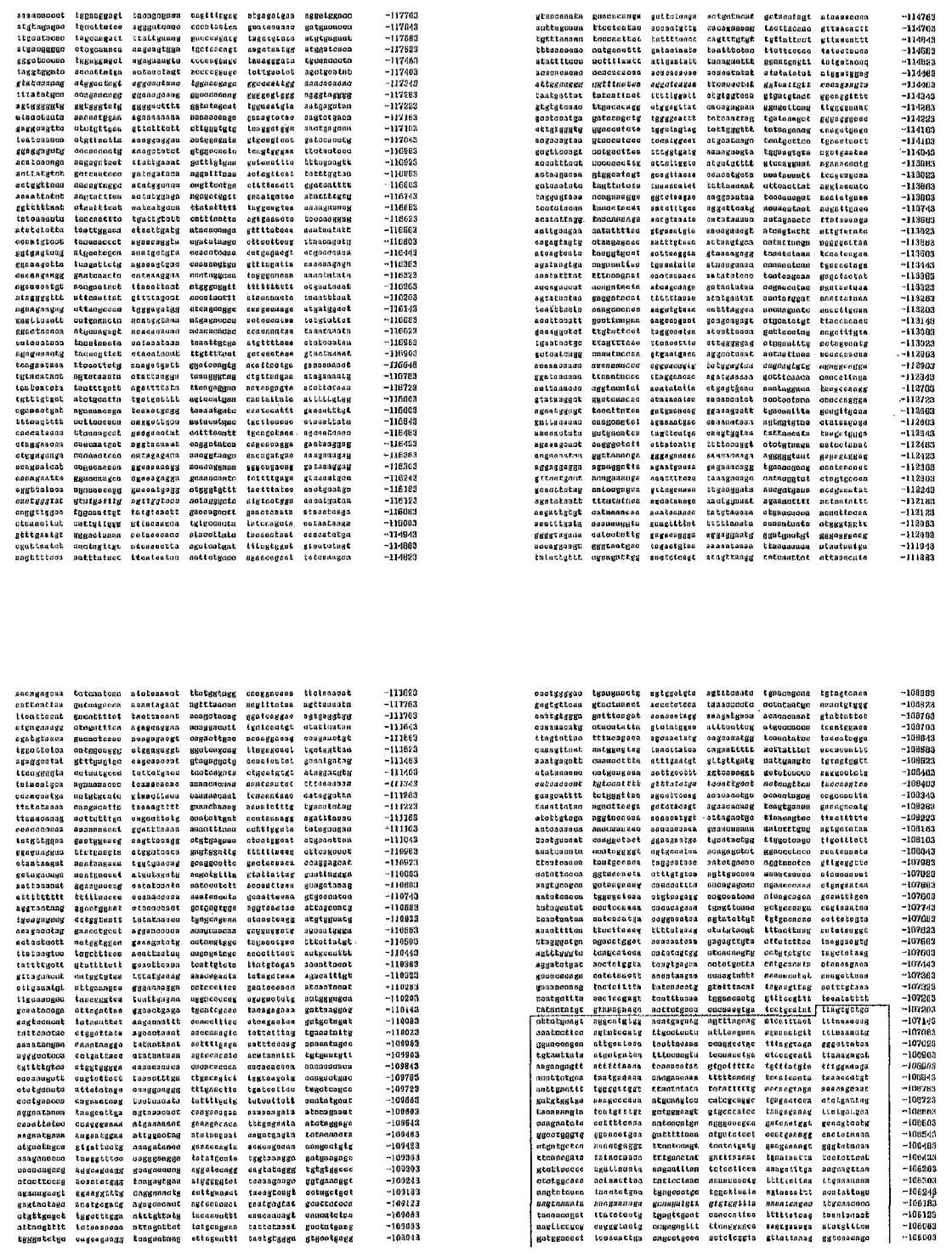
Figure 6J:
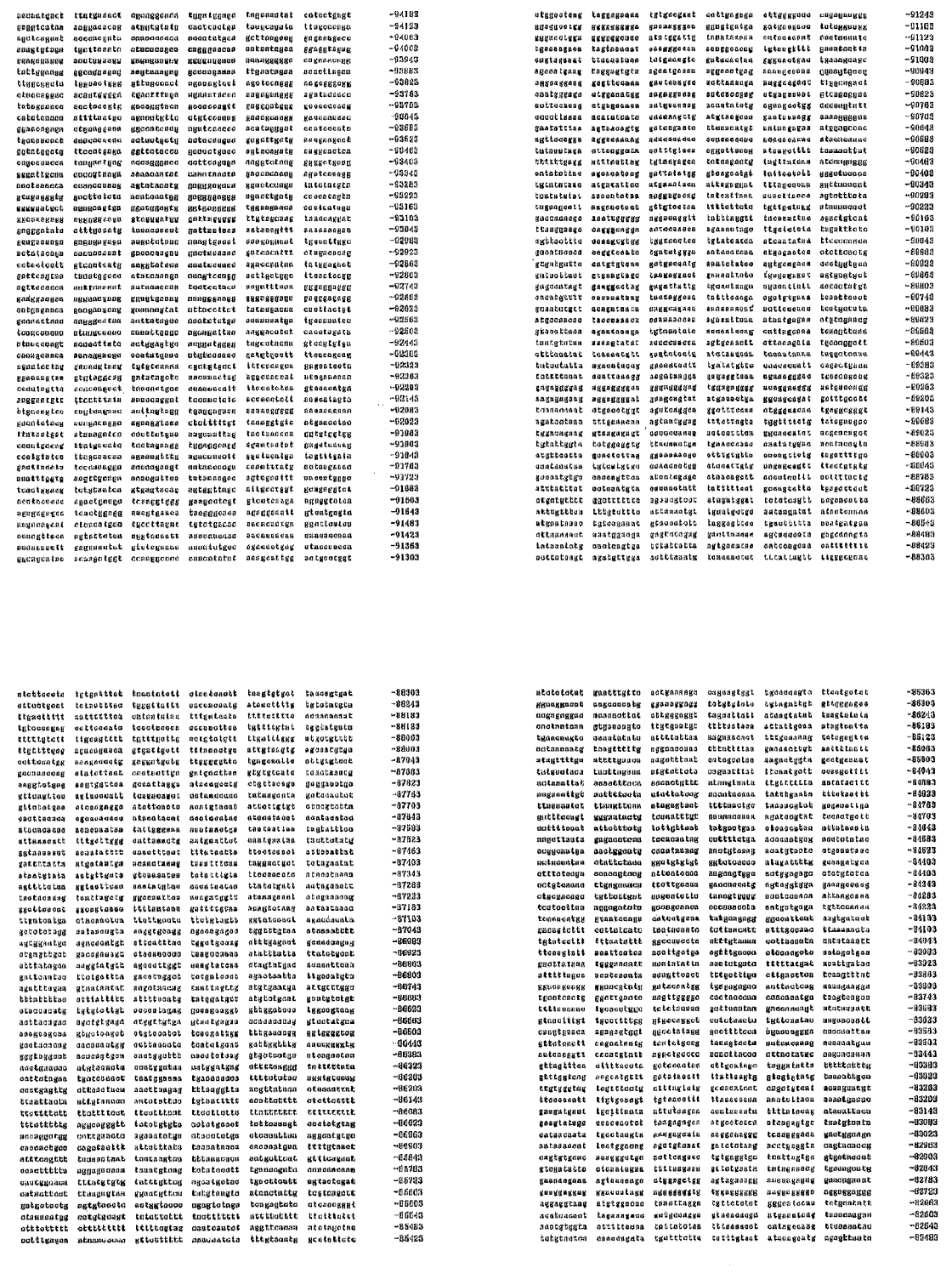
Figure 6K:
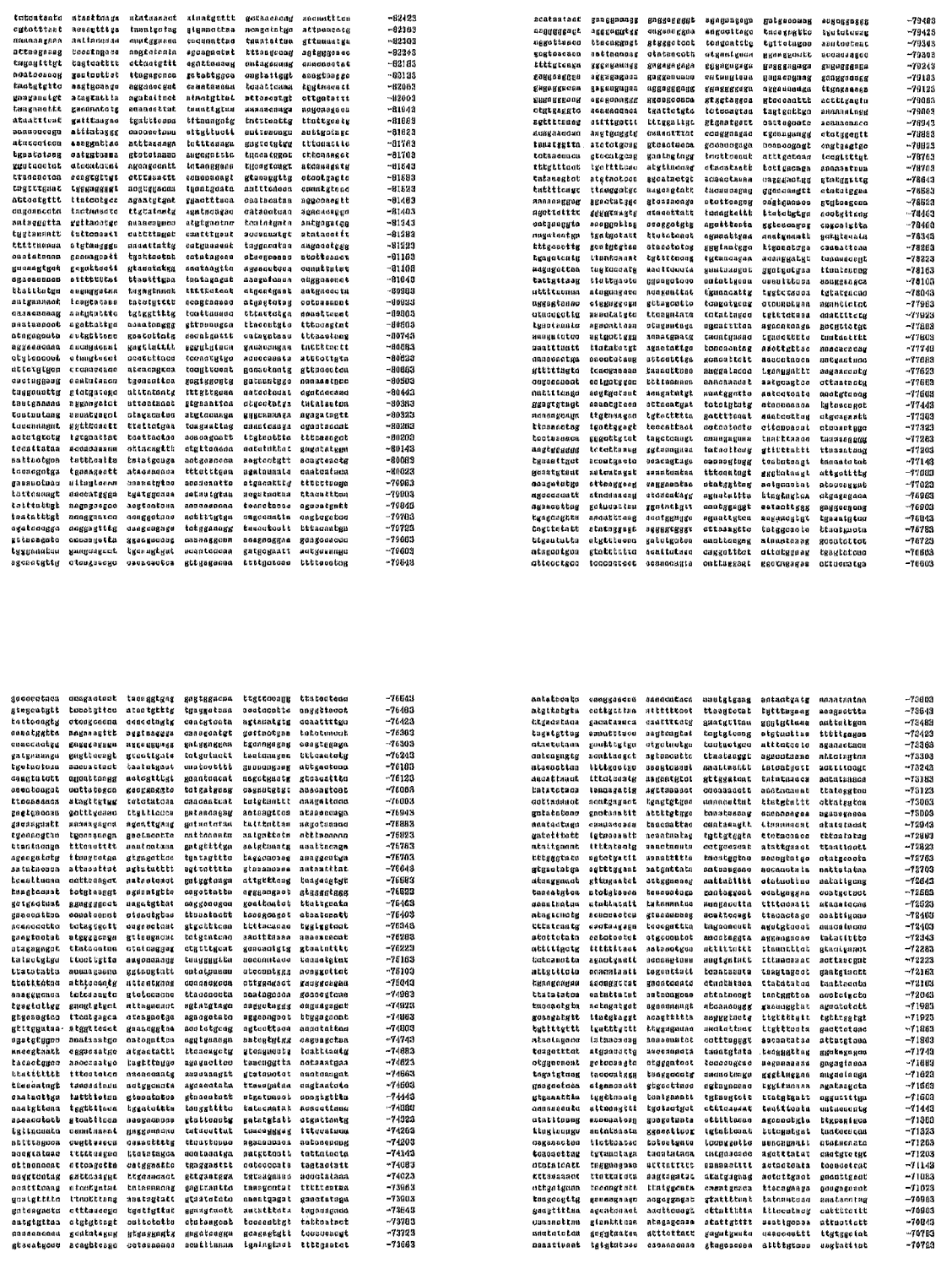
Figure 6L:
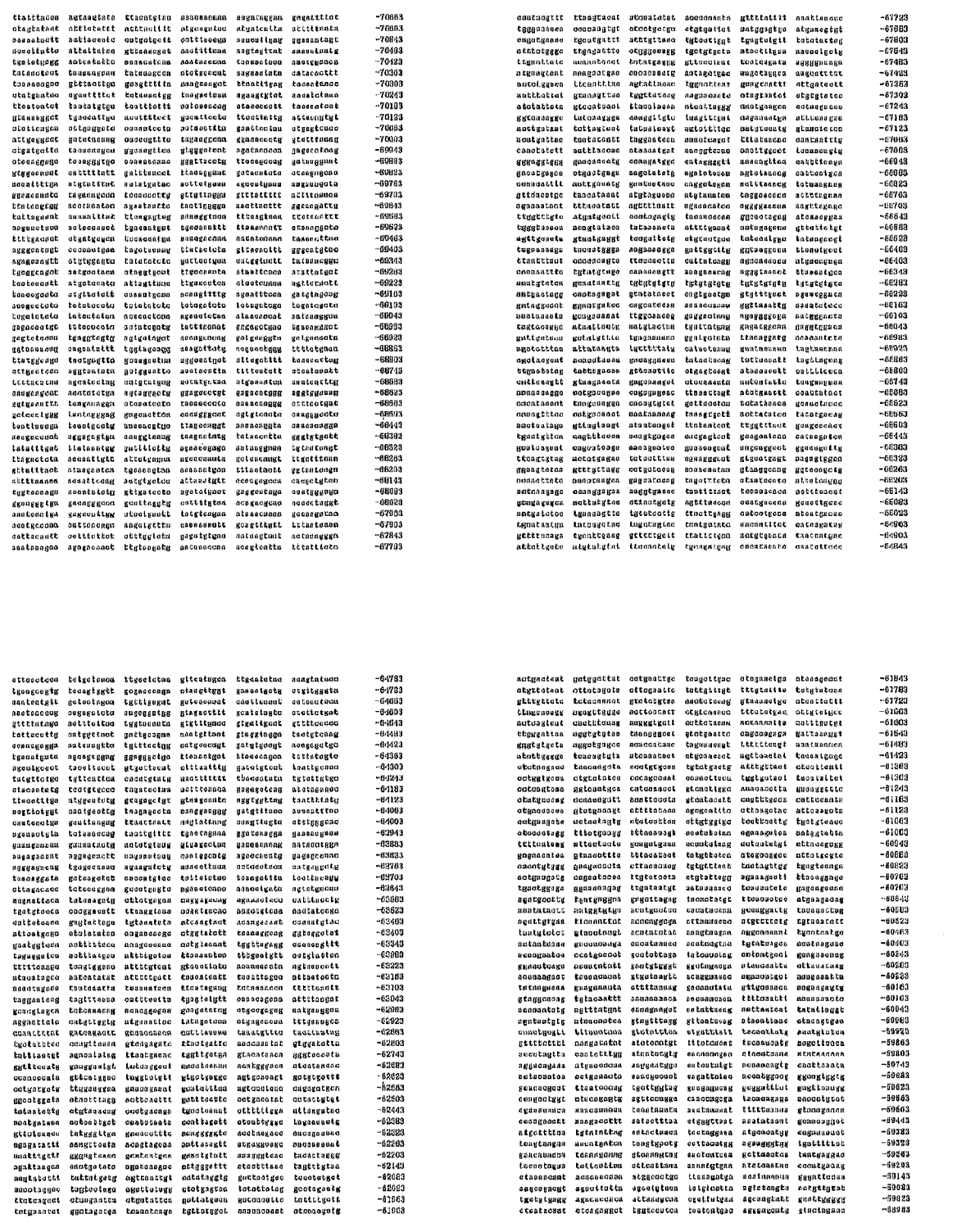
Figure 6M:
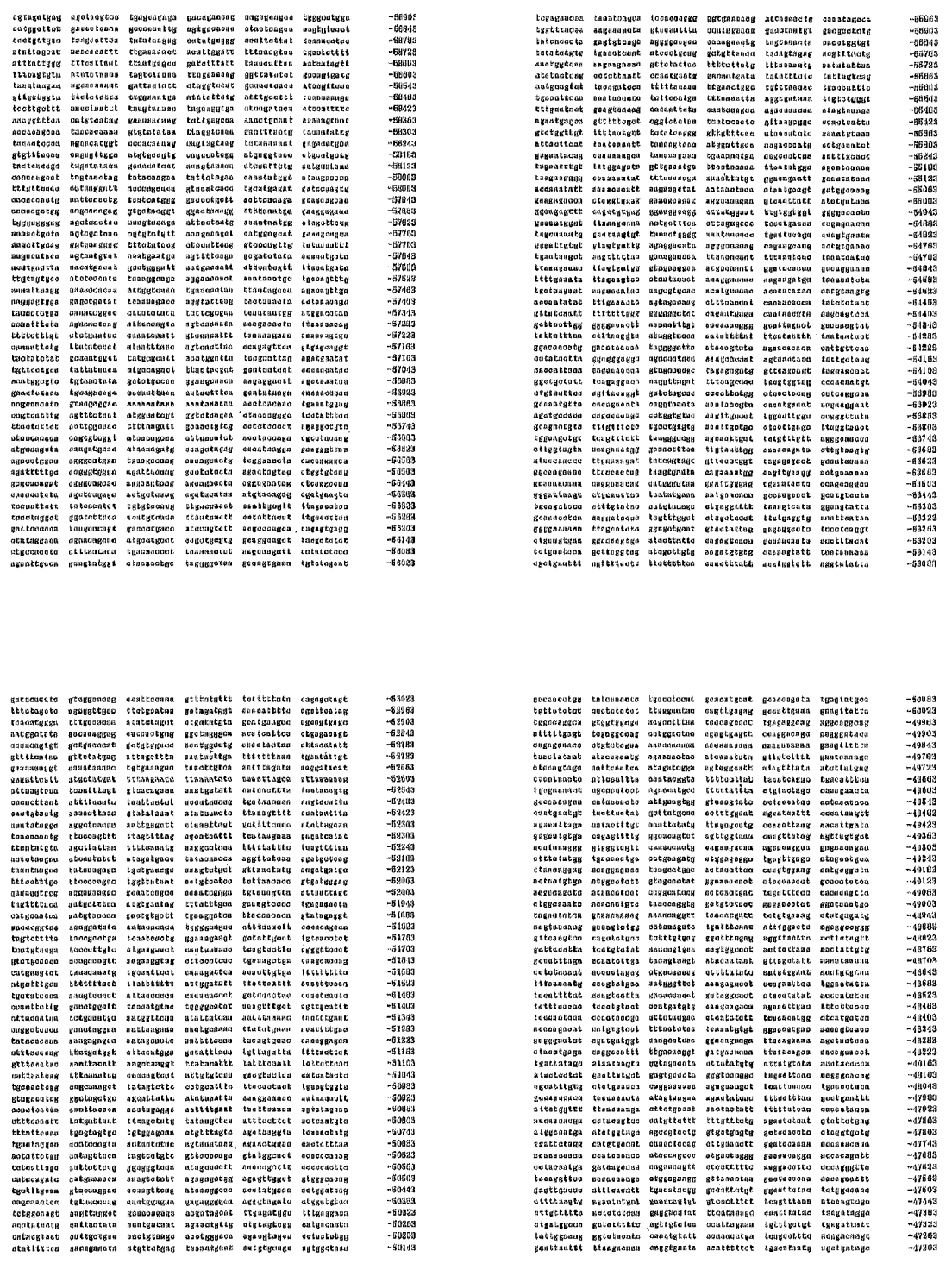
Figure 6N:
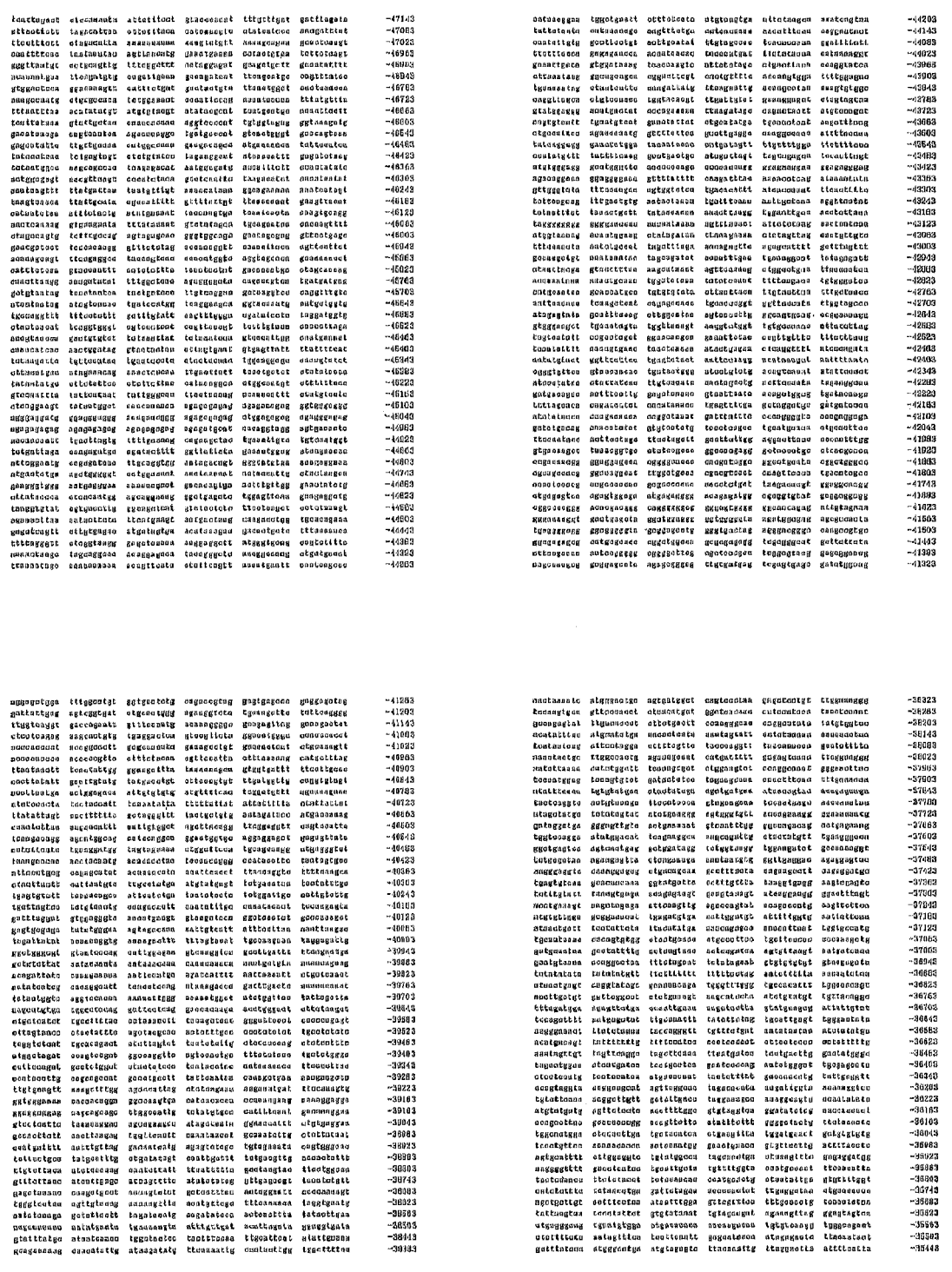
Figure 6P:
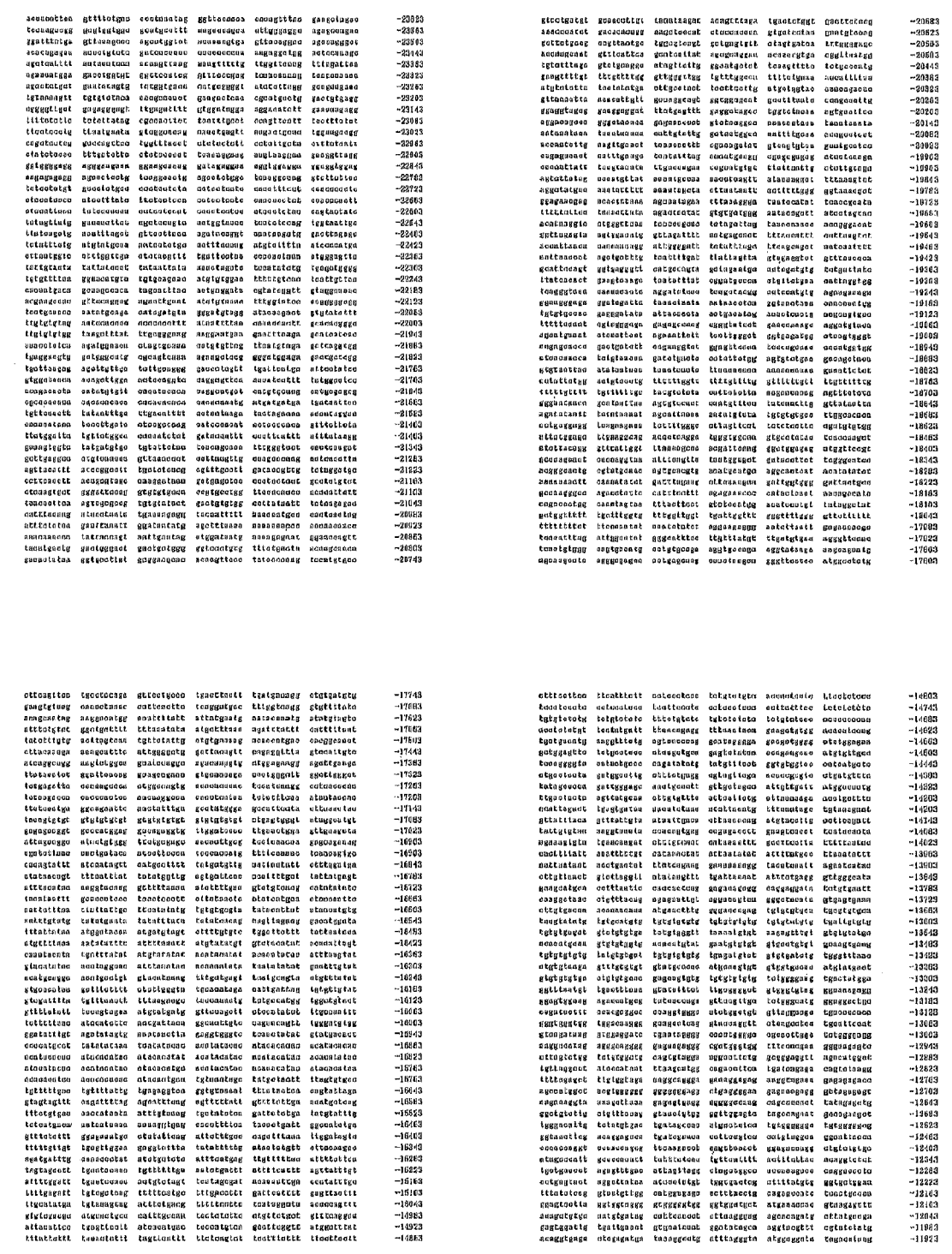
Figure 6Q:
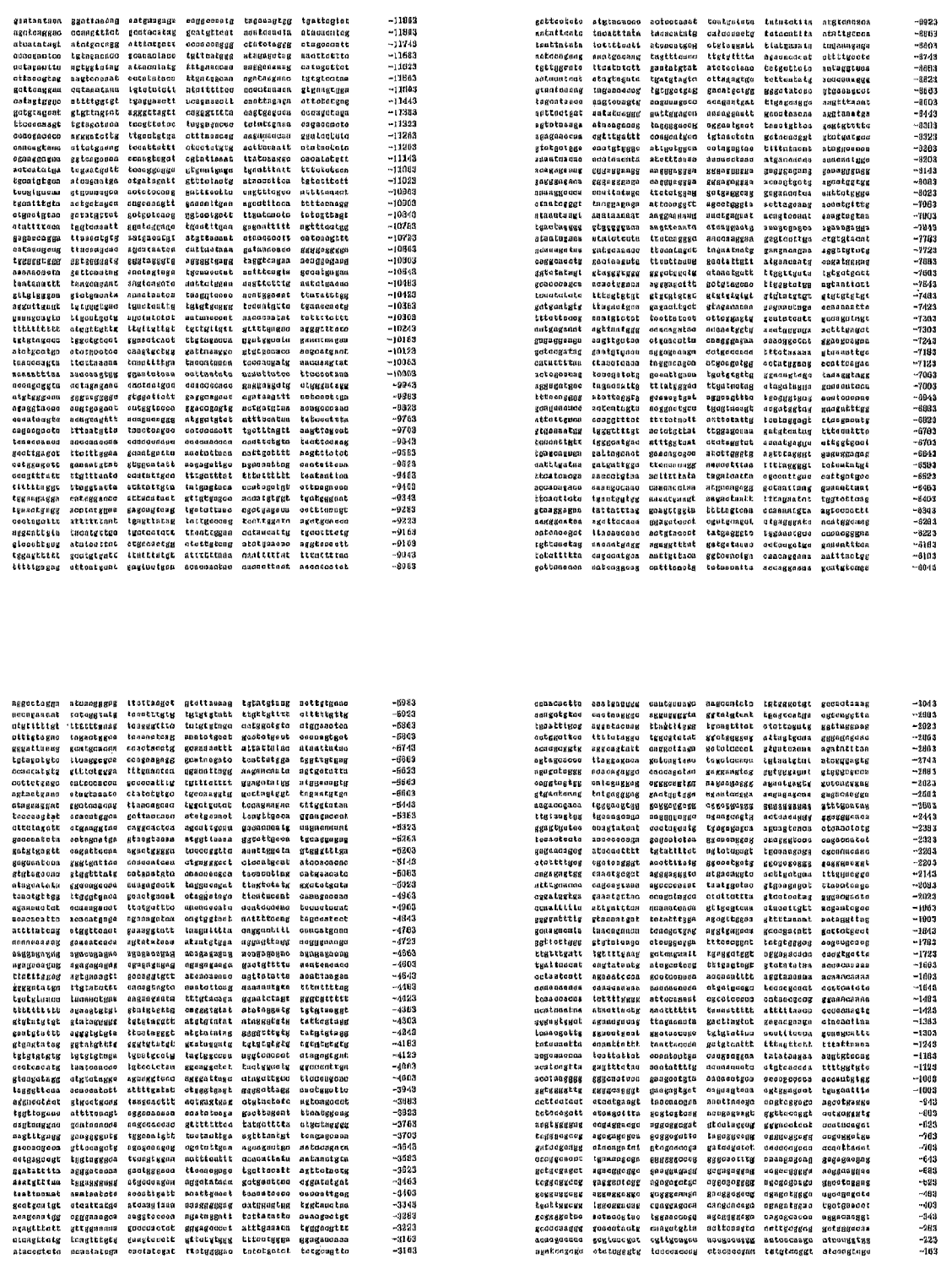

FIGS. 6A-6R is the base sequence of an about 200 kb region comprising exon 1, a part of exon 2, intron 1 and about 100 kb upstream of the exon 1, of Runx2 and corresponds to SEQ ID NO: 2.

FIG. 7 is a drawing showing the sequence of the 1.3 kb enhancer region of human Runx2 (SEQ ID NO: 4). The inset shows the sequence of the 0.34 kb enhancer region (SEQ ID NO: 5).

In FIG. 8, the mouse 0.34 kb enhancer region (SEQ ID NO: 3) and the human 0.34 kb enhancer region (SEQ ID NO: 5) correspond to positions 787-1206 of the mouse 1.3 kb enhancer region (SEQ ID NO: 1) and the human 1.3 kb enhancer region (SEQ ID NO: 4), respectively. The consensus sequence corresponds to SEQ ID NO: 6.

DESCRIPTION OF EMBODIMENTS

Figure 2:
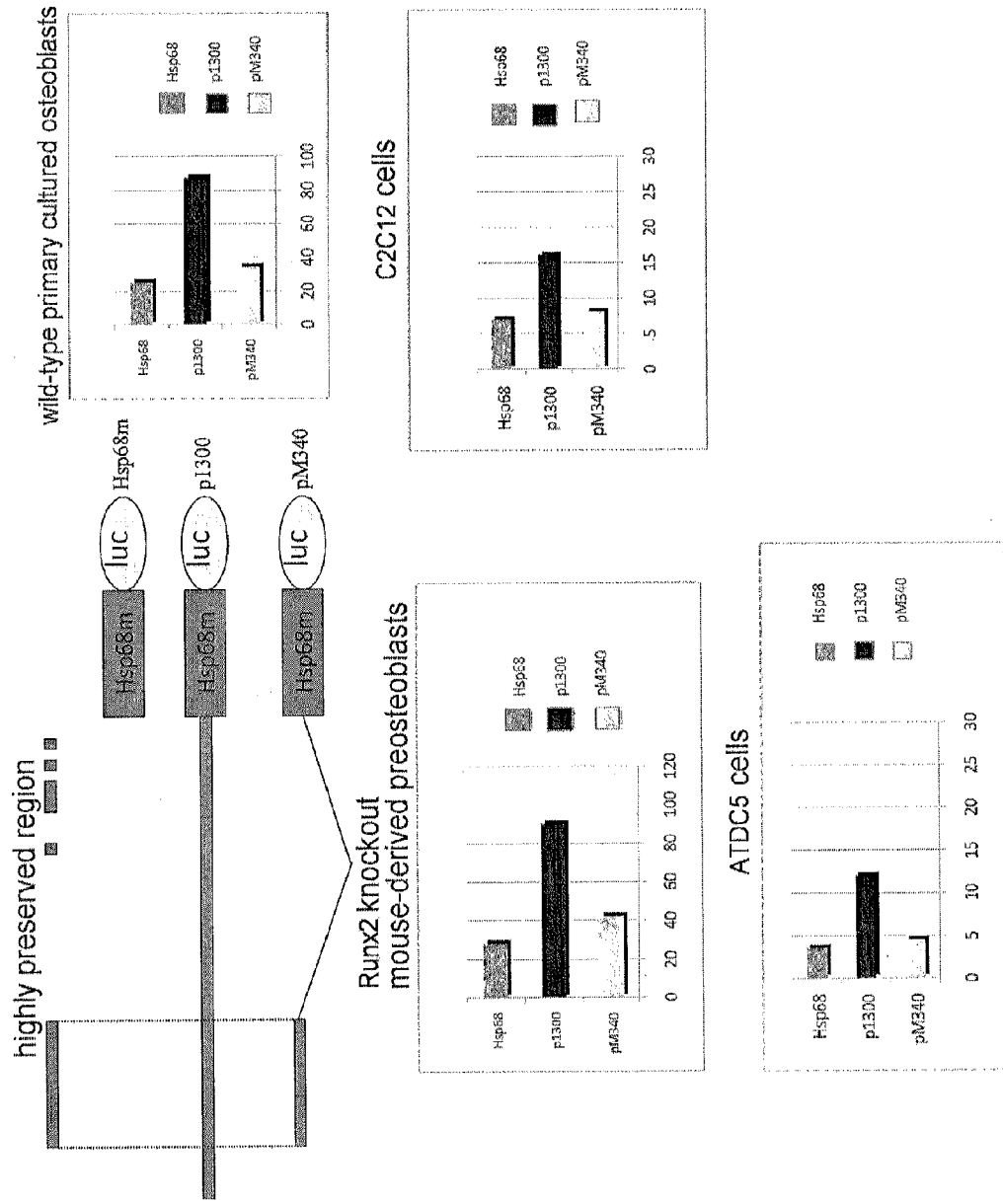
FIG. 2 is a drawing showing the results of a reporter assay using the 1.3 kb enhancer and a deletion variant thereof. Wild-type osteoblast progenitor cells (primary cultured osteoblasts), Runx2 knockout mouse osteoblast progenitor cells, C2C12 cells, and ATDC5 cells were used. Contained in the 1.3 kb are two roughly divided conserved regions; the 0.34 kb is a particularly highly conserved region.

The present invention provides an enhancer consisting of the following DNA (a), (b) or (c):
(a) a DNA consisting of the base sequence shown by SEQ ID NO: 1
(b) a DNA consisting of the base sequence shown by SEQ ID NO: 1 wherein one or more bases are deleted, substituted or added, which has a function of osteoblast-specifically enhancing the gene expression efficiency
(c) a DNA consisting of a base sequence capable of hybridizing under stringent conditions to a base sequence complementary to the base sequence shown by SEQ ID NO: 1, which has a function of osteoblast-specifically enhancing the gene expression efficiency.

Enhancer refers to a base sequence region on DNA, which is bound to a transcription factor to regulate the gene expression, and the enhancer activates transcription in cooperation with a promoter. The enhancer of the present invention is specifically a DNA consisting of the base sequence shown by SEQ ID NO: 1. The base sequence shown by SEQ ID NO: 1 corresponds to the −107205th to −105938th region of mouse Runx2 gene (92878th-94145th region of SEQ ID NO: 2). A DNA fragment consisting of the base sequence shown by SEQ ID NO: 1 is an enhancer having a function of osteoblast-specifically enhancing the gene expression efficiency.

As for human Runx2 gene, the −107205th to −105938th region of mouse Runx2 gene (−163410th to −162149th of human Runx2 gene) also has a function of as enhancer to osteoblast-specifically enhance the gene expression efficiency. That is, another embodiment of the present invention is an enhancer derived from human Runx2, which consists of the following DNA (a), (b) or (c):
(a) a DNA consisting of the base sequence shown by SEQ ID NO: 4

(b) a DNA consisting of the base sequence shown by SEQ ID NO: 4 wherein one or more bases are deleted, substituted or added, which has a function of osteoblast-specifically enhancing the gene expression efficiency
(c) a DNA consisting of a base sequence capable of hybridizing under stringent conditions to a base sequence complementary to the base sequence shown by SEQ ID NO: 4, which has a function of osteoblast-specifically enhancing the gene expression efficiency.

As mentioned below in the Examples, the present inventors have successfully identified the about 0.34 kb region (to be also referred conveniently to a 0.34 kb enhancer in the present specification) necessary for osteoblast-specific expression in the above-mentioned about 1.3 kb enhancer (to be also referred conveniently to a 1.3 kb enhancer in the present specification) region. Therefore, another embodiment of the present invention provides an enhancer derived from mouse Runx2 and consisting of the following DNA (a), (b) or (c):
(a) a DNA consisting of the base sequence shown by SEQ ID NO: 3
(b) a DNA consisting of the base sequence shown by SEQ ID NO: 3 wherein one or more bases are deleted, substituted or added, which has a function of osteoblast-specifically enhancing the gene expression efficiency
(c) a DNA consisting of a base sequence capable of hybridizing under stringent conditions to a base sequence complementary to the base sequence shown by SEQ ID NO: 3, which has a function of osteoblast-specifically enhancing the gene expression efficiency, or
an enhancer derived from human Runx2 and consisting of the following DNA (a), (b) or (c):
(a) a DNA consisting of the base sequence shown by SEQ ID NO: 5
(b) a DNA consisting of the base sequence shown by SEQ ID NO: 5 wherein one or more bases are deleted, substituted or added, which has a function of osteoblast-specifically enhancing the gene expression efficiency
(c) a DNA consisting of a base sequence capable of hybridizing under stringent conditions to a base sequence complementary to the base sequence shown by SEQ ID NO: 5, which has a function of osteoblast-specifically enhancing the gene expression efficiency.

Moreover, the enhancer in the present invention may have the base sequences shown by SEQ ID NOs: 1, 3, 4 and 5 (in the 20 present specification, to be also conveniently referred to as an enhancer sequence of the present invention), wherein one or more bases are deleted, substituted or added, or a base sequence capable of hybridizing to a base sequence complementary to the enhancer sequence of the present invention under stringent conditions, as long as it has a function to enhance the gene expression efficiency in an osteoblast-specific fashion.

Here, in the enhancer sequence of the present invention, a base sequence wherein one or more bases are deleted, substituted or added means, for example, a base sequence wherein 1-30 bases, preferably 1-20 bases, more preferably 1-10 bases, still more preferably 1 to several bases, are deleted, substituted or added.

When deleting, substituting or adding one or more bases to the enhancer sequence of the present invention, conventionally publicly known techniques and appropriate combinations thereof can be used. For example, a method of artificial mutagenesis can be performed by a commonly used method of site-directed mutagenesis and the like. Methods that can be used to introduce site-directed mutagenesis include, for example, the method utilizing an amber mutation [gapped duplex method, Nucleic Acids Research, 12, 9441-9456 (1984)], the method utilizing a host deficient in the dut (dUTPase) and ung (uracyl-DNA glycosylase) genes [Kunkel method, Proc. Natl. Acad. Sci. USA, 82, 488-492 (1985)], the method based on PCR using an amber mutation (WO98/02535) and the like.

Moreover, hybridizing to a base sequence complementary to the enhancer sequence of the present invention under stringent conditions means that a specific hybrid is formed and a non-specific hybrid is not formed under stringent conditions. For example, nucleic acids with high homology of not less than 60%, preferably not less than 80%, are hybridized to each other, and DNAs having a lower homology are not hybridized.

As for the stringent hybridization conditions, those of ordinary skill in the art can select appropriate conditions. In one embodiment, prehybridization is performed in a hybridization solution containing in 25% formamide, under more stringent conditions in 50% formamide, 4×SSC, 50 mM Hepes pH 7.0, 10× Denhardt's solution and 20 µg/mL, denatured sermon sperm DNA, at 42° C. overnight, and hybridization is performed by adding a labeled probe and incubating at 42° C. overnight. The washing and temperature conditions for washing thereafter can be about "1×SSC, 0.1% SDS, 37° C.", more stringent conditions are about "0.5×SSC, 0.1% SDS, 42° C", still more stringent conditions are about "0.2×SSC, 0.1% SDS, 65° C.". With more stringent washing conditions for hybridization, isolation of a DNA having a higher homology with a probe sequence can be expected. However, the combination of SSC, SDS and temperature conditions is an example and those of ordinary skill in the art can realize the stringency similar to the above-mentioned by appropriately combining the above-mentioned or other factors (for example, probe concentration, probe length, reaction time of hybridization etc.).

Furthermore, the DNA in the present invention includes an isolated DNA having at least 60%, preferably not less than 70%, more preferably not less than 80%, of sequence identity with a DNA having the base sequence shown by SEQ ID NO: 1, 3, 4 or 5, which shows osteoblast specific enhancer activity.

Herein, "sequence identity" refers to residue sequence similarity between two polynucleotides. The aforementioned "sequence identity" is determined by comparing the two sequences aligned in the optimum state over the region of the sequence to be compared. Here, the polynucleotide to be compared may have an addition or a deletion (for example, gaps and the like) compared with a reference sequence (for example, consensus sequence and the like) for the optimum alignment of the two sequences.

Numerical values (percentages) of sequence identity can be calculated by identifying the same nucleic acid bases present in both sequences to determine the number of fitting sites, then dividing the number of fitting sites by the total number of bases in the sequence region to be compared, and multiplying the obtained numerical value by 100. Algorithms for obtaining the optimum alignment and homology include, for example, the localized homology algorithm of Smith et al. [Add. APL. Math., 2, 482 (1981)], the homology alignment algorithm of Needleman et al. [J. Mol. Biol., 48, 443(1970)], and the homology search method of Pearson et al. [Proc. Natl. Acad. Sci. USA, 85, 2444 (1988)], more specifically including the dynamic programming method, gap penalty method, Smith-Waterman algorithm, Good-Kanehisa algorithm, BLAST algorithm, FASTA algorithm and the like.

The sequence identity of such DNA can be measured, for example, by using a sequence analysis software, specifically, BLASTN and the like. Such software is generally available from homepage address www.ncbi.nlm.nih.gov/BLAST/. A default parameter for comparison of two base sequences by BLASTN is, for example, Matrix: BLOSUM62, Gap existence cost: 11, Per residue gap cost: 1, Lambda ratio: 0.85.

"The function of enhancing the gene expression efficiency in an osteoblast-specific fashion" means that the function of enhancing the transcription efficiency for an optionally chosen gene in particular appears specifically in osteoblasts. Whether or not the DNA fragment having an optionally chosen base sequence possesses the function can be determined by, for example, integrating the DNA fragment into a vector having an optionally chosen promoter and a reporter gene to generate a recombinant vector, introducing the vector into a transgenic animal, and determining whether or not the expression of the reporter gene in osteoblasts has increased. If the expression of the reporter gene in the osteoblasts of the transgenic animal has increased, the DNA fragment possesses the above-mentioned function.

While the transgenic animal to be prepared here is not particularly limited, a transgenic animal permitting easy determination of reporter gene expression in an osteoblast is preferably prepared and, for example, a transgenic mouse and the like can be used (detail to be mentioned below).

In addition, the function of a DNA fragment can also be examined by introducing an expression vector containing the DNA fragment into a cultured osteoblast.

As the reporter gene here, β-galactosidase (sometimes to be abbreviated as β-gal) gene, alkaliphosphatase gene, chloramphenicol acetyltransferase gene, growth hormone gene, luciferase gene, green fluorescence protein gene (sometimes to be abbreviated as GFP), blue fluorescence protein gene, yellow fluorescence protein gene, red fluorescence protein gene and derivatives thereof and the like can be mentioned. The aforementioned "derivative" includes artificially prepared variants.

As the promoter usable for the vector of the present invention, promoter of Runx2 gene (e.g., about 200 kb region containing upstream and intron of Runx2 gene; see Example for the detail), minimal promoter (e.g., HSP68 minimal promoter, CMV minimal promoter, SV40 minimal promoter, minimal promoter (MinP) of PGL4 vector), human-derived promoter (e.g., β-globin promoter etc.) and the like can be used. Preferred is a minimal promoter since a shorter DNA construct can be obtained. Particularly preferably, a promoter maintaining specificity of enhancer, capable of suppressing gene expression in other tissues, and showing almost no transcription activation ability by itself is used. From such aspect, HSP68 minimal promoter is preferable as a minimal promoter.

The minimal promoter refers to a DNA region that determines the starting site for transcription by RNA polymerase II, and is involved in the maintenance of the lowest required level of transcription, also known as the core promoter, is normally seen in a relatively narrow portion in the vicinity of transcription starting site for the gene. The minimal promoter is incapable of expressing downstream gene when used alone, but is capable of expressing a downstream gene with the provision that an enhancer is present in the vicinity.

The present invention provides a vector harboring the above-mentioned osteoblast specific enhancer. The vector is exemplified by an expression vector capable of specifically increasing the expression level of the gene whose expression is desired to increase in osteoblasts using the enhancer of the present invention. This expression vector comprises, for example, a promoter and the coding region of the gene whose expression is desired to increase. Also, the expression vector may be one comprising a promoter and a reporter gene. As the promoter, the above-mentioned various promoters can be used. As the reporter gene, the above-mentioned various reporter genes can be used. In particular, in the case of an expression vector for gene therapy in humans, the HSP68 minimal promoter is suitably used, as the promoter, but a Runx2 promoter is also suitable.

Although the arrangement of the various constituents in the vector of the present invention is not particularly limited, as far as they are able to work appropriately, it is preferable that the promoter and the reporter gene (and/or the gene whose expression is desired to increase) be joined in this order from 5' to 3', and this is obtained by cloning each constituent into the vector serving as the backbone by a method known per se. The position where the enhancer is joined may be either of the 5' side of the promoter and the 3' side of the reporter gene (and/or the gene whose expression is desired to increase). As the vector serving as the backbone, an appropriate vector can be chosen according to the purpose.

Specifically, mammal-derived vectors (e.g., pcDNA3 (manufactured by Invitrogen), pEGF-BOS (Nucleic Acids. Res., 18(17), p. 5322, 1990), pEF, pCDM8, pCXN), insect cell-derived vectors (for example, "Bac-to-BAC baculovirus expression system" (manufactured by Invitrogen), pBac-PAK8), plant-derived expression vectors (for example, pMH1, pMH2), animal virus-derived vectors (e.g., pHSV, pMV, pAdexLcw), retrovirus-derived vectors (e.g., pZIP-neo), yeast-derived vectors (for example, "*Pichia* Expression Kit" (manufactured by Invitrogen), pNV11, SP-Q01), *Bacillus subtilis*-derived vectors (for example, pPL608, pKTH50), *Escherichia coli* vectors (M13-series vectors, pUC-series vector, pBR322, pBluescript, pCR-Script) and the like can be mentioned. In the present invention, it is preferable to use a vector expressible in mammalian cells.

Furthermore, a bacterial artificial chromosome (BAC) vector enabling a larger DNA fragment to be integrated can also be suitably used. For example, pBACe3.6, pBeloBAC11, pECBAC1, pCLD04501, pBiBAClac1, BiBAC2, V41 and the like can be nonlimitatively mentioned.

The vector of the present invention may comprise, in addition to the above-mentioned various constituents, a vector-derived optionally chosen base sequence or an optionally chosen base sequence resulting from a restriction endonuclease site added in the process of cloning and the like, as far as the objects of the present invention can be accomplished.

The thus-obtained vector can be confirmed by sequencing and the like to have been cloned at a desired position in a desired direction.

The gene comprising the coding region contained in the vector of the present invention is exemplified by a gene that encodes a protein whose amount expressed in osteoblasts is desired to increase specifically, and also encodes a protein for treating a wide variety of target diseases. The target disease is a disease treatable by, for example, expression of an exogenous gene in an osteoblast-specific fashion. Specifically, metabolic bone diseases such as osteoporosis and the like; bone defect, bone fracture, chondral defect, loss of teeth, cartilage associated diseases such as rheumatism associated with bone•cartilage destruction, osteoarthritis and the like, ectopic ossification, ectopic calcification, rickets, osteomalacia, Paget's disease, bone metastasis of cancer and similar ones and the like can be mentioned. For example, it is a disease selected from the group consisting of osteoporosis, bone fracture, bone defect, periodontal disease, osteosarcoma, chondrosarcoma, cyst and benign tumor developed in the bone, bone metastasis of cancer, infiltration of cancer into the bone, alveolar bone resorption due to loss of teeth, fibrodysplasia ossificans progressiva, arteriosclerosis, ossification of spine ligament and osteoarthritis. In the present specification, the "loss of bone•cartilage•teeth" refers to a disease or damaged state in a mammal having bone tissues or cartilage tissues. That is, a disease characterized by bone fracture, loss and/or denaturation of bone or cartilage caused by aging, dynamic load, external physical force.

Examples of the protein for treating target diseases include, but are not limited to, growth factors such as BMP, FGF, IGF, EGF, VEGF, PDGF, TGF, PTH, PTHrP, chondromodulin, Wnt, interleukin, interferon, TNF, Notch and the like, peptide hormones, cytokines, chemokines and receptors thereof; transcription factors and transcriptional regulatory factors such as Cbf, SOX, Smad, HOX, CREB, nuclear receptor, STAT, AP-1, CBP, NCoR and the like; adhesion factors such as ICAM, VCAM, Selectin and the like; intracellular information regulating factors such as p38, ERK, JNK, CaMK, PTP and the like; bone•cartilage matrix proteins such as collagen, osteopontin, osteocalcin, aggrecan and the like; cytoskeleton proteins such as NuMA, actin and the like, and the like.

As a part of gene therapy, examples of the gene for which increased expression in osteoblast is beneficial include, but are not limited to Runx2, Osterix, NFAT, Sp3, Sox4, Dlx5, ΔFosB, Wnt, b-catenin, Tcf7, BMP, BMP receptor, Ihh, Shh, Fgf, Fgf receptor, IGF, IGF receptor, Smad, Akt, retinoic acid, Noggin, Chordin, Follistatin, Smurf1, dominant negative Runx2, dominant negative Osterix, dominant negative Tcf7 and the like.

The present invention provides a transduced cell having the above-mentioned vector. The transduced cell can be obtained by introducing a vector having the enhancer of the present invention, particularly an expression vector having the enhancer, a promoter and a gene comprising a coding region (a gene that encodes a protein whose amount expressed in osteoblasts is desired to increase specifically) into an optionally chosen cell.

For introduction of vector into the cell, for example, calcium phosphate method (Virology, Vol. 52, p. 456, 1973), DEAE dextran method, a method using cationic liposome DOTAP (manufactured by Roche Diagnostics), electroporation method (Nucleic Acids Res., Vol. 15, p. 1311, 1987), lipofection method (J. Clin. Biochem. Nutr., Vol. 7, p. 175, 1989), virus infection introduction method (pMX, pMSCV and the like; Sci. Am., p. 34, 1994), particle gun and the like can be used.

The cell into which the vector of the present invention is introduced is appropriately selected according to the object thereof and the vector to be used.

When, for example, expression of a gene having a coding region in a transduced cell is desired, the vector of the present invention is introduced into a cultured osteoblast and the like.

Specifically, mouse osteoblast progenitor cells can be prepared by cutting out the calvaria of a fetal mouse on embryonic day 18.5 or a newborn baby, and shredding the same with scissors into fine fragments, then adding collagen gel (cell matrix type I-A), and then adding αMEM after the gel solidifies, and culturing the cells for 10 to 14 days. Thereafter, the cells are treated with 0.2% collagenase and collected via centrifugation, resuspended in αMEM (containing 10% FBS), and seeded to and cultured on a culture plate.

Also, the vector can also be introduced into rat femoral-tibial marrow-derived mesenchymal stem cells and human bone marrow monocytes. Rat femoral-tibial marrow-derived mesenchymal stem cells can be prepared by taking out the femur-tibia, then flushing out the bone marrow with a culture broth and pipetting the same, then performing centrifugation, discarding the supernatant, resuspending the cells in αMEM (containing 10% FBS), seeding the cells to a laminin-coated culture plate and culturing the same, adding bFGF to a final concentration of 3 ng/ml on day 9 after seeding, and culturing the cells.

A human bone marrow monocyte fraction is available from ALLCELLS or LONZA. After thawing, the culture is treated as mentioned above.

The enhancer of the present invention (and vector containing same) can be used in the presence of various factors that enhance the osteoblast specific enhancer activity thereof. For example, BMP2, TGFβ, retinoic acid, Wnt3A, shh, Ihh and the like can be mentioned. For mouse 0.34 kb enhancer, BMP2, TGFβ and Ihn are preferable, and the enhancer of the present invention is activated in the presence of these factors.

The vector of the present invention is also useful in being introduced into pluripotent stem cells. In the present invention, a pluripotent stem cell refers to a cell that can be cultured in vitro and has the pluripotency for differentiating into all cells that constitute a living organism. Specifically, embryonic stem cells (ES cell), pluripotent stem cells derived from fetal primordial germ cells (EG cell: Proc Natl Acad Sci USA. 1998, 95:13726-31), testis-derived pluripotent stem cells (GS cell: Nature. 2008, 456:344-9.), somatic cell-derived induced pluripotent stem cells (induced pluripotent stem cells; iPS cell) and the like can be mentioned.

A method of introducing the vector of the present invention into a pluripotent stem cell is not particularly limited, and the above-mentioned method for introduction of a vector into a cell can be used. For example, an injecting method using a microscope, electroporation and the like can be mentioned.

Then, a pluripotent stem cell incorporating the vector of the present invention is induced to differentiate into an osteoblast. Examples of the differentiation induction method include the following methods.

In plate culture, differentiation can be induced by culture in DMEM (containing 10% FBS, $10^{-7}$ M Dexamethason, 10 mM b-glycerophosphate, 50 mg/ml Ascorbate 2-phosphate).

Alternatively, with OSferion (OLYMPUS), APAC-ERAM-AM (PENTAX) and the like as scaffold materials, osteoblast differentiation can be induced three dimensionally. In both plate culture and 3-dimensional culture, differentiation can be further promoted by adding a differentiation induction factor such as BMP.

Subsequently, the expression of a reporter gene in differentiation-induced pluripotent stem cells is tested. That is, a cell with a significantly increased amount of reporter gene expressed, compared with control, can be judged as having differentiated into an osteoblast. By selecting cells wherein the amount of reporter gene expressed has increased significantly, osteoblasts differentiating from pluripotent stem cells can easily and accurately sorted.

The selected osteoblast can be used for what is called regenerative medicine.

The vector of the present invention is capable of enhancing the expression efficiency for a transgene in an osteoblast-specific fashion, and hence capable of providing a method of regulating the gene expression. By inducing the expression of a transgene in an osteoblast specific fashion, a wide variety of gene therapies can be performed.

Here, examples of the transgene include a gene encoding a protein desired to show a specific increase in the expression level in an osteoblast, and those similar to the above-mentioned can be recited.

A method of introducing the vector of the present invention into an osteoblast is not particularly limited, and the above-mentioned method for introduction of a vector into a cell can be used. For example, an adenovirus vector, a herpes virus vector, a retrovirus vector and the like, which containing the enhancer of the present invention, a promoter and an introduction target gene can be used (hereinafter the vector containing the enhancer of the present invention, a promoter and a gene to be introduced is also referred to as the gene expression agent of the present invention).

The gene expression agent of the present invention finds different use applications depending on the gene to be introduced, and can be used for, for example, a variety of gene therapies as described below (hereinafter, such an agent is also referred to as a gene therapy agent).

1. Introduction into the femur neck or vertebral body of a patient with severe osteoporosis enables the prevention of femur neck fractures or vertebral body fractures.
2. Introduction into a bone fracture site enables the promotion of healing of the bone fracture.
3. Osteogenesis promotion after leg extension surgery for taller growth is possible.
4. It is possible to culture bone marrow mesenchymal cells and propagate them in large amounts, and it is also possible to increase whole body bone mass. Treatment of bone diseases caused by osteoblast abnormalities, for example, osteogenesis imperfecta and the like caused by type I collagen disorders, is possible. Amelioration of dysostosis is possible.
5. It is possible to treat ectopic calcification (for example, vascular calcification and posterior longitudinal ligament calcification (ossification of posterior longitudinal ligament)).
6. It is possible to treat fibrodysplasia ossificans congenita, which occurs due to an activating mutation of BMP receptor.

The disease to be the treatment target of the gene therapy agent of the present invention includes metabolic bone diseases such as osteoporosis and the like; bone defect, bone fracture, chondral defect, loss of teeth, cartilage associated diseases such as rheumatism associated with bone cartilage destruction, osteoarthritis and the like, ectopic ossification, ectopic calcification, rickets, osteomalacia, Paget's disease, bone metastasis of cancer and similar ones and the like. For example, it is a disease selected from the group consisting of osteoporosis, bone fracture, bone defect, periodontal disease, osteosarcoma, chondrosarcoma, cyst and benign tumor developed in the bone, bone metastasis of cancer, infiltration of cancer into the bone, alveolar bone resorption due to loss of teeth, fibrodysplasia ossificans progressiva, arteriosclerosis, ossification of spine ligament and osteoarthritis. For such diseases, the gene therapy agent of the present invention can be used for bone regeneration, distraction osteogenesis and/or suppression of osteophyte formation.

Methods of introducing a gene therapy agent into a patient include the in vivo method, wherein the gene therapy agent is introduced directly into the body, and the ex vivo method, wherein a certain kind of cells are taken out from a human, the gene therapy agent is introduced into the cells ex vivo, and returned to the body (Nikkei-science, 1994, April issue, page 20-45, Gekkan Yakuji (Pharmaceuticals Monthly), 36(1), 23-48, 1994, Experiment Medicine extra number, 12(15), 1994, Japan Society of Gene Therapy ed., Handbook for Development and Research of Gene Therapy, NTS, 1999).

For administration by an in vivo method, the gene therapy agent can be administered, for example, intravenously, arterially, subcutaneously, intradermally, intramuscularly and the like, or directly administered topically to the target osteoblast itself.

Regarding the form of the preparation, a wide variety of preparation forms (for example, liquids and the like) comporting with the above-mentioned various dosage forms can be assumed. For example, in the case of an injection containing a gene therapy agent, the injection can be prepared by a conventional method by, for example, dissolving the same in an appropriate solvent (buffer solution such as PBS, physiological saline, sterile water and the like), thereafter, as the case may be, performing filtration sterilization using a filter and the like, and then filling the same in a sterile container. The injection may be supplemented with a commonly used carrier and the like as required. Also, liposomes such as HVJ-liposome can be in the form of liposome preparations of suspensions, frozen agents, centrifugally concentrated frozen agents and the like.

It is also possible to prepare a sustained-release preparation (mini-pellet preparations and the like) and indwell the same in the vicinity of an affected portion, or it is also possible to continuously gradually administer the same to an affected portion using an osmotic pump and the like.

As for the administration form of the gene therapy agent, for example, formulation method, administration method and the like are explained in detail in experiment guide and the like (separate volume experiment medicine, basic technology of gene therapy, Yodosha, 1996, separate volume experiment medicine, transgene & expression analysis experiment method, Yodosha, 1997, Japan Society of Gene Therapy ed., Handbook for Development and Research of Gene Therapy, NTS, 1999).

Specific examples are given for explanation in the following.

When non-virus vector is used for constructing the expression vector of the present invention, by the following means, the gene therapy agent of the present invention can be introduced into a cell or tissue.

Examples of the gene transfer method into a cell include lipofection method, phosphoric acid-calcium coprecipitation method; direct injection method using a micro glass tube and the like.

Examples of the gene transfer method into a tissue include gene transfer method using an internal liposome, gene transfer method using an electrostatic liposome, HVJ-liposome method, improved HVJ-liposome method (HVJ-AVE liposome method), receptor mediated gene transfer method, a method of transferring an active ingredient together with a carrier (metal particles) into a cell by a particle gun, direct introduction method of naked-DNA, introduction method using a positively-charged polymer and the like.

When a virus vector is used for construction of the expression vector of the present invention, examples of the virus vector include recombinant adenovirus, retrovirus and the like. More specifically, for example, DNA of the present invention and an exogenous gene operably linked to the DNA are introduced into a DNA virus or RNA virus such as detoxified retrovirus, adenovirus, adeno-associated virus, herpes virus, vaccinia virus, poxvirus, polio virus, sindbisvirus, Hemagglutinating Virus of Japan, SV40, human immunodeficiency virus (HIV) and the like and the obtained expression vector is used for infection, whereby the gene can be introduced into the cell. Of the aforementioned virus vectors, an adenovirus vector is preferably used since high infection efficiency can be achieved.

The pharmacological effect of the gene therapy agent of the present invention varies depending on the gene to be introduced and the target disease; for example, when using a gene therapy agent containing BMP2 as an exogenous gene for a bone mass-reducing disease, bone mass gain and elevations of osteogenesis markers (alkali phosphatase, osteocalcin and the like) are expected [J. Cell Biol., 113: 681-687 (1991), Biochem. Biophys. Res. Commun., 172: 295-299 (1990), Science 286: 1946-1949 (1999)], so that the effect thereof can be confirmed by bone mass measurements by the DXA method, measurements of blood osteogenesis markers by ELISA and the like, and the like.

Provided by the gene therapy agent of the present invention are methods of treating bone/cartilage diseases and ectopic calcification. These methods of treatment are also included in the scope of the present invention.

In the treatment method of the present invention, the introduction method of the gene therapy agent is the same as that mentioned above. The dose can be appropriately controlled according to the treatment object disease, and the age, body weight and the like of the patients. For example, the amount of an expression vector contained in a gene therapy agent is desirably 0.0001-100 mg, preferably 0.001-10 mg. Such administration dose is desirably administered once in several days to several months.

The treatment method of the present invention can be applied to amphibias, birds, mammals, specifically human; and non-human animals such as monkey, horse, sheep, rabbit, rat, mouse and the like.

The present invention provides a transgenic non-human animal incorporating the above-mentioned vector having the osteoblast-specific enhancer of the present invention. The transgenic non-human animal of the present invention is a transgenic non-human animal retaining the aforementioned expression vector and has one feature of the osteoblast-specific expression of the exogenous gene in the expression vector. A transgenic non-human animal retaining an expression vector comprising a reporter gene as the exogenoue gene has the excellent property of making it possible to conveniently screen for a compound that influences the activity of osteoblasts in the presence or absence and intensity of the expression of an osteoblast-specific reporter gene as an index. Also, a transgenic non-human animal retaining an expression vector comprising the gene that encodes a protein for treating the target disease as an exogenous gene makes it possible to evaluate the therapeutic effect of the protein when expressed in osteoblasts.

The transgenic non-human animal of the present invention may contain an expression vector incorporated in the chromosome of a mammal.

Examples of the "non-human animal" include mammals other than human, for example, mammals such as mouse, rat, rabbit, swine, dog, sheep, goat and the like, and the like. Of these, rodent animals represented by mouse, rat and the like are preferable, since they are used for drug research purposes, pathology model is easy to make, and the like, and mouse is particularly preferable.

The transgenic non-human animal of the present invention can be obtained by, for example, microinjecting the expression vector of the present invention into a fertilized egg of a non-human animal. Specifically, first, a superovulated female and a sire are mated. About 12 hours (varies depending on the animal species) after mating, the oviduct is taken out from the female, and a fertilized egg in the single-cell stage (pronucleus stage) is collected and placed in appropriate culture broth. Next, the expression vector of the present invention is microinjected into the pronucleus of the fertilized egg. Meanwhile, a female that has reached sexual maturity is mated with a vasectomized male to generate a pseudopregnant female. After microinjection, a surviving fertilized egg is transplanted into the oviduct of the aforementioned pseudopregnant female. Thereafter, a fetus that has developed from a fertilized egg after intrafallopian transplantation is taken out by natural delivery or surgical operation. Genomic DNA is prepared from a portion of the tail of an offspring obtained. The DNA obtained is analyzed to determine whether or not the offspring obtained are transgenic animals. Such transgenic animals are mated to establish a line. An exogenous gene (for example, reporter genes such as GFP) present in the expression vector in the established transgenic animal is subjected to expressional analysis, and osteoblast-specific expression is confirmed. By the operations above, the transgenic non-human animal of the present invention can be obtained.

For a detailed preparation method of the aforementioned transgenic non-human animal, for example, mouse embryo operation manual (Kindai Shuppan Co., Ltd, 1989), Molecular biology protocols (Nankodo Co., Ltd., 1994), gene targeting (Yodosha, 1995) and the like can be referred to.

The present invention provides a method of confirming differentiation of a pluripotent stem cell into an osteoblast (method 1). The method comprises, for example, the following steps:

(a) a step of introducing an expression vector comprising the osteoblast-specific enhancer of the present invention, a promoter and a reporter gene into a pluripotent stem cell, (b) a step of inducing differentiation of the aforementioned pluripotent stem cell, and (c) a step of determining whether or not the above-mentioned pluripotent stem cell has differentiated into an osteoblast by measuring the expression level and/or activity of the reporter gene.

The various constituents used in the various steps (e.g., osteoblast specific enhancer, promoter, reporter genes, pluripotent stem cells), and various operating methods (e.g., introduction of vector into cells, differentiation induction) are the same as those described above, and are performed in the same manners.

In the step (c) for determining whether or not the above-mentioned pluripotent stem cell has differentiated into an osteoblast by measuring the expression level and/or activity of the reporter gene, specifically, degree of expression level and/or activity of the reporter gene in pluripotent stem cells after differentiation induction is measured; if an increase in expression level and/or activity is noted, it is judged that the pluripotent stem cell has differentiated into an osteoblast. A method of measuring the degree of expression level and/or activity of the reporter gene is chosen as appropriate according to the kind of reporter gene used; for example, when the GFP gene is used as the reporter gene, the degree of the expression of the reporter gene can be measured by measuring the fluorescence intensity thereof.

Moreover, the present invention provides a method of screening for a compound that influences the differentiation of a pluripotent stem cell into an osteoblast (method 2). The method comprises, for example, the following steps:

(a) a step of introducing an expression vector comprising the osteoblast-specific enhancer of the present invention, a promoter and a reporter gene into a pluripotent stem cell,
(b) a step of inducing differentiation of the aforementioned pluripotent stem cell in the presence or absence of a test substance,
(c) a step of measuring the expression level and/or activity of the reporter gene in the pluripotent stem cell differentiation induced in the presence of a test substance and comparing the level with that in a pluripotent stem cell differentiation induced in the absence of a test substance, and
(d) a step of screening for a compound that influences the differentiation of the pluripotent stem cell into an osteoblast, based on the aforementioned comparison results.

The various constituents used in the various steps (e.g., osteoblast specific enhancer, promoter, reporter genes, pluripotent stem cells), and various operating methods (e.g., introduction of vector into cells, differentiation induction) are the same as those described above, and are performed in the same manners. As a method of measuring the expression level and/or activity of the reporter gene, those similar to the method used in the above-mentioned (method 1) can be mentioned.

The "test substance" may be any commonly known substance or a novel substance; such substances include, for example, nucleic acids, glucides, lipids, proteins, peptides, organic low molecular compounds, compound libraries prepared using combinatorial chemistry technology, random peptide libraries prepared by solid phase synthesis or the phage display method, or naturally occurring ingredients derived from microorganisms, animals, plants, marine organisms and the like, and the like. A mixture of two or kinds or more of these compounds can also be supplied as a sample. "To induce differentiation in the presence of a test substance" is, for example, to perform differentiation induction of pluripotent stem cells in a culture broth containing a test substance, and "to induce differentiation in the absence of a test substance" is, for example, to perform differentiation induction of pluripotent stem cells in a culture broth not containing a test substance.

The expression level and/or activity of the reporter gene in the presence and absence of a test substance are compared; if a significant change in the expression level and/or activity of the reporter gene is produced, it is judged that the test substance has influenced the differentiation of pluripotent stem cell into osteoblasts. A substance that significantly reduces the expression level and/or activity of the reporter gene can have the action of suppressing the differentiation of pluripotent stem cell into osteoblasts; a substance that significantly increases the expression level and/or activity of the reporter gene can have the action of promoting the differentiation of a pluripotent stem cell into an osteoblast.

Furthermore, the present invention provides a method of screening for a compound that influences the activities of an osteoblast. The method is largely divided into a method using a cultured osteoblast (method 3) and a method using a transgenic animal (method 4).

(Method 3)
A method of screening for a compound that influences the activities of an osteoblast, comprising the following steps:
(a) a step of introducing an expression vector comprising the osteoblast specific enhancer of the present invention, a promoter and a reporter gene into a cultured osteoblast,
(b) a step of contacting or not contacting the aforementioned cultured osteoblast with a test substance,
(c) a step of measuring the expression level and/or activity of the reporter gene in the cultured osteoblast contacted with the aforementioned test substance and comparing the level and/or activity with those/that in a cultured osteoblast not contacted with the test substance, and
(d) a step of screening for a compound that influences the activity of the osteoblast, based on the aforementioned comparison results.

The various constituents used in the various steps (e.g., osteoblast specific enhancer, promoter, reporter genes, pluripotent stem cells, test substances), and various operating methods (e.g., introduction of vector into cells, method of measuring expression level and/or activity of the reporter gene) are the same as those described above, and are performed in the same manners.

The "contacting cultured osteoblast with a test substance" means, for example, cultivating the cultured osteoblast in a culture medium containing the test substance, and "not contacting cultured osteoblast with a test substance" means, for example, cultivating the cultured osteoblast in a culture medium free of the test substance.

The expression levels and/or activities of the reporter gene when contacted with a test substance and not contacted therewith are compared, and when the expression level and/or activity of the reporter gene significantly varies, the activities of an osteoblast is considered to be influenced. Here, "having an influence on an activity of osteoblasts" is intended to enhance (or suppress) gene expression efficiency in osteoblasts under the control of the osteoblast-specific enhancer of the present invention. A substance that enhances the expression efficiency can become an osteogenesis promoter because the expression of for example, Runx2 (the master gene for osteogenesis) can be increased.

A compound that enhances the expression efficiency for the desired gene by acting on the osteoblast-specific enhancer of the present invention to enhance the activity thereof is also encompassed in compounds "that have an influence on an activity of osteoblasts". In this case, for example, BMP2 and TGFβ, which have enhancer activating action (see Example 2) can be used as positive controls.

(Method 4)
A method of screening for a compound that influences the activities of an osteoblast, comprising the following steps:
(a) a step of preparing a transgenic non-human animal by introducing an expression vector comprising the osteoblast specific enhancer of the present invention, a promoter and a reporter gene,
(b) a step of administering or not administering a test substance to the aforementioned transgenic non-human animal,
(c) a step of measuring the expression level and/or activity of the reporter gene in the transgenic non-human animal administered with the aforementioned test substance and comparing the level and/or activity with those/that in a transgenic non-human animal not administered with the test substance, and
(d) a step of screening for a compound that influences the activity of the osteoblast, based on the aforementioned comparison results.

The various constituents used in the various steps (e.g., osteoblast specific enhancer, promoter, reporter genes, pluripotent stem cells, test substances, transgenic non-human animals), and various operating methods (e.g., method of measuring expression level and/or activity of the reporter gene) are the same as those described above, and are performed in the same manners.

The administration of a test substance to a transgenic non-human animal is performed orally or parenterally. Examples of the parenteral administration route include systemic administration such as intravenous, arterial, intramuscular, intraperitoneal and the like, and topical administration into the airway, near target cell (e.g., conjunctiva etc.) and the like.

The expression levels and/or activities of the reporter gene when administered with a test substance and not administered therewith are compared, and when the expression level and/or activity of the reporter gene significantly varies, the activities of an osteoblast is considered to be influenced. A measurement of the expression level and/or activity of the reporter gene can also be performed by, for example, organ-culturing and examining a metatarsal bone of a transgenic animal. Here, "having an influence on an activity of osteoblasts" is intended to enhance (or suppress) gene expression efficiency in osteoblasts under the control of the osteoblast-specific enhancer of the present invention. A substance that enhances the expression efficiency can become an osteogenesis promoter because the expression of for example, Runx2 (the master gene for osteogenesis) can be increased.

A compound that enhances the expression efficiency for the desired gene by acting on the osteoblast-specific enhancer of the present invention to enhance the activity thereof is also encompassed in compounds "that have an influence on an activity of osteoblasts". In this case, for example, BMP2 and TGFβ, which have enhancer activating action (see Example 2) can be used as positive controls.

EXAMPLES

The present invention is explained in more detail in the following by referring to Examples, which are not to be construed as limitative.

Example 1

Identification of Enhancer Region

Using a BAC modification kit, IRES-EGFP-polyA was inserted into the downstream of BAC clone (RP23-356F5) of about 200 kb (−200082 to +126 region of mouse Runx2 gene: SEQ ID NO: 2) containing exon 1, a part of exon 2, intron 1 and about 100 kb upstream of exon 1, each of Runx2. This vector was microinjected into the pronucleus of a zygote of B6C3HF1, which was transferred to the oviduct of a recipient mother to prepare a transgenic founder. The caudal vertebral end was cut off, the skin was removed, and mice that expressed GFP (green fluorescent protein) on the caudal vertebrae by observation under a fluorescence stereomicroscope were selected. The caudal vertebrae of the expressing mice was fixed, and tissue sections were prepared and subjected to immunostaining of the tissue using GFP antibody, whereby expression in osteoblast and chondrocyte was confirmed. Of the confirmed transgenic founders, those showing high expression levels were crossed with B6C3HF1 to prepare Runx2 promoter EGFP transgenic mouse [RP-full (−200082/+126)].

Furthermore, vectors defective by 30-50 kb each from 200 kb were produced, and 6 kinds of EGFP transgenic founders were prepared. In the same manner as above, 6 kinds of Runx2 promoter EGFP transgenic mice partly defective in the Runx2 genome region were prepared [RP-D(−30822/−882), RP-D(−55791/−25843), RP-D(−78042/−50853), RP-D(−122442/−78503), RP-D(−1661442/−117453), RP-D(−200032/−156463)]. Using tissue sections of the Runx2 promoter EGFP transgenic mice containing full-length Runx2 genome region and 6 kinds of the Runx2 promoter EGFP transgenic mice partly defective in Runx2 genome region, the pattern of systemic expression of GFP was examined by immunostaining of the tissue using GFP antibody. In RP-D(−122442/−78503), disappearance of the expression in chondrocytes, decreased expression in osteoblasts and disappearance of expression in a part of osteoblasts were observed. In those regions, therefore, the region preserved among species (mouse, human, chimpanzee, bovine, dog, horse, macaque, opossum, orangutan, platypus, chicken, Xenopus) was searched in www.ensembl.org. In this deletion region was found a 1.3 kb region highly preserved among the above-mentioned species (1.3 kb enhancer). The 1.3 kb region was connected to Hsp68 minimal promoter to produce a transgenic founder for expression of EGFP. By GFP immunostaining of the tissue sections, expression specific to preosteoblast and osteoblast was observed (FIG. 1).

As the result, the enhancer confirmed in the present Example is located about 30 kb distant from the transcription start point (the 200083rd-position of SEQ ID NO: 2) and a conventional promoter analysis generally cannot detect the enhancer.

Example 2

Reporter Assay

<Method>
1. Cell Culture

Primary Osteoblast (POB) was obtained by collecting the skull of a normal mouse (SLC) on embryonic day 18.5, culturing cells from the skull for 10 days according to a collagen gel culturing method and separating the cells. The separated POB was cultured in 10% Minimum Essential Medium containing FBS, alpha modified (αMEM), for 2-3 days, seeded in a 24-well plate at $1.5 \times 10^4$ cells/well and subjected to a reporter assay about 24 hr later.

Runx2 knockout (Runx2 KO) cell was obtained by collecting the skull of a Runx2 knockout mouse on embryonic day 18.5, culturing cells from the skull for 10 days according to a collagen gel culturing method and separating the cells. The Runx2 knockout mouse used was prepared by Komori et al. (Cell (1997), 89, 755-764, JP-A-H10-309148). The separated Runx2 KO cells were cultured in αMEM containing 10% FBS for 2-3 days, seeded in a 24-well plate at $1.5 \times 10^4$ cells/well and subjected to a reporter assay about 24 hr later.

C2C12 cells were cultured in Dulbecco's Modified Eagle's Medium (DMEM) (SIGMA) containing 10% FBS, seeded in a 24-well plate at $1.5 \times 10^4$ cells/well and subjected to a reporter assay about 24 hr later.

ATDC5 cells were cultured in Dulbecco's Modified Eagle's Medium/Ham's F12 (1:1) hybrid medium (DMEM/HAM F12) (SIGMA) containing 5% FBS and 10 μg/mL transferrin, seeded in a 24-well plate at $1.5 \times 10^4$ cells/well and subjected to a reporter assay about 24 hr later.

2. Reporter Assay

For transfection, used were pGL 4.10 (Promega) plasmid DNA and pRL-tk plasmid DNA, into which Runx2 1.3 kb enhancer or Runx2 0.34 kb enhancer and mouse HSP68 minimal promoter (mHSP68) had been inserted. As a control, pGL 4.10 plasmid DNA, into which only mHsp68 promoter had been inserted, was used. Plasmid DNA (each 0.1 μg) to be introduced was transfected to the cell cultured in the 24-well plate, by using FuGENE 6 Transfection Reagent (Roche). After culture for 12 hr, the medium of C2C12 cells was exchanged to DMEM medium containing 2.5% FBS, and the media of the ATDC5 cell, POB and Runx2 KO cell were exchanged to each medium containing 1% FBS. 36 hr later, the cells were washed with PBS, Passive Lysis Buffer (Promega, 80 μL) was added, and the mixture was preserved at −80° C. until measurement. The reporter activity was measured using Dual-luciferase Reporter Assay System (Promega).

3. Influence of Factor

To the ATDC5 cells was transfected plasmid DNA (0.1 μL) according to the above-mentioned method, and after culture for 12 hr, the medium was exchanged to a medium containing 1% FBS. Furthermore, after culture for 12 hr, various factors were added. After stimulation for 24 hr, the cell was washed with PBS, Passive Lysis Buffer (80 μL) was added, and the mixture was preserved at −80° C. until measurement. The reporter activity was measured using Dual-luciferase Reporter Assay System. The concentration of each factor was Fibroblast growth factor 2 (FGF-2, 30 ng/mL), Fibroblast growth factor 18 (FGF-18, 30 ng/mL), Bone morphogenetic protein 2 (BMP2, 50 ng/mL), Transforming growth factor-beta (TGFβ, 1 ng/mL), retinoic acid $10^{-8}$M, Wingless-type MMTV integration site family, member 3A (Wnt3A, 10 ng/mL), Sonic hedgehog (Shh, 200 ng/mL), and Indian hedgehog (Ihh, 200 ng/mL).

<Results>

The reporter activity of the Runx2 1.3 kb enhancer/Hsp68 minimal promoter and Runx2 0.34 kb enhancer/Hsp68 minimal promoter in the POB, Runx2 KO cell, C2C12 cell and ATDC5 cell was examined. The schematic diagram of each construct and reporter assay results thereof are shown in FIG. 2.

As a result, the Runx2 1.3 kb enhancer/Hsp68 minimal promoter showed 2- to 3-fold reporter activity as compared to that using only a Hsp68 minimal promoter, and the Runx2 0.34 kb enhancer/Hsp68 minimal promoter showed about 1.2- to 1.5-fold reporter activity as compared to that using only Hsp68 minimal promoter, thus showing increased activity in all cells.

Figure 3:
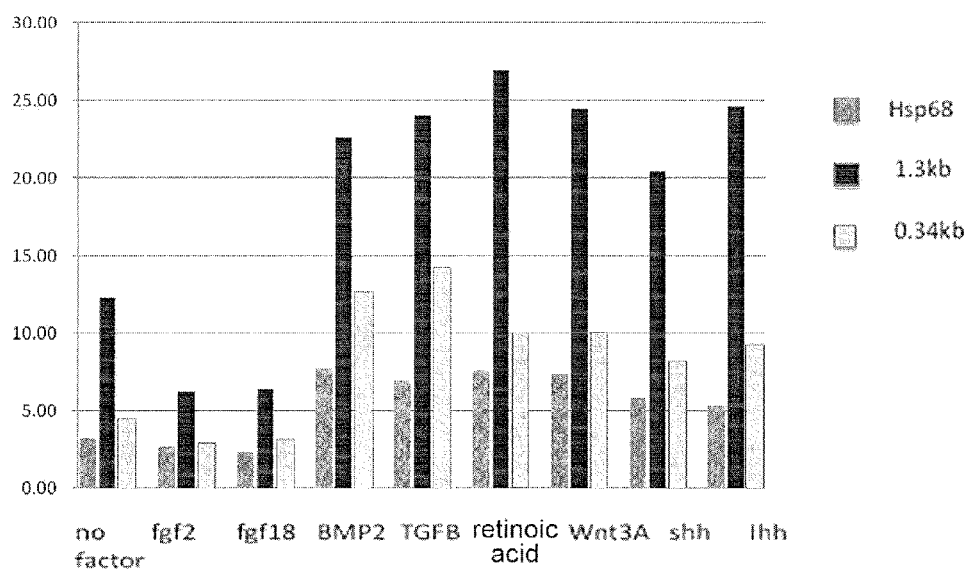
FIG. 3 is a graph showing the results of an examination of the reporter activities of the 1.3 kb enhancer and the 0.34 kb enhancer in the presence of the Hsp68 minimal promoter. Examined were changes in the enhancer activities with various factors.

Furthermore, activation of an enhancer by various factors of reporter vector of the 1.3 kb and 0.34 kb enhancer/Hsp68 minimal promoter was examined. The results are shown in FIG. 3.

To the report assay of the Runx2 1.3 kb enhancer and 0.34 kb enhancer using ATDC5 cells were added FGF-2, FGF-18, BMP2, TGFβ, retinoic acid, Wnt3A, Shh and Ihh as factors, and variation of the activity due to various factors was examined.

As a result, the 1.3 kb enhancer was suppressed by FGF-2 and FGF-18, and promoted by BMP2, TGFβ, retinoic acid, Wnt3A, Shh and Ihh. The 0.34 kb enhancer was suppressed by FGF-2 and FGF-18, and promoted by BMP2, TGFβ and Ihh.

Example 3

Further Refining of Enhancer Region

Figure 4:
FIG. 4 is a picture of an EGFP transgenic mouse by fluorescent stereoscopic microscope (embryonic day 16.5) generated using the 0.34 kb enhancer and the HSP68 minimal promoter. GFP is detected in the skeleton.
Figure 5A:
FIG. 5A is an immunohistologically stained image taken using a section of tibia from an EGFP transgenic mouse (day 5 after birth) generated using the 0.34 kb enhancer and the HSP68 minimal promoter.
Figure 5B:
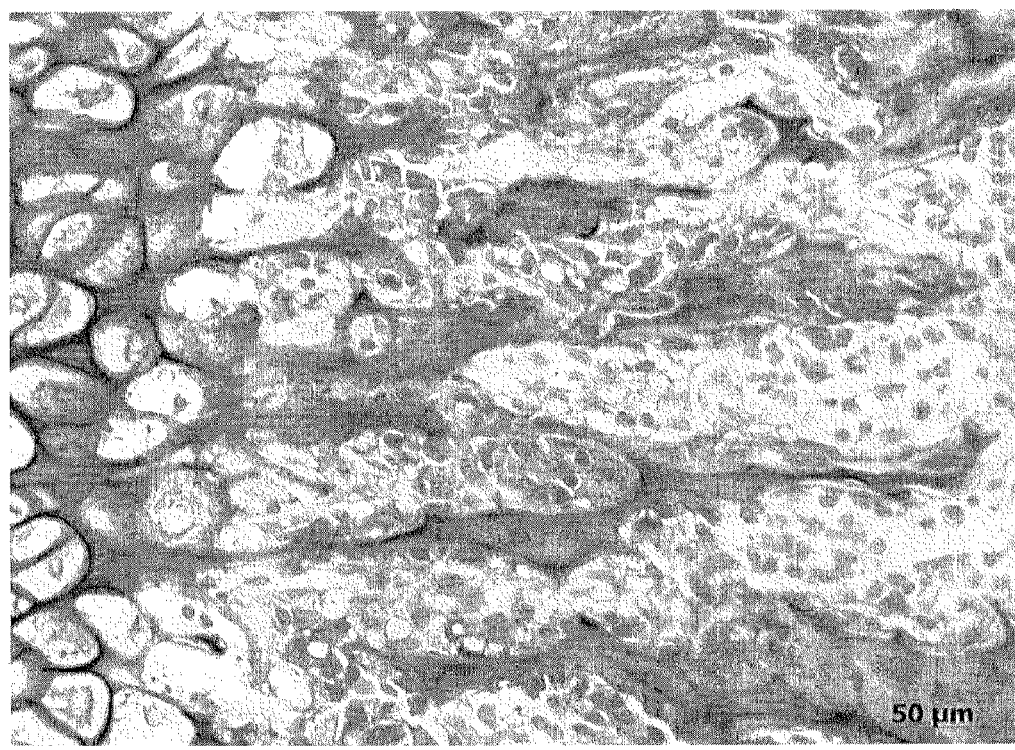
FIG. 5B is an enlarged view of the enclosed part on the left side of FIG. 5A.
Figure 5C:
FIG. 5C is an enlarged view of the enclosed part on the right side of FIG. 5A. Expression of GFP was observed only in the osteoblast.
Figure 8:
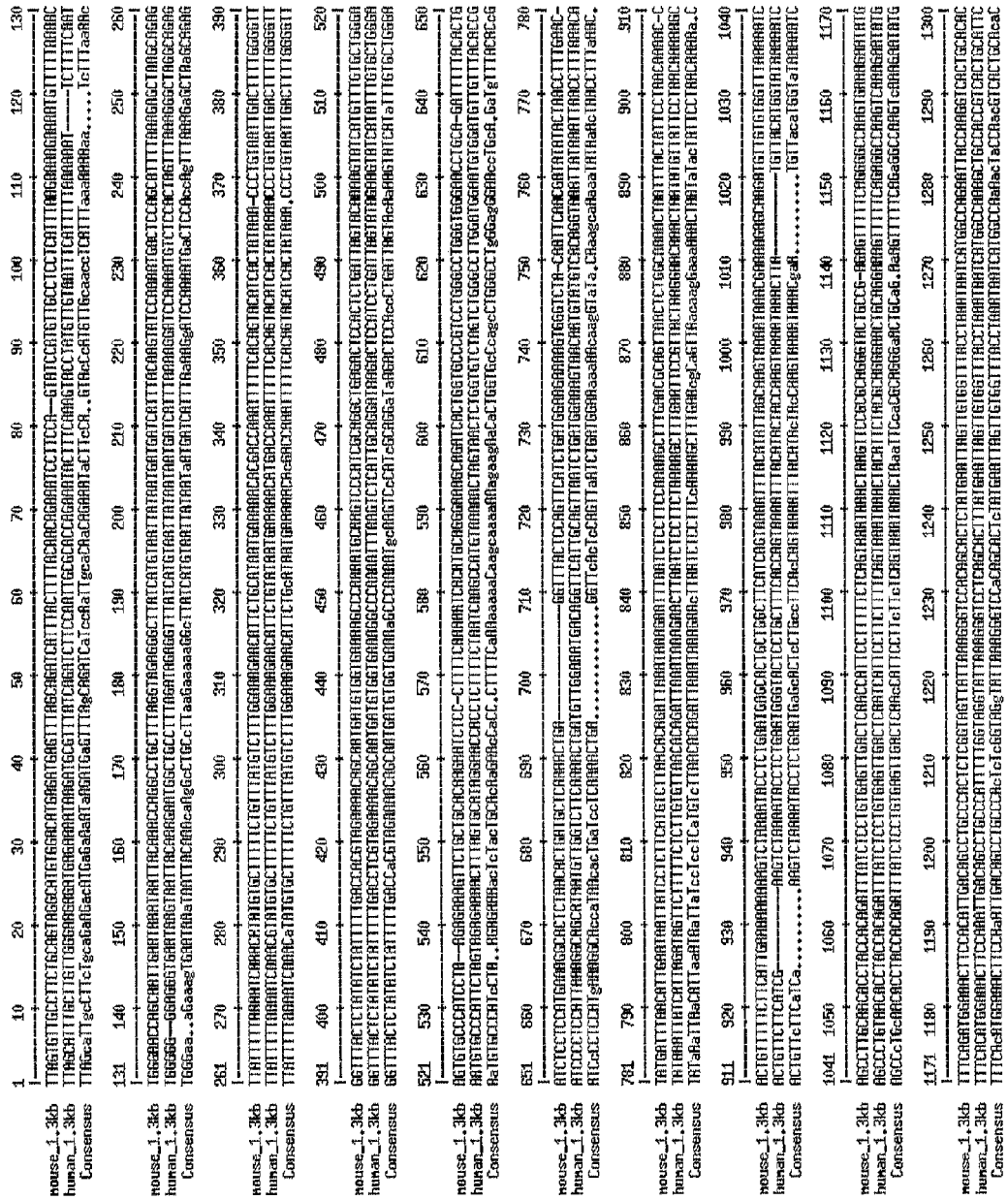
FIG. 8 is a drawing showing the results of a comparison of the sequences of the Runx2 enhancer regions in mice and humans. The mouse 1.3 kb enhancer region (SEQ ID NO: 1) and the human 1.3 kb enhancer region (SEQ ID NO: 4) are illustrated.
Figure 9:
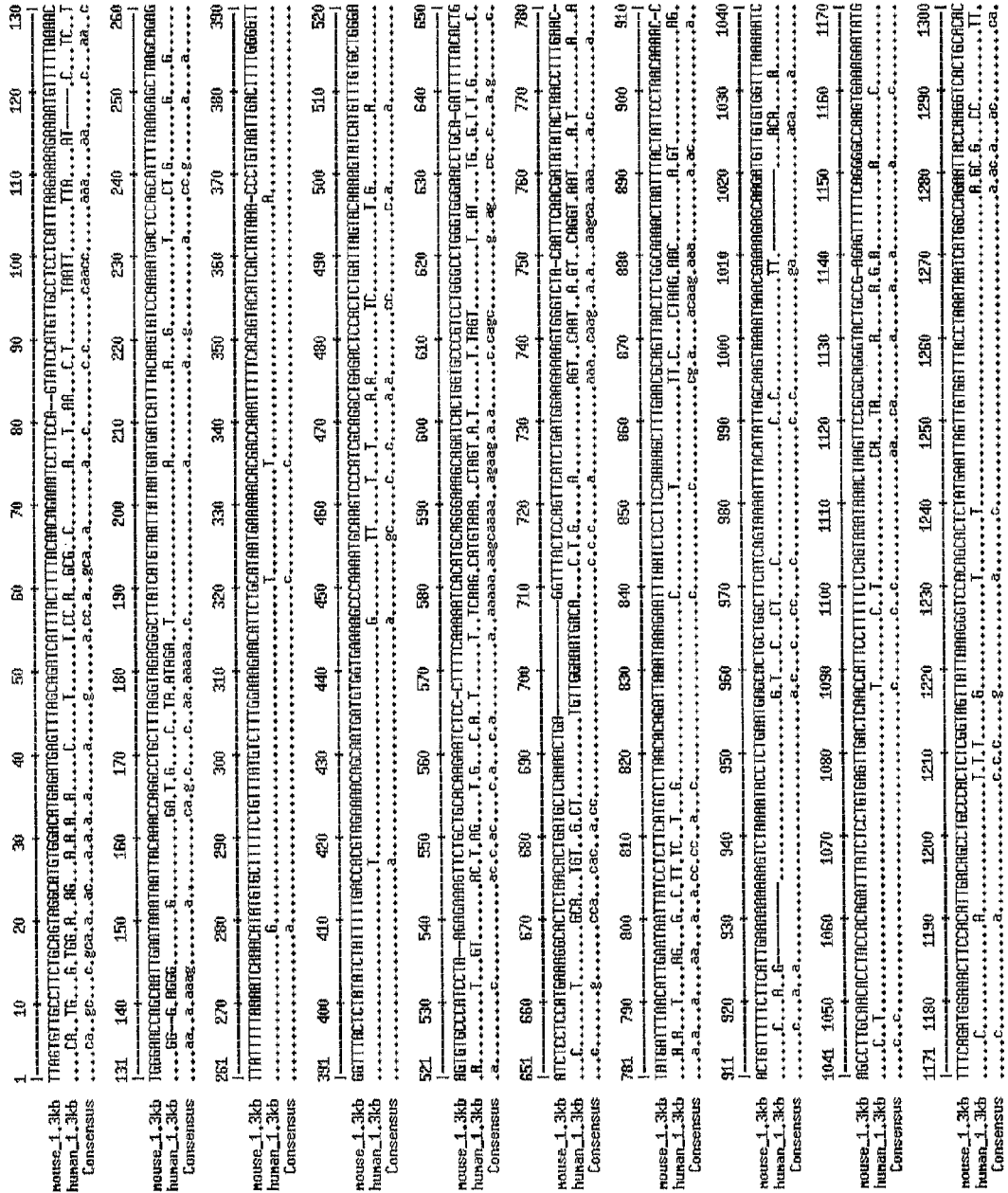
FIG. 9 is a drawing showing the results of a comparison of the sequences of the Runx2 enhancer regions in mice and humans. A homologous sequence is represented by dots, and homology is schematically shown. As noted with respect to FIG. 8, the mouse 1.3 kb enhancer region, the human 1.3 kb enhancer region, and the consensus sequence correspond to SEQ ID NOs: 1, 4 and 6, respectively.

Among the mouse 1.3 kb enhancers, the following region (about 340 bp) showing particular high homology beyond species [having homology even with chicken and Xenopus (a kind of frog)]:

(SEQ ID NO: 3)
ttatcatgtaattataatgatgatcatttacaagtatccaaaatgactcc agcattttaaagagctaagcagagttattttaaaatcaaacatatgtgc tttttctgtttatgtctttggaaagaacattctgcataatgaaaaacacg accaaatttttcacagtacatcactataaaccctgtaattgactttggg gttggtttactctatatctattttgaccacgtagaaaacagcaatgatg tggtgaaaagcccaaaatgcaagtcccatcgcaggctgagactccactct gattagtacaaaagtatcatgtttgtgctgggaagtgtgcccat was noted, and EGFP transgenic mouse was prepared in the same manner as in Example 1 and using an Hsp68 minimal promoter. The lineage was established, and the expression of GFP of a fetus on embryonic day 16.5 and a transgenic mouse on day 5 after birth was examined by using a fluorescent stereoscopic microscope or immunostaining of tissue with anti-GFP antibody. FIG. 4 shows observation images of the fetus on embryonic day 16.5 by a fluorescent stereoscopic microscope, and FIG. 5 shows observation images of the tissue immunostained with anti-GFP antibody. As a result, expression of GFP was observed only in osteoblast, thus clarifying that the about 340 bp region contains a part necessary for osteoblast-specific expression of Runx2.

The enhancer of the present invention is favorable with the features shown below.

1. Capable of inducing osteoblast specific expression. Furthermore, expression can be induced from the early stage of osteoblast differentiation, which is advantageous in inducing osteoblast differentiation.

2. High expression in living organisms is expectable. The HSP68 minimal promoter falls in the category with the lowest transcription activation potential among the minimal promoters, but when joined with the enhancer of the present invention DNA, sufficiently high gene expression could be induced in living organisms.

3. By variously changing the minimal promoter to be joined, the expression level can be further enhanced.

4. Practical because of the short DNA.

5. High gene expression is expectable even in cultured osteoblasts.

INDUSTRIAL APPLICABILITY

By using the enhancer of the present invention, osteoblast-specific expression of a specified gene can be induced. This induction enables a wide variety of gene therapies (prevention and treatment of bone fractures, osteogenesis imperfecta, bone calcification and the like). Furthermore, by using the enhancer of the present invention, it is possible to screen for a compound that influences an osteoblast activity (for example, differentiation of osteoblasts), specifically enabling the provision of an osteogenesis promoter, an osteogenesis suppressant and the like.

This application is based on patent application No. 2009-183366 filed in Japan, the contents of which are incorporated in full herein.

The invention claimed is:

1. A recombinant expression vector comprising an enhancer, a minimal promoter and a gene containing a coding region, wherein the enhancer consists of
   a DNA consisting of the base sequence shown by SEQ ID NO: 5,
   wherein the minimal promoter is selected from the group consisting of HSP68 minimal promoter, CMV minimal promoter, SV40 minimal promoter, and minimal promoter of PGL4 vector (MinP).

2. The recombinant expression vector of claim 1, which further comprises a reporter gene.

3. The recombinant expression vector of claim 2, wherein the reporter gene is selected from the group consisting of β-galactosidase gene, alkaliphosphatase gene, chloramphenicol acetyltransferase gene, growth hormone gene, luciferase gene, green fluorescence protein gene, and blue fluorescence protein gene.

4. A method of screening for a compound that influences differentiation of a pluripotent stem cell into an osteoblast, comprising the following steps:
   (a) introducing a recombinant expression vector comprising an enhancer, a minimal promoter and a reporter gene into a pluripotent stem cell,
   (b) inducing differentiation of the pluripotent stem cell into an osteoblast in the presence of a test substance,
   (c) measuring an expression level of the reporter gene in the pluripotent stem cell differentiation induced in the presence of the test substance and comparing the expression level with that in the pluripotent stem cell differentiation induced in the absence of a test substance, and
   (d) screening for a compound that influences the differentiation of the pluripotent stem cell into an osteoblast based on the comparison results,
   wherein the enhancer consists of a DNA consisting of the base sequence shown by SEQ ID NO: 5.

5. A method of screening for a compound that influences activities of an osteoblast, comprising the following steps:
   (a) introducing a recombinant expression vector comprising an enhancer, a minimal promoter and a reporter gene into a cultured osteoblast,
   (b) contacting the cultured osteoblast with a test substance,
   (c) measuring an expression level and/or activity of the reporter gene in the cultured osteoblast contacted with the test substance and comparing the expression level and/or activity with those/that in the cultured osteoblast not contacted with the test substance, and
   (d) screening for a compound that influences the activity of the osteoblast based on the comparison results,
   wherein the enhancer consists of a DNA consisting of the base sequence shown by SEQ ID NO: 5.

6. A method of screening for a compound that influences activities of an osteoblast, comprising the following steps:
   (a) preparing a transgenic non-human animal by introducing a recombinant expression vector comprising an enhancer, a minimal promoter and a reporter gene,
   (b) administering a test substance to the transgenic non-human animal,
   (c) measuring an expression level and/or activity of the reporter gene in the transgenic non-human animal administered the test substance and comparing the expression level and/or activity with those/that in the transgenic non-human animal not administered the test substance, and
   (d) screening for a compound that influences the activity of the osteoblast based on the comparison results,
   wherein the enhancer consists of a DNA consisting of the base sequence shown by SEQ ID NO: 5.

* * * * *

SEQUENCE LISTING

<160> NUMBER OF SEQ ID NOS: 6

<210> SEQ ID NO 1
<211> LENGTH: 1268
<212> TYPE: DNA
<213> ORGANISM: Mus musculus

<400> SEQUENCE: 1

| | | | | | |
|---|---|---|---|---|---|
| tgccttctgc | agtaggcatg | tggacatgag | atgagtttag | cagatcattt | acttttacaa | 60 |
| cagaaatcct | tccagtatcc | atgttgcctc | ctcatttaag | aaaagaaaat | gtttttaaaa | 120 |
| ctgggaacca | gcaattgaat | aaataattac | aaaccaggcc | tgctttaggt | agagggctta | 180 |
| tcatgtaatt | ataatgatga | tcatttacaa | gtatccaaaa | tgactccagc | attttaaaga | 240 |
| gctaagcaga | gttatttta | aaatcaaaca | tatgtgcttt | ttctgtttat | gtctttggaa | 300 |
| agaacattct | gcataatgaa | aaacacgacc | aaattttca | cagtacatca | ctataaaccc | 360 |
| tgtaattgac | ttttggggtt | ggtttactct | atatctattt | ttgaccacgt | agaaaacagc | 420 |
| aatgatgtgg | tgaaaagccc | aaaatgcaag | tcccatcgca | ggctgagact | ccactctgat | 480 |
| tagtacaaaa | gtatcatgtt | tgtgctggga | agtgtgccca | tcctaagaga | aagttctgct | 540 |
| gcacaagaat | ctcccttttc | aaaaatcaca | tgcagggaaa | gcagatcact | ggtgcccgtc | 600 |
| ctgggcctgg | gtgggaacct | gcagattttt | acactgatct | cctccatgaa | aggcactcta | 660 |
| acactgatgc | tcaaaactga | ggtttactcc | agttcatctg | atggaagaaa | agtgggtcta | 720 |
| caattcaacg | atatatacta | acctttgaac | tatgatttaa | cattgaataa | ttatcctctt | 780 |
| catgtcttaa | cacagattaa | ataaagaatt | taatctcctt | ccaaaagctt | tgaacgcagt | 840 |
| taactctggc | aaaactaatt | tactattcct | aacaaaacca | ctgttttct | tcattgaaaa | 900 |
| aaaaagtcta | aataccctct | gaatgagcac | tgctggcttc | atcagtaaaa | tttacatatt | 960 |
| agcaagtaaa | ataaacgaaa | agagcaagat | gttgtgtggt | ttaaaaatca | gccttgcaac | 1020 |
| acctaccaca | gatttatctc | ctgtgagttg | actcaaccat | tccttttct | cagtaaataa | 1080 |
| actaagttcc | gcgcagggta | ctgccgagag | ttttcaggg | gccaagtgaa | agaatatgtt | 1140 |
| tcagatggaa | acttccacat | tgacagcctg | cccactctcg | gtagttatta | aagggtccac | 1200 |
| agcactctat | gaattagttg | tggtttacct | aaataatcat | ggccagaatt | accaaggtca | 1260 |
| ctgcacac | | | | | | 1268 |

<210> SEQ ID NO 2
<211> LENGTH: 200208
<212> TYPE: DNA
<213> ORGANISM: Mus musculus
<220> FEATURE:
<221> NAME/KEY: transcription initiation site
<222> LOCATION: (200083)..(200083)

<400> SEQUENCE: 2

| | | | | | |
|---|---|---|---|---|---|
| tcagccatca | taacctataa | aatgataatt | tcaatttgtg | caaatttaca | tgatttctca | 60 |
| ggtatgagac | aatgtaaaaa | tgctattctt | cagaatatgg | gcctgaagca | atggaagagt | 120 |
| gtcagtgctg | gcctcctgct | acaaggctgt | gattttggtc | gttagtgcta | aatatatgat | 180 |
| acatggcaaa | gttctatgac | taatccgttc | tagaagaaaa | aagatcaact | gattttcaga | 240 |
| ttttaacctc | cagttttcat | tagttaacat | attttatagc | tcacatgtag | aaatgatcaa | 300 |
| aaagcaatca | gtgaggccca | agccattcat | aactagaaaa | ctgaacagag | agaagggact | 360 |
| tacttgaata | gagggtgtct | tattaaagta | ctgagtagga | attgggggtt | agaaggcaaa | 420 |

```
gattacatgg aaaatgtatg tcaaacaagg ggggagccaa acaaatttag ggaaaaacta    480
agtttatagc tagcctgcct gccagcatgc ccgtgtttct tccctctgtc ttcctgtctc    540
cctttcttcc ctccctagct ccctcccttc gcgctacttt caaaatgact tccttatgta    600
tccccagctt ggagtgtgta gccacctgcc ttccctccc actggagaca tactgcttc      660 accctacgc catgcataac tagaatgagt cttactgtaa agtattccgt ggatgaactg     720
ttatggagcc acatggtgct caccttaacc tgctatcatg agaagcagaa acatgccaat    780
ttccaacagt gatctggctg atgggttata tagtgaagga agaatccaat tcttttctac    840
ctgccatgtt gaaatacagt tttcttactc gaaggcacta tcctgaacaa ctattaacag    900
tccacaagag aaaaatgaaa acaaaatcct caaagataaa aagagcaca cttaaccaat     960 tatttaaaaa aaggggggg gggcaggaga aagggatgg acaacttat gacagacatc      1020 aacctcaggc tctttctctt gccgctttgg tcattccata caaacagatg aagatgggc    1080 ttgaaagaat tcagaaggaa gcaagagcta ggtcttggga gttagcatta acctttcaag    1140
atgatcattt cagccatata tgtcaagcct gaaataaagg aataataaat ctgactggta    1200
ttttattata ttaggttaaa tttgttggct aatttatata atctacataa tttctattat    1260
ttctccatgt ctttaaaatg aatatattgc agtccataaa ctgttcagag tttgtctttc    1320
actgtgcatt gtaatgctat gtgtgggccc caagcctggt gtctgtaaat agattgggga    1380
ccctgccaca atgatatttc taattggtaa ataaagatgc caacagccaa tagctgggca    1440
aaagagacaa aggaggggtt taggtttcca gggtttgggg tctaaggaga aacacagaag    1500
gaggagaagg tacaagaaga gagaagagac gccaccatat ggctaggagt caaaaaaagt    1560
ggtcctgagg gctggccaat tggagttaag agtggcccag atgaaacatg gtaagtaata    1620 actcaggggtt atagatagga aagtagattc taataacata gagggtagga ttttgcccag    1680
ctcttgtgct gtttaaggct tattgtaaat ataaagttg tatatggttt ttatccagga     1740
acttaatggt caaaggtagg gtagaaaccc caggggtggta ttaaataatt tctacaacaa    1800
taaatctgat aacatgaatt atttatataa attattataa tgacattctt ttaatacaaa    1860
actggaatga ctccatttga tgttcagcga gcatttaaat gttcaccaac acatgtggct    1920
atttgcatcc ttttttttag tttaatttta tttataattc attttttaca ctccatattc    1980
cattccccac tccacccatc cacattttga ctgttccaca tcccacacct cctcccaccc    2040
cgttgtctcc atgtggatgc ccccaaaccc caccctacgt gacctctaaa ctccctgggg    2100
cctccagtct cttgagggtt aggtgcatca tctctgaatg aacacagacc cagaagtcgt    2160
ctactgtatg tgtgttgggg gcctcatatc agctggtgta tgctgtcttt tggtggtcca    2220
gtgtttgaga gacctcaggg gtccagatta attgagactg ctggtcctcc tacaggatca    2280
cccttctcct cagcttcttt cagccttccc taattcaaca cagggggtca gctgtttctg    2340
tccattggtt gggtgcaaat atctgcatcg gactctttca gctgcttgtt ggatctttgg    2400
gggacagtcg tgataggtcc cttttttgtga atgctccata gcctcagtaa tagtgtcagg    2460
cctttggacc tcgtgttgag ctggaccgca ctttgggccc gtatttgcaa tcttaagca    2520 ttactgaaag tttttatgct atcttaaggt gatcttttg agagagaaaa gtattcagat    2580
atattgatga ataaagtaat caatcagttc tttgacataa gagtcaaatt tcatattata    2640
aagtaatatt tttacataat gactatattt tgctcatcta attgatagtc atgtctttaa    2700
tgctttgagt ttagaaataa cctggcaatt tgatagtcta gtcctactta caaatcagtc    2760
agaattctaa actgatactt acaaagtgga gatttgtact actgagatat caaagatccc    2820
```

```
cagggcatat ttaaaatagc aatagagctg gggttcattc ctgtctgcac cagcccctca   2880
ccagcttggg tgcaaactca gcagatagtc tccggaggac tctccatgca gaaggtaccc   2940
ttgcacatcc aggatcttgg gatcactggt gagtggaacg aaacatctgc tctaaaacaa   3000
ccaggagtgg cctgtgtgag caggaacaag gacacaggaa acccaccgaa ccagcagctg   3060
gggttctttc cagtctgtat caggatctgg ccatcttcgg tgagaactcg gtgaacagtc   3120
cccagaggac ctcccacgca gcaagcaccc tagcacatcc gggatcttag gatcgctgag   3180
gagattcggc ctccagagag ggctctgacc ccgggactca agtgagagca ccatctttata  3240 tcctaggtct cacatagacc agtccactca ggagagtgcc tgggccacag aagcaacaga   3300 gttttttttgg acaggggccc tacaggcctt catcctctgt cagaaggcag agctgagctc   3360
cagacctctg tgcaccttcg ctgccagagg agagcttgcc tgaagagagt gctctgacca   3420
ctgggactca ggagagagtt ggactcccag gagtgctgac agaggctaag agaatcacag   3480
aaggaacaag ctccagccag agacagctag aacatctaac accagagatt accagatggc   3540
aaaaggcaaa tgcaagaatc ttaataacag aaacaaagac tattctgcat catcagagcc   3600
cagtataccc accacaacga gtcctggata ctccaacaca cccaaaaagc aagattcaga   3660
tttaaaaatc atatctcatg atgctggtaa aggattttaa gaagggcatt aataactcac   3720
ttaaagaaat acgggagaac actgctaaac aggtagaaga cttttaaagag gaagcacaaa   3780 aatccctcaa agaattacag gaaaacactg ctaaagaggt agaagtcctt aaagaagaaa   3840
caaaaaaacc cttaaagaat tacaggaaaa cacaaccaaa caggtgatgg aattgaacaa   3900
aatcatccaa gatctaaaaa tggaaggaga acaataaag aaaacccaaa gggaaacaac    3960
tctggagata gaaatccaag gaaagaaatc aggaaccata gatgcaagca tcagcgacag   4020
aatacaagag atggaagaga gaatctcagg tgcagaagat accatagaaa acattgacaa   4080
aacaatcaaa gaaaatgcaa aatgcaaaaa gatcctaact caaaacatcc aggaaatcca   4140
ggacacaatg agatgaccaa accgaaggat tataggtata gatgagaatg aagattttc    4200 aacgtaaagg accagtaaat atcttcaaca aaattataga gaaaatttc cctaacctaa    4260 agaaggagat gcccatgaac atacaagaag cctacagaac tccaaataga ctgaaccaga   4320
aaagaaattc ttcccgacac ataataatca aaacaacaaa ttcactaaat aaagatagaa   4380
tattaaaagc agtaagggga aaggtcaag taacatataa aggcagacct attacaccag   4440
acttatcatc agagactatg aaagccagaa atcatggac agatgttata taaaacctaa    4500
gagaacacaa atgccagccc aggctactat acccagaaaa actctcaatt accatagatg   4560
gagaaaccaa agtattccat gacaaaacca aattcacaca atatctttcc acgaatccag   4620 ccccttcaaag gataataaag ggaaacccc aacacaagaa gggaaattat gcccagaaa    4680 aagcaagaaa gtaatccttc aataaaccta aagaagata gctgcaagaa cagaatccca   4740
actctaaaaa caaaataac aagaagaaac aattactttt ccttaatatc tcttaatatc    4800
aatggattca attcccacaa taaaagata tacactaaca gactggatac ataaacagga   4860
cccaacattt tgctgcatac aggaaaccca cctcagggac aaagacagac actgccttag   4920
agtaaaaggc tggaaaacaa ttttccaagc atacggtaac aagctggagt agccattcta   4980
atatctaata aaatcaattt ccaaccccaa tttatcaaaa aaaaatcaa agaggggcac    5040 ttcatactca tcaaagataa aaatcttcca agatgaactc agttctgaat atctatgctc   5100
caaatgcaga ggcattcaca ttcattaata ggaaactcta gtaaagctca aacgacacat   5160
```

```
tgcacctcac acaaaaatag tgggagactt caacacccca ctctcatcaa tgggcagatc    5220
ctagaaacag aaattaaaca gagacacatt aaactgatgg aagttatgaa acaaatggat    5280
ttaacagatg ctacataaca ttttatccta caacaaaagg atataccttc ttctgagcac    5340
ctcatggtac cttctccaaa actgaccatt taattggtaa caaaacaggc ctcaacagat    5400
aaaaaaaata ctgaaattat cccaatgcat cctatcagat cactacagac taaggctgat    5460
cttcaataac aacataaata atagaaagcc aactttcatg tgggagctga acaatactct    5520
actcaatgat aacttggtca aggaagaact aaaaaagagg ttaaagactt tatagagttt    5580
aatgaaaatg aagccacacc atacccgaaa ttatgggaca taatgaaagc attcctaaga    5640
ggaaaactca tagctctgag tgcagccaaa aaaaaaaaaa aaaaaaacta gagagagcat    5700
acactagcag cctgacagca tacctacaag ctctagaaca aaagaaagca aattcaccca    5760
agaggagtag ctggcaggaa ataatcaaac ttagggctga aatcaaccaa gttgggggaa    5820
aaaaaaaaaa ctatacaaag aatcaaacaa accagaagct ggttctttga gaaaatcaac    5880
aagatagatg aacccttagc cagactaagt agagggcaca gagacagtat cctaactaac    5940
aaaatcagaa atgaaaaggg agacataaca acagaacctg aggaaatcca aaacatcatc    6000
agatcctatc acaaaagact atactcaata aaactggaaa acatggatga attggacaat    6060
ttcctagaca gataccaggt accaaagtta aatcaggatc aggtaaacta tctaaaaagt    6120
cccatttccc ctaaagaatt agaagcagtc aataaacgtc tcccaaccaa aaagagccca    6180
ggaccagatg ggtttaatgc aaagttctat cagaccttca agaagacct aattccaatt    6240 ctcctcaaac tattccacaa aatagaaaca gaaggtactc taccccattc attctatgaa    6300
gccacaatta ctctgatact aaatcacat aaagacccaa caagaaaga gaacttcaga    6360 ccaaaattcc cttatgaata tcaatgcaaa atactcaat aaaatacttg caatccaaat    6420
ccaagaacac atcaaaacga tcatcccaca tgatcaagta ggtttcattc cagggatgca    6480
gggatggttt aatatacagg aatccatcaa cttaatccac tatataaaca aactcaaaga    6540
caaaaattac atgatcatct cattagatgc ggagaaagca tttgacaaaa tccaacaccc    6600
attcatgaaa aaagtcttgg agagatcagg aattcaaggc ccatacctaa acatgataaa    6660
agcaatatac atattctatt gtacagcaaa ccagtagcca atgtcaaact aaatggagag    6720
aaacttgaag caatcccact aaaatcaggg actagacaag ctgtccact ctcgccctac    6780 ctattagata tagtacttga agtcctaggc agaacaattg gacaacaaaa ggagatcaag    6840
gggatacaaa atagaaagga agaagtcaaa atatcactat ttgcagatga tatgatagta    6900
tatataagtg accctaaaaa ttccaccaga gaattcctaa acctgataaa cagcttcgat    6960
gaagtagctg gatataaaat taactgaaac aagtcagtgg cctttctcta cacaaagaat    7020
aaataggctg agaaagaagt tagggaaaca acaccttca caatagtcgc aaataatata    7080
aaataccttg gtgtgactct aactgaggaa gtgaaatatc tgtatgataa gaacttcaag    7140
tctttgaatg aagaaagaaa tcgaggaaga tctcagaaga tggaaagatc tcccatgctc    7200
acggattggc gggatcaata tagtaaaaat ggttatcctg ccaaaagcaa tctacagttt    7260
caacgcaatc cccatcaaaa tttcaactca attcttcact gaactagaaa gggcaatttg    7320
caaattcatc tggaataaca aaaaactag gacagcaaaa actcttctca acaagaaaag    7380
atcctttggg ggaatcacca tgcctgacct caagctgtac tacagagcaa ttgtgattaa    7440
aaactgcatg gttctggtac agagacagac aggtagatca atggaataga attgaagacc    7500
cagaaatgaa ccacacacct atggtcactt gatctttgac aagggagcta aaatcatcca    7560
```

| | |
|---|---|
| gtggaaaaaa gacagcattt tcaacaaatg gtgctggcta aactggcagt tatcatgtag | 7620 |
| aagaatgcga attgatccat tcttatttcc ttttacaaag ctcaagtcta agtggatcaa | 7680 |
| ggaaatccac ataaaaccag aaacactaaa acttatacag gagaaagtgg gaaaaagctt | 7740 |
| cgaagatatg ggcacagggg aaaatttcct gaacaaaaca gcaattgctt gtgctgtaag | 7800 |
| atcaagaatc gacaaatagg acctcataaa attgcaaagc ttctgtaagt caaaagacac | 7860 |
| tgtcaataag acaaaaaggc caccaacaga ttgggaaagg ttcttcaaca atcctaaatc | 7920 |
| caatagggga ctaatatcaa atatatacaa agatctcaag aagcgggact ccagaaattc | 7980 |
| aaataacccc attgaaaaat ggggttcaga gctaaacaaa gaattctcac ctgaggaata | 8040 |
| ctgaatggct gagaagcacc tgaaacaatg ttcagtatcc ttaatcatca aggaaatgga | 8100 |
| aatcaaaaca accctgagat tccacctcat accagtcaga atggctaaga tcaaaaacta | 8160 |
| aggtgagagc agacgctggc gaggatgtgg agaaagagga acactcctcc attgttggtg | 8220 |
| ggattgcaag tttgtacaag tactctggaa attagtctgg cggtttctca gaaaattgga | 8280 |
| catagtacta ccggaggatc cagcaatctc tctcctgggc atatacccag aaggtgttcc | 8340 |
| aacttgtaag aaggacacat gctccactat gttcatagca gccttattta taatagccag | 8400 |
| aagctggaaa gaacccagat gtgcctcaac agaaaaatgg atacagaaaa tgtggtaaat | 8460 |
| ttacacaatg gggtactact cagctttaa aaacaataaa tttataaaat tcttaggcaa | 8520 |
| atggatggat ctggaggata tcatcctgat tgaggtaacc cagtcacaaa agaactcaca | 8580 |
| tgacatgcac tcactgctaa gtgatattag cccagaaact tagaatacct aagatataat | 8640 |
| ttgcaaaaca catgaaactc aagaagaagg aagaccaaag tgtggatact tgttcctcc | 8700 |
| ttagaatggg aaacaaaata cccatggaag gagttacaga gacagagttt ggagctgaga | 8760 |
| cagaaggaag aaccagagac tgccccaccg gggatccatc ccataaacat ccacaaaacc | 8820 |
| cacacactat tgcacatgcc agcaaaattt tgctgacagg accctggtat agctgtctct | 8880 |
| tgtgaggcta agccagtgcc tggcatatat agaagtggat gctcacagtc atctattgga | 8940 |
| tggaacacag gaccccaat tgaggagcta gagaaaatac ccaaggagct gaaggggtcg | 9000 |
| gcaaactata ggaggaagaa caatatgaac taaccagtat ccttagaact tatgtctcta | 9060 |
| gctgcatatg tagcagaaga tggcctagtt tgacatcact gggaggagag gcccttgatc | 9120 |
| ttgggaagat tatatgccac agtacagggg aatgccaggg ccaggaagtg ggtgggttgg | 9180 |
| ggagcagggc agggggggggg agggtatagg ggactttcaa gatagcattt gaaatgtaaa | 9240 |
| tgatgaaaat catctaataa aaaataaat aaaataatag ctattcctga tcctctctac | 9300 |
| gacctcccac aaaagaatct actggaaata caggccagga agctgtatct ttgtgtggcc | 9360 |
| tataaagcat cttccccaa cctgacatgc gacattgaat ctctgcttca gaggaactga | 9420 |
| cattgttggg ggtttaagaa cattaaaata agaccactat gaacgtagtg gatcacgtgt | 9480 |
| ccctgtgaca tgttggggca cctttggagt atatgctggg tcttaggtta gatctatttc | 9540 |
| caattttctg aggaacctcc agattgattt ccttagtggt tttaacagtt tgcaatccct | 9600 |
| ccatcaatgg aggagtgttc ctctttctct acatctagcc agcatgtgct gtcacctgag | 9660 |
| tttttgatct tagccattat gattattgta aggttaaatc tcaggttcat gtgatttgaa | 9720 |
| cttccctgat cactaaggac cttgaacatt tctttaggtg tttctcagcc attcgagatt | 9780 |
| cctttgctgt gaattctctg tttagttcta caccccattt tttaattttt ttgattgggt | 9840 |
| tgttcagttt cttggtggtt aacttcttga gttctttatt ttttggatat tagccttcta | 9900 |

```
taggatatgg ggttagcgaa aacttttttcc ccatctgtag gttggcaatt tgtcttatta    9960
gctatgtcct ttgccttata aaagttgtcc cgtttcatga ggttccattt atcaattctt   10020
gatcttagag cctgaaccat tggagttctg tttagaacat ttccccctg tgccagtgag    10080
tttgaggctc tttccaattt tctcttctat tagattcagt gtatctgggt ttatgttaag   10140
gtcctcaata catttggact tgggctttgt acaaggtgac aaatatggat ctattttcat   10200
ttttctacat acagattgcc agttagacca gcaccattta ttgaggatgc tttcttttttt  10260
ccattgtata ttttttggctt ctttgtcaaa gttcaaatgt ctataagtgt gtggttaaca  10320
atatttacat taaaaaataa gcaaacaatt tcccttcta tttgggctac tttgcatcca    10380
acatcacaag ggaatttgta gaaagttta taaatgtaac atctctctta aataaatttc    10440
ttgaacacta gaacctatat atcaccaatc agtctggtaa ctatggagga agctaggtgg   10500
ctaatggaca ggtgggtaca tataacatag atattgggac aaaggtaata tacatctggg   10560
gtaaggtgat tgcaatagat tcaccacaag acttgcaatg gattgtaatt taaaatgaat   10620
ttaattgttc acttctggaa ttctccatta aatgttttca ggctgtaatc agctacaggt   10680
aactggaacc ttacaaaggg aaaacataga taagggaaa tgattatagc acactaacac    10740
agactagcta gaaaaggaag gggtgggggt agcatagccc aaaatctcta gaatatagca   10800
tatgacacac agagtaagca aaagtcaccc aagtaccaaa acagacaaac tagtaaagaa   10860
tataaactag aactacatct ccttacacac acacacacac acacacacac aattgggctg   10920
ataaagaagg cagtctaagt cagtgggggg aaagacaggc ttttaatgaa tgttgacaat   10980
aaaactgggt agctattcag gaaaagacaa aattggttcc acatataaaa aatggattaa   11040
acaaactaag gatatataag aaaaattgaa atcatttta aaatactgga agaaattca    11100
agtgaattat tctttaaatt cactatgcaa actggaactc gtgattcaaa attcaacata   11160
aataaagatc atatggtaaa gtaaaagtat ttcaagccaa acaaaatctc tgatagcaaa   11220
cttttaaaac tgataaaatt aacacactgt aagggtatct ttgctccata tactacagat   11280
gaagtgttgg ggtcataatg tatttgggac acgcgttagc tgagaaatgg atgtgcagcc   11340
cctggtcagc acttaactag cctgagtaat cctgagtaat aacaagggta acactgggta   11400
atggcaccca ggaaataaca acatgggga agaagacagc tcttcagtta agaagaatag    11460
gagtgataaa taggagagcc tggaaaagtc actcctatgc agacactaga gtaataattt   11520
tataaaatt cttgatgagc tataaggttc atagttgaaa tgtactctgg aaaagaaaat    11580
attacatagc tataaaacta tatgtcccag tatattttac taacctagcc taaatatcta   11640
aaataacacc aatgtgggtt tggagtatag ctcagtacaa ctataggcac taaacatgca   11700
aaaagcccac caaccaaaca agcaaaccta cacagcaaaa taactcagca tatagcacct   11760
ccaaagggtg atccaagaaa tgggcacaat aagaagtatc agtaacaaga caggatacccc  11820
ttgacatgcc acactgaata gatcccatca cttccccaac aatcttgttc agaatgtggg   11880
accacattct actgtaagag aagagcaata gaacagaagc acacgctgct tcttggaaat   11940
gttcagatca cgaaaggtca ggaggtactg aagctaaagc agagacagaa agagacagcc   12000
gcgacaaggc aacaatagtc tatcagccaa tgtgggagcc ttcactgcac ttctgaaaag   12060
aaactgggat tagtgccaag gaagatggaa ttcaaataag gctgtgaagg tattgtggca   12120
ggattatttta caggttttca taactgttat atgagatatt gacattagag agagctgaat  12180
ggcatctgag aactctatac cagttgtaga tattttcgtt acagtcaagt gaattctaag   12240
aaacctttgg tgaaaagaat gcagttgtaa aaagtactgt tgctatggca tcatccttct   12300
```

```
gttagagtga atctgtttac gcacttaaac cagaattatt atatttatgt catatctcaa    12360
tagtgccaaa aatcttgctg ctaattaaag ctttgttctt taatgtgttg ggttggaaca    12420
acaatagaag cagaataaaa aagagatacc aaatagggat ggttctgtgt gaccttacca    12480
ggttaattag ttgtgtatga accacatctt ccaccaaaac tgcagtttca tggagaggcc    12540
tcctagcatc acctagagaa aacctgcagg aaaaataaaa cacaccacta ttaaggatgc    12600
agaacaggta cagcaaataa ttaatatata cttctcattg taaggatcag ctgtataaaa    12660
gaggcaataa actgctctta aacaattcaa cagtgcacac ttacttctag tctaagaaaa    12720
taatgccttg tttataaagt gtaacttgcc aaaaaaaaca tattattacc tgcagtcctt    12780
gtttacagag tatgctaaaa ggtgaaaggc tttgaggtct taaatgctca agctatatcc    12840
agaagaagat atatacagtg ccctgctgcc tgcagatcaa gatggagaac cctcagctcc    12900
tccagcatta tgttttcctg aaggctgcca tgcttcctaa cataataata gtggactcaa    12960
cccatactga aagtcagccc caattaaatt ttttacttta tacaggttgc cttggtcatg    13020
gtgtctcttc acagcaatgg caaccttaac taagacagac accctaaaac tacaataaat    13080
tcaatattgc ctaaacaatc tgtagcattg atagtatagt tcactgacag aataggtgcc    13140
taccaaattc aggcttcagg actgcaaatt acaagcaaaa tatcctgcaa aaatgtaact    13200
atatatgaac caagaatcag agagcttcat gaaaattagt tacctatggg ataagcacga    13260
gaaagtaaca aatgatttag atgattacat agacagagga tgcacaatca gaccttaact    13320
gaatcatatg aatgtacaca gataacaagt atccttgtaa tgcttccttg attgtttttg    13380
aaaacagttt attcttcaat taaatggaat tggaaatctc ccggtattac tgtctatgac    13440
taaatgtaag ttaccctatt agatgctctg agatgttctc caagaaagaa ctgtgatcac    13500
caatgttctt gccattacaa gattattctc taagctgtgt taattacaca acattgcaca    13560
tcaattcagg aacattctgg aggaaaagac tccaaatgac ttaaagcctt tggcaaaagg    13620
attccaaata tactcagcct aagatgctag aaccctgttc ttcagttta aacaaagatg    13680 atgatggtaa tgagagcaaa cactgaggct tttaaagaat tgtttacac attcaaaaaa    13740 tatttcttgt gggtctatat caagcactgg ttttcttaca aacaggggaa cggattttc    13800 tgactaataa actagtgact gattttcag ttgctgtggt attaagcagc taccactcca    13860
ggtcaaacag gaaggattcc tttcaatgaa cacatctctg aacaatgaac agtgtgtctt    13920
ctcaaagact cttttttttt ttttgatgtg ctaaaatttt ttgttttttt tttttttta    13980 ggtattttcc tcatttacat tttcaatgct atcccaaagg tccccatac ccactccccc    14040 aatcccctaa ccacccactc cccttttttg gccctggagt tcccctgtac tggggcatat    14100
aaagtttgca agtccaatgg gcctctcttt gcagtgatgg ccgactaggc catcttttga    14160
tacatatgca gctaaatatt tcttgtgggt ctatatcaag cactggtttt cttacaaaca    14220
ggggaagaga tttttctgac taataaacta gtgactgatt tttcagttgc tgtggtatta    14280
agcagctacc actccaggtc aaacaggaag gattcctttc aatgaacaca tctctgaaca    14340
atgaacagtg tgtcttctca gagactcttc tatagaggat gtcaacctcc agaaaaccag    14400
tctaggacct ccatgctctc tcacaacagg agacaccgca tcttcacaca gcatcttcac    14460
ctgtaagaaa cttcctacac acaagctcct ggtaagaagc aatgatctga ttttctggtt    14520
tattcctgtg ctgaataatc tcagtattta tgatacagtg tttgcaaagg ttttctcct    14580 aaacctaatc agtcccaccc ctctcctttc cttttttttt atattaatac ctttattacc    14640
```

```
acgattggtt tatgtatgaa ctattatgat acaatctatt actatgctct tattttata   14700
caagcatgta gacatgtcag ggagttagtt agattgagga aagtatattt attgttactt   14760
agcctgcttg gttgtggtat tctgttggtt gaaagtgtgt agaggcctcc aatgctgctg   14820
tctaagagct aataccactg ggaagacagg ttataatttt catgttcttt tttttaattt   14880
ttttaaaaa atattttat taggtatttt cctcatttac atttccaatg ctatcccaaa   14940
attccccat accctccccc cactcaccta ccgacccact cccactttt gtccctggca   15000
tgtccctgta ctgaggcata taaagtttgc atgaccaatg ggcctctctt tccactgatg   15060
gccgactagg ctatcttttg atacatatgc agctagagtc aagagctccg gggtactggt   15120
tagttcataa tgttgttcca cctataggt tgcagatccc tttagctcct tgggtacttt   15180
ctctagctcc tccattgggg gccctgtgat ccatccaata gctgactgtg agcatccact   15240
tctgtgtttg ctaggccccg gcatagtctc acaagacaca gctatatctg ggtcctttca   15300
gcaaaatctt gctagtgtat gcaatggtgt cagcatttgg aggctgatta tgtgatggat   15360
ccctggatat ggcagtctct agatggtcca tcccttgtc tctgctccaa actttgtctc   15420
tgtaactctt tccatgggtg ttttgttccc aattctaaaa aggggcaaag tgtccacact   15480
ttggtcttcc ttcttcttga gtttcatgtg tttcctaatt gtatcttata tcttgggtat   15540
cctaagtttc tgggctaatg tccaattatc agtgaataca tatcatttaa gttcttttgt   15600
gattgtgtta cctcactcag gaagatgccc tccatgtcca accatttgcc taggaatttc   15660
ataaattcat tcttttaac agcttagtag tattccatgg tgtacatgta ccacattttt   15720
tgtatccatt cctctgatga ggggcatctg ggttctttcc agcttctggc tattataaat   15780
aaggctgcta tgaacatagt ggagcatgtg tccttcttac cggttgggc atcttctgga   15840
tatatgccca ggagaggtat tgcgggatcc tccggtagta ctatgtccaa ttttctgagg   15900
aaccaccaga ctgatttcca gagtggttgt acaagcttgc aatcccacca acaatggagg   15960
agtgttcctc tttctccaca tcctcgccag catctgctgt cacctgaatt tttgatctta   16020
gccattctga ctggtgtgac atgaaatctc agggttgttt tgatttccat ttccctgatg   16080
attaaggata ctgaacattg tttcaggtgc ttctcagcca ttcagtattc ctcaggtgag   16140
aattctttct ttagctctga gccccatttt ttaattagat tttctggagt ccaacttctt   16200
cagttcttta tataaattgg atattagtcc cctatctgat ttaggatggg taaagatcct   16260
ttcccaatct gttggtggcc ttttgtctt attgacagtg tcttttccct tacagaagct   16320
ttgcagtttt atgaggtccc atttgtctat tctcgatctt acagcacaag ccattgctgt   16380
tctattcagg aattttcc ctgtgcccat atcttccagg ctttccccca ctttctccac   16440
tataagtttc agtgtctctg attttatgtg gagttccttg atccacttag ctttgacctt   16500
agtacaatga gataggaatg gatcaatttg caatcttcta catgataacc gccagttgtg   16560
ccagcaccat ttgttgaaaa tgctgtcttt tttccactgg atggttttag ctcccttgtc   16620
acagatcaag tgaccataag tgtgtgggtt catttctggg tcttaaattc tattccattg   16680
gtctacttgt ctgtcgctat accagtacca ttcagttttt atcaatattg ctctgtacta   16740
cagcttagg tcaggcatgg tgattcctcc agaggttctt ctatccttaa gaagagtttt   16800
tgctatccta ggttttttgt tattccagat gaatttgcag attgctcttt ctaattcgtt   16860
gaagaattga gttggaattt tgatggggat tgcattgaat ctgtagattg cttttggcaa   16920
gatggtcatt tttacaatgt tgatcctgcc aatccatgag catgggagat cttttccatct   16980
tctgagatct tcttaatttt ctttcctcag agacttgaag ttcttatcat acagatcttt   17040
```

```
cacatcctta gttagagtca cgccaaggta ttttatatta tttgtaacta ttgagaaggg   17100
tgttgtttcc ctaatttctt tctccgcctg tttattcttt gtgtagagaa aggccattga   17160
cttatttgag ttaattttgt atccatctac ttcatcgaag ctggtatagg agatctctgg   17220
tggaattttt agggtcactt atatatatta tcatatcacc tgcaatagtg atattttgac   17280
gtcttccttt ccaatttgta tccccttgat ctccttttgt tgtcaaactg gtctaaagtt   17340
ctctatcttt gttggatctt tctgtggttt aggtatcaga gtaattgtgg cttcatagaa   17400
tgagttgggt agagtacctt ctgtttctat tttgtggaat agtttgtgca gaactggaat   17460
tagatcttct ttgaaggtct gatagaactc tacactaaac ccatctgttc ctgggctttt   17520
tttggttggg agattattaa tgacttcttc tatttcttta ggggaaatgg gactgtttag   17580
atcattaact tgatcctgat ataactttgg tacctggtat ctgtctagaa atttgtccat   17640
ttcatccatg ttttccagtt ttgttgagta tagccttttg tagaaggatc tgatggtgtt   17700
ttggatttct tcaagatatg ttgttatgtc ttccttttca tttctgattt tgttaattat   17760
gatgctttcc ctgtgccctc tagtgagtct ggctaagggt ttatctatct tgttgatttt   17820
ctcaaagaac cagctccttg gttgattctt taaatagttc ttcttctttc cacttggttg   17880
atttcgcccc tgagtttgat tatttcctgc tgtctactcc tcttgggtga atttgcttcc   17940
ttcttttcta gagcttttag gtgtgttgtc aagctgctag tgtgtgctct ctctagtttc   18000
tttttggagg caatcagagc tatgagtttc cctcttagaa atgctttcat tgtgtcccat   18060
aagtttgggt atattatggc ttcattttca ttaagctcta aaaagtcttt aatttctttc   18120
tttattcgtt ccttgaccaa ggtatcattg agaagagtgt tgttcagttt ccacatgaat   18180
gttggctttc cattatttat gttgttattg aagatcagcc ttagtccatg gtggtctgat   18240
aggatgcatg ggacaatttt aatatttttg tatctgttga ggcctgtttt gtgacaaatt   18300
atatgatcag ttttggagaa ggtcctgtga ggtgctgaga agaaggtcta tccttttgtt   18360
ttaggataaa atgttctgta gatatctgtt aagtccattt gtttcataac ttctgttagt   18420
ttcactgggt ccctgtttag tttctgtttc cctgatctgt ccattgatga aagtggtgtg   18480
ttgaagtctc ccactattac tgtgtgaggt gcaatgtgtg ctttgagctt tactaaagtt   18540
tctttaatga atgtggctgc ccttgcattt gcagcataga tattcagaat tgagagttcc   18600
tcttggagga ttttacccttt gatgagtatg aagtgtccct ccttgtcttt tttgataact   18660
ttgggttgga agtcgatttt attcaatatt agaatggcta ctccagcttg tttcttcata   18720
ccatttgctt ggaaaattgt tttccagcct ttcactctga ggtagtgtct gtcttttttcc   18780 ctgagatgga tttcctgtaa gcagcaaaat gttgagtcct gtttgtatag ccagtctgtt   18840
agtctatgtc tttttattgg ggaattgagt ccattgatat taagagatat taaggaaaag   18900
taattgttgc ttcctattat ttctgttgtt agagttggca ttctgttctt gtggctgtct   18960 tcttttggt tgttgaagg attactttct tgctttttgt agggcgtggt ttccgtcctt   19020
gtattggttt ttttctgtt attatccttt gaagggctgg attcgaggaa agataatgtg   19080
tgaatttggt tttgtcatgg aatactttag tttctccatc tatggtaatt gagagtttgg   19140
ctgggtatag aagcatgggc tggcatttgt gttctcttag ggtataacat ctgtccagga   19200
tcttctgtct ttcatagtct ctggtgaaaa gtctggtgta attctgatag gcctgccttt   19260
atatgttact tgaccttttt cccttactgc ttttaatatt ctatctttat ttagtgcatt   19320
tgttgttctg attattatgt gtagggagga atttcttttc tggtccagtc tatttggagt   19380
```

```
tctgtaggct tcttatatgt tcatgggcat ctctttcttt agttttagga agttttcttc    19440
tataaatttg ttgaagatat ttgctggcct tttaagttga aaatcttcat tctcatctac    19500
tcctattatc cgtaggtttg gtcttctcat tgagtcctgg atttcctgga tgttttgagt    19560
tagtatcatt ttgcattttg cattttctct gattgttgtg cccatgttct ctatggaatc    19620
ttctgcacct gagattctct cttccatctc ttgtattctg ttgctgatgt ctgcatctat    19680
ggtttcacat ttcttttccta gggttttctat ctccagcatt gcctcacttt ggttttctt    19740 tattgtgtct acttcccttt ttaggtctcg gatggtttta ttcaattcca tcacctgttt    19800
ggtcgttttt tcctgcaatt ctttaaggga cttttgtgct tcctctttaa ggtcttctat    19860
ctgtttagca gtgttctcct gtatttcttt aagtgagtta ttaaagtcct tcttgatgtc    19920
ctctaccatc atcataaaat atgcttttaa atccgggtct agcttttcgg atgtgttggg    19980
gtgcccagga ctggtggtgt gggagtgctg cgttctgatg atggtgagtg gtcttggtct    20040
ctgtttgtaa gattcttacg tttgcctttg ccatctggta atctctggag ttagttgtta    20100
tagttgtctc tggatagagc tagttcctca ggtgattatg ttagcctcta tcagcagacc    20160
ttggagacta actctctcct gagttttcagt ggtcagatta ctctctgcag gcaagctctc    20220
ctcttgcagg gaaggtgccc agatatctga tgttcgaacc tgcctcctgg cagaagttgt    20280
gttccactca ccagaggtcc taaaatccca tggagagtcc tgtggggacc ttggggatgt    20340
cttcagactc agcgcccaag gtgccctgat gctggtgcct accagaaggg acttgtgacc    20400
ttggtcaggc cagattttct gcttccctaa ttaatgccct ctcctttctt ttttacctct    20460
tcgatatttt taacccagag acaaattcaa agatccacac aatggaccct tatttgtatc    20520
ctaagagaga tatcttggtg gcctcttagt gcctgtgctc tttctctttc aaattcatac    20580
tttacacaca catccttatc aatgtctatt atccttttaag caacaaatat gcactgaatg    20640
atttacatgt gagagcatta ctgcacatgc tgagtcatgg aaacctatta ttctctaagc    20700
tgccattact gttcctgtct tctgcctcga ggggaaatgc tctgtattta ggtaggattc    20760
tgtttctttt gtgatttcca aacatcaagc ttagttgaaa atacaaaatc ctactttcaa    20820
aattatgaag cattgttttc aaaagttttg ttttgtttgc taaaggataa tcatacatac    20880
atatatatat atatatatat atatatatat atatatatat atatatacca gctcaatata    20940
ttatttacat agtttgtaaa cttgattttt taaagtaatc actttaatga ttttttaagta    21000 aacttacaga gcagtgtgcc cacctcatct ataaaataca gttttatgac tttctctagt    21060
accccaaaac cttatttctc ttgacaataa ccccccatttt catctccagt tcagggcaaa    21120
ctatgagaaa aacctagttg aggtcaccag acatcaggtt tcccttccag gttcaacatt    21180
cctcatttct tagcatgtaa gtctgttgta cagccatttt caaaacactg agacaggcct    21240
ttctggaggg agaagagagg atgctataca taaccaggac aaacgacctg agagagtcag    21300
aggactcaca aggctgtata agcagacaag ccttgaggct ctagtcctag aactgcctgt    21360
gtattgtgca gagagtgctg ggagagtggt tttcttgggc agttactgac acagctgcgt    21420
tggacttcag ttaagctctc agtttcaaca acctagactc agtgaattat ttctttgtcc    21480
tctagtcagc atcctttcta gaatgaacag acatcttttg gtatctcccc aagtaaattc    21540
tacgattttc ccaaagacca ctatggcaat tttcagttta aaaacagtag tatagtattc    21600
ccttggctat atattaatgc ctaagttttg attttgaata gaaagttac cagttttttaa    21660 tgaataaaca acaattaaaa acaaagcagc tctctaacct acacagtgaa caagcccaat    21720
gtagacaaca gatggcataa tcaacatttc tgtggacagt gaagagctga actagcttca    21780
```

```
ggtctatctt tgagctagtt tgccatcttg tccagaataa tatcatgtca tatgacatgg    21840
aatattctgc tggaattttt accctgttcc atagtattac tccatacaca aactatctta    21900
tggactatga atccattcac attcctaaat aattaaagat ccatatttt cttgaggtca     21960 gaaaatttaa tgtgtttatt gtgtgtggta gtgtatacct ttaatcccag tgctcaggag    22020 gcagggtag agttcaagtt agatgggcct aaattaagac cttgactcaa aataaattaa     22080
aaaattaaaa aatattgtaa aaactgagca atttttaaaag tgttccctga ctaaactcaa   22140
ccttcctaca acattttaga agcaaatcaa aattatgcca aaagcctaac ttaattttac    22200
ttcttataaa aaaaacagac aataatttat atcactattt aattaataag aatcttatgc    22260
caagcttttc tcctgagaat tatattcaca gaagccaaag tattagtcca gcccaaaaca    22320
agagtatgca aatgcaaaca taaacaaaca ctgcaaagcc agaggaatca ctacagatat    22380
gtgaaaagta actatgcaaa tatctgtgac tgccaaaagg aaaatacata atatattcca    22440
gttgtactac ataatatatt ccatttgcgt actcagaaaa ggattcaatt taaatcatga    22500
agcatacaag acaactatct ttatagacta tgtaaactag acaatgatca gcgacttttg    22560
ttcagagaaa ataagaaaa catttatctc tagtctcaac aatattcctc caatcaaaat    22620
ggaatttagt atacccagaa aaagatgcag tttcaaatta ttctctagaa catgtataaa    22680
aaagtgatga catgagaaag atgttaagat ataattatat gttatgattc tattgagaat    22740
aaacatagag catacattaa atgatctttt aggttcactt tagattatag accagaattt    22800
caaattttgg tatgtataaa taactttta tacaagtcta cacaaactat cattataaat     22860
catatattaa aatgtaccat tgaaagcttc atcggtacgt taaccatgaa catatgaggg    22920
aatcgaagta tactaaaaac accattaaaa ggtattgttg ctcggtatct gcagagtact    22980
agttggaggt ttcacataga cacaattaag tccttatgta agagaggata tttgcacaaa    23040
acctcaacac acccttttgt cagattagtt cctacaatat gaatgctaca taggagtta    23100 ttctacagta ttgtttagga actgacagca gagtctaaag atgaatccac agacattaaa    23160
tccatagatg tggagggcca actatcctgt atactggcac cgccagacta cacgcgtaaa    23220
catcatcaca gataccaacg ttgaggtaat gtacttacac cagcatagta catcaaaacg    23280
taggtgagca cctacactat tcttcccttt tacataatta ttaatagtgt ttgttctttc    23340
catcgcaggt ctagttgtgc aagggtatgt attcaatgga gagctcagtg ggatttccat    23400
tcccagtatt ctgaccagga gctctaacat tagcctattt tatactacaa tgtttcacca    23460
acgccttaga cacttaggct atttcaactt ctaccaggaa aaacagaat gggataaaag      23520 atgatatgcg cataattcaa actaagtgct tgcagtaggc ttctggatga cttttttgaca    23580 actaaatgtg ggccatgcag aaataccaat cttgtgtaag gaacacagct gctgaactca    23640
tgaaggtgaa agggagaagc aacttaataa tgatttttaca gcactattag aataaagaca    23700
aagattttat gtgatattga tttaaatgcc tctctctcaa tatgctttcc atgggaacag    23760
tgggctcttc agggtcagaa atcactttac acatttgcct ggcacccagc tttctttgca    23820
acacttgaga ataaacattt taacagtaaa tcattctgaa tgctaactct accagcagag    23880
atgctcactg cgttgtataa gttttgagta tactcaattg aagtgtgtga catttttcatt   23940 tatttccaag gttatttttt taaaacttaa taaaacgggg ggggggaat tccctggtaa     24000 cccaccccctt gataaagacc tatgacaaat taactactgc tgagaaaaga attattcttc   24060
cttagggatg agctaagtga ctgttcaata ccaagtggtc aagcctaaaa acatacatga   24120
```

```
aacaacagtg aacagactga gcaggtttgt gtaaatgtaa caataataat taagaaaaa   24180
gagaacaggc atatgagagg ggaagcttta agaggatgtg attactataa ataaaaataa   24240
aatatattta aaaataaaat taaaataaaa agtggatttg gggctgtaaa atgtatggaa   24300
tgctaatgta atgtaaatac aaaagtagaa actcatttaa aaatagaata atcacaata    24360
caggtaacta aaacaatttg ggtataagag tattctttct gttctgcaaa atggtactat   24420
ttctaagcta taaggaggaa acaattagga gtatagttga agattcatag gaatttttta   24480
ttaattcaag gcagtatatt ttctgtttaa gttccattga ggctattctt tcagactcaa   24540
tgaacaatta actgtctaca aattccaagt tctcaaatgt gttaatgata taattgagca   24600
tacactctat aaacccagta gtttatagat aataggttaa atacccatt attagctaaa    24660
tttcatagct acataggtca attctaaaag tttacctagc aataataaaa taagccttgt   24720
ttgctaattg ggtttccaga taaaaatgtc cactacatat atgcatgtgg acatttacat   24780
acatatacca aaatctatat agaagcttaa ttcacctttc cagtattttc tgatgcaaac   24840
ctgaataaag ccaaacccct tggtctctatg aaggctaggc actcccaagg acttgcacaa   24900
ggcttgcttt cagtctaaca taaactgtat tgagaccaca gaagatatga aattctggaa   24960
gaataagctt taaattatct acttttaaaa tatactatta cataatttaa aaatcatttt   25020
actgagtgaa cgaaaaaaac tgttgttaca attcaggggt cacttattaa ttcactttc    25080
tggaacaggg tcataaagtc tttgtcgcaa acacacagcc caccaaagct gcaatgcaca   25140
atcaggcaca gtcatggtct ggttcagcgg tgtgactgga ctctgaaatt caatgggaa    25200
ctggaagaga acatgaaata ctactcttct tttgtaagtc ccccaagaat ttaaaactgt   25260
gaagaacaaa aggtgccttc ttacttaaac aggctgggca aaaagagggg actctactgg   25320
atagctctat gttaacttga cacaaactag agtcttttag aagagggagc ctcaattgag   25380
aaaacacctg acgctggttt gcaagcctgc agtgattttt cctggatgat ggttaatgtg   25440
aaagggtcca gttcactgta ggaaggggca ccaatgggta ggtggtccta ggtgctctta   25500
gaaagcacac tgagcaagcc atggagagaa gccatgaaag agcatttctc cacggcatct   25560
acttcagttc ctgcgctgac ctcccttcgt gagaacagga aagttgtaag gtgagataac   25620
acgtttcctc cccaagttat ttattgtcaa ggtgtttatc atgggaatag aaaccaaatt   25680
aagcacccca atacctcaaa atatgaccat cctggacaca ggacatagga caaaggaaat   25740
aaatgtaaaa caatgacatt aaagcaggtt ctagtgcgat atagtaagta ccgtgattaa   25800
aaggggaaat tggacaagag acacacagat ggaaaactaa catgagcact taggaggaag   25860
ccaggtaact gacgtcacac ttcgggaagc tgaggaaggt aaggacccgt cagaggcaca   25920
ggaagaacat cagcttcggc ctcaaagact ccacactcat ttattttac ttttgaaac     25980
agaagctcat gtagcccagg ttggcctaga agttgctata tagtcagtca agcataacta   26040
tgagatcctg aacctaatac ctcaggtctt aagtgccaga attacagaca tgtcaccatt   26100
cctggctgac atctaaagcc tcaggctgtg gaaaataaac tgctgttgtc tcggattttt   26160
gaacctttgc tacagaagcc ctaggaaaca gtacagaaac agagcagttt aacacaacag   26220
cactcaaata acatcataat ttaatgacca gataaataaa atgattagat ccaaaataaa   26280
atgcgccaag gattacacat agttgtcaag ctaaaattaa gtcaattttc tacatatgat   26340
acagctatga aggaagtttc ttttaaagcc ccccaaacat gtgtgctaat aggtgaaagg   26400
aaacactaaa ggcctatttta cccatcttgt cttggtgtaa aatggaagca ttctgaatga   26460
agacatgcgt tgcctcagtt actaggtcgt ggatcttcaa tatccaaagt gttctgtggg   26520
```

```
gcattaagtc tagttggccc tgaataagtc cagcaatgac ctccaagaat gccttctttc    26580
caaatggagg gaacacaggc aaatgaaaag ttcatttaga tccatgtcac tcttgttttc    26640 cttttttgaga ctaggtttca tatgggagat ggctcagcaa ttcagagcac atgctacgaa   26700
agcacaagaa cccaagttcc aacccagctt ccacccaaaa cctggccact gtcatgactg    26760
cctgtcaacc ctagtgttgg cggatacaga gaagtggatc ccagaagctc actgccactg    26820
ccagccagtc tagccaagag tgaacttcag gctcagggag agattacacc aggaaaaaaa    26880
aaaaaaaaaa ggtggagggt gacagaaaaa gacatgcaat gttcttacct acctcctcct    26940
gtgtgtgcat actcatgcat acactgaaca cagaaattgt aagaaaatgg actgtctttt    27000
gttagttatg ctttcacatg gtcatgaaat ggacagtagg aggtttggaa gcacagccac    27060
actctattat ggacagaagt gatggagaat caatgagaca cagctaaagt aatgccatga    27120
tggttacaag agctgggaca tggtcttttt tgatatctta ttcaggaatc atcgacttaa    27180 aattttata gaatgcacaa cactatgact attgaaatag actcaaatta tttgtactat     27240
attttaagaa aacctgaaaa tgtgagctta ccaggtatga aaataaaaaa agaaaagga    27300 aaaaaaaaaa aaaaagccg gcatggtgg cacacacctt taatcccagc actcgggagg     27360
cagaggcagg cagatttctg agtttgaggc cagcctggtc tacaaagtga gttccaggaa    27420
acacagggct atacagagaa tccttgtctc gaaaaagcaa aaaaaaaaaa aaagcttgc    27480 tttaattttt ttttgttgtt gttgttttct ttttttttat tacatatttt cctcaattac    27540
atttccaatg ctatcccaaa agtccccac acctccccc ccccacaca cacacacccc      27600 taaccaccca ttcccatttt ttggccctgg cgttcccctg tactggggca tataaagttt    27660
gcctgtccaa tgggccttc tttccagtga tggccgacta ggccatcttt tgatacatat     27720
gcagctagag tcaggagctc cggggtactg gttagttcat aatgttgcac ctacagggtt    27780
gcagatctct ttagctcctt ggatactttc tctagctcct ccattggggg cgctgtgatc    27840
catccaatag ttgactgtga ccatccactt ctgtgtttgc taggccccgg cctagtctca    27900
caagagacag ctatatcatg gtccttgaaa caaacgcttg ctagtgtatg caatggtgtc    27960
atcgtttgga ggctaattat gggatggatc cctggatatg gcagtctcta catggtccat    28020
ccttttgtct caggtccaaa cttttgtctct gtaactcctt cgatgggtga ttgtttccaa   28080
ttctaagaag gggcaaagtg tccacacttt ggtcttcgtt cttcttcagt ttaatgtgtt    28140
ttgcaaattg taccttatat ctcgctatac taagtttctg ggctaatatc cacttttcag    28200
tgagtacata tcatttgagt tcttttgtga ttgtgttacc tcactcagga tgatgccctc    28260
caggtccaac catttgccta ggaatttcac aaattcattc tttttaatag ctgagtagta    28320
ctccattgtg taaatgtacc acatttttg tatccattcc tctgttgagg ggcatctggg    28380
ttctttccag cttctggcta ttataaataa ggctgctatg aacatagtgg agcatgtgtc    28440
cttcttactg gttggggcat cttctggata tatgcccagg agaggtattg cgggatcctc    28500
cggtagtact atgtccaatt ttctgaggaa ccaccagtct gatttccaga gtggttgtac    28560
aagcttgcaa tcccaccaac aatggaggag tgttcctctt tctccacatc ctcaccagca    28620
tctgctgtca cctgaatttt tgatcttagc cattctgact gtgattgttt ctactcttct    28680
agaagaaaac gatcaatcta ggccgcacta accatcatga catctcgttt tattaacctt    28740
cttgggattc caattctctt taccaagaat cacttctaat ctgctctcca ggctctactg    28800
tctataacat acagaattaa gtatgatggc tggttctaaa gcaagttttt aaccatcatc    28860
```

```
ctcaaacttt attggcctaa aatggctcta aaactaaaac tacaaacaaa caaataaata    28920
cttattcttg gcaacaacta tgactcataa acaaacaaac aataagcttg tatgtaagtt    28980
ggagaaatac aaggaacaat gtggagagtc aggtcccact gatatttaca actgaagtta    29040
ggagttctga ctgtagaact atgtatgtgt cacacataaa tatgggtgta acagcatcag    29100
cggagtatgg taaacagaag actatctgga ctcttgatgc cataaacata gcaacttcaa    29160
aactcgctgt tgacagtgtg gccaaaatac ctcatctcat atcgtcatac agattctagg    29220
gaaaacatcc ccatgtatct tgaaacaaaa ggcagaagac cccaaggctc gcagttgttt    29280
cctataggtg ggttgtgggc actgctttgg gcaatgggaa actaagtgga aggaatgctg    29340
agggtctcaa atcacttaag ccagaattgc acaatagaca gtggcatggc aaaacgattt    29400
ttcatacagt gccagttatc cactatcttg cttctctttc tattttgatt tgtgatttgg    29460
gagaacttgg gacaacatat agtatacaga cttccattta ttctcttgcc ttataaattt    29520
ggttgggttt tcaacaaaac ttgaagtata tagtttactg ctcaactaag atctcatcct    29580
ggtgtgtgtg tgtgtgtgtg tgtgtgtgtg tgtgcatata taattcaaag gaataacatg    29640
ttaggaatct ttagatgact gtttaaatca aagtcattt ctagtttatt tgtctttcat    29700
ccattaaaaa tgttttagaa aaggagatct gcataatgcc agctggaatt ccagaagat    29760
cttggaaaca taacatctca cagtataaac ttgcaggccc tatgtcttgt ttgagatctg    29820
cgccatttca agtcacctgg atgtgcacat ttctgctaga ggcctgctta tcaagcacag    29880
aaactgaaac cctgcactac actctcaagt gtgcaaggga gtgaataccc actggaaaga    29940
gccctgattt acagggtggc ccatttaaaa tgttcccatt taataatgtg gctgtgcaca    30000
gggcctcttt taaatgggcc accctgcatg aagctttggt ccaagataaa aaatgtcctc    30060
cctcgagaat ttttaaaaac caaaacact gtaggtttag tggtttattt ttaaggtttg    30120
agatggtttc tttggactcc tttggaactg aaaaaagatg gatacacatt ttaaaaatga    30180
aatgttacaa ccacacatct gtaatgagaa ctggtgccag tggatatttt taaaagaaat    30240
taaaacggtc aattttttt tatttaggtt aggcaaacgg ctgctgcaca cacagctcac    30300
agtaactact tttcagcaaa ccttcacaag aaatttccta atgaagattt ataggatgtt    30360
ctgagattga taattaaagg ctcccccaaa agatatgaat gacagcatca gagatgtcag    30420
ggtgagggc ttgccctcta aaggagggc cagtgactta aaataaagat gcatggcagt    30480
tataacagac aaaataccga aaaacaggc ctagagcaaa gctttgctgt tggacttttc    30540
cctattcata ttaagggctc tgacaaataa ccccattgct ccacaatgca cacatgtaga    30600
taacccagt gctccacaat gcacacaggg gagaaatgaa ctcctgattt agaagggtat    30660
gcaatggaga gaaaggaaa aggcttctct taagaatatt ctgacaaaaa agatgattct    30720
caaaccctat gtctggctca ttcctcccat aaaccaatac tagcgatgac aaaaagtata    30780
aggatgatga agggtctttg tgctgacact tttcatagaa gcctaacgtt attgcatcat    30840
ttaatcccac tgcaatacta tggggtaagt actgagactc gattttacag atgggataag    30900
tgacacacta aaatattata tagtctatac aaggtataca catagaaaca aaaatacaca    30960
gagagagaca ctcagagaga gacagagaga gagagacaga gagacagaga gagagcacaa    31020
tataatgttt tctaaagaga gggccattaa gtgctgaagg catgaggtac ttgtattcaa    31080
aggtaaccac tagggaccag aaatattaaa cacagagtgt tgtctcttca aagaaagaaa    31140
tgtataacct gtttccttcc tagaaggcca ggaatggatg tggtcaatac cttggtgaca    31200
tctgtgctat tgtatggcca ggccacatct ggctccctca cacttgtgtg cttatctcat    31260
```

```
cctccagacc cttagcttga acacggtttc tcagtcaata taattcatct ttacagaaaa   31320
agtcacacgt actttacaaa gagttttgat gtaatcatgc cttaagcttt attatgcacc   31380
tgggattgag ttaattatca gcaggaacat ttctgcccaa cccccaaact atgctgtgct   31440
taaatacacc tgaaataaac tacctgaggt cagaatcttg aagtatggac caacactggc   31500
ttttgagtca cgttgaacca gattcctgta tacattgtgt ggatcattaa tctgctggtt   31560
gtgttgtttg tatagacacc ccacaattag gtcattctcc atctctaaat ggaacaagag   31620
cacaaaatcc tctgatggta cccactccaa gtacccattc gttaatatat tggactctta   31680
agtgatatat ccatgttttc ttaagagcca tagccagggt cttcctcaag cctaacgtgt   31740
tactgacaga ctccacatct gtggactcat aatattctag ctaaaatatt ctaagacaaa   31800
gaaaaagaaa aaagagcaaa actgaaactg aatgtgtaca gactttctaa atttcctggt   31860
cataaatccc aaaataatat taatgcagca tgatagtata ttaaatatta taaaatcgat   31920
agattatctc aagtatattg gagcatatgt gaagattata cgtatatgct atgctcattt   31980
tccctaaggg tcctaaatat ctgtagatta gggtaaccaa gggactcctc cagacaaccc   32040
cctatacata ccaagggaca aataagcaca ttcactcaac acacatgtat taagtaagca   32100
cttcttttgt atctttcact cttttaggca tttgtcaata agtagagtat gaaagagact   32160
aaaccgttat ctgaattatc tcatttttca ggatgtagga tgagtctaac ctaaagatat   32220
atatttactt atgccagcca gaaaataatg ggaatatgag aatgctagtt ctgctctccg   32280
aatatgatct aattgaattt atacacttag aaaaggacca aggagcaggc agaggagtag   32340
gtagaagtga ggccacaaag gagaacacgg tactggacag tcaagcaaga ggcccatatc   32400
atcaaacacc cctagaaatg aaagatggag aaaggtgaga gggaagagct aattggaggg   32460
agcaacacga cagggaaggg ggccacagaa acacagaaa gaaccagaaa ggatcatcac   32520
aaagtaggaa gctactgctg agtgtgcatc agggtgtctt actataattt atacttcaaa   32580
tactaaaatg ttcactacat ttccatgtgc ttattggcat tttgtgtgcc ttcctcccta   32640
aagtgttagt tcatgtcttt tgccaagctt ttattggttt acttaacttt tttttttaat   32700
ggggaagtag gggttgaag ctttatattt tatacttctg tgggcatgca cacacagaca   32760
cacacatata tatatataca caggcattgc aaacatctgt tactaagata tttctccatc   32820
acagaatcac cttggtacat ttgcagaaag gcgctgccta caaatatggg tcttttcctg   32880
gactctgttc ctaacactga tcgacctgtc catcctgctg ccagtcctgc actgtactga   32940
cccagtagca tttatttg taaatcttaa aaccagacac tctgaagctt gcaatttct   33000 cctttcctct cactgtgacc gtcccctgac ccctgtgtgt gtgtgtgtgt gtgtgtgtgt   33060
gtgtgtgtgt gtgtacatga gtgcatgttg tgttgtgcat gtgcacatgt ggaggtcaga   33120
ggacaacttg aagaattctc tggggacaga ccttggttta ccaggctctg ctgtccttca   33180
ctgagctatc cagttggttc tgcttttgtc cttcctttga aacttttggc tatgttttat   33240
tgaacagaga tgttaagtac cttttattaa cccaactgca gttttaattt tattatcaac   33300
aaatagaagt aaaattggaa gtaactgaca ataaatttaa gaagcatttt ctctcatcag   33360
tcacaggctc agagctttga tgttttctga aggtgttatc aatgatactg ttctaaagtt   33420
ctgacttata ggaagatagt aatttacatc cttcaaatta acataacctt tgtaccctgt   33480
gattgtgata tttttggtca ggtctaacac cttttaaagc attttcaat gtacaagatt   33540 cttaccattc tctatataca aaatatgatt gcaaataaca actgacttat tttccagagg   33600
```

-continued

```
gaatgcttcc tatcttactt cccttcttgc actgtgcgat agtttcagta taacaaagag   33660
aactggctct gtcttaacta tgtcctaagg aggctgacca tgttaactgc tttgagcaga   33720
ttttcattta taactcactg gtttaataca cacgttgact cccgctctct atgggtttct   33780
ctctagagcg cagggatggt gtgcactgtg tctgtaccac ctctgcattt tctgtagaaa   33840
tacgcatcac ctaaggtaat ttaagggcac ctcttacccc tctgaacttg aaagtgagtc   33900
cttactggag acatgcatta caggaagggg gaagtgtact tagaaatata tgtgtgagtg   33960
caaagaaaga gaggtagact gtgaagcagg agtcccaggt tagcatctca ctgctaaggc   34020
taccacaaca ctgcctaggt ttttccttct gagagaacat acatttcctt aaccataccc   34080
aaggatcctg ggctataaca cactgaaaac atggtttgag ttctcaggtg ctatgaccaa   34140
tatcttactc ttttgtacat acattaaaat aagtgacact tattccttaa tgttcttttct  34200 gattttagtg tgattcacaa agttacagta aatcaagaat atattttctc taattatatc   34260
tcttatgcag gactgagctt aacaatgtgt tcacaccca caaggtatct tagtcagggt    34320
ttctattccg gcacaaacat catgaccaag aagcagttgg ggaggaaagg gtttattcag   34380
cttacacttc catactgctg ttcatcacca aaggaagtca ggactggatc tcaagcaggt   34440
caggaagcag gagctgatgc agaggccatg gagggatgtt ccttactggc ttgcttcccc   34500
tggcttgctc agcctgctct cttatagaac ccaagaccac cagcccagag atggtcccac   34560
ccacaagggg ccttccccc ttgagcacta attgagaaaa tgccttacag ttggatctca    34620
tggaggcatt tcctcaactg aagcttcttt ctctgtgata actccagctg tgtcaagttg    34680
acacaaaact agccagtaca caaggtaacc acaatacttc atgcagacat gggtttctaa   34740
taacaattaa tctaaaaaca tgcatattaa tagtttacat gtcagttttg aagtgaaatt   34800
gctgtgtata agcacaaacc acaaacaggt atttaaagtt tagagggtcc cccgctccag   34860
agatccttga aattaagaaa cgatttacaa cttaactata agattaaatt aaaaaaaaaa   34920
aaacaagtca aacaatcact atataatgat caaaagaatc agagaaggta atacaaaaat   34980
ctcagaagat aaagtggttt tataatgatt atatcaaatt caactgtata gaaacatcaa   35040
atgctatttc ttaagcaccc agggtgatag aatttctttt tagtgtaatt tcacatgtgg   35100
aaaccagcag atgctattct catttcttta ttgtattttc ctcatcttct gccttgatta   35160
tacatttaga tgatagtaat gatatttcat gtggtaagac attaacccag catggtttga   35220
ctcacactgc tgtctattct gcagattcct ttctcagatg tgacaataaa agctcaggga   35280
agtgtgagtg actatgtcaa gataatttgc ccaagaagag caaaaatatc aacacaggtc   35340
tttctgccac tatttccaag gcacttttta ctaataggta actaacagta tttattaaat   35400
gagcaagcct gggttttctt gtaagaatca catgacttct aaataacaga ataaactttt   35460
tctgtggcat attaagtaaa aataaataat actaatgaca aaggctctaa acttcagaaa   35520
cagtctacga gtaagcactg atcagaatct tcatgctagg agcaaataca ttcaatccca   35580
ggttttaaga ttgccttcta tttctggggg tgtgggggga gagcaactgg gatgtaaagt   35640
gaataagata tatggatggg tggttggatg gatggataga tggatggatg aatggatgga   35700
tggatggaca gacagacaga cagacagaca ggaaaaatat tgttttctag caatagttgg   35760
aaggagagga gggggcagga aaggcactcc gatagagaca gtaattaggg actccagaac   35820
accacaggct atcactttga aggctggcac tcagaacaca aataagataa tgcatataat   35880
gcagtggggg tagaagccac tcctgctgac atcgggcaga actccattat atgtaccaat   35940
caaaaattag tggaatctga gaacctgacc ttggtgctaa gaaagaaaat aaaagtggtt   36000
```

```
tagtgagtac atgagtttga tcacatcatt tcaaaataca tccaaaatat agatcaaaaa   36060
catttagtcc ttactccaca gagtaaggta tctatggagg atgtagtcag gagtagataa   36120
agggtgcctt cttcaggcac cctccacttt attttaggaa aactggagcc tgccaagtct   36180
gctagactgc agggacacct ctgtctccac ctcagcaaca ttaggatttt aggtgggaga   36240
cccagctctg catttacatg ggtgctgatg atcaaacaca aatgctcaag ttttggcagt   36300
gagtacttta ctaactgtgg tggttagaat aagaatgacc tgatacactc atatatttca   36360
atggctaata tcaggaagtg acactaaaga agatgacagg ctgaggaggt gtggccttct   36420
tggagtaggt gtagagttgt tggagaaagt atgacactgg agtggccttt ggggtttcaa   36480
aagtggaggc ctggcccagt cttagtttct ctctctgctg tctgtgaatc acaatgtaga   36540
actcccagat agttctccag caccatgtct acctattaat tgaatcactt ccctagcctt   36600
ggattctttc tttgaacctt ctctgtaaat gagatgcagc agctaataca ggactcagta   36660
gtaaaacaca ggaacgcttc tactgagtg aggaacaaga cacagctacc tgctaattaa   36720
gaatcttacc agcagtgtaa acagaaattc tcattatagg aggtgccaag gatggaaaac   36780
atgtcaggaa aaaaaaaaa aaactgtcca catgtgtata ggataaactt ttcacccttg   36840
atgattgcat caagtatcac aagtagtgtt taagaacata ggaaggaggg cacatacaag   36900
aataaccaaa aattataact ttcatattta tcaccactaa taataacaag ttccataaga   36960
aaatacaaaa atttacaaca gaaactaaga aatatgcaac ctgtataaga agaaacttcc   37020
ctgatatata catgctctaa aaaatatcag aaatggaaaa ccatactagc ccatgtacaa   37080
agatgaggta aatttttggt tgtagcaaaa gcatcagccc cgtttcccaa ttcagaaatt   37140
caagacactc aacataaatt aggaaattta tctggaagat gaaatatagt aaactggcta   37200
aaataaatga gtatatagtc ttctataatg gtatgagagt gaaccactat ctactctagc   37260
ctttggacag acactctggg aatgccacta cagcactgag ctctatgagg cacactggca   37320
cttataactg atgtgtaagg cattgatttc atggctgctg cacccattag gcattccac    37380 tttgtatcat cttgcttgat ttacttaggt gatccaggta catttaatat ttcaaaaatg   37440
gaccagggca cagcaacata accatttctc taaaagtcca actttgcctt tctgtttatc   37500
tgtatatatg tccatgtact gcttgtgtgt caggtgtcca tggaaggcag agaagggtat   37560
aggagccctg gaaactagag ttacaggcag ttagctctca tgggaaaaac tcaggtcttc   37620
tggaaaaaca gccaatactc ttacacccat ttctgtattc atacaaattt acttttttata  37680 aaaaggggtg tgtgtgtgtg tgtgtgtgtg tgtgtgtgtg tgtgtgtgtg tagggggtgag   37740 tatatacgca agacaggtgc ccattggggc cagaagagag tatcagaacc cctggggctg   37800
gagatagatg tctgtgggcc atctgacaat ggtgctggga cccaaaccta ggtcctctag   37860
aagagaacta attactgtta aaagctgagc tattctctac ttccatttat tagacagcat   37920
tctatgtaca ggtgatggag agctcacata ttatatagca ttcataacca aagcagtttt   37980
agattatatg cacttaaaat aatcaggaag tttacattct tggaaatgct aagattatac   38040
aaagatcaat atacataaac tacactgtta cacatgggag tgaagcaagc aaatgcctaa   38100
gtcagacctc aaggcttgta gcttcatgaa acaataaggt ttttaacaa tgaggttttt    38160 aaaaacagat gaaattatgt gtggatgcag tcaactatac tcatgcatgc atgtggagga   38220
cagaggatat tctcagattt tgttcattgg attgctatcc tttctttgac tgagggtctc   38280
tcattggcct ggaactggtc aagcaggcta agtaggctaa ggcaggcaag taagctagtt   38340
```

```
aggaagcccc cggaagctct ctcttgcttc cccagtgcta ccatataagc ttactccatc    38400 atttttaaaaa tgggttctag agagcaaact cggggctttt aatgattctg cgatctgtcc    38460
agccttcaac atgaaacact tctggtggca tctgggacac caccttctac tggatttcct    38520
ttatctccat ggcagcaaca tctcacattc tgtggttgtt tccttcattt ctggaaataa    38580
cacactcaaa gtgattcagg gctcagacta actttgttat acaaatacac acctctatgg    38640
atgagtggtc tccctagctt ctaccacatg tccctgaagc aggacagact ttcttatcca    38700
attgctaagt tagcataaca aaaagaatgc atgcaaatct caaacccaaa tttcctcttc    38760
tgaattttag ttattagcac atctttttgg cacgattata ctatatggat atcaaatatt    38820
actggcacga tcattcatcc aattctccag aattaaggcc tcagaattat ctctaaattc    38880
tttattttgc ttgtgttcta tatttgatcc atcagtaaat attcaactac cttgaaaagg    38940
tccccagaac tgatgagctg ggggcatagc tcactaaaaa acttcttgcc taacatatat    39000
aaggttctgg gttctagtgt tagctctgcc ctcctaaaaa attattataa ttctggaatt    39060
gctcagaaac acctcaagct actaatgccc taatccaaaa gaccatcacc tctgataaga    39120
actaccatgc cacgccatat ctcctatcct cctacatgca tctacagtaa ctctgtcctt    39180 gtgagttttcc tcgcctatat tctccaataa ggaaaacata taattcagtc aggtatggta    39240
atacacactt gtattcccca acagtcagga ggcaaagagg agatccatga gctccttgcc    39300
agcctgcact acacagtgag accctgtcaa tccatgaaaa ttgtatacat ttaaataaaa    39360
ccatgatttc tatggccagc ttgtgtcttc atctacagta gtccttaaac tatcaacttc    39420
cctgccgttc tgaaaacaca ctaaacactc ccatctagac agttttttata cttcctatgg    39480 agtataaaaa gtagatggaa attgctcttt ccctagagat tgcataattt catccaaatt    39540
tccattccca ttgtcccttc agaatggcct cttttttggtc atcacattga aaacactagt    39600
ttctatattt ttttccttgt acctttttatt cctaggtaag atggcaggtg cacacgtcaa    39660
tgcccaggga agcctcacaa gtgcagacac ttcattctgc tgaccaaact tgtgaagaga    39720
acaccgcaga cggtgccaca ctgatgtatt ccaacaatga aaataatcc aataaggagt    39780 ttgaatgagt aagtctttaa aggaagagat gagtaacaac aataaaaaaa tcattcgctt    39840
acaaagtgtc taatgttcat gaattagctc caatcaccct gtaagaagta cttgaatata    39900
tacccatgta aaacccctttt acatattctg catagactta gttttttgctg acaggatatg    39960 gaaaaaatct ttcacataat ttaaaagtca agaaagtatg atttttatct tcatattata    40020
ggcatcttag aataacaatt ttactccaac aagacagtaa gggaagagaa gagatataaa    40080
ggttatctat cccagttgtc ttacggtatt tccttgcttt tctaagttgg atcctatctt    40140
ttaagtgttc tctcacatga agtataagc ataaaatata atcaaagctt tttaaggtaa    40200
gaggtaaagg gaattgttag ttacaattac tagaatggtc atatcaaggt cttagtaaca    40260
gctgtcaatc aaattctttt atgcagtcat gctgcctctc acccaaacag aaaggattgt    40320
gagactattt aaaatagaag atcttgtctg aggaggcagt ttctttgcaa ttcacaacta    40380
attaaaacaa agaaaagcct tcggaagaat atgttgtttt atctgtatca aaatataggt    40440
catttcatat ctggctcatc cattcactca tccaaatttt atttactact ggggtcatcc    40500
ttatttgtaa cttcctagta ttttttataag tcctggggat tcaatcctag cactgcaaaa    40560
tatatatgca ctaagtattc acattccaaa gattgtaaaa cttttagaaa caaaatacct    40620
agattataat gcttagtgaa tgttactttta aaaataaaat aactacaaat ggactggta    40680 ggccataccct ttaagcctag cactcagaag gcagagacag gaagatctct atggattcaa    40740
```

```
ggccagctga tctaagatgc cagttccagg ctagtaatgg tacatagaaa gtcactctta    40800
aaacaaacaa acaatcctga aaggaaagaa gagaagaaga cttgaaggaa tgtttggtaa    40860
cttggggagc cagagagacg actcagaggt taatatcact ttcagtgctc tcgcagagga    40920
tccaagctca gtaccaagca cccacactgg atggtgcaga ggctcccttta actctcgttc   40980 cgggagatcc aacacactct tctgccctcc ttgattacct gcactgctat ggataatata    41040
tttttaaaga gagatagcat gcctgaatcc ctggtttacg gactgtcacg tttcctatgg    41100
aaacggtagt gtttgagcta gatttggaga atagaagaca agacatttca aaatacaaat    41160
cagtgagtct gaaaaggaaa gtacaccaaa actaaaacaa acagaaacta aaaaagaga    41220 accttactgg gaatatcaga atgtatgact aaggtggttc ctcccaaatt ctagacatat    41280
ataaaacggc aaagttttct cataaagata gaaaactgtt ttaccttatt aacaattaat    41340
tgagatgttt taaaaatgaa ccacaggaaa ggggttaaga agagtgatat tttaggtcac    41400
agtgctcagg gaagaagcct gaggactaca gcaatggctg tatggtggct gttaggaacc    41460
attcctaatg aacactacac ataactgagc atcctgtcca tgaagtacgt aaatgcccag    41520
ttctaaaata cacactttac agcaaatgat ttatctgaca ttcaaatgaa caaggataaa    41580
agaagacata tgttgaactt cacaaattaa tgtttatatg tgatattata aatatttca    41640 aatatacagt atacaattaa gaaaaaaatc tatcgatgat tagattttaa aatacattgc    41700
tttaaaagta atgcttttaa atgcttatgc aaggtattgg taattcatcc ttatgactat    41760
ataattcaga gaattatcaa cacttataat gtaagagatc ccaggacaaa tgctcctaag    41820
acacacaaag gtttaaaaat atagtccaca ctatttgcat acataacttg ttttcctcat    41880
tgtctaagac tagcagaacc aaggaaaccc acatcctaag ccacagaaca gagacacctg    41940
gttttgttct tatcacagga tgacaaatgc tttcaatacc ctaatagcag acagacatcc    42000
tcaacatttg tatagtgttc tttaactaac aaaacggtgt gtccttcctg agttctagaa    42060
tggtgaaagg ctcaatgcaa acacttctta gaataccttt gtcagtccat ttaaagagac    42120
agggccaaga gcatgggctt cacagcattc tgtttctttt gttgctctaa tgcttacatg    42180
gttgagtgtg acttcaaaaa ggttctataa ctcatcgtgg tggtgcacga ttgaaatccc    42240
agcacaacag gcaggggaag gatgagatca caagagaatc tacaagttca tgaccaccct    42300
gggctacaca gccagatagt ccctgaaaac cagaccaaag agggggactga aaagaaacca   42360 gaaaaaaaaa tagtatctct gggtttatac ttataaatat atctacatgt cgatatctgc    42420
tttggtagga aaatagtaat gattttcatc agtacaacaa agaaaagatt ttaatactct    42480
attcatgtta taggaattaa aaacatgagg aaacacatat ttaaaaggc ttgtctttcc     42540 gtgtgtgtgt gtgtgtgtgt gtgtgtgtgt gtgtgtgtgt aattagaatg atgaaaagag    42600
ctattacttt tctttatttt tgaccagtat aattttataa caatttctaa agacactact    42660
ttatagtgtt ttgtaattta gcttttaaa ataaattcta aaattaatgg cattattatc     42720
atggttccag tgaaaaataa tgctgattta ggtaatctag ttaaaatgtt ttttaaaaac    42780
tatttcaaga atgtaacagc cttcaacgta tttgctttaa aagcacaagg gcctgagttt    42840
cctgagtaga gtggtctgta cttgtactag tagtgctagg gaggcaacga tgggcagatc    42900
cggggctgct tatttggcca cttggtctaa ccaggcctac ttgcctagct ctaagccaat    42960
gggaaatact atctcaaaaa caaggtggac agctgctgag gaaaacacct ccggtttgtt    43020
tgctctggct ttcacacata tgtaacagac acacatagag accacacaaa cacagataca    43080
```

```
cattttcata tacaaacaaa caagaatttg gaaaatgcca ctcataactg atctctgtag    43140
atttgatcac aaaagtgcaa ataacttaaa gaagtgaaat gtagcagggc atggtggcgc    43200
actcgggagg tagaggcagg cggatttctg agttcgaggc cagcctggtc tacaaagtga    43260
gtttcaggac agccagggct acacagagaa atcttgtctc aaaaaaccaa aaaaaaaaaa    43320
aaaaagtaaa atgaattccc atgccatcca actatcaggc aaaagtagct tttcaaatga    43380
aaagtattgt taggaggctg atgtcctttc ttttcaccat ccagatgaca actccatcct    43440
aatcttccta ttcattgcac tgtaaagact tcaatgatat cataatgctt ggaaagacat    43500
gccaacaatg cacaatcaat tttgaaatgc tcagttactc tacaaggctg tcacttaaaa    43560
cagatttcca aaactctaat tactatttta cataggagat accaactcct ggttttcttt    43620
agtctctctc accccagtg caaattaaaa gcccctacct aggcagggcg gtggtggcgc    43680
acgcctttaa tcccagcact cgggaggcag aggcaggtgg atttctaagt tcgaggccag    43740
cctggtctac aaagagagtt ccaggtcagc cagggctaca cagagaaact ctgtctcgaa    43800
aaacaaaaca aaacaaaaca tccctaccta aagcacaggg agaacctgag cccccacaa    43860
gagactacaa ctcaattgtt cttgaaatga acagccaatg ttgaaaatct ttactctgta    43920
tcacaatcag catcctaaaa tgtgtatttc taaaattact caaagctatc tattacaact    43980
gctttgcaac tcaaagccct aatgaagtca tcttttccta actttaatct atacagaact    44040
ctgctgcctc tacaatttga cttgacaaag tatagtgtct ctgggaagca ttggctctgt    44100
ctgtctataa aactgaccct tgggaccag aataagaaat gctagtttgc agccacttta    44160
taaacctcag cttgaccaca gatacctcag aagacatggc aactatgcag aataataccc    44220
atctagagat cacatcttca gaatcttgtt atgggaagga tgagaggaca cctatcacct    44280
aatattagta catgtagtag cctacagggg cttccttgtt cagcttagtg ctatggtaca    44340
gaaatggcat ccagaaatat ttctattacc caccacagta actcccttgt aattcattat    44400
tatgaaagca cagaaccaag ggtcatatcc taatgtgaac atgtgccaca atacacaagc    44460
ttgcttatct atggagataa tgagaaaatg acatcagaca ccttacttca aattactctg    44520
cagaagatag tccttgctag ttattcaatt ttgctcatga aggaagtaca aaggaaggag    44580
ggtaaatata ctcaaactaa aaggtcagaa ataaacccct tattgtgact gtttatccaa    44640
cactacttgg tgtattccaa attccatagg gaaatgtgtc aaaataaagg tggagtcctg    44700
ccctttctctg tgggaagcca catgtgccgt tgcagagtgg cactgactac tgctggccac    44760
cacgcataag tttggacaaa caaccaatgt gtacatatgc agtaaagttt tttgcaaaga    44820
cactgcctgg cccgggcatg ataatgaggt tctgtaaggt actgagagta taaccaatca    44880
gatgtgagac atgcaaatga ggtatgataa tgaggttctg taaggtactg agagagta    44940
accaatcaga tgtgagacat gcaaatgagg tataataatg aggctctgtg aggtacagag    45000
agagagagta gccaatcaga tgaggaacat gcaaatgagg cgtagtgcat aaccaatccg    45060
ggtataagac acgcctctcc taggcctata aaagcagcac cagttctggg ctcagggtct    45120
tttcgcctct acaatcaagc tctcccaata aacgtgtgca gaaggatcct gttgcagcgt    45180
cgttcttcct ggccagtcga gcgcgcgcaa gacttctcca ccttcacaca ttctcagtcc    45240
tactgaagag tcaagttgct tcatactgca gtcacattta caagggacca ggcccttacc    45300
acgcaaggac agagtgctat accactgaca agatttgatc aagctgcact gaacagcagc    45360
aggaagatca tttcccttatg gtgttatggc aacaatgaga gagccaaaac tgagtccacc    45420
actccaggaa taagagatga taactggaca catctgtaag cacctgttca ggcaatgtct    45480
```

```
caccaagtca cagttctaaa ctatttcact cctccaaagt cagcagtgct aggcctgagg   45540
cacagatgga aaacatcacc tcaggaaagg agctattgac atgtaggctg tggtctgaac   45600
ttgtgatgct atcatagcct caaccaacat ttaaacaaaa agctttctgc aaggctggga   45660
tcacgaatat cagccagagc catgcagttt gggttgtaac tcaaaattta tctacatagt   45720
ttataatcag ggagagtttt tctctctctt tttctaaaat ttgtggggtg tgtgtgtgtg   45780
agagagagag agacagagac agagagagac acagagacag acagacagac agacagactt   45840
gttttggatc ctcagagcta gttaaaggca gttgtgagat gcccagtgtg gagcctaaga   45900
accaaactca gatgctctgg atgaacagga agcagtcttt acagctgaac cacacctcca   45960
gccctgagat cccatctctt atagaggcta aaatgtatag tttctacatg gcttggtcat   46020
aaatttaaag ctttagggct agggatgagg ctcatctatt aagatttgcc ctaggtcact   46080
agcagtgaac acaccaaatg tgcagacatg cctgagatgc tagcacttga gtgttggagg   46140
caagaggatc agaagctcaa aatcagtttc tgtttcagaa ggagctcaag acaaacctgg   46200
gatatatcag accttgccac aaataataga agaaaaatgg ctggggatgc agttcactaa   46260
ggtgtgtgcc aatgtgaatg gaaccctgag ttcaattcct agttcccat aaaactgaac   46320 atgataatat aaggcctgta atccttcaat gccatcattg gctatatagt aagttcaggg   46380
aaagtatggg ctatataaac gcttgtctca aagataaata aatgaaaaat gtttataact   46440
ttgaaacact ttcttttctg tgaacactga ggcccagata tagttagcat ctcattgctt   46500
tttctttgtt gttgttggtt ggtgtcttag ttagggtttt actgctgtga acagacacca   46560
tgaccaaggc aagtcttata aaaacaacat ttaattgggg ctggcttaca ggttcagagg   46620
ttcagtccat tatcatcaag gtgggagcat ggcagcatcc aggcaggcat ggcgcaggag   46680
gagcggagag ttctacattt tcatccaaag gctgctagtg aaagactgac ttccaagcaa   46740
ctagggtgag gatcttatgc ccacacccac agtgacacac ccattccaac caggtcacac   46800
ctattcgaac aaggccacac ctccaaatgg tgccactccc tggcccaaga atatacaaac   46860
cgtcacagtt ggccttgata tcaaattatt ttaattgtat aagtcaaata ttagcacatt   46920
tcaatttgat cattagagaa cactatcaga aaggcaaaaa tcaggccatc ttttctcttg   46980
aaagtagatt gagatggtgc tattacatct gcccatccag aaggtggggt caaggtcaac   47040
aatctcaaac accaaacaag tctgggtctg aaataatcaa ttatggcata gttatctgag   47100
aaggaaaaca gaactttaat atactgtcta gaaagaagat ccaaaggtgg ccataaatca   47160
aggtatacta ataacatatt aatccagtga ctaaagccaa ggtcatttat aataacacta   47220
gtatgtttca attaagcagt catttgggag gctgaagtat gactcattta tagtcttatc   47280
aattaaacta caaataact agaacagagt ttacactaaa agttactaat aagaagcaag   47340
actccaaagg cagcaattac aagtttctga atattcaag gagagctacc aagtgatcta   47400
cggcaaacac tgggagagca gaacaacagt acagctttgg ggttaaaaag aaaatgtgtc   47460
aaatgtatga acgagtgatt tcttgggagc agtctaaaat tagatgatca aaaatataag   47520
cactatggct caagtgtgga gatacaaaga ttttccatga aaacgagcaa gtataacaca   47580
tatagattct gcaagcgaag caaaacctga aactgaaaat attgttttag ctggtaaaaa   47640
catttttata tgtaagtgaa ttatggtgtt tcctaactgc ctgaagtgct tagtgaattg   47700 acattttaa aagtctgtac aatttgtatg cttcaatggg aaagatagag taagaaatta   47760
aagtgtaaag gcagagaagc gatggacaca ggacaagcac tgggaagcaa actgtgccca   47820
```

```
gaggactggc tctgcagtct gaacccacat ccccaagccc agctcaagat ctccataggc    47880
agtcccccaa gaaagccatc aacaagccca ggagcttccc cacctctgta gtaggtaccg    47940
acaatctcat aagttgcagt gcccaggaaa aggcaattcc agggacttgg taggacactg    48000
acgctcagac ctcaggaaaa cagtagctcc aagtcacaaa agctacaaat gctcagtgga    48060
gagaactggg agatggctca gtcagtaaac gcaggaggac caggatttac ttccccatca    48120
tctaggccac aaaggcaggc atggtagtgc ctgtctgtca tcctgagaag gggaggtaga    48180
gacaatcaga tccttggaac cccacagttg gccagccagc ctacctaagt cggtgagttc    48240
taggttcaga taaagaaact ggactcagaa catgcaaaga gaatcacaca ggaacccaat    48300
cctaaacaaa gaacttcagg aaactaagga aagctgagag atagaagaga tagaaagggt    48360
tttctccaga aaaaagtcc ctgggggtg gggtagagag agacaatttc aactgaaact     48420
ggggaacctg aggaaagaaa gcatgttgca gttctaggga cttatcactt tgaccaagaa    48480
aaaaataaaa gcccttccat caaattctaa ctatttcttt tagcctaaat tccactaaat    48540
acacgtgcct agctcttagg caagagtagg aagataaccc tactgatcct cgggctttct    48600
ttccccaggt tcaatgttga tttcagttga aattgtctca gatgcaaatg tgtgcctatt    48660
gataataggg ttggtattga agttgacctc ttaaaacaaa ttgtagcgtt accttatcac    48720
ttcattcatt catttattca ttcattcatg agacatgttt gtaatgtctc gctgtacttg    48780
tgcacatagc atacttgtaa cataccatgt tcaggatctt tacaagaaac aagaaagatg    48840
ataaaatgac ctgtccgtgt gaactcctcc ttcgtggcgc ccacacaaag tctaaggaga    48900
cactgcctcc tccttcagat cccacgagtg gtgatcagag ggtacagaca gtcatgattg    48960
cttgtgaaat accctccacc aggctcatgg ttgtaatcat agtcctcagc ttgtagccat    49020
tctgtttaag gagggagagg gttatggaac atttagaaaa tggagcctat ctgtaataag    49080
caaacatgga aggctgaggg taggaagcaa cgtcttacag ccctgtgttg ccatgttgcc    49140
tgttttcttc ctgcctctag atccatctag attgtgagca aaaccttcca ttcctgctcc    49200
cacagcgaaa ggcataccag gacctccagc atgccttcct taccaaaagc aactggaccc    49260
tcaaactcct ggccaacata attccttcat ccctcctact gcttcatggt aagaattagt    49320
cactggaggg gagaaacagc taacacagag agcctactgg gcagcacagt agactacaaa    49380
tggcttttat tcaggatcta gctggatggg aaacctcaaa aactcaactc catccacaat    49440
ctcaggtgat tgttgttgtt agacaaagaa aacagaatct actagagtta gttgtcttta    49500
gcattaaaga tccatacaac tacacaacat atatttagag acattttcct aagagtaaca    49560
tgtcagtatt tgtaatttgg catctgtggc aatcttagat atcctataac aagagtggtc    49620
tggagagaca actcagaagt taagaacact ggctgttctt caagctggaa atcatgtggg    49680
tttgattccc agcacccaca tgataattac aacagtctgt aactcaagct cttgggatc     49740
tagctacatc tgtgccctct cccggcttct attatcagcg cttatcaagt gcccatttgg    49800
tatcttgtta cttctgtgct gtgaggagct ctggacaagt tcggatttcg tagagtttat    49860
taaatttttc tttaattcat ttaattgaga gatgatgaac tcatggtcac cagactactg    49920
aatttgattt tattttcctg taatgcccca aatctggcaa ctcttccaga agactacact    49980
acttctgcca tttcctcttt tcttctttcc ctgctgtgcc cctccctga tgaaatctaa      50040
agatgtatta tcttttatag ctaaagcaca catttactg aataaaccca actctgctct      50100
atccaataaa taagaaaata gaatctgaga cttggtattc tcacctattt aagccttttt    50160
aaaaaaataa agtaatttaa tattacttaa caatgatcct acaactccct taatgtccat    50220
```

```
ctggcctacc ccttccccag gaactccaga gctgctactt ccattaacac tagaatgatg   50280
gtataacttg tttaaatttt ctgttcaaaa tagatactgt acaaaatagt atgagttcaa   50340
tattgataaa aagtaatttt aagattcaga catccttgaa atcataagca agattttcct   50400
tccttagtac tgcacaagga agtgggagct gccttctaca catcatggca gctttctgac   50460
atcttgtgag ctctaagatg cttcatctgg taccagtcat cttgatatca atatatcaaa   50520
attaagtata aatgtaagaa atccagtagt acctgaagat tgtagagaaa attcaaggtc   50580
agatttaata cacaagggcc tagtaagcca aatcatacat cttacaatgc taagagtgct   50640
ctgtgacgga aagaccagcc caaataacca ccagagccac caatctccat gtggacctga   50700
aaaccaatag agctggtaag cctgatgacc tgggtttaat gtttaaacct aaagacgttc   50760
cctgaccgcc atccacatgt ggtgaaaaca caaacataca catacatgta cacgtacaca   50820
cactatacga acacacacag aaataataat gaatttaaaa acataagaaa atcaatagat   50880
gattcataag catattttat atttaaatac aatcataaga actgaaaaaa atagggatct   50940
tctgtccaca caaggctcta ttaatgttga gtattagaca tatactagct attgctgtct   51000
ggatttctga atatttgta cctatatttg actcacacat gagctctaac atgaggaaga   51060
cagcaacaag tcttcattac actcagggct gtgtcactaa gtattaatgg tggcagtgca   51120
ggcgatgacg ctgatgtacc ctgaaacgga taacttattt aatgctgtaa attgtgtgtc   51180
atttcacgtc ttcagttttg tttgctcaga attacacaca aacaagacat aaatacactt   51240
aagaaaaaag ttgctggaaa taaggtagt accaacactg ggcaaatgta acaaatatg   51300 gtaagcacac ctacacagaa tcagtacagg ctattttat cccaaaaccc caaaaccacc   51360
atggcatttt tatggcttat gactgaagag aacctttcaa accaaaatgt ccccaatttg   51420
aacagtaagt cacttcagga ttgataaaat ataatataat ataataccaa tatgttagca   51480
ccatcaaact tagaaacctc aatgaactat cccttcctgg ttatgaattt ataaaaatgt   51540
cacttttgtt aaaagatggg attccagtga agtacagtat ttatatgtat tttttctca   51600 catgtactag ttgggatatc attcctatat cacctctgta tgctttatac tgacggtgag   51660
tcagatcatg aaattcctca agctagggat tataattttt tatgattaaa tatgaaccaa   51720
atatagtccc aaaagcaaca aaaaaagtaa agataaatcc caacaacagg acacacaaat   51780
agaacttgag aaaccaaatt ctcaattttt caacagataa aagacgtgat caaaattcag   51840
cagggaagct ccacctggga atccatgaag aacacattga atataagaa cagggactcc   51900 aagtaccggg gacgagactt acaagacttg taaagaaccg aaggccatct cctaatgcca   51960
cagagtgagg aatggtgggt aaatttctgg tagacttctt agaaaaggtt taatatctgt   52020
ttaccaaaat aggaatgttc ttaattctta cttcttcaca cgtatttaaa tttgtggcta   52080
ctacagaaaa tactatgtct atataaactt aaatagaaca acttttttaag tacaaactta   52140 gctctaaagc aacgtttgct aaaccattaa gttttcaaat taatgtaata ctcatttatt   52200
ggtaaatgtg aatactagtg aactggtaac aggccttata gacatcgcta cctgcttttc   52260
aacatattac tgtagaactg tctacctgta cgtgtggaat ttcaattagc agagtctgtg   52320
gaacactaga gctgactcgg atctaccaaa aaacagtcaa ggttctgtgg agagctacta   52380
tcactgatat ccctcacatc tagtaatata aaggtttcat tctaatagtt ctaaacctat   52440
gcctgtaagc cacagcttct caatgagggc ttggaatagg agcgctaggt caatgtaaag   52500
tcacagagag ctacctatgt acctagaaag aggccaaaag tctcctctca gagagggcat   52560
```

| | |
|---|---|
| cacagatggc atctgatgac caatcataca gagcagcact gaccacaaag cattattact | 52620 |
| atttctttct ctacccactc cgcaaccctc tgtattttt tcaattgtgc acaatgccac | 52680 |
| aaagttatta aaacatggta catttcttgc aaatcatagt aagtacctat gttgggaatc | 52740 |
| taacctaata attcttagat tcagtgatat atggagccta cctggtctat tgttctaggt | 52800 |
| ccttttagca gtgactagac attctttgaa atcttcattt atttctcctc atatgcttca | 52860 |
| tcttaaaaca tcactttttt gtcaacattt tacccagaa gccaacctaa gctatatacc | 52920 |
| aacatagaac ttcctgccat aagtttagaa tctaataaaa gtttattgta catgtgttca | 52980 |
| tatctctgag tgtgcaaata tgaattttca ctgttagatt gcacttccaa acaagagggg | 53040 |
| ttgttcctta ctgtcttaag aggtttattg ctatgaagag acaccatgac caaggcaact | 53100 |
| cttataaagg aagacattta actgaggctg gctgacaatt cagacgttga gtccattatc | 53160 |
| atgtggtgga aagcatggca gtgtgaaggc agatatggtg ctagaaactg agtacatcta | 53220 |
| catcttgatc tgcaggcagc aaggagagta gcttgattgt atcaaaccct gcctccattg | 53280 |
| tgacacacat ccgctaaggt cacacctatt ccagtaaggc cataccttct aatagtacca | 53340 |
| ctccttttat aagcattcaa acaacatgag tctatggggg gcattcctat tcacaccact | 53400 |
| acagttacca accttgtctc tgcaacctca tacacaagct ctttaaataa actaaaaaaa | 53460 |
| ttgttgaaga caacagtacc acactttgaa gctgatgtaa tagaaaaaat ggttgtttgg | 53520 |
| ggcaagttac ttataacaga tctcaaactc atatgtgact atattcagaa ttccataaaa | 53580 |
| gtaaggcatc ttccctgaca agaggtaggt agttctagga tttaaaactt ctctttacag | 53640 |
| atatcatttc atattacaga ttatatcaag cataacatga ctagtagatt cctttaggat | 53700 |
| taaatgaggc attggggtga cgatcttacc aacttgttcc taatgagtat tcccaactag | 53760 |
| tatctcctga taacttgatc agactaccac aagggttcag gattgatggc tacagttggc | 53820 |
| ttcatctacc cgaaactgct ttagaaagtg actatataat tgtatgctta caggtacagt | 53880 |
| acaatgatag ctatgttcct gaaggcccgg tggggctgg gaataaatct cctttgtgat | 53940 |
| tttcttgaat ataacaccag gttaccttt aaccttcgtt cctttttat actataaggc | 54000 |
| agttttatgc actgacgtca cttgagctca tgccatcaag aggacggtgt gacagggggt | 54060 |
| gacagggttg agtacagctc tgctcagcat tgtggttcgt gaaggagtaa tcactacttc | 54120 |
| tacctctaca gtgagcttat gaacaaacag cacattttct tgtttgttta cagtactttt | 54180 |
| atactcaaaa caagaagtat caagttttc agacagacag gattaagtac agtgaagctg | 54240 |
| aagaaaacta gatgtagaag ggaccaacaa gagctgtcag ggaagtgatc tcagaagaga | 54300 |
| tgtaacagtt gacaattgag taagagcatg aaaatactgg gtaggatagg ttggggagag | 54360 |
| aatcccagct ttgtctctgg tccagctctc ttcacatggt agtggcctct gcctcaatgc | 54420 |
| tgacatctga taccattttt ataggtaatg tgaacacaag tcactacaat cattgttctg | 54480 |
| atatctgggg ggaacaaatg ctttaagcta gttcgatcac tgccattttc ttggaacttt | 54540 |
| ccccccatat tgttttaaga ggagtcttac tatccaggct caggtaacca acccttccta | 54600 |
| ggctaggcct ctggggaggc ttaaactata ggccaatgcc accatatcca acaggaaaag | 54660 |
| cttttataaa aataaacaag agatcatttg tcttgtttac caataaaact gtattatgca | 54720 |
| aaataaattt tggtctttaa aagtagtggg aaaatgtgga ccttcatctg tgagctttgt | 54780 |
| ggagggagca gaacatctca gaaaggaagg tccgggttgc catggcattt tcattccagtt | 54840 |
| attgtgatgt cctatcagtt aaaggaatag tagcttgggg cctctggcag cttttcctgg | 54900 |
| accccattct acaatatttc ttcatttgta cctcgaaccc tacaaaacct aagaagtgag | 54960 |

```
aggaaaagag aaaccaaggt actaactttc ctgaatactg actctgaggc cattggaata    55020
agaaaagtac aactcccact ggtcctgaaa ctctgttctt ttgcagctgt gaagtggcta    55080
aaagcagtta acaaactcct tggcagcctt ggactcgcat tacctttttga ggccactctg   55140 aacaagctag cctccctcac cttctttggg aggaattctg ggcaattgta aggttttggc    55200
ttgacagagg catctaaaga taacagtcag ctaaaaggca agagtctcca ttggcatact    55260
ggttcttgcc tctgaaatgt aggtggtgtg cacacaacag cagcaagcca ccggaggact    55320
agaaagcatc agagggtaag acacttctct tgactactgg cttaccaaag cagtcttacc    55380
atgataaagc aacagtggaa atgatgagga gaaagactca ggcagtgaca caagggcaga    55440
agcaacacag cacatgaagg gaggcaaaca ttcctgttca gtactggaga agaggggaa     55500 ggagactaaa cggcaagcgc agcccacagg ccggggccaga gagggtgcaa acagactgtg   55560
tagatgcttc cccagtgaag ggctgccaag aattgtgcat gatgccccca cagcacagac    55620
aagacagcag gtaaaaaaga gggaacgggt gcaaatcaaa gaccaccagg agcgcatgct    55680
tcgagggagg gaactcacag agcaaagact caaagaacaa ctcatgcaga aagaccagag    55740
ccagctccct tcacttgaga agctccatcg agtgaagaaa gagatgaagg actgtgaaag    55800
ggccaatgca cacccacttc tgcagctacg cactaaaagt ctcattaagt tggagagtct    55860
tttggagaag tctcaggcag gagatgaagg gaaaacagct gtaaagccca atcaaaagaa    55920
atgcttggcc ctgccaccat tttttgagaag tcatgtacga aaaatcaaag atcagtaaaa   55980
ttttgttgcc ttttgtggaa aaaaaattac taggaattaa ataaaaaact tcttagaagc    56040
actgtgtcat ttggcaagat tgttcagcaa ttctgacacc ctaccttgct tctgaaagag    56100
ctagaaggga cagagatagc tcagtggtta agcacgtgct gctcttgcag aggacccagg    56160
ttcagttccc agcatgacca gcacccatgc agtagctcac aaccgtctgt aacactagtt    56220
ctaagggaac tgatctcctc ttctggactc cacaggcacc aaatatgcta gcacaaagat    56280
atgcatacag gcaaaacact ggttatacac ataaaatcct ttttaaaaag tttgaaatga    56340
acattattct ccatattctg ctttttctttt gagttttttt tttttaaaaa aaacaaagca   56400
caaaacatcc taaaaagtct cctaaacttg ggaattatgt attgcacatt catagaacaa    56460
caaaaccaaa acattcaagg aaaaaagtgt aagtgtgtaa ggggattcag gaaaggggat    56520
acaattaaac taaaaattcc aaatgcacaa aacactttaa gaacaaagaa aagaccagta    56580
attttcataa acgacatact ggcatgaaat actcagaagc ttaagttaga aacaattgct    56640
atgaaatagt ctttaaaatg taaatgatgt gattttaata tgaacatagt tcatttcaac    56700
taatcaaatt ctcacaaggc aagcctcaaa aagacccatg agctaatcat attcatttgg    56760
ccaatttaac aaaggaaaca ggggtggtag gcagagcaaa taggagagga gctgtagcta    56820
ctggggtggt gggtggagta agtaggagag gagaaggggc tagtggggtg gtgggtgggg    56880
taagtaggag aggaggagtg gctagtgggg tggtgggtgg ggtaagtagg agaggaggag    56940
tggctagtgg ggtggtgggt ggggtaagta ggagaggagg agtggctatt tgtcagaaga    57000
ggcaaagtaa tatttggtat catgccccaa gcaaaagacc acccaaagac acgatccctg    57060
gtgaagctga gatcaaagca gagctcatca gcactgacaa agacaattct cttccagaat    57120
ttatttacaa aataaaccag aaactatact ttttgagacc cttttctata gatgagtacc    57180
acactgacat tttgattaga aaaccattaa gtagtaagcc cttgcttctt catatctcac    57240
actacaggaa acacaaatgg ccacgtttgg catgtagggg attggaaata tttctgaaa    57300
```

```
aattaccaca aaaaaaaaat ctcacagtaa aaatttaaac tttgtaacag acctcccccg    57360
cacactaggc caagaattcc ccacatcatg aggccctctg gcctcacttc ctcactactg    57420
tcctgaatga gacactggga aagttctaga agttttcatc caagaaccat ttttgtttta    57480
aagaacttaa cctctttcat ggaacaaata gagttcttca atggagagtt agaattttag    57540
tacacactga aactctgtaa acgctatagt atgaggtatt tcctcaaaat gagacaagag    57600
aatgaaaaaa tcgatggaat aaaaagaatc ttgcagactt cttgaaaaat agtcaaactt    57660
cagaattcta attttttacca aagttatcaa atgagctgaa tgcaaagctt ctcaaagcaa    57720
aacagtgagc gcctttaagt ccggccattc attttcatga gtgcttatat atttaacttc    57780
tataaacaat cttttgctga aatatgcgag gggaaaacta tgtaatgatt tctcgtcttt    57840
catttggacc actggactga cttgggagta gatcttcaag aaggaataaa agcaaatctg    57900
aaacatttcg aataggttaa gattcaaaca ggagatacCC actgacgctc tgaccatcag    57960
attaaaggac tgacataaaa aggcctagac agtccttaca acttcgtgag aaatagctca    58020
taaccagagg ccgggagcct ccttggaagg gattctgatg gagtctggtg tggtggagca    58080
cacctttaat cctagccctt agagccatta gtcctggcag aggcaggcag agctctgtgg    58140
atttgaaacc agcctagtct acaagttctg gcctacacag gctgcacaga gagattttct    58200
ctcaaaagaa aaaaatgtgc aatagcaaat acatacatgg aaacatagtc agcaagtgca    58260
cctgaggaac tgagaatgaa aataaagcat tactaaaatc attaaggcac aaaagatgac    58320
caaatcctgt catttgtagc aacaaagtg aaactgaaga tattgagtgg aataaaccag    58380
gcaggaaaaa aacaaaccat tacatgcttt cacctacata gaatagaata taaacaggct    58440
gagttgagga aaataaaaca aataaacaac aacaatacaa tgagcagaaa gaacagtggc    58500
tagtattgtc cagagggaa gacacagagg gaactaagga aatattggtt aaggagcgca    58560
aaccatggcc agacaagatg gcttgggcta atgtgcagtg ggcacttaca gttaacatac    58620
agtgctcttg aatccaggtt ttgaatgttc ttcccagaag caagcaagtt ttaaatgaca    58680
gataacctac acatgtatgg aagaccaata tacaaagtac taatgcaccc aacaacagac    58740
tgtgatatag aaaaacaatt atcaataaac atttacaata attttactat gcacttcaaa    58800
gaaaattaat gcagatacta acaatctgc agtcaaattt cttggcattt accaatataa    58860
atatataagc ttaatatata aatataaata taaacttaat tatgtaaaata taaaacttaa    58920 acatgcctcc caggcctacc cacatgccac tataattgag gccttttctt aatggatgtt    58980
ccctcttcca agatgaatgc agcttgtatc ctgttgacaa aatctaggca gcacacatga    59040
aaatctgctc aaccattttg gggggtgagg gtgagacagg gtttctctgt gtagccctgg    59100
ctgtcctgga gctctctcta tagaccaagc tgcccttgaa ctcagaaatc cacctgcttc    59160
tgcctcccaa gtgctgggaa taaagccatg cgccaccact gcccagcttc gagtctaact    59220
cttaatgtaa agttcggctt taaatgatac tgatgaacac tcactgacca actgtaatca    59280
acactggagg aggggtaaga aagcaatgga ggatgaggta caggggaaga gtctttctgc    59340
aacataaaac tgaactaata actacagtca ataaaagcaa aagaaatgtg ggtattttgg    59400
tatactcaaa ttttatgaca aactgtttat caaaacagtt cttatcaaag cacaaattct    59460
ttgtgaagac cagtttagaa ctatgcctgc cactgcctgt atcaaaaaca tgtagcacac    59520
atgcccagaa ctcataatgt cacagaagaa tgaggtgcga tgaaacaatt atcaaattac    59580
tgagtttctg aaattggcct actcatattt gatacctaca tgtctttaac attctttact    59640
gtactctcat gttcactagc tttcctgagt aaagagatat cgaaagaaca gaaatgttca    59700
```

```
agagagcaac aaaatggctt aaaagggctc actgccagtc actgcacagc cagccctggc    59760
cgccagctca gtgcccccat gcactgaggc ctttccactt tctggaacac tttcctcaca    59820
tcttgcagcc actcacatgg gtgctttgtc atctggttct ctgagaagtt caggttttga    59880
gtctggcttt acaggtctta tctctgatac tgaccttgtg aaatgatcaa ggcttacggg    59940
ggatatgaca ctcctaccac attctgattt atctaagcaa acactatgaa aaacaaaaa    60000 tatgactgtg ggaacaatgc tttagaatgg gaagatgtaa acaaatctgg ataacattaa    60060
aaaatttaat gagattgagg agtgggagag atggtgtagt agttaggaaa acttgctgct    60120
cttccagagg acctgaatat ggttccctgc acccacactg agccaatcac aacctgcatg    60180
gagctctagc ttcaagaaga tgtgatatct ctgacctctg tggaggggca caagcactca    60240
cacaaacaaa caaaacacac aaacatactt tgaaaaaaaa ttttttaatg aataaagttt    60300
aagtcatttt ataagaagca tggtagtatc aattcaagtt ggcatcccag agataattaa    60360
ataaattttc tttttgtttt gctctaaatt atactaattt attatttaaa taaaatgttc    60420
ttaatcaaga attcagaaat ttttctgaa tctcaaaagg atttctctca tgaaaaaaag    60480
caaaattctg ccaatactct tctgtcttgg tatttctaaa atgctcaagc ggatagtcga    60540
gggaatgaaa agtacaaaga atttaacaac tttgatatta cagctaatat catccaaggt    60600
agccatgtcc tgcagagaat taaagtaata tatatatatt acacacacac acacacacat    60660
atagtcaaat cagaaataaa actatatgta aaatcttaaa tgcaaaagta acaaccctga    60720
ctttggatac acagataaca ggattattga agatatgaga aaacacatct tcctatagtt    60780
gcattgcatg ggaagtttct gtcatggcta ggttaacttc catatgttaa gagtcaatgt    60840
tatctattct aaaaccaaga caaacgcagt aactatggtg acacttgtga agaacctta    60900 atgattctat ttttcaaact ctgcagctga ggttcattaa ggaatcaaca caccacttat    60960
tttcaaaacg aaacatactg ttagggataa cattcagggg tagggggttc atatcaggtg    61020
ggaggctata ggctataatc ctggcactgt aggaaagtag ggagaagaat tataaaagtt    61080
atggttaatg gggaagggaa acgagatgga gtgggacagg aaagaggtca aagatcagag    61140
tgcaagtctg tgcagttagg aacaagattt gctcttggaa accataaagt caaaaataag    61200
agaatgttta tacattcata tgtgtgtgtg tgttacttaa tagaaatgtt taataaatgc    61260
atattgatag atcaagaacc aattggggaa taggacctta gcatcagaac cacccctaca    61320
tctcaccttt tctgtccaat aaaatatatt ctctgagagg gggctggtag agcggcccgt    61380
ttccaggact taaaacaggg tatcaaaagc tacacactac aaatgcacaa taatcaggaa    61440
agcttagagt cataaataat tttacaaatt caattacaaa tttgaaattt gtttaaagct    61500
gacagtttta aaatgattgt ttttagtatt ttaagattat atcataataa aactgttctg    61560
taatataaag ttaaatatca agacattgca tcaaattact gtccaggacc aaacagtatg    61620
tgcccaaaaa atacacactg aagaaatgta atataatgca tatatctctt agaaaaacct    61680
agtaattcat atgagataag gaaagtaaga atttgatctt caagattata aatatagaat    61740
tcgagataaa gtaagctcat agatgacatg attttaacac acaatcaaag ataaattaat    61800
cctctaagct aatatacttt tgaaattatt ttaagtcaaa ttatcttaaa tttaaaaggc    61860
acaatatgat acatacacac acacatacac acactattat acatgtgtgt tacatgttcc    61920
tttgccaagt cattcgctca ttagcgatca gccatatgag ggcaggcctg atggcagacc    61980 cccttttaccc acagcacttg cagttgggag gcagaagcat attgatctgt gggttcgagg    62040
```

-continued

```
ccagcctgat ctacataaca ggatgcaggc cagccagggc tacatacata ataagaccac   62100
aatctcaaaa ttaatttatt aattaattaa caaacacaaa gaccatacag aaatctgtgg   62160
taccattttg gtctttatat ggaatatgtt gatgtttctc aaataacatg ccttcaaaac   62220
caagaagaat ctattagctc tataatttat agttattttt tactaaactt attagtgaca   62280
aaaacacagc tttcaatcat catttatact gttaactata atcttgtgag gtaccatttt   62340
tcaggtgaag ttttacagat gtaatactgg gaacttgcaa gttttcaata atatttcttt   62400 ttcttttta ttatctttat tcttatacac atttgtgggt tttgttttaa atgaactggc   62460
agataaaggc tctttgtggc aggataacag gaatggggcg agaacgaaga tatgaatga   62520 ggctaagtta ctgcacaaat agtggccaaa caactgtgtg attttgtaat aagtggacta   62580
gagaaaaggt ggcaggaatg gatgtggatg aagaaaggtg gtaatgatca gaactttgag   62640
tctgtattgg aagattgctc agtcaggaa gagtttgcca tgtaccatga agacctaagt   62700
ttggatatcc aaaacctacc aacagccatg tgcatcaatg catgcttgta ttggggaggc   62760
agaggcagga gaatccttag aacttgctag tctgatttta gtttcagggt ctgtgagaaa   62820
tactctcaaa ctaaggtgaa gagtgattaa gagagacatc cataattgac ctctggcttt   62880
cacacagaca tacacacata agcacacata tagatatact caacaaaaga agaaaaggaa   62940
gaacttctca gttgtgcagg taggtggagg gtagtgtgtg tcttagccac ctcactttgc   63000
ctgtgtagta ttgtcgggc agacgaagga ggaacttgct tggcttttcc caaagtctta   63060
tgaaaaccta gagccttgac actcagggct ctgggaatat taccatgttc tgttttcacc   63120
atgaaatgaa aaacactgct aaccactggg aatcagcgat aaagctctta cgtaatggta   63180
aggacactta tttgcaggac agaaaatcaa ttccatcaga ctaaagccat catttggatt   63240
ctgaataatg tcgtgtttct ttttatttat aaatatgtct tggctttata atttcattat   63300
atttaaatgt ctggagtttc tatctagaag gctaacaact tgggttagtg agggaagtaa   63360
cctgaattgt aggactactg tgataagtgt tgtaacagac cttgcctcct tgcttactcc   63420
gttttcctac tagtatgagg atgttaatga caatctcaac tgtgggagtg ttgggggaag   63480
agaagggcta tcaattggtt gagcctggta cctggcatat gactagcatt tacactctgg   63540
caaggggctg gcacagggat gataactggt ttctgtccgt caaaagcaga ctttgggttc   63600 aacatttaa tctatcatat aagacaaaag aagcctgaca ttctatgggt gccaatagtc   63660
ccctgttttg aaaaatggag tagggggtgc ttgcatggct ttaggactta ggctaccatt   63720
ctaaaaatac tgtcccgcag ctgtttaaaa tttatttttt tagaccatag caccactgtt   63780
tggttgtttc caatttctca gaccacaaat agtaaaagtg tactcagtct actgcaaaca   63840
taaatagcaa atgcacgctt cagcactttt taaaggatat ggaaattggc aacaaaaacg   63900
cagttcatgt tgaaaattta cgacagcctg ccatatttct tcagaaatac aatcaggtag   63960
aaattaggaa gatctctccc agctgggtgg tatttttatg ttttttcact tatattttg   64020 ctcgctgaaa gactttcatt atgcagcttc tggcacttga taaatagag caatggtacc   64080 tttgctaaaa ccacagtttc tctggttatg tttagcatta cacaaacatc cttcacctta   64140
gatatccttt cccatcgggc atttaattgg acatgcactg aaaagatgat cttttttccag   64200 aatagtatac tttctggata tcattaactg gcagaattgt gttttgaaa cttcacagaa   64260 gtatatgtgt gcacgcattt caactattaa gtatttggtt ccataaaagg tattgtgaag   64320
attcagagaa aaggcatgaa tacaaagcaa ttcagactga cctgttgtgc acctacaact   64380
aaaggaagga aacaaaacag taggaaatat gtaaaaggcc acaacatgaa ctgtatgtct   64440
```

```
cttaactgtt ctgggaatgt aagaaataac acaacctctg actgtaggtt tcaagaaaga    64500
aagaaaacat tcatggtgtg taaggttgtt aaataagtaa cacataaagt taaattcaac    64560
aaagaaaaac agttttaata actaggaata aatattcaaa gtctatatct tacttcaatg    64620
ttaacatatc ttcctttgca taggtaaaca agaaatacta aaaattttaa aacccgtaga    64680
acttaacact gaaggaacag acgatcaaat cattaaatac ctggagaaaa aaatagcact    64740
ttgtaatttt agagaattta tttatatatt ttgcttttct tgaaaaaaaa aacaaatgaa    64800
taattcaaaa cttggtgatt tggggtatgg tgtcccatgc ctgtggtcaa aggatcattt    64860
gagcctagga tctagcctgg gcaacatgag aacaattctc aagaacaaac aaaatttaat    64920
gacaacagtc tacacttcac tctacttatt taaattgagt tcaaaggaaa gaaagcctaa    64980
caaactactt taaggggcca ctgctcatca tctgaatttt agcaatctca cttcatagat    65040
aaacattttc atattcacta tgtacatgtt ttttcactgc atgagagtat gtcttttgaa    65100
agacacaagt tcagttatac tactaccaaa aatttaaaat ttcaatttgt gcagtggaac    65160
aaaactaaga ttagctgaat gaaagagaca tctaaaatgc tcttgagtat tggtaaaaac    65220
tcaatgtatt gctttcttag ctcactgaaa gcaagattaa gactgagatc tacaggcact    65280
gtgaagccct tttctaccgg ctaagcagtg gctctttcca atcttccact aaacgtatga    65340
tttggccaga taatgttgaa tgtgcaaact gaaaatgga cctataaatt ctgagttaaa    65400
tatcaaagaa agtagaagga tcagattata ccatagctta agacaggtag ccgtgtgttt    65460
gtctcctccc cactagcact cactgaaaaa agaaacctat gagtctgggt tagttttacc    65520
ctattttaga tgctgggtag gagacacagt tctgacagta tgtcatgact gtggttctag    65580
ggttatctag aagtcacagt tatatctttt ggtctgctca atgatataag taaggttagc    65640
ttctcaaaat ggctcattat tgctttagaa tgtcatttaa tcatgttttc ctaaaaataa    65700
gagtagatct aatcaatatg aaaactagaa acataataac attttcaaa gggattttta    65760 agtgggaatt tatgttctag tgatgcattt ttcttatgtg aaacaagatc acttttacaa    65820
aattgaatgt tatttatat tcagaacagc agagaataaa gaatgaaagt ataagtatct    65880
acttcatttg ctataataat aagttctgaa atggaaagaa atacagaatt caacactggc    65940
agctaatgga acatacaaac cttgcaattt aaaacgaaaa agcttcctcc tgatactgta    66000
taatcgcttt gggttaaaaa aaattttccc cttaaattaa ccatgagaaa cggagagaat    66060 gaaaagaaa tcactgccaa cacattacaa ggacttactg aatatttaac gtatggaaac    66120
aaatctagat tgggaacctg ggcatggcca cacaggagtg agccatgcct catctatgac    66180
aacacacaga gcctgcatct ctgaatggag gaggtgcact gatcctgaga agctcccga    66240 atagtgagtt gattagagca tctgacagtt ccttccatag tctgtgagtg gtctgaggaa    66300
agccatccta cctgaaacta tggctatggt gacaccaaca ttaattaatt acaatcatat    66360
agtaggcatc tgtcccttc gaggatgcac aataacctcc accatcatgt ttatcatgag    66420
ctctagacaa ccagaaacca atcacatgct cagagttaga gacatgggag gaaatcgcta    66480
ccattagact gaggacatcc tctacaaatg tttccacggc tttatcacag tttaaatcc    66540 taacaagtaa ttcatagta ctccctccta cttttaaaat tttgtttaac tgaaggtagt    66600
gacctatatt tattttttaaa tattttttaa atgttcgttt agctggattg aatatctata    66660
cataattaat agttacttgg aatatagtac atttaatttt tcctgcaccc tccctgcaaa    66720
aattaccata atttaaact acttttttcac atcatttgga acttaaatta catacaagta    66780
```

```
atgtaatcta agacctttc tgtctggtca cttgaggaat tagcaattaa agaatgaatt    66840
ttcatggtca gttatatctt cattttatga aaaagtaatt tttcatatta agactgtttc    66900
ctgggctttt tatagtttaa aaaaaaatta ctactttggg agcaaagaca aggacttggg    66960
aagacagcag cctcctttg ggtcccaggc aggccagcag agaagccctc caaggtggga    67020
gagtgacaag gcaggcagtt caacaagagg cagtaactgc aggagctcag gggagcaccc    67080
tgtcatgtta cttaaaccac tggtcacccg gcaccagctt ctgtttcact gtgagtgttc    67140
tatcttaaa catgatagtc ctatcttcta catgtcagta gcaccagaag cattcataat    67200
tcagaaatgt tttccatttt tgcaatgcag gattttaaac ctgactttaa aaaaaaacca    67260
gttaaagcct gtatttcttt aagaccagag tcttatttat gggagtctgt ggcttaactg    67320
aaaacaattt ttctgttgca agaaaagtca gtcagtatga gtctgaaatg tacaaactag    67380
cgcccatccg ccaatagaac cctgtggaaa aggcaccaag atcaatgtta taactctcat    67440
taattaaatc agagacttga aactaaaagt caaactagag aaaataaaac attcataatt    67500
tttaaaatta caatgtatca taaatgtaaa cacatgtact acatcactta tttaggtcag    67560
caaatactta ataaagccaa tatatgtaaa tatggtgagt gccagactta tgacgccatg    67620
acccaccct catacaacaa gcatgtagaa attcctcagt gctattgtgc aaagtttgtt    67680
cactaaatac tcgtgtataa tttacttatt tctaaaatgt tagcaatatt aaataaaagt    67740
ttaaaattgg tatgttaatt gaaaataaga atgaattaat gaaaaattaa cccacaacca    67800
aaatatttaa taaagtagct atagtatata aatatcacat aatcttaaaa tcagtattta    67860
tattaactac ctcacataca tgctaaggaa acctaccagg aatgagctat gagaaaccat    67920
ttgcagtcaa aatatgctgc acttaacaga tgagcagaaa cactcaagaa cgtcagtagc    67980
acagacacaa accagtgggc agtggggtcc agaggtctct gtccatgaag gcctaccttat    68040
ctttgtacac atcacagcaa cacaggaatc cttaacacag gaagatttaa aacaaaacaa    68100
aaagacaaaa aaaaaaaaaa aaaaaaacac aaaaaaccag cactcactgc tatcatttta    68160
aaagcaaatt tgtagtattt acatacttga ttaccccaa accttctaga aaattaatat    68220
agttgtaata aatgatcatt ctctatcttt taccacctat attaaaaata acaagatgaa    68280
atgagcaatt ggttttaagt aaccatgtat aaatattcat ataaattcat agatgtcact    68340
gttatgagag gataaaaatt tcaatctaag caaaattgtt aaaataaaaa aatgttctgg    68400
ttgtaagtaa ctcatatata agaaaatagt tatatatcta catctttcct tatcttaatt    68460
tattgaattt ttcatactta aataatacag atagcataat catacactat aaacataat    68520
catacattat tacaccttat tgtaaaataa tagttattct ataactgtct tctgcattaa    68580
aaaacaaaac agaaattcta cagcaagcta taagaactgg caaatgcaag tgtgctcact    68640
cagcaactga aacatgagcc ttccgtttca ttgctggttt gttgttcact aagaaaaagt    68700
ggcttctttc tcaatgaatg atgcttccta tttggataaa cacgggaagt catgccacca    68760
acagaatgtg attatctata gtgagagtta gttactctgt gtccccttct aaacaataaa    68820
ttaacatatc aacaccctcc aacacatttg tataaacatt aaaatacaat ctatcagaaa    68880
gtgaaaggca taatgggtt aattttagag tgtgcacaca gacttgagct gcccagtatg    68940
ggatggacta gaatgaatgt attggacaca tgatgttact cattctacag gaagtacaga    69000
gaaggacaga gagccaaatc ttcattcaca tcaaacattc gtggacgccg ctgtaattga    69060
aagaccgttt ccaaacagat agctacagac ttcagttttcc attaaaataa tatgccttca    69120
catctgctcc aacaaaaaca gtcctgtcct taagctttac caaaatgcct tatgcttaat    69180
```

```
tttgtaaaat attaccactt tgttttgctt taatttacaa ttagttaaac taataaaatg   69240
ttgttcaaat ttccaaatta tgttaacatg ttagaaagtg ctaccatggt gcctaatcaa   69300
cattttacac cagtggcttt ccaagctttc aaatttcact tgcttcatgc aacttcctag   69360
aatgatacaa atcatataaa ttttcaatta caaatttgat tatacctcct cccaaaagag   69420
gatcaatttt acaaatcaag ctttcatact caatgctaac agttctcact ttttgaacct   69480
atacaataat tagaaattaa atataagaca acacataggc tattgggtca tgatatattg   69540
taacagtatc taactggtga tgatgcattt cttgaaactt ataaaagaat gcaaacatgt   69600
taagagtaca gataactatg aaataaatta aagaggttt taaaatccat tattttaaaa   69660
ataataagag aattaaaaac acagagaaaa ggaaaacaat agaggcctc atccttcctt   69720 gagaaatact gaaacagctg acactgacaa cacaacttta atctactatt tatctgacag   69780
taaattcaaa accattaata aagttaatgg aaacttaatc acattgcttg tactcaatga   69840 tgttttgta ctaaacagtc aaatgtccca tttagaaaga ctgcctaaat aattttattc   69900
ataaactttt cctaatagct gaaactataa aaatgtgcaa tatcactact cctcaaaaag   69960
atgcctacct tgaaacagcc ttcacattta acgcggaata ctgactaagg tgagcacaga   70020
aagctccatt caaagcaaat caccaatgca agccacgggt tttactcttc tccgagtttc   70080
aggtacacgg attcatcgct ttgaaaaaaa atgcaatgca aattggagaa acctcgccgt   70140
ttatgaataa tagcctctgt gttgtaccta ctaacgacaa agcatattgt acacaataag   70200
ggcctactga tgacagattc cacaagggaa gttttgtctg gtggtttgga gagagattcc   70260
aaaattattt aaagcacaag tcaaaaaaac catgggagaa tatgaaggtg tggtgcagat   70320
ggtgacaatg atggagaatg tgaagacagc ataggaaaag acatggagga ggcacacacc   70380
cgtacccagt aaacctcaac ccctctgtct cagccgtcct cctcctcctc ctctctcctc   70440
ttcctctgct gctgctgctg ccctcctcct cttcatccct catcctctcc ttttctgagc   70500
tcaactacat cgttctgaaa gatgcctttg accacccctc tataaaagtt ctcaagcaca   70560
aagcttttat agggatctta atgtgaattc attttaact ttattttaaa cttcggctat   70620
ctttaataaa ctgtaagttc cactgggaag gaatcttgaa tcgttcttgt attctactag   70680
tcctgaaact caaaacaaaa gtctaaaaga ataagtattt actgactgct aaggcaagca   70740
aacagagaag atttaaagat gcaggtgagc aggcagtcag atgaaggact ggggtcacca   70800
taaatgtatg gcacacagag gatcctgatt tctggtgata ctcctaccac acatcccctc   70860 cattttgct tcactcctct ctctccaggg attttacata ttgactctca caaacactc   70920 cattgaaagg ggggaaagt ttgaaagctg gtgcgatgag tcatgtccaa accttgacgg   70980
tctcactcag actgtcctgt cttcttggta gcatagctga cacccatcta atagaaagca   71040
ccctagctac ccaggctgag ctcaaagcat ggagggccac tcctgggtct cacatctggc   71100
caatcgtgtg ctggtgattc tctcttccct ctttctcctc ttgtcagttc tcactgctgc   71160
cagcttaaat gaagggctgc gtttgttcct ggaactaagc tgcagcttct taaagcagga   71220
cacttgattc cagtaacgct ttgatatacc cacatgctgg atttagattt ctcagagtcc   71280
tgctgtttta ccaataataa aaaactggtg agggattgtg gtatcatatc ctaacaaaac   71340
caaagcccct cccttgttcg ttttttttt tgttttgttt tttgtttttt tttttttaaa   71400
cttactctag aacagtggtt ctcaacttgt aggttgtgac cctttgaggt gttgaacaac   71460
tttttcattg gggtcaccta agaccatcag aaaacacaga tatttacatt atggttcata   71520
```

```
acagtagcaa tattaaagtt ataaggtacc aacaaaatta tttttatggt cgagagttac   71580
tacaacatga gtaactatat taaagggtca cagtattagg aaggttgaga gccactgctc   71640
tagaaccata gattcaacat aatggcctcc tgttctcttt gatcaagttc acctgttttc   71700
ctaaaacaca cattcactca agcagcatgt gttgtcctct ctatgcacat agagacctaa   71760
agttgcatgg cccaagaatg gaagcacatt gcttgagctc caggagtgag ttttagttct   71820
tcctccattt ctgtagtttg tatgtccact acacggggca gcacccacaa tgtgcatctt   71880
atagatggat actcaaggtg gcaaagtcag ctggtagtgc tggtagtaat ttacgccacc   71940
ttccagattt ttctcatagt ccagctgtct tcacaggggc catcttagca caattataaa   72000
agaggattct acatgcaaat gcaattgagt aaaattagta ttccattata ttaagcttta   72060
gctatttgtg ttttttcttg ttaaagatgc cttcatttaa taaccatttt ctgggatgct   72120
gccatgtgct gaaaagaatc taccttaaca gggaaggctg atgagtccac atgaatagtc   72180
aaatgcatac catacaccgc gtcagacagc aggtgcaggt accagtgaag ggagcagatg   72240
ctatcgtaaa tgtggtaact tatgaggcct tcaacgatga tgtagtcttg aggaaaagcc   72300
atgaaggagg taaagacgta gggagtgtga ggatctccaa gtaaagattc taacaggctt   72360
ttaagtacag aatggcccta aggcagttca gttgcagtgt tctttgtagg attgtaagca   72420
gatggtaaga aagatgctgc tagcactagg aacaaacacc agaagatggg agtcatctgc   72480
ctagcttgaa acatgcagct ttcattccta taacaagaaa gagttctgaa ctggagcaaa   72540
gggacatcgt tgggatttct gaagtttctc tggtcatcat atgaagatta cagtgagggg   72600
tagggacagg gctaggggtt gaaaatcaaa gggaaagaca gatagggttt tctttaaaac   72660
tccaatggaa aggcagtggc gccaatgatt caatgtgagc agaaaataga tatatgatga   72720
gagttaagat gctgtcattg attactacaa gatagagtag acggaaagat tccaacctac   72780
acatttgatc ttgaatctgc tcccaagtta cataggtagc ctatatctgt atgcttgtat   72840
tcagcccggt ttctactgac ctagttagtg cctaccagct gatgacagat atcaccagac   72900
attttgggtt gtttgctttt agtttatcat tattgttttt tggggttgtc tgtcggcttt   72960
tattttatca ttgttgtgta tgtatgatac atgtaggggg caaaagtgta ccagatcaca   73020
catgtagagt caagagtaca gctctgtgag gttgggtctc tcctcccacc tttctgtgga   73080
ctccagggat cagactcagg gtattaggct tccccagtca tgactttccc tcataggctg   73140
tattcccaac ccacttacct agacttttgg tcatagtctt ctgtcttgtc ttactcagct   73200
cttaacattt ggctgcattc cttggccttt ggcttcttct cccattctca gcactaacag   73260
ggtagttggt cctcagtctg tgattcagtt ttcaaagtcg catctgcctg gagttcaact   73320
ctcctgcctc ctttaagagt ttctgtcaac acactgggga ccatgctgat aatcctagtg   73380
attgtgtaat ttaaagatat ctaattggat cacattcata aatcccttttt agcatgtata  73440 gtaacacatt cgatagttca aggataagga ttataaaccct cactgggtcc tattagtctg   73500
tctatcacaa taattgaagg gtttacgaat atgggtttgg tagtgctttt agatctatgg   73560
ttccaagatg actgccaaag cttgttatca agcccaaatt caagaggaca gggcaaaatg   73620
agctgagccc tcagctgacc tgagtccttt gatacactgc ccccaaaact ctccaacccc   73680
agtgaagttc attcccactg atcattctgt caggacgtgt gtattaaatg tactgttctg   73740
cttcttgttc aaaaagggaa aaatcaaaga agctagaagt cttccaccat aaacaactac   73800
aactgaaaat aataacagaa aatctgtaag catgcaaact tgaggttaga aaactctaaa   73860
ttttgtaaaa cttaaacact ttcatttctt aatattccag agatattttt gtaccatgaa   73920
```

```
gatagttagg tgcaacttgt ctgcccctcc tgtctgactt agttcttctg tgaagctgta    73980
ggaatagcac agatcaaaca cacaccacac acatgcattg agtacatacc agaaaacctg    74040
ctactgagct acttgctcag tcatggtcct gtgacttatc attcatccat cccacagggc    74100
tcttcatacc ataacttctt atcatgatgg catcgagaat tacattgcta acatcaaagc    74160
tttgaaagac acacatagca ttcctcttca ttattaagat gcatattcta ggtgctaagg    74220
agttgactca gttgccaagt gcttggattg caagcttgag gatgtcagat ctgaagaacc    74280
gcaacacaga ggtaaaaagg caggtatggc agcacacacc tgtatctcag cactgggaag    74340
atggagacag ggagatccct agggcttctc tgctagccag tttggccaat cagcaagttc    74400
caggttcagt atacacataa aagattccta cttgtccctt aaacacattt aagttgccta    74460
tgcctgaacc acaaaatgac cctgaagccc aatacaaatg gcagcctgtg cttatccagc    74520
tatatttagg ctaattaaaa gaaatagtct agtaggaaag tttaacatac ttggtcttct    74580
acatgattgc tcacttaaaa tcatgattta tagccgggcg gtggtggcgc acgcctttaa    74640
tcccagcact tgggaggcag aggcaggccg atttctgagt ttgaggccaa cctggtctac    74700
aaaagtgagt tccaggacag ccagggcatt acagagaaac cctgtctcga acccctcccc    74760
cccaaaaagt catgatttat tttatgtagt tcatctcttc catgcatttc ttatgcaatt    74820
tctcaggccc atattggttg ctttctttta gctgaaacat ctctcttgct gttcccactt    74880
ctactcagta aatcagtcat caggactcca acacaaggtg tccctttttcc tggaagctgc    74940
ccttccggcg gtctcagttc tggcactagc cttgaaggtc tgcatgtgca cgtacaggcc    75000
tgtgcaagag atccatagct ctcggggtct tcttactagt ttttttgatt atctgtactc    75060
agccttggtg ccctcttgtt tcccttggct taagaatctc aacacactgc cctacatgac    75120
aagtcaggat ccaccccttca aacagctctg agcacacaca ctctagtgtt caaatgaccc    75180
cagagtggct atctagacaa gagaatacag cagacacaga aggtttggct gtgtgtgtgt    75240
gtgtatatat tatatatagc tgtgttttat atataaaatc tacttcatta ggattcaaat    75300
gaaaagaaa atgagccatt tgtagtttac agagggaaaa cataaatggc taaaacattt    75360
ttcaatgtgc agtatcagta aaaaaaaaaa aaaaacaca tgtagatcaa acaaattagc    75420
agtcttattt ggcaaagaca aaatgtattg gtaaattgcc agggaaacaa atattcatag    75480
ccactgttag tgagcagaaa tggacagaca ttaaaaattt tgataatggg actgaggagg    75540
tgacttagtc aataaagtga ctactgtata agcatgcaga tgtcagttca atccccagtt    75600
ttagtactca cattaaaaca aaacaaaaca aacaaagcca ggtgtgacaa tctctcaggc    75660
aggaagctgt aacaagagga tctcataggc tcaatactca gcctaaccta gacaaacacg    75720
caagctcctg gctctgtgag acaacctgtc ttaccaaaat acagtagaca gcaatagaag    75780
acaaccacac acatgggcac acacatgcac atgcatacat gtaaaagaca tatacactag    75840
aaacattagt tataattcca agtttctacc ctgtgaaaac cctggtctca cttactgaac    75900
tgaagtttat gactaacttc ataaagagtt attaaagaca aagaaattga ctaagtgctg    75960
gctgactaag tctgtaacca tgtaagtgcc tggtgttctt agccttaatt acaaaagaga    76020
aaatgtaagg gctggggaga tggctcagag gctaagagcc tttctttctt gcttaaggac    76080
ctagattcag ttctcagcac ccacacagca gttcacaacc attcccagcg actgtaactc    76140
cattcccagg ggagctagaa ccactatctg gacctggagg gcactagata tacacatggt    76200
acacagacat acatgcaggc aaaatattca agcacataaa ataaaatctt tttttaaaag    76260
```

```
aaatgttaga atgaaaacaa tggcttgatc actgattcct tatatttact atatgattta    76320
ctatattctc attgtgactc aatgcactat gggaaacttt gaaacttggt actgaataaa    76380
gattacttca aagctcctac aaagcattga agtttacata agttactact taaatgtaaa    76440
cagccatgcc aataatgtca ttagcattca aaataattcc aagattgtaa aatgaaaaaa    76500
aaagttaaca tattgaaagc aattaactcc aggaagaggt cgaaacaata aagcaatgta    76560
taaatgagca agcataacac agaacactgt atcaaagagg ccagtgacca cccaagtaca    76620
gagcagctca gaaggaagaa atcagttctc tacaacacct taggaaaaag tttacatgtg    76680
gccacacaca tgcccaattc atgcagtttg agaggagaga aaataactgg gggaaaatta    76740
tctaaaattt aagcaaaaga ataaattatg ccaaacagga aagtcatgtg actgacagca    76800
gtaaaatctg aagataataa aatgggggaa ggaagtcagc tctaacacta agaaacacga    76860
aaggcgtgag aacattcctg cccggtgtta ggttaactct ctggagggaa acactgaaaa    76920
cacaccgtcg taaaatatgg atcacagagt attgagtagc ttaaaatgag atgtttccaa    76980
cccacctctt atgaatagtc aggagaaaca cgtttatgag gacattgagg gtggctgtta    77040
gataccagtt cacaaagtaa agtagggaaa ccaagtgcca agagcataaa cagcccgaac    77100
ttcctgcaag gtaaaacatg tccatgaact atttactatg cctatactct cagcaattgg    77160
aaggtggaag aaataataac tggagaccag cctgggctac ataatcagac tctctcaaaa    77220
acataagaaa agtgaaaaaa acaaaaacaa aaacaaaaac ccacacacat ttaattatct    77280
gctttctaac gttcccaaag aagctgagca cactgtactt acaacaagag ctggcaccag    77340
tagtgtggtt cagtgggtag ggctccaatc cccgtgcctg tgctgtgcgt agcacgtgca    77400
catgagcgcc tcccatgcat actaaagaaa tgaggatgaa gatgaagact gacgatattg    77460
tgacctttaa gatgttttag cttttaactc cttaagggta aaaacaaaa caaaacaaat    77520 tacatagcta aaagctctaa agcattgcta tcactgctta tacatcaaac actctaacca    77580
cttcttcagt gcatgatagc acactaataa cattccactc attcccacaa acaacagtat    77640
atgtcattta tatagtgctc tgggatggtt ttaataccac tgagacatgt gtcctgacaa    77700
agcacagtca cattaacatt ttattctatt atttttaagt aaattaagga atttgtactt    77760
aaaactttga tagaaagttc ttaataaagt actgggggg gggaatcttg gagaatcatt    77820
tacctaaaaa acacaaaaga gtgaaatgtt tgctatatgc tataaaatga cattttcccg    77880
tgatttaaag ttatgtttta aaccaaaaca aaaattattt aaaaaaaaac caaaactaat    77940
gataaagtta atatttaaga gagagacagt taaggtaacc taagtagaaa taagagtgtg    78000
gggcttcacc tgaagaatca aaatgctgcg gccatagact ccaagtcact tatggccaaa    78060
gcaatcaata tgcaaattat gtgtcattaa ataaaatgta ctaaaacatg ctgtaaatca    78120
agagaaaaac attcatatag gcagaaaagc actcatatag gaagaaaaga ctagaaaagt    78180
cgatagaaaa aatgaaatga gaaaaaaatc tgtaatatta aactaagttt catgaaaata    78240
gctaaaatat accatttaag aggtcagggt tggacagttt atataaaaat aatcctttgt    78300
gtaacagatg tctaagataa taaagtatat taattatcca aattctatat tttataacat    78360
ctaaaagtat caaatagca caccatactc catacacata atgtaacgaa cacatctgct    78420
ctgtacagac tatattcttg ttggaatttc ttctaattat accctccctg gtacaaagag    78480
agggaggtag tgtgggccat gaaagcaaag caagtaaaac acacaccaat acatgaacat    78540
cagagcctca acactgacgt gaataattag acttcagaga caggaacgag acacagaaaa    78600
aggcattgtg ttacgaacaa agagtcaact cagtaggaaa acaggacgat tctatagatg    78660
```

-continued

```
ctaacctgtt gtggatcagg tttaatgctt gtattatgtt atttgggttc ctatatgtga   78720
aatgctgagg gtccctgccc tccagctaat tctgactggt aaataaagtt ggcagcagcc   78780
aatggctggt cagggagcca gaggtgggac tttagaattc atgggcaagg tgaccaagga   78840
agaagcagaa ttgccctgct gagaaaggct tgagaactgc aggaagagat acatatcaat   78900
catgtaagat cctggggaca gtggcactgc tcccccacc acacactggg tcagggtag    78960 caaagctaga atacagattt tagtaggtaa taattcagaa gtatcagagg ggaggaagtt   79020
tgagctgatt aaggcatatt aaatataagg ctgtgtgtgt ctgcatacat ttcgttagag   79080
atgccagagc tttggggtgg gtagcaaggg actcagctgg ggacactaga gcagattaat   79140
caactacaac aatactaacc aaataacaaa gtcacaaaga cacacaggaa aactatggaa   79200
gtcgacgcag cacctgtaga ttccaacagc tagagaacca gtcaaaaagt catcaaagat   79260
ctaagaactc taaacacata ccaagaacat caaattgaaa acatgttgta acgggagaca   79320
gcacatacta gcagcttgac aacacatcta aaaagcccta gaaaaaaagg aagcaaattc   79380
acccaagagg agtagatggc aggaaataat caaactcagg ggtgaaatca accaagtgga   79440
aacaagaaga actattcaaa gaattaacca acgaggagt tggttctttg agaaaatcaa    79500
caagatagat aaaccctag ctagactcac taaagggcac agggacaaaa tcctaattaa    79560
caaaatcaga aatgaaaagg gagacataac aacaaatcct gaagaaatcc aaaacaccat   79620
cagatccttc tacaaaaggc tatactcaaa aaaactggaa aacctggatg aaatggacaa   79680
atttctggac agataccagg taccaaagtt gaatcaggat caagttgacc atctaaacag   79740
tcccatatca cctaaagaaa tagaagcagt tattaatagt ctcccaacca aaaaagccc    79800 aggaccagat gggtttagtg cagagttcta tcagaccttc aaagaagatc taattccagt   79860
tctgcacaaa ctattccaca aaatagaagt agaaggtact ctacccaact cattttatga   79920
agccactatt actctgatac ctaaaccaca gaaagaccca acaaagatag agaacttcag   79980
accaatttct cttatgaata tcgatgcaaa aatcctcaat aaaattcttg ctaaccaaat   80040
ccaagaacac attaaagcaa tcatccatcc tgaccaagta ggttttattc cagggatgca   80100
gggatggttt aatatacgaa aatccatcaa tgtaatccat tatataaaca aactcaaaga   80160
caaaaaccac atgatcatct cgttagatgc agaaaaagca tttgacaaga tccaacaccc   80220
attcatgata aaagtgttgg aaagatcagg aattcaaggc ccatatctaa acatgataaa   80280
agcaatctac agcacaccag tagccaacat caaagtaaat ggagagaagc tggaagcaat   80340
cccactaaaa tcagggacta gacaaggctg cccactttct ccctaccttt tcaacatagt   80400
acttgaagta ctagccagag caattcgaca acaaaggag atcaagggga tacaaattgg   80460
aaaagaggaa gtcaaaatat cacttttgc agatgatatg atagtatata taagtgaccc   80520
taaaaattct accagagaac tcctaaacct gataaacagc ttcggtgaag tagctggata   80580
taaaataaac tcaaacaagt caatggcctt tctctataca aagaataaac aggctgaaaa   80640
agaaattagg gaaacaacac ccttctcaat agtcacaaat aatataaaat atcttggcgt   80700
gactctaact aaggaagtga aagatctgta tgataaaaac ttcaaatctc tgaagaaaga   80760
aattaaggaa gatctcagaa gatggaaaga tctcccatgc tcatggattg gcaggatcaa   80820
cattgtaaaa atggctatct tgccaaaagc aatctacaga ttcaatgcaa tccccatcaa   80880
aattccaact caattcttca acgaattgga aggagcaatt tgcaaattca tctggaataa   80940
caaaaaacct aggatagcaa aaactcttct caaggataaa agaacctctg gtggaatcac   81000
```

| | |
|---|---|
| catgcctgac ctaaagcttt actacagagc aattttggta aaaactgcat ggtactggta | 81060 |
| tagagacaga caagtagacc aatggaatag aattgaagac ccagaaatga acccacacac | 81120 |
| ctatgtgggt tcattcgaca agggagctaa aaccatccag tggaagaaag acagcatttt | 81180 |
| caacaattgg tgctggcaca actggttgtt atcatgtaga agaatgcgaa tcgatccata | 81240 |
| cttatctcct tgtactaagg tcaaatctaa atggatcaaa gaacttcaca taaaaccaga | 81300 |
| gacactgaaa cttatagagg agaaagtggg gaaaagcctt gaagatatgg gcacagggga | 81360 |
| aaaattcctg aacagaacag caatggcttg tgctgtaaga tcgagaatcg acaaatggga | 81420 |
| cctaatgaaa ctccaaagtt tctgcaaggc aaaagacact gtcaataaga caaagagacc | 81480 |
| accaacagat tgggaaagga tctttaccta tcctaaatca gatagggac taatatccaa | 81540 |
| catatataaa gaactcaaga aggtggactt cagaaaatca ataaccccca ttaaaaaatg | 81600 |
| gggctcagaa ctgaacaaag aattctcacc tgaggaatac cgaatggcag agaagcacct | 81660 |
| gaaaaaatgt tcaacatcct taatcatcag ggaaatgcaa atcaaaacaa ccctgagatt | 81720 |
| ccacctcaca ccagtcagaa tgtctaagat caaaaattca ggtgacagca gatgctggcg | 81780 |
| aggatgtgga gaaagaggaa cactcctcca ttgttggtgg gattgcaggc ttgtacaacc | 81840 |
| actctggaaa tccgtctggc ggttcctcag aaaattggac atagtactac cggaggatcc | 81900 |
| agcaatacct ctcctgggca tatatccaga agatgcccca actggtaaga aggacacatg | 81960 |
| ctccactatg ttcatagcag ccttatttat aatagccaga agctggaaag aacccagatg | 82020 |
| cccctcaaca gaggaatgga tacagaaaat gtggtacatc tacacaatgg agtactactc | 82080 |
| agctattaaa aagaatgaat ttatgaaatt cctagccaaa tggatggacc tggagggcat | 82140 |
| catcctgagt gaggtaacac attcacaaag gaactcacac aatatgtaat cactgataag | 82200 |
| tggatattag cccaaaacct aggataccca agatataaga tacaaatttcc taaacacatg | 82260 |
| aaactcaaga gaatgaaga ctgaagtgtg gacactatgc ccctccttag aagtgggaac | 82320 |
| aaaacacct tggaaggagt tacagagaca aagtttggag ctgagatgaa aggatggacc | 82380 |
| atgtagagac tgccttatcc agggatccac cccataatca gcatccaaac gctgacacca | 82440 |
| ttgcatacac tagcaagatt ttattgaaag gacccgatg tagctgtctc atgtgagact | 82500 |
| atgccggggc ctagcaaaca cagaagtgga tgctcacagt cagctaatgg atggatcaca | 82560 |
| gggctcccaa tggaggagct agagaaagta cccaaggagc taaagggatc tgcaacccta | 82620 |
| taggtggatc aacattatga actaactagt accccggagc tcttgactct agctgcatat | 82680 |
| gtatcaaaag atggcctagt cggccatcac tggaaagaga ggcccattgg acacacaaac | 82740 |
| tttatatgcc ccagaacagg ggaacgccag ggccaaaaag ggggagtggg cgggtagggg | 82800 |
| agtggggtg ggtgggtatg ggggactttt ggtatagcat tggaaatgta atgagctaa | 82860 |
| atacctaata aaaaatggaa agaaaaaaaa aaaaaaaga gaaagtctac cagtctgaca | 82920 |
| gaggcagttc ctctgttgaa gttctttctt cttgggtgtg tcaggctggc aactgagcca | 82980 |
| tcatcaaaca ctgttactta aaaggaggaa aatggagata gtgcagtcct gatccacctg | 83040 |
| ggaggagctg cccacccatg aaagctatct gtggacactc tcagtgggaa ttctactccc | 83100 |
| acatcacagc aagagctact ttcttgaaat gctttgtgaa gctcactttc tttcgcagtt | 83160 |
| acttatgtct gctcaatccc gatcgataca aggatttaaa actcgttcat tctttggtaa | 83220 |
| actggttaaa aacagtaggc atatggcacc aagttcctga cttttaactt ggatcatttt | 83280 |
| aaaattatat aagtatttca actatggaga agcgctggtt gaaatgatac atattttgtg | 83340 |
| ggttttttaat ctaatttcat catcatgcca ttatattttt taggcagtaa acaagccccg | 83400 |

```
tatcaaacta taacaatttc tgattgtctt catttaatta agtgaaactc tcccaaggag   83460
atctctcttc taattggaaa ctccttgatg atacacaaga gttttataaa acataatatt   83520
cccatgtcct taaaaaccct agaacaggta agatataagc cttccttcag ttaacagctg   83580
ggtgagtcag atgcctcgca aaatgctgta ccacctccaa catgagacgt ctgccccaca   83640
ggaaagctta tcagattctg agaaagtgac caaaaagtga gtttagatta caaaagaga    83700 caaagaagg gaatcaactc cataaaggaa ccctaggcaa tagggaccaa aaactatata   83760
agcaacatgt acagaatact ttaaattact atgggaggtt ttttttttt ctgaatcaat    83820 atagggtttt attcaattat gttttagcct cccctacttt ataaaaacta taaatttaat   83880
agcagaagag cttaagcaac tgggagatgg ctcagcaggc aaagccaagc atgatggcct   83940
gagttcaatt cctgagactc acatggtaaa atgagaccca actcccataa tctgtcttct   84000
ggactccaca atgcaagagt acacacacac acacacacac acacaaataa taaataaata   84060
aataaataaa taaataaata aataaataaa taaattgtga atgttttaaa ctatccataa   84120
agagcaactg tacccgttct ctacatacat ttgttttaat gctcactaaa gtactaaaat   84180
tcagaataaa ttcccttctg aaagctgctt ggctcaagtg acattactga gaaacaaact   84240
tgtacatact agtctaaata ctattaagga taaagggtag ctgttaagaa atagaaaatg   84300
taatcatcta taatttgatt agcttttata ttcagaggaa aatcagagtc atcttctaaa   84360
tgtttgtgct atctgcatta tgctgctttt agtccatgaa cactattatc attttgtgg   84420 agaaactgat agaaaacaga tcaactgcgg taaaatgatc caatccattt gaaaatttgt   84480
tttcagtttt ccttcacaaa aaggcttgca aatacatgac tgcttcccac ctacattata   84540
caccataaac ttaacagcat gcagacatat actttacatt tgcagataaa agcaatccac   84600
ctaggaacca caacaatgat aggtacaaat caggctatca cagaacagga gaataaggag   84660
ctggagcaga caaaactcac catagagaca aacggtaaga aacagatgac aaagaaagag   84720
acagaatcat cagacaaaaa ggcaaaaagg aaacaggaaa gggcagacag gataaaggag   84780
aacagaatta ggaacaagca agaaagagga gcaaacaatc tcttttgaga gtaaaatgca   84840
aggttataca agaaaccagg gaccatgcgg atgggtgttt tactttatcc aactgcctgc   84900
cactgggtat gtatgatttg agttggtccc actagggctc atgtactgga aacatgataa   84960
caggttggcc tggaaattgt tatgtcactt gaccagcctt gaactcaata atacctcaga   85020
ctcaacttct cattgttggg gttacaagca tgtgccacta tatccagcta cctaataaga   85080
gtttgaatgt gggactaaaa cctacccacc ataccttatc tacaactaat ccacatctga   85140
cgattaatct cactagttgt ctcaaccta agctcatgat tttcgtggat gtactctagt   85200
aagttttcca aatttatact ttcatcatca aattctgccc agaacagcat tctcaaagca   85260
gtaccaaata gaacacaaga gcttctcaga actgctacat gctacatagt ataaaaccca   85320
acttagcaaa ttcctcatac accactgttg cacagaaaag tacttacaac gttaacattt   85380
tgtttaaaac tcccaattat tcttttccct cagtttgtgt tgttattcct gttaaccttt   85440
tttcaaccac aatgcacttt gatactaatc taatttctac ttcttccccc tatcctccca   85500
atattttccc acttttaatt attgaatatt taagaatttt ggaatgagtt tatgatacac   85560
acacacacac acacacacac acacacacac acacatatat atatatatat atggatggag   85620
attggaaggg ggtttactca aggctcagaa ttcacactat ggtcattgtt cccagaagta   85680
taatgattct tatcattact ttttggatt ctgtggtcca gtgatgtact ggcaggtttt   85740
```

```
gtgtgtcaac ttgacacagg ctggagttat cacagagaaa ggagcttcag ttggggaaat    85800
gcctccatga gatccagctg tggggcattt tctcaattag tgatcaagct gggagggccc    85860
cttgtgggtg ggaccatctc tggctagtag tcttgggttt tataagaaag caagctgagc    85920
aagccagtaa gtaacatccc tccatggcct ctgcatcagc tcctgcttcc tgacctactt    85980
gagttccagt cctgacttcc tttggtgatg aaaagcagta tggaagtgta agctgaataa    86040
acccttccct ccccaacttg cttcttggtc atgatgtttt gtccaggaat agaaccctg     86100 actaagacaa gtggcatagt gcagttacaa ccacatgcta aaataaaatt tcagcagcaa    86160
gctcaatctc tagttatctc taaaacatct ttttaaaaat cttcacttat aggtaccatc    86220
taggagtaaa acagaaaggc ggtctaagac caggcaataa tccaaaagat acatatgaaa    86280
tcctctacaa taaactacat aatctttgca aggattcatg aaaacatact aagattgacc    86340
acatcttagg tcacaaaaga aatgtaaata catataaaaa aatagaactc ttataaaaga    86400
aattgaagaa aatattttaa gtgaaatgta aacagaacgt atcagtatttt attgtatatc    86460 cagagtagtg ctaagagaac aatttgtaac attaagtgca catattacga aggggcttaa    86520
atcagtaatc taaggtgcct acttaaggaa gtaaagagg taaatctaaa tcaatcagaa     86580
agataagtga cagaaattaa tgaaatatta ataagaaaa caaaactcaa tgaaactaga     86640
aaatatttct tttccagaat cactaaaacc aatatctccc taatcagcaa gagctactat    86700
aacagaccct acagatacta atcagcaaga gctactataa cagacccctac agatactaaa   86760 agtatactaa gaggatacat tttttttaaac atatgaatat aactatggat aaattctaaa   86820
tcatttccta aaagcacacc aagctgtaaa cctttaggaa acaagaatc aaccttgcaa     86880 accttccatt gccttcagaa aagccagact gcagcagagt ctgcatctgt ttaccacact    86940
gaaaggctct ttgtcttcct taggcactaa atccttacca gcttcccctag aagctttgta   87000 tgaatactgc ttagtttaac ttcaccttttc cttgggggag ctggaatttg actagcaatg   87060
gctcatcagg caaataccaa gtgaatgaca aggcctaaat aataattaaa aaacaaacaa    87120
acaaacaaac aaaaaaaccc cggcacagtg tctggagtca cagcagtgtg agaggcagga    87180
ggatcacaaa ttcaataccc ttaggaacac agatgaaaaa gctttcaaca caacattaga   87240
aattaaaccc aggtacatat acatatatta ctgagtgaac aaataggaca taagccaagg   87300
gtataaggct ggctcaacac ctaaacatca aacaccatct acctcataaa caaccaggga   87360
agcatggcgt tcccttatca gatgaaacag ggaaagaatt tgacaattta gcagttgcaa   87420
gattaaaaac caagcagtct agaaaatgac caaacataaa agtggtgtaa ctataagaga    87480
aaacactata gctgacatca tagttcatga caagtggtaa tattaacata taagctggga   87540
agaaagcact aagggctctt cttatcattg ttttccaggt ctctgtaaga aatcctaaat   87600
aagacaataa ggttaaaaga gggagaaaaa aaacacaaga agggggtaat gagagaggag   87660
aggaggagga agaaggctta agaatgaaaa gagaaacagg tgaaaagaag aaataaaact    87720
gttcctgcct acagaaaaga caattttcaa taaagaaagc cataaggtat ctagtgccca   87780
gcacttctag aatcagagaa gttcgcaaaa ttgcaggata aacgctgaaa acagaaatat   87840
agatctaatt tttatataca agcataaagc aactggaaat agaaactttt actaatattt   87900
aagattgtgt cataaaacaa acatacaaac tatgtaaaaa ctgaacacca acacttacaa    87960
aaatttgatg aaaaaaggta gaagtttatt ttttttaaata caaaataatc atgggtggtt    88020
ggggtagaaa catcctcttg gagacaggga aggaggaatg ggatgactgt gggagggcag    88080
accaggaagt gggtaatgac tagactgtaa aaaaataaaa ttaaaaaaaa ataataatga    88140
```

```
tatcttgttt cgcagattgg aactctcagt atagttaagg tatcaattct cttaaacatc    88200
aacagagcaa tctcaatcaa atctcaaact ttctggtagg caaggacaaa ttctaaacat    88260
cattcattaa gataagacca aaatagaat agtttaacac aagtttctaa agttaaaata     88320
ttcattccat gacattttct tacttaccat aaagctacag ggatcaggac agtgaggtgg    88380
ctgagaaagg ctagatttca agagcaggaa aaaggacatt tgctcactgt ctattcataa    88440
agatgtaaca gacactcaac acagagacgt cagacttgac acaaggacag ccagaactgt    88500
tggcttctca catggcaggg ctggagaggt ggctcagcag ttagagcact tgctggttaa    88560
agaggcctat gtttgagtgc cagcaaccat gtagaggctg acaatcatct gcaatgctag    88620
ttccggggta cctaatgccc tcttctgacc tcctcagata ctgcatgtgt ataggatgtg    88680
tatacatgca agaaaaacac tcaaacacac aaaacacaaa aataaatct tttaaaaaaa     88740 ccaacaatga cctgtgcatc gtaacttaca caaaacaat tcaaataac cataggctta      88800 ttatctaaaa caagacatta taaaagtttt gaaacaaaag aaaatctttg tgacctctag    88860
ttaaacaaag acttctttga cagaattctg aaatcttgat acataaaagg agatttacac    88920 cccccccaa aaaaaaact ggatttaaac aaaatttaaa cctttggctc tctagaagaa      88980
tctgttggaa gaatggaaag aagttacagg ctgtgagaaa ctcatggcat ctgcacttca    89040
ggagaaggac ttctgaagta ctggatccca gagtggattg ttttttaaag cttcagccct    89100
ctaataagat aaataagaaa tggtgaacag gcaggccttc gactacaaca ccaggagcat    89160
gctagacagc aaatgaccat atgctagatg aagatgtttg gtattattag gcattaggga    89220
aattaaaaat ggaagcacag catatcaatc aatacctctt accaattaaa gcagctaaag    89280
attttttttt ttttaacca ccaaacccaa aaataaccta gcaattccaa gtgccaatca     89340
aggtactaag ggcctggaat ctcaaccact gctgagtgga aggtaactac attagccatg    89400
tgcagagcag cttggtcatt tctataaaac tgagcagaaa ctacctcagg atgtggcatg    89460
ccagccctag gaacctgcct aggaaccoca acagcaacaa gaggaggctg agcaatggga    89520
actcctcctt cctggtggaa gaaagctctg cctaagtggc tagaactgac tttcttatgt    89580
ttatcagtcc tcgctttccc acattactaa cagagatagc aacctttcct actgcacttt    89640
tattttgctt gtattttctt gcacttcaaa tcattgtcta ttatgtagat aaaattacat    89700
gttagcacct catggtgtaa tttatgaaag aaacagaata tctagctaaa agacatttgt    89760
cttgaaatgt cttgaaagca gggaaaagga cctcccttca gactcccacc atcactccat    89820
ttgcaaagac taaagggtca tcattgagaa aggacaccag agagactctg actgggagca    89880
gcaatacaga cttagattaa ggcactgaga tgcatcgaac tacagagaaa gcttaaggag    89940
aagtccacat tctacattct aagaaaattt acacctttac ctcagactca gctgctagat    90000
tattcactac ctggcttata agccctaaat aaccaaagtc tcttctttag tgaaatattg    90060
aaaataagaa aaaataaggc tataattaat aattttgaga aatttcccag aaaaatagcc    90120
agggcctcca cctgattacc ctataataaa agtccacctc acataaattt tgtgaatgtt    90180
tgttttgtca ctggtgggga cacacacaca cacacacaca cacacacaca cacacacaca    90240
cacaaagctt cagtcttctt taaactttga ttgcagtct tggtaagctg ccagcctgac     90300
ctctgaactc attctatagc ccaggcaggg tttgaacttc tgatccttcc tagctcagcc    90360
ccctgaacca cagaactcag tcctcacata tattttgatg tctcattctt aaatatgaat    90420
aggcataaaa taagcattga agtaaacact caagaaagaa aaaaaagata atccagaaat    90480
```

```
caaattatac ccagggaaaa atgaaaaaat gaaagacaca tttgagaata atctaggaga    90540
aagaatgaaa aagaatggaa attggactag atataagaat cagctgagta tctacaacta    90600
ctgaatagca gtgattcctg aaagataaaa gaaacaagta acacagaaaa caagactgtg    90660
aaagaaacaa taaggtttcc aagggaagga tatatgcatc tggtaaagga gatgaagagc    90720
cacacagcag aggcagcagg gcagacccag aggctccagg cagtataggg tgtgtggccc    90780
ctccttccag acactctggg tcagagtgaa atgggggtct tccaagcagc ggtgaaaggt    90840
agaaagaagt ggaaggtttg caggaaactg acttgaaact taaagtcagt cctagctgct    90900
gagtactagc aaatgcgatg agagcacact agtccacact gcatgcgtat gcattctcca    90960
ctgttgagct tggctttgga atttgttatg tacaaccttt caacaacagt caacatctaa    91020
attacgtttt tctaaaacaa attagcttct tctgcagaca tattctaaat gactatgaag    91080
tgggatctgc cagcagaagg tcagaataag cttagcattt tactgtggga gtgcctgagg    91140
cactggggac tgaagaactg agtggctgtc agtttcaatc tgaacagcaa tgtagtcaca    91200
gagtgttcaa gtcctaaact accctctcca taaacccctc cctctaatgc caactgtggg    91260
cattgtggga gatttcagat ccacactagg aaagatgaca acacacaaat gtattattct    91320
caaaaacatg ctacatatta gtctatggac atttccttcg atgcccacca tcaatggaca    91380
ttagtcttac tttacagaca agcaactatg ccgcaaatgg tcaaatatac taccataggc    91440
caaagttcat aatggagtag taacttatca cagaattttt acttatttct accacaattt    91500
aaatgagatt caaaacttta atttgaatgt gttgttgatg cattgaagtc tgtagtggtt    91560
ctataaaaac catgaagcaa aattgccttt ggtcaaaggt gctctcccca agggcctctg    91620
catcacacat tgtccatttt gtttatctgc tccattgact actcagttca taccaagtca    91680
gaagcatttt tctgggttac agccttccag acacaactgc acacctagag cagacactta    91740
taaattctac agacttaaga gctctacagt agaacacaag tcagtgaaaa gaaagacatg    91800
ctcttgtcga aggtacacaa aaaacatggt cttagactgc ttcacagtac ttactttttc    91860
actcaaaaca aaacaaaaac aaaaacaaaa gaaacaaaaa aatctttgag agtgctctaa    91920
tcctgcccat caaggctact ggaagaatgc tgcctactgg ttggctcagc ttgctttctt    91980
aaatcaccta ccatcggggt agtgccatcc acagagctct ggaccctccc acatcaaata    92040
ttcatcaaaa taatgccaca taggcatacc aatctgacac aggtaactca gttgcggttc    92100
cctcttccca ggtaacacta ctttgtgtca agttgacaaa aaaataaaaa ataaaaacat    92160
aagtgcagca gctaagaaag caaccatttc aacagagcac agaacccaaa ctgagaataa    92220
aatctcacca tggagctcaa ctgtcagagg aagccatcaa ataagcagca gccatttgca    92280
tatagcatat acctccaaaa cacacagaaa tgagttcaaa gctgaaaaga cagtaaataa    92340
tcactaataa aatcaaatga aaggacatca agtatcttgt tgtgacacac ccttctcgta    92400
aaacttttca ttccttaaag ttttctgaag ctatgtacgt tttacttaag aatataaggt    92460
ttagggctga agaaatggct caacaatcaa gagagttgta cttctcttac taaggacgtg    92520
agtttgggtc tcagcatcca catctcgtgg ctcacaagtg cctgtctgtc tagctctaag    92580
aggatctgat acctctggta tcagtgagca ccctctgctta catgcacata ctcacagaca    92640
gacacacaga catataactt aaaataagaa acaagtattt aaaaacatat aaagcttaaa    92700
gaaaacaaag tactatttta tatcaccctg gtatttacat tagaagttag actttgtaaa    92760
tcatgcttta aactcagagt tcatttacaa tggaccaatg gtttccgttt tccatatttt    92820
tatactatgt gtaaagaagc acttctgccc cacaaagtga tcctgcatat ttagtgttgc    92880
```

-continued

```
cttctgcagt aggcatgtgg acatgagatg agtttagcag atcatttact tttacaacag   92940
aaatccttcc agtatccatg ttgcctcctc atttaagaaa agaaaatgtt tttaaaactg   93000
ggaaccagca attgaataaa taattacaaa ccaggcctgc tttaggtaga gggcttatca   93060
tgtaattata atgatgatca tttacaagta tccaaaatga ctccagcatt ttaaagagct   93120
aagcagagtt attttttaaaa tcaaacatat gtgctttttc tgtttatgtc tttggaaaga   93180
acattctgca taatgaaaaa cacgaccaaa ttttcacag tacatcacta taaaccctgt   93240
aattgacttt tggggttggt ttactctata tctattttg accacgtaga aaacagcaat   93300
gatgtggtga aaagcccaaa atgcaagtcc catcgcaggc tgagactcca ctctgattag   93360
tacaaaagta tcatgtttgt gctgggaagt gtgcccatcc taagagaaag ttctgctgca   93420
caagaatctc cctttcaaa aatcacatgc agggaaagca gatcactggt gcccgtcctg   93480
ggcctgggtg ggaacctgca gattttaca ctgatctcct ccatgaaagg cactctaaca   93540
ctgatgctca aaactgaggt ttactccagt tcatctgatg gaagaaaagt gggtctacaa   93600
ttcaacgata tatactaacc tttgaactat gatttaacat tgaataatta tcctcttcat   93660
gtcttaacac agattaaata aagaatttaa tctccttcca aaagctttga acgcagttaa   93720
ctctggcaaa actaatttac tattcctaac aaaaccactg tttttcttca ttgaaaaaaa   93780
aagtctaaaa tacctctgaa tgagcactgc tggcttcatc agtaaaattt acatattagc   93840
aagtaaaata aacgaaaaga gcaagatgtt gtgtggttta aaaatcagcc ttgcaacacc   93900
taccacagat ttatctcctg tgagttgact caaccattcc ttttctcag taaataaact   93960 aagttccgcg cagggtactg ccgagagttt tcaggggcc aagtgaaaga atatgtttca   94020
gatgaaaact tccacattga cagcctgccc actctcggta gttattaaag ggtccacagc   94080
actctatgaa ttagttgtgg tttacctaaa taatcatggc cagaattacc aaggtcactg   94140
cacacttgga atactatcta aaatcggtgc acctttaaag ccattactcc tctgaaaatc   94200
taagctgaag tagcaacttt cagccagctg ttgattaaaa ggtacgtcat atttaaatta   94260
caataaaatt tataagtcaa ctattaacat ttggtctcat aagagcagct aatcatcctt   94320
taatgcaagt aataaaacag tatgtggcct acctatattc aacatcacct ctaaacaaaa   94380
gaattcttac taagccaatg aaatgaaaca tcacaatctg atgtctactc tcaaagtaaa   94440
gtaagactga atacagtagc tgagtttcag aagtcagcac aaaggagtca gtctaggaa   94500 gaggctaggg atgcatctca gccacagctt cagctctagt ctgtagaaaa cgtctctacg   94560
cagttaaagt cgaccacagt acctcaccta gaccactcag tgagttgggt gctgtttaca   94620
acaacataaa accaaagcta agaacaagaa gtattttaa aaaatagatt caaataagta   94680
ggcatttaaa caataagtcc ttttataagg aattgagtgt aatcttttca caaattacaa   94740
attatttgta catcaatgtc ttcttaaaat ccactcattt aatagagaaa taagaataag   94800
aaaaggataa aactaacttt aaaaacagaa accatactca tcatgagcaa gtcagtttgt   94860
tatttatatc atagatgtta ttgatcttat tcccttataa tccacatata aaccccaccc   94920
tccactattt tacaggtcag tatctataaa agtaatgtaa tttcaaacat cttcacacag   94980
caataaggta gctaagaatg tgatccagat ctacaaagct ctatagaatt gccatcaatt   95040
ttacatgttt aaaatagaat ttgctttcca tcaatgcttc ttaagatagt taactatacc   95100
agacttattg aagcagtcac tctggatcca gcaaatcatt tgagttctta catcctgttc   95160
ccaccacctt tatattgcag gaagcgctca atttcaagaa taacagcaca aattccacag   95220
```

```
gcaaagaagt tattgggatg tatatggcca tatatttgcc aaggtttcaa gggaaaaaca   95280
agagattcag gcaaataaac agaacactag atgacctgca attaaaagtt gtatttgaag   95340
gtgcctctgc ttctttgcac acttcaggtt tattcagagt cagaacgtaa agcaagtctt   95400
acagcatcag cacagtgctc cccagagcgt ggagtaattg acagctcagg aaagagagca   95460
gtgctgcccg tggccagtga ctgcaacagg ggactcctga ctgcacactg ctttggggtc   95520
ctcttccttt cagacttgcc gccactttct ccattctctt catcagtttg tctttcctcc   95580
tccgtcttcc tattctcacc tcctctcctg cttcacactg atccatgtaa aagaactagt   95640
gtgatactaa ccgggaagga ccagtcccac ccaatgtgtg cttgacagct ggaaacccta   95700
tgacttaggg aaccgcatcc tggcactttg cagagccttt ttgctttaaa aagattttaa   95760
ctattaaaat ctgccttgga tcatagagag gaatagagtt ttaaaagata gagacagaat   95820
caaagggcca tggaaatgca cagaagactc caggtgtgct gcacaaagac aaagcaagct   95880
cttggactcc caacagcctc cagttcagta agacataaa cacagctcct tctctccagc   95940
agacgcacct ttcctcagca gacaattgtg accactacac aaaagcacca tggtgatgtc   96000
agagttttat tacgaattat aattaatttt ctattaaaaa gaagagattt catataaata   96060
ctccattaag aaagataata caacgtagtt atcagtttta ttaaatgtct tattaccctg   96120
tttaaatatt ttctatccaa cataaagtaa aactcaaacc catatcaagc aagcaaatct   96180
gacttactga aaatgcttcc tgatctttcg gtcattgcca ttaccatgaa catagcgaca   96240
gtccacgaga agtcggaatc tattaacact gcatcaacta ctagaaatag aattgattaa   96300
tcacaactca attactactt atagttatta cttattatta cttataaagg tataaagttg   96360
tactttcaga aaagtcttaa actcttctat ataaagtgtc ttcacagact tttaacttgt   96420
ggtaaaaaaa aaaaaaaaaa aaaaaaaaaa aagtgggtaa aatataccag ccaacttggg   96480
attttgctca ctaagttttt caggaaaact gacctcatgg taaggatgaa ggaagaaatg   96540
agctcctcat tagtgaagga cattacaatt tcctcagcat atccggcctt cctcttagca   96600
cagcccatca tctctggtgg tctggataac cttttgcagt gtatctcaga acacaagcaa   96660
acaaatggta cctttactgt aatagatctc gtgaggaagg ttttacataa gtaactgcca   96720
gctgcacaat ccgtagtaca gcaaccagga cagaagctct gaagagacag tgacaagagt   96780
tagaccactg acaggacccc atcaactgtt tgagtttcca tacttgttaa gccccacact   96840
ggccatcgaa ggctcaattt caaagaggat accttcttaa gcatgaaata ccttatctaa   96900
cagtaggtca gggatagata ccgtgagtaa ctgaaggaca gtgttataac tgggacagca   96960
ggacagacag ggaaggaagg cactggtaaa agtctgggag tgaagaagtt aactggtttg   97020
gtagctaggg aagagactgt gcacttgagt gatgaagatg aagcctgaga agagtgtatg   97080
tacagaaaca ccaaaatgat ctaaattacg ataaagacat tttgaacaaa tatacattat   97140
tacatttcaa ttaagccatt actcatgctg tgttatgagt ggcatttgtc tggatgtctg   97200
gcacgagggt gaggtggctc atgcagtgtt tatctctctg cctgtgctcc cttcctctct   97260
ttaataagca ggtggttttg aagaagaaga aaaaatagg atcaggaaca aaggtcactg   97320
aaaaagaaac ataggtattc ctctctctag tgcttcgtta ctctatcttt ccgtttctgc   97380
ttgtgagatt cggtctgtag tgccagttct tccttcttga atctagaatc agaagatggg   97440
gatgaggatg tcctaagagc agaatgctct taagtacagt tatatactta atacctgaca   97500
gtcaaatgca cattcacttt ttaaatctgt aaagagtatt tgttgccatc taatgtggtt   97560
gcctcgtgga gttttgatga ggtataaatg aacaattaaa tcagatatga atataaatat   97620
```

```
ttaatgtaga aactatatag acgttgtcaa tataagctag agagctccag atatccacct   97680
ctgtgactct tctctttagc tttccagact ccagtacata acccacccac gttgctcctc   97740
caccacccct agtaaagtta acacagatca gaacatggga tcagtggcca cctgacctat   97800
acccagtgca tgaaggttca aagtctgaca actccaaggc agtctttcca aacacctttc   97860
tccattgtgc ccatcactaa gagactcctg tatggtctga atgaataaag cacctggtct   97920
caaattctgg tgcattatgc tggaaaccat actgggacta tccaacaagc cctgctagat   97980
tttgacatcc ttgagaaaga tagccaccac cattaacaaa cctttgcata tagcaaaaac   98040
gggagggata ggaaatgtca aactaaatgg caaaagattc agtgccaagg atgggacaag   98100
taaattcccc caaagtatgt gtcccatata tttcccactg aaattgatcc agtccccaaa   98160
agcagacatt gtggaacatg gaaggatgct cacaggctgt ttctctaaat gagtaaattc   98220
ttcacctcgt cagaaagtac cacctaccct cagagtagag gcatttccag aatagacagg   98280
ctctctctcc tagttctatt gaacatcaat ccttatacaa gtctttctct gcttctcttc   98340
ctactaagca catctctatt cccccttaag ctcaaagttc ctggcagaat tccatatcct   98400
gtgtaaagag atttaggctt agattccaga tattactatg ttttccatag gaaatataaa   98460
ttagtaatat tcaaacaggg actggcccct aatctattca gatatactgg ccttcatata   98520
aacacaagtc acactaagca tgctgagtgc taactgcagc cattcaaatg ctgtatcatc   98580
ttctattttg taatacacaa aaataagtgg gtggggatgt gtaatttcaa atatttgggc   98640
aaagaaaaag ctctctatga ctaaaacaag atggcaaatg acttcatctt cttttggaaa   98700
ataacctcat tatgacagct tgctaaccaa cttgtttcca aagccactaa cagtagccta   98760
taaagtcaca gctgctactg ttgcaaacta ctaaatgttg atttcattct caatgtcatt   98820
ttgaaagaac taatgagttc tttaaagcac tacaatgtat gacgaagaaa ttatactgag   98880
aagactacaa tgagaatttt atgtcttgct cagtaaagat gattatatgg gatgacagac   98940
accagactga aaaggcatga ctgtgaaatt cctagacaac aggcacacgt attcagagag   99000
gctagaagtc attagagagt aagacagtca acaagtgcct attctgatct tcaagccatg   99060
gaaatgtgac aggctacgtg caagttctga gagccaccTT atttcaaaag gaatgttatt   99120
tataggaatg ataaaaataa ctcataaaat ttgaaactct cagatcccaa gtatagtgga   99180
aaagaactgt caatttaaac tgtgcttaat tcacaattaa attttgtttt ttctttgcac   99240
ttgttatcat atattaaaac tgctttgaaa tattggccaa aattaactga ttaaaccaaa   99300
ttacagtaca accatggaaa ggaatactat gtagccatta aacaagacat tagaaagaat   99360
acagtactca taaatattc atgatattta atgaaaaatt tttgagaaat catttaagtc   99420
tcatgttatg tgtgacagaa aaagatacat atacaaaagt tttcacagta ttgaactcca   99480
tactcatact taactgtcta aatgatattt caacttgaac atgtaagaga tgcatcaaag   99540
tttgcctggg ggaaccagac tattgatgag cctgctctcc tggggctac tttgctgacc    99600
ttcttcagtt gtgtaggcgg cggcttcaca tccttcttgc tgaccttcag ttgtgtaggt   99660
ggcaggcttc acatcctttt gactccttct ctccttgcaa agctcacact gaaccactca   99720
gcagggtctc tggcttccac cttttaaatg ctctcagatt ctaaccatgt agctacttct   99780
ttcagttact ctcatggacc gagtcacttg aatccctac tgcctccatt ctgacagagt    99840
ccccagtact cccagtgact tgctatagtc tgctttcaac agtgatgaac cttgactcat   99900
gtcactgctt tgcttacttt actagcctgg aatgcacacc ttatgaagat gttcggaatc   99960
```

```
ctgcataaca aactccaggg catctttcgt ctcattttca catgcccaca gcctattact   100020
aaccacacta cgccaagata tttaaaaagt agccaactga gttgatgcac agattactgt   100080
cctaacagtg gaggactctg aagtaaccta agcaaagcac aatcttgggt tactgagcag   100140
caccatggct tcctgcctcc tccatactaa attgatgctc ttcttctctg acgtacctaa   100200
catcagtccc ttgcttcccc tggaaccact gtgtgcatct gtaggtgtat gtaagtgcca   100260
tggcacatgt ggaagtcaga ggaaacttgg tacttctctc catctaccac ggaggtcctg   100320
gggatgactg tcacgcttgg cagcaagtgc ctttactcat cagccctatc tttttttatt   100380
ttactccaat tttataaagg ctcatgtttg agtttctatt acaacattcc aggaacatac   100440
cagagattaa agtaaagatt caaaaccggg ttttttgttt tgttttgttt ttgtttttct   100500
gtttggttgg ggtttgttgt tgttgttgct gctgctgttt tgttgctgtt ttctgggaca   100560
ggatttcatt atgtagctaa ggctggtctg aactcacta  tgtaacccag attagacata   100620
aaatttacag aaatcctcct ggtctcagcc tgctgagtac tgagattggt atgagccatc   100680
atgcatggat ggctctatgg gctttttatt attattacga ttatctattg tgtgtatgta   100740
catgtatatg tgcatggatt agtggtatga cacatatgtg gaggtcagag gaaaatatgt   100800
gaaagttagt cctctctatc atgtgggttg tgggcatcga attcaggtta tgctgaatgc   100860
caagcatctt tcccagctga gccacctcct agtctgcatc acagtttgtc agaatgcaat   100920
cttacttcaa ggcatgtctt agaaaaaact aaggtaaaat ggatgtatga tttaagtctg   100980
atttcagttt aaacatataa aagcatctcc acagtgcttt atgatattcc aaatgtttta   101040
tctgccaagt tatttgactt tcaaagtaat cgtgggatga gttcaatttc aagcagaagt   101100
gtgtgcacac tcatatgaac gaccaaaaag taagggttgg caagcatgta gagaagtggg   101160
atccaagtga gacacaaaga ggatcccatc tcccccttggg cattagctgg ggtaaaatat   101220
ggttgaaagc attgttaaaa tcattttcct gtaaataaac aaaaatggtg gggcatagag   101280
cagcttgcct ctctcattac cagctactgg cctctcttgc ccctgtagta atgagaaaaa   101340
ggatggccaa acagccagac caccctcccg cctgcatcag ctgttttgag cacgccatga   101400
ttccttgatc cagctctata aaagactgca gctgccctcc ctggctcctg agaacacagg   101460
cctagctgtg actctttaaa gcagattata tcatcctttt tgcaactgta aaccatttgt   101520
actctaacca gagaaagact acttcccttg gtggactgac tatgattact agcaaggctg   101580
tgaatggtcc acagtaaatg attgtgatta gccaaagaag tatctgtgat tgatccaaac   101640
atctctttgg gggctacata agcaggctat aggaggacac ttgaggagca ctgctccgtg   101700
ctatctccct tggtattgca gcatcaggtc taataaagta gctatgtggt tttgttttgg   101760
ctactttcag taaaagcaac tgaattggaa tcaaagtaac aacagtgaga acaggagaga   101820
gatggtcaag aatcaaggta aggaagcagt acctaggaac caacacacca cacaggcact   101880
gtgcacatgt ggtatgccca cccagtcagt gcttgtgacc tgcagattcc atgggtgtgg   101940
atgaatctga cagtttctgg agccatgcaa acccaacact gtcctgtacc tggtacctct   102000
gatcctgaca ttggacttct gggtttggca agaaaagt tctggtggca ttggaggtac   102060
cccaaaagtt catacccagc ttctaatacc tggcatggag ctcccaaaca cccctacttg   102120
tgccaagccc cagggcccag cttcttaaat gtaaacacca gtcaacaact gcttgtcagt   102180
tgaagcaaca gcagggtggc agtcttggca tagctgcttg acagatgaaa aggtggtacc   102240
ccacccacag gcatcactca taggcaggca tctactctga gattcccatc tagcagtgca   102300
atccttcttt cagtgtgtgg ggggggatgt ctgaggggg  actaatgcct gcacctaaat   102360
```

```
gttcccatcc acgcctgggg ccatacctga agagtcttcc agatgccct gctcctgaat 102420 gctgttatag gcaggcagcc taagtcactc tggcagtagc cactaataac ataaggagaa 102480
gctgaagagt tcaaatgcag ccaggccaag aagaaagtc tgaacagagg agaggatagt 102540
agagagctgt taaatgctga ggagcctgag agaagaacct gaaggccctg acaccaatg 102600 agttccacag agctggcaag gcattagagc caagtgtctc acaccttcc ccgagagctg 102660 caaccctggc tgctgtcaac ggtcatcata cctgagtgtt gcacagggct gttacacaga 102720
ggcaccattt gctgatgctt tcacctgcct actgcctcga ctgctgctgt caaaccccag 102780
ggaaggaaac ctgcaagatg ccagcatctg gaagtcttct ttcctagcca gatacaggga 102840
aaaggccctc aaccagctgg agggtgacca tagcacactg ctagtagact tgtaatgtga 102900
atcagcagct ttggaaaata gcttcagcct cccaacaaga ttcaacacag aattattaca 102960
aacacagtaa ttccagtcta ggtattatca gtggctgaca tcattgacgg gtgtgttgct 103020
tgtttgtttg ggggttatca aggcaaatta aaagtggctg cttactgagt ttaggattat 103080
aatatggact ggtgagaaag ctctgattcc acagtttta tacttaaagc tttgtgctag 103140
ggtgtcttga tctaatcaaa tacagtggta tccagcacaa agcaagcagc aaacattctg 103200
aaaacaagtc ctgacaacca cccaccctac gccaacattt agttagtgct gggttagtaa 103260
gacacaggct gcaagacttt gacaagtggc tattgaggag gaaatgtttt cacctttaa 103320 aggaaacttg aaaaaatatt tattcagttt tttaaaaaag gaaggaaaat ctaattcagc 103380
aagaatcagt tctactgtta ccagtgtgct tagaagaaat ggctggtaat gtcttggagg 103440
atactggggg ggggggggaga atggggaggt ctggtaattt atcttactaa gagtccactg 103500
gtaccccaaa aagaaaaggt tctgaaatta atgaatattt gaacaatatt gcaaacatac 103560
ttgacctcaa tgaattacac actttaaatg tcaacttta tactaccata aaaatgtgta 103620
cttcttgata tagctgtctc ctgagaggct ctgccagtgc ctgacaaata cataggtaga 103680
tctcacagcc atccactgga cggagcacag ggtcccaaat gaaggagctg cagaaaagac 103740
ccaaggagct gaaggggttt gtagccccat aggaggaaca acaatatgaa ctaaccagta 103800
ccttccctag gactaaaacca ttaatcaaag aaaacacatg gtgggactca tggctccagc 103860
tgcatatgta gcagaggatg gccttgtcac tcatcaatgg gaggaaaggc ccttggtcct 103920
gtgaaggttc tatgccccag taaaggggaa tgccagggcc aggaagtggg aatgggtggg 103980
ttggtgagca gggggagggg agaggggata ggggattttt ggagggggaaa ctaggaaagg 104040 ggataacata tgaaatgtaa ataagaaaa tatctaataa aaatgtgtac ttaataataa 104100
tttgaaaagt aggaggagtt aagttcctgg acacaaaat ctaagacaac aaatctatac 104160
atgactgagg gagtatttttt tttttttaagt atagaataga gtttatttag ggcaatgaga 104220
gaggagttaa gaggatagta gtggcaggga aaggcagaga gagggagaga atagagaagt 104280
agaggctggc catgaacacg tggagttagg ggggaaggga agtagggaag ggagggagga 104340
agtgactagc ccaagagggc aagagagaaa caagagcaag tcatcatatc ttgaaacaag 104400
tccaaccctg tatcccatac atcagccagt cacccaccac cctggggcaa gtggtaactg 104460
aatcccacag caggcctatg gctatggtaa gaacagacct gtgagccatc agctctatag 104520
gtgagaagta gggagctttg tcatcccagt gggctgtgca actgcctact actaagggaa 104580
gaaaatgctc caatccccta ggatttcagg gtgacaatgg aacaggaagt ctcccccatt 104640
tgaccaatgc acagatttca gctaaaaaaa cacagtatgg tcatcattgc cctccagttt 104700
```

```
tgtccatgtt cactcctcta tccttgactt aggctcatga tttccttctg ttttgagact    104760 ttcttttttgg agatgttttt ggatggctgg tttgaagaag agcatggatg gtttccttca    104820
ctctttcaca aacaatttct gccatcatct ctcttccatg ccaaagccct agtttatgta    104880
ataaagtgac aaagtgtgac aaaccgttag gtgtgtgtac atgcatgtac acatacacac    104940
acacacacac acacacagag agagagagag agagagagag agagagagag agagagagac    105000
ttgctcagtc tttacactgt cattactttg aaaacaacca cagactggct tacaactatc    105060
tgtaactcca gtcccagaga atttgacacc ctcttcgggc ctccttggga agcagtacac    105120
agacacacat gcaggcaaaa cacccatata cataaattta aataataat aataatgtct    105180 ctgtctctgg tgaggctctg ccagtgccta gcaaatacag atgctcacag tcatctatag    105240
gatggaacac agggccccca atcgaggagc tagagaaagt acccaaggag ctgaaggggt    105300
ctgcaaccct ataggtagaa caacaatatg aactaaccag taccccggga gctcgtgtct    105360
ctagctgcat atgtagcaga agatagccta gttggccatc attgggaaga gaggcccctt    105420
ggtcttgcaa actttatatc ccccagtgca gggaaacgcc agggcaagaa gtgggagtg    105480 ggtgggtagg ggatcagggc aggggaaggg tatagggac tttcgggata gcatttgaaa    105540
tgtaaatgaa gaaaatatcc gataaaaaat tgaaaaaaaa gaaatcctaa atattgcaac    105600
aaagatatag acaagtaagc aaaactttaa aacttaaaaa tcatgacact aagagatgcc    105660 aattttaaa agatgaacaa agccttagcc aaactaagaa aaataaaaaa aggagcaata    105720
ttcacagcag ccttatttat aatagccaga agctggaaag aacccagatg tccctcagca    105780
gaggaatgga tacagaaaat gtggtacatt tacacaaaga agtactactc agctattaaa    105840
aacaatgact ttatgaaact cgcaggcaaa tggatggagc tagaaaatat catcctgagt    105900
gaggtcataa aaggacacag atggtgtatg cactcactga taagcagata ttagcccaga    105960
agctcagaat acccacgata caaaccacaa accatatgca gcttaagaag gagaaagacc    106020
aaagtgtaga tgcttcaatc ctacacagaa caggaacaa aataatcgca ggaggtagag    106080
ggagagaggg acctggaagg gagagaagag ggggaggaaa aaaggggggc cagaaacagg    106140
tattggaagg ggcaggagag aagtaaagag gcccagaaaa ttgaatagaa acacttagca    106200
ttggaggata tggaactggg gttagccact agaaagtcct agctccaggg aagcgggagg    106260
ctaccaggac acaatgggga tgactttaga agaaataccc aagagaaggg agatacaacc    106320
tatagaaacc acctccagtg gacaggtaca gcccccagtt gagggatggg gccacccaag    106380
catctcaaaa atttttaatgc agaaatgttc ctgtccaaag gaaagaaagg gacaaaaaac    106440
ggaacagaga ctgaaggaaa ggccatcaag agatcacccc acatagggat ccatcccatc    106500
tgcaaacact aaaccccccac actactgctg actccaagaa gcgcttgctg acagaagcct    106560
ggtatggctg ttccctgaga ggttctacca gcacctgacc agtacagatg caggcactca    106620
cagccaacca tcagactgag cccagggacc ccttcagaga aaggtctaag ggggctgaag    106680
gggattgcaa ccccgtaaga aaaacaatat caactaacta gaccacccag agctccaagg    106740
aactaaacca ccaaccaaag agtatacatg gagggagcca ggactccaga tatctatgta    106800
gtagagggtg gccttatcta acatcaatgg gaggggaggg agacttgatg ccccatcgta    106860
gggggatgct agagcagtga ggctggagtg ggtgagggg tggaagaaca ccctcataga    106920
ggcaaagagg aggggggaaga gtcgggatgg gattagggg ttgtagcaag taaccaggat    106980
gagggatatc atttgaaatg taaacaaaat gattaataaa aataaagttt aaaaaaagaa    107040
gaagaaaaga gagagagaga aagctctaac aaagtgacat aaagagacat tgccattggc    107100
```

```
actatacaga cacacaaaat gacacaagaa gactaaaaac gatcacattt ctagacacag   107160
cctactcatt gtcaatcatg aaggtataca aaatcaaaac agaccaataa tatggagact   107220
gattcagtaa taaatggccc ctatcaaaga aaagtccagg acttgatggc ttcactccgg   107280
agttccacca aattcaaaat aataaaccaa tcctcctaca aagatttaaa gggaggaggg   107340
gaaggaagaa aggaaagaag ggagtgaaag aaagggaagg gggagggaga gagggagagg   107400
aatgagaaca gaagaagaag gaaaaagtat attaccttct tataagacca cacttactgt   107460
gccacttaac aagggcataa aattatagcc aaatatctga aaaaaaatga tgcaaaatcc   107520
tcagcaaaac ataagcaaac caaattgagc agcagattaa aaggacctct cacctagata   107580
ataaccaagt acaacttatc actggagtgc acggatgggg tagcatacaa gtcagtgtga   107640
cacagcaaca aaaaggacgc ccatatgaac atgtcaaaac gctgtgcctt ttcacagcag   107700
agaatcctag gaaaagtaag tgtgtcaaaa cgctgtgcct tttcacagca gagaatccta   107760
ggaaaagtaa gtgtaggcag gatatagctc aacaaactag aggccaccat atagaacaaa   107820
cccatagtta acaccagact taacactgaa aaaaaacatt ttccctctaa gtaaacatga   107880
aaggaatgtt ttcctttata aaaacaggat tccaactctc accacctctt aaacatagta   107940
ctgaaagtcc cagtcagaac acttagtagg tgaggagaaa aaaaggggg aaaaaaaaa   108000 gacatctaag acagacagga agaaggtaaa ctcttttttgt taaaggtgtc atgaacctac   108060
ttataatgat ataaagatcc cacttctgaa aagcaattag tactaaccca ggtgtggtgg   108120
cacatgccag ttatgccatc tcctagaagg tggaggcagg agaataatat gagctaaaag   108180
ccatgtatcc ttagcaacaa agaaagtttg agacaaactt ggctacatga tagtttgata   108240
gacttaacta tcccaaagga aacaagaagt aataacacga caaatttatg actaagaaac   108300
aaatttggtg aagttgcaga acacgattca tataaaagcc agtagaattt aaccatgggc   108360
tcactggaag tctgtaatca gtgagtacag agtggttagc attgcctggt gcagaggtct   108420
acatacacac agactgcagc tcaaggtggg gaagcctcgt gtcctcaaga agaggtctca   108480
agagagagcc tcactggagg aaagtgaaca taagggcaca agaggaaatt gtcatgagta   108540
aagacagcat ctcacatgcc tgccttagat tgtctgacac aacacactga ggcttcatca   108600
aaaagttaca agtattctaa aggtcaaatt aaaaaaaaaa aacaaaacaa caacaacaaa   108660
aaaaaaactt gagaaactct gtctcgaaaa aaaatctgcc agacactgag ctaccaacca   108720
ggcagcatac acaagctggt ccaaggcccc caacatatat aaagcattgg actgcctggt   108780
ctggcctcag taggagaaaa tgtgccgaat ccttgagaga cttggggccc cagagaaggg   108840
ggaggcctgg ggggggggga gacaagggaa ggagtgatga gatgaagaac tataggaagg   108900
gggacctgga gggggcaac atatggattg taaataaaaa aataaaaaat aaataaaatc   108960
tgaaaagaca tagtaaacat caagggccaa aaaggcacag tgtaagtttt gaatccctta   109020
cagtagaaat ttaaaataac tctgaacgtc gatacactaa gggcactgac tgaaagcagc   109080
agccatgaag taggagtgta agcatgcaaa aggccctgag aaaagcaaaa ggaagtgccg   109140
aggaaggaag gagttccaaa gactcaagcc acttaaaaga aaggaagact ttggcagact   109200
caatgggagc ctggaaatgg aagaggaaag aatcaccgag ctgagaaaat gtcagaggaa   109260
acttccacag ctgagaaaaa aatgaaaaag aaaatatctg agaagcctgg aaaaagtatt   109320
ccccttaaaa acatatcatc cacaaagttg atgtaagcaa gaataaaagg aaaagggaa   109380 gaatatttaa agtaacagtg gctcagaatc ttccacatgt aataagagaa atggagccac   109440
```

```
agttccagga aggccaaaag acacacacac acacacacac acacacacac atacacaaac    109500
tataaataga cttcaggcta catttgtaca cggcttaaag ataagctttt taaaacttat    109560 tttttttgagg atttcattag tgtaagagca tctcagactg tagttatcaa atccagaggg   109620
catatcttac agcacatcag gattatatgg gtcagcctgt tattcatctt gggctacaaa    109680
tgtatataac atgatattcc atgaaataca attagaggat tttagcacaa ggttaaacat    109740
tcatatatat aaacatctaa aaggagacag tatcattaaa aaacttaccc agtctttcta    109800
tagaagcatt aagaactaat gttgtcctaa ttttcttctc tgttgctagg ataaaacact    109860
gaccaaacgc aacttggggg aggaaaggtt tatttaggtt tacaaattac agactgtcat    109920
ttaaggaagc cagggcagga actccaaaca agaaactagc ttgctctctc tagatttctc    109980
agttactttc caaagtgtgg tggtccctcc tgtatcatca atcaatataa ttcccccaca    110040 gacatacccca caggtcaatc tgatctggga aatccctcaa ctgagactcc ctcttcactg   110100
gtgatgcttc catgtgtcaa gctgacaatg aaatctatcc agtgcagaca ccctggtgca    110160
gatacttact gtgaagtagc taagaggact gaaacttctc tgagagagct agtgagtgct    110220
gagccatagt gaaggcctag gagattattg tgcactaagc agacattatt aacactatgt    110280
cacatgtttt cacaaataag tactaggcaa tatttcaaga agatgtgaaa tcaattcact    110340
gcaatctgtt ccagataata caggcagaaa aaaaaaaaat acttcccacc tcatgctata    110400
atgccaacac tacccaaaca ccaaaaccaa agaaattcaa ataatgagaa ctgtagaacg    110460
gtaccttcca agaataaaga tgtaaatatc accaatacag cattagcaaa tcaagttcaa    110520
taatgtctaa aaaagtatat aacccaacca agtgcaactt cttccagata tgcaaggctt    110580
ctttcaatat tcaaaatgtt gagtctcctg atctaagcca tccaataaaa taggctccaa    110640
tatcctatta agacatacag gaaaataatt tgatatgttc caacaccatt cagactgaaa    110700
tcttttcaat aaattaaagg acgataagga gagaggtaaa agaaagggac tgaacagaag    110760
gagaggggag aggaggggaa gggaggggag tggagagggg acaggaaggg aatgaacagg    110820
aagagagaag aggaggggat gcagcagtat atgaaactga ggcagcagat gctttgcctt    110880
tcaaaccaat ctgacctggt agctcaggca ggctttccaa ctgggaacac tgaggcgggt    110940
agatcctaac tttgcaacaa agtaatggag tttcttagta tggttttctg tctagaagac    111000
tggacagaag gtaagagagt cccccccaaag actccttttca ggcaccatct acgcacagct    111060
tgtattggta tctggaggtg ttacaactga tgaacccaac caatatggac acatacagta    111120
ctgttcatta gaactcttag ggaaaaaagc ctttgtgtta cacagttctg tagatttgc     111180 caataaataa tgtcatgtgc ccaacactgg ctccattgtg cagagcagtt ttactgtgtg    111240
gcccatgtgc caccagttca atcctcgagc ctaacagctt cccctccttt ccttttactg    111300
atttatttct cctaaatgta cacaactatt tattttcct gccagtcttc tgagcttcct     111360
ctgctgtttt ggcttttttc agaacgtcct atagatggat tctctcagtt acgcacattc    111420
atttgtttca tttgtctttc attaaactgt tgaatgctgc aataagatat atactcaaaa    111480
atgaataaac tgtcagaaat gtacaatctt taggagttcc tgactttta aaatgatgaa     111540 cttaaaaact aaatggacga gagtctcgag gacttaaaac agtacccata gagcaaagta    111600
tataaatctg cactcagtga tttattatta agtgacatac cattcagcaa cattttttt     111660 ccttctaagt agatgttgga actttaaatg tcaaaactct tttattagtt ttgggcgcat    111720
atcttcccta tgtgatttat taaatatctt ctaatcactt taagtgtgat taacagtgat    111780
cttcctgcct tctaatttac tgggttattt caccacaatg ataccttttg tgtctatgta    111840
```

```
ttgactttt    aatttttttca   cataatataa    tttgatcata   ttttcttttc    ccaacacaat    111900
tgtccaagag   ccttcccatc    tccctaccca    cccaacttca   tgttttgtat    tggtatgata    111960
tttttgtctt   ttgcagtttt    tgtttgcttg    cctgtctgtt   ttgatttggg    atgctgtttt    112020
ttgttttgag   agaaagaaca    gtgattgctt    tttaaactgc   attgtaagtg    agcaatgtga    112080
ccttccatgg   aaagaccctg    gaggatgctg    ttgggggttc   tgagcacttc    cttgtgtcct    112140
gccaaacaag   ctatcttaat    cactacttgc    gatgacttaa   gtgtgtcatc    tcactaaatg    112200
aaggtctgag   aagtggttca    gccattagga    atacagcctg   ctgttacaga    gaggacctga    112260
gttcagttcc   agtacccatt    tcagacagct    cctaaccccc   tataagccta    gctccactct    112320
gttctctgaa   ctcaagaggc    atcttcactc    acatgtacat   attcttgtgt    ctccgtctta    112380
cacttacaca   cgcacacacc    atacatacat    acatacatac   atacatacat    acatacatac    112440
atacacacac   acacaaataa    tattgggaaa    aaataactga   taataattaa    tagtatttca    112500
attaaacatt   tttgcttggg    cattaaactg    aatgaattct   caatgaataa    tacttctatg    112560
ggtaaaaaat   acaatatttt    caactttact    tttataatta   ttcctcaact    attccattat    112620
gattttatta   atgataatga    acaactaaag    taaatttcaa   taggactgct    tctagaaat     112680
ataatgtata   aatgttgcta    gtcaaaataa    tctatttgta   ttccaacctc    ataccta aaa    112740
agttttctaa   ggtacttcac    aaatatgtac    aacataataa   ttatatgatt    aatagaaatt    112800
tactacaaag   tcattagctg    ggccaattca    acagatggtt   ataaagcact    ctcgacacag    112860
ggcttcacat   ggcagtaaac    ttttaataaa    gattttgtaa   acagtctaag    aataataaac    112920
ttgatcatga   ctacaactca    ttcttgcctc    ttctgtagtt   ggtatccact    agaccacata    112980
gctctctagg   aataacagta    caggtgcagg    agccagagcc   tggtttgtaa    ataaaatttt    113040
agtggaatgc   agacacatgt    attcatttac    tggctgccag   ctttgagact    gcaaccagag    113100
ctgagttgct   gacagaaagt    ctacaacccc    taagccaaaa   atattttatta   ttatctgcct    113160
ctttatagaa   aaggtatgtt    agcccttggt    aaagtatcaa   ctagtatgac    acaaattcaa    113220
gattcaatac   ttctgattta    gacataggct    tctgatccct   agactaattc    ttgaaatgta    113280
agatttagaa   gtaataatat    aagctaacag    taattagttg   atgtgaatga    attgtttggc    113340
tttatttac    ctttattttt    attttacatg    tatggatgtt   atgtctgcat    gcatgtctgt    113400
ctaccacatg   tgtgtcttgt    ccccatagag    gccagaaggt   gttggatccc    tggaagtaag    113460
acttacagac   agctgtgagc    ctggttgtga    gtactgagaa   ccaaacccag    gtcctatgca    113520
aaagcagcaa   gtgctcagct    ctgtccatct    tcacgattgg   tttgaaccgg    ggtgggtcg     113580
gcctacacag   cacacactgg    ctttaacctc    tcatctgcat   gattggtttg    aaccggggtg    113640
gggtcggcct   acacagtgca    cactggcttt    aacctctcag   gtgctcctgc    ctcagcctcc    113700
acctgaacac   atgtacacta    ccatggctaa    aatggatgag   cttttaaggg    tatttttata    113760
cattctagaa   tgatccaact    taatggaaaa    tgacacacca   ttttctctac    aggtgtccag    113820
ccctgagttg   cttcactaca    aacttaagag    tttaaggtta   acgttataaa    ctaaaattat    113880
ttaattacta   attgtaaccc    aatctattcc    tgtaattttt   cccttctttt    ctcttctttt    113940
ttctttctt    ttctttccct    ttcctttcct    ttccttcttc   ttctttttt     tttttttttt    114000
tttcttttg    aggcagggtt    tctctgtgta    actctgacct   tcttcaaagt    ccctctgtag    114060
accaggctgg   ccttgaactc    agaaatctgc    atacctctgc   ctcaaattaa    aggcatgtgc    114120
caccactgcc   cagctaattt    attctttata    taccatacca   cacaaatgaa    ttttgtaact    114180
```

```
atttcagttt taaaactaat tcctaagtca tttaaacaca aatgcttcat gtttcagaat    114240
ccacttttta aggagaaaaa taaatgtcag tctatccctt tgaacagatc ccacaacaaa    114300
cactggcaca tttatgtgtg tatttgttcg agcatgctac tgacttcatt agtactcgat    114360
catacttcct ttaagagtaa ggactgttcc tatgtaagtc atcactattg tcgtcagctt    114420
gatgctcctg agtgtaactc actggtaccc agagtctaga tcagagtctc ctcaacgggt    114480
ctaaaaatgg cctgtgcagt tctcttcttt tccttttttt attttctttt ttctttcttt    114540
cttttctttt cttttttttt ttttcgtag caatcaatct aggttcacaa atatagctaa    114600
cctttgagaa ataaacacca gttctttttt aaacaatcta tttgtacatg gcatattctc    114660
atctctctat gaatttgttc actgaaaagc cagaagtggt tgccccagtc ttcatgctct    114720
ggaaggacat cagccacatg ggaaggagg tctgtgtctc tgtagattgt gttgggagaa    114780
cagagaggac acaaacttat cttgggaggt tagaattatt ataagtatat taagtatata    114840
cactaatcaa gtgaaaagtc ttgtgaatgt ttttaataca attattgcaa atagtaatta    114900
tgaacaagtc caaatatatc attttattaa agaaacact tttgcaaaag tctagagttc    114960
actaaaaatg tcagttttg aggcaccaac tttcttttaa gaaaacttgt aattttaatt    115020
atagttttga attttgaaca aagctttaat catcgcataa aagactggta gcctgcaaat    115080
tatgcctaca tacttagaaa ctgtcttctc cagaatttat ttcaatgctt ccaagctttt    115140
actaaattat aaaatttaca aacactgttt ataagtaata ttgttttta aatatacttt    115200 aagaaattgt aattttccta atattatcag aaaatacaaa tatttgaata tttctaattt    115260
ttaaaaatct ttaagttcaa atagagtaat ttttaactgc taaaacgtct gagaaattga    115320
gatttccagt gggaatactg tcaaatttgt aaaaacaaaa agatccgtat tccactgctt    115380
cattttcaat attctttctg tattgttaat tatgcctgaa ctcaccataa attatacata    115440
aagcttaata gagacctcaa tccacaatag cctttctga acccaatgag aaatctatac    115500
acggcaatga aactggcatg caaataaaag aactgtcaag acatgtactc ctgaaataac    115560
cctacaataa ctattctaaa ggctgtgtgt ggtctcaccc atagattttg gcaagatgca    115620
ctttctccga ccacagtcag attcatccaa aagcagtggc actggagagc ctctgtctca    115680
cctgtcaaac ttgagaaaca ttcttgcaaa gaccaccatg agtcggtgga gaaagccacg    115740
ctgcgacagc tgttcttgat aagcatcttc taaagtgggg aactccaaca attaagcaaa    115800
tcatccttaa aggagatata gacagcaaca cccaaaccta aatgctgaga tgttccaaaa    115860
tcaaacatgg gtaatccaga catcctgcaa tatgcagagg ggccattcat aagtgatact    115920
gacagtcttt ccttatcatc taatacaatc tcttaacatt atttgccaac ttaaaaacta    115980
tgtatccttt tttaatattt ggccaacctc ctttgtaaaa ccttaaaata catataaatt    116040
ttcaagtatt aaattcatca aaattgctga agtttgacaa ctaaaagctc aatagctgaa    116100
gacttataaa tgggaacatt aaatatatta aaatctgatc tttttatgat acattgatac    116160 attttttagcc acatcaaata aaagttcact tttgctttgc cttgacttca tcaagtttat    116220
ggacagaagg ggaacgtatg gatacaatgg tgagagagac aattactcag aaaagaagga    116280
tgcctcactg ggcttgactc aagttggggc cactacccaa caacaaatga taagtcagac    116340
ttttaaaaac tgcacctggc tctctacaaa gcttacataa gaccaacagt atctaaaatt    116400
gtaactttgt tgccttttgg gtgacaggct cctctaactc tgttcaatac aagaacaatt    116460
caagtgaaca agagagtggt ggcctatagg gccttttcca agacaaggga caccaattaa    116520
gttctcactt cagaataatg tcatctgcag taaagtccta aatcacaaag acaaaatgac    116580
```

```
aatcaaggtt cccatgtatt aggctgcccc acacttaccc cttactatgc aagcacaaaa    116640
gttagtttca cttttcccta gatacactaa cttgcatagc taggatatta tttttctttg    116700
gtttggtcag aagcatgttt gatataaatt ttattaagtg gtagtgtatg taacattgca    116760
ttgtgggtag tcgtttcctg ctttagtctg gccacatcct cagctgtcat acaagcatgt    116820
ttcccacatt ttgtgcaagt tgtcaccttt ttaaaaaaaa aaatcttaca aaaatgacac    116880
gaagatgaat tgctttaata attataagaa acataaaata ttttatacag atacattaca    116940
gaagtataga ccaccactct tcagagagca atgcctcaca atcagagtgc taatgtcata    117000
cataacaata tgcctaagta aaagagcata aaggaaaggg tcaagggaca gactggcaga    117060
aataaaacat tcctggacag agctgtcaat gatctctaag acctgaggta cagtacaccg    117120
cagtgtgcac aaagggctgc acttcagacc tgtgaggtgc tcattagtga gtgctacaat    117180
gtcgatattc ctcaatagaa ttttaagaaa gttctgaata tatagaaacg tgaaagcatg    117240 gaaaagaaa agtaaaaagc ctggagctgg agtagaaagg aaaagagag gaacagaaat    117300 gaaggaggag ggaccatagg aggggggtg tggagggggg aaggagggga aggaggaggg    117360
aggaggtaag atgtggacac taacttagga tgttctctct gggcatccaa tctgcatatt    117420
acatcacact tagaaagacc actgccagga gtacacacgc atgaaatcag taaacaagaa    117480
aactgtggta ctttttaaaa tattatctaa tttaaaacct catagccaag ttcaaaaatac    117540 tctgtactca caaccagata tgctttctta tatttgtaat ataaagcatg agagttaata    117600
tctcataatc ataattcaga atataaaact ataatgtttt gctaacacag aacaatttca    117660
cgtctttaat aaaagtttga taaatgctag gtgaacttaa acagctatgc attaaacctg    117720 aaaaagaaa aattacccac caatggaaaa cacaaattac taaatattaa gttaaaatga    117780
attaagaaag tccctagccc aagtctcata agcagactat tttaagccag agtgggcacc    117840
tagagtttgt tagtcatttt cttactgttt cgattaaaag aatagaaaag caacaactat    117900
acatccaaag gaatccttct ttagagcaca gatattggca cagtattggt aaagtaaggc    117960
tactgtgttc aagtgcaagc aggaaccgat caaataaaaa tcaattcaaa tggtaacatt    118020
gaagaaatgt atagtattta agatattact atactgttat attcacatgt cttgatattt    118080
taagaacttt gacaaatctg aaaaaattat taaattgtaa aaaaacaaga aagcaagaca    118140
ataatttcat gatttaagac tgatttcaaa tttaaagctg tatttcattg ttattgcatg    118200
aaaacacaga atttataggg cacaactaaa cttgttactt acttcacagc aattgctagc    118260
atatcctcca aaaggattac atttaaaaga tcttttaaaga gagtctgtgg tttccatttc    118320
tgaatataag catggtaaaa gtctctaaac aagcgctttc tgccatggct tttcaaagct    118380
ggctccctct ctccatctct agcagccatt tctaaggaaa tgcagtcagt atcaaagatg    118440
ttaccactca ccagtgttgt ctttaaattt ccaccacagt gtacaggttg ctcctgagtc    118500
tagtttgaat tgggaggggt acgtggacaa tgaatgcata aatttaacca caaatgtaac    118560
attcctgttt ttatcctgcc agaatgtgat ggactttaca caatacataa aggccacgtt    118620
cagcaacctc tactaaactc ttgtatcatg agatacagac cataactcac agacacagga    118680
aatagggtta ggttacctgc aaaacagacc atgtgactac tcatctgata aatgagatgg    118740
tggtaaaatt tattcaaatt catttagat caatttgaat accaaaatgt atatacccttt    118800 ttttaaaaa atgtaaggga aaattattg catgaaaaat taggacataa aagacctggg    118860
cactctaaaa gaaaagcatt tgcttactat cctatagcaa ctacgcaaac atcttcaact    118920
```

```
gccaagtgct gcgattcctt gtacatatgg aactaagttc agaaactcca caaattatat    118980
agacaaaacc cttttttat ttactttgaa taatagagat aaagatcaca ctggcacact     119040
ttatttatga agaggataa tagagtaact ttttctcct ctgcatgaat aatgaccta      119100 aatgaaaact tcagtataaa tatctgtttt acagtaaaac atgagtctag cctcaaaaat    119160
caaacaaaag aatgtatttc tgtggttttg tcattaaaac tttattctga aaattaaat    119220 aaataaacct agattcttga aaaataaggg gttaaaagca ttaccatgtc tttccagtat    119280
atagagaata aatgtttaaa gaatcttatg aacatgattt catagataac tttaactaag    119340
aggaaacaaa aacagacaat gagttatttt ggggtgtaca gacacaagaa tattttactt    119400
ctgtcaccct ctaagtcact ccctcttacc tccactgtgc accccaaata atttcttgta    119460
cttctgtgcc cccacccacc atcacagtca tccgttccat gccactcctg gttaccatca    119520
cactaggaag aaatctaaca tgcaaattca gagtggcgtg gataaatggc aaaaaatgcc    119580
taggaaattg gtctgctcgc ctttataatg tttgttgaaa aatcctccat cgctcccaac    119640
taatgaaaac aggaagctct attcataaat gtgaaattca ctgcctatga tatataatca    119700
tcctaataag aaaatgagct ctagacatac atgtccaaga gggcaaaaga agagatagtt    119760
tcccaaagat ggtttcaatt ttcttctgaa tcagaattag caaatcaaga cgactaacat    119820
actctgtctg tgtgcattat tccttactac acacagcatt ttgtaattta tttcaaagct    119880
tccattataa acaacaaaaa cttacagttt ctgttaaccc cctctattct gagctatgga    119940
aattactgca tatttcatta tatatgcaga actgcaccca aagtcctgtt acagtcactg    120000
tccacgctga tgaagaatt atacaaaaca tttctttgaa agataaaatc caatcataca    120060
gaaaactaac attagtccaa caaaatgtcc accacaattc ctgacatttg ttttttaaga    120120
tcttcaaagt aaccatggga tgatggcaaa aataatgtaa acgatactaa ttacatttaa    120180
tctttattgt aagagccgcc acgtaataaa aaaaaaaaa tcaactacac agccatgatt    120240
taatatttgt aaaggaatcc ccaggctaac acttttgtga cagccaatta cagtcgatcc    120300
cgatcccggc aaggagtttg caagcagagc tctggaaagg taaactcctt tttacaatga    120360
gttacagatc cccaagctta ggaagacaag caaaaggcaa acagaaggaa gcagccaccc    120420
tgggaaatcc gaagcagcct tgcaagtgat acaatcccaa gatgcgaatt actgcaaagc    120480
agcactgttg ctcagaacgc cacacactca gttgagacaa ttttgctcac ttttccatag    120540
acataataat gaaggaaagg gaggagggt agagaagaga gatgaaaaag cagaggaggg     120600 aaggggggagt agggaggtgg cagaaaggaa aagccttagc tacagagttc tgctctccag    120660
aggcttaacc ttacaggagt gtgggctcct tcagcatttg tgttctagcc aaatcctcat    120720
gagtcacaaa aattaaaaag ctataacctt ctgaatgcca ggaaggcctt accacaagcc    120780
ttttgtcaga gggagaaagg gagagagaga gggagagaga gagggagaga gagagggaga    120840
gaggaaggga aggagagaca gaggaacacc cataagtaaa gagacagaag gaaggaaagg    120900
gagaggacaa gagaagagaa aggagggagg ggaggggaga aggaaaaaga ttgagaaaga    120960
gggagggaag agagcaaggg ggaagccaca gtggtaggca gtcccacttt actttgagta    121020
ctgtgaggtc acaaaccaca tgattctgtc tctccagtaa tagtgcttgc aaaaaatagg    121080
agttttaaag cttttgcttt tttggattgt gtgaatgctt cattcgcctc acaaacaacc    121140
acagaaccac aagtgcggtg caaactttct ccaggaagac tgcaagaagg ctctggcgtt    121200
taaatggtta atctctgcag gtcactacca gccaccgaga ccaaccgagt cagtgagtgc    121260
tctaaccaca gtccatgcag gaatagtagg tccttcaaat atttgctcac tccgttttgt    121320
```

```
tttgtttcct tgcttttcac atgttaccag ctacataatt tcttgacaga aaaaaataaa   121380
tataaagtct atgtactcca ggcatactgt acaactaaaa cagggactgg gtatggtttg   121440
tattttcagt ttaaggctgc aagcagtatt tacaacagag ggcacaagtt ctatctggaa   121500
aaaaaaggag ggactatggc gtcaaacagc ctcttcagcg cagtgacacc gtgtcagcaa   121560
agcttctttt ggggtaagtg ctaccttatt tcaagtcttt ttctctgtga acctgttaag   121620
catgaaggta caaggcttag cccggctgtg agctttccta ggtcacagcg cagcatgtta   121680
aagatcatga tgatgctatt ttctctcact agaaattgaa aaatgaaatt gctgtaaata   121740
tttgcacttg gcatgtgtaa ctaactctcg gggtaatggc ttgaaatcga caaaattaaa   121800
tgagctcatg ttaatcaaat tgttttccag tgtaacagaa acaaggatgt taaaaacagt   121860
aagagcttaa tagtcccatg aacttcccta gaataaagct ggatgctgaa ttaatcaaag   121920
tattgttaag ttattgactc ggcagctccc aatattgaaa caaatttcca aaaggaagca   121980
attttacaaa atagcagacc acagaattat tgaaacattg tggtctacca tgtatgacac   122040
aggagtaaac ctggaggcga gttagcattc tcagctgccg ctccactgaa agaattctct   122100
ctaccgcttg aaactatgtc ttcagatatc tctattagcc tgtttctaaa caattttctg   122160
tgactaaatc agacattcaa ctagaataga agcattttca agacatcaga gctgttctgt   122220
aaagatctcc agtgcttggg acaatgaatg tacatgaaac tgaacttttc taataatttt   122280
aaatttaatt ttatatctgt agactattgc tcccacatag aacttgttac aaacacacag   122340
caaacactga aacctctaag attcctttga gcacattctt aaacctacca aatgaatacc   122400 gttttagtc tcacgaaaaa taaacttcac aaggataccc tgaaggattt aagaaccatg   122460
ccgacaaaat catgctggac ttttaaaaca aaacaaacat aatgcagtcc cttaatactg   122520
aattttcagc aagtgctaat acagatatgt aaatggcttc aatcctcatc aactgtcacg   122580
ggagtgtagt aaaatgtcca cttacatgat tctctgtatg ctacccaaca tgtcccagct   122640
acacagcaga ttgtaaagac tgtctttta gcttttaaat aaatccttag ctgcagaatt   122700
ttcaaactag tgattggagt tcccattact cctcctcctc cttcacacat ctcaactggc   122760
tcctaaaaca gggcttgtct tagctcaagt caaagagaaa taatttaacc taaaaggggg   122820
aagtgggggg tctcttaaag ggtaaagaaa tatacttcag gttttttattt ttaaaataag   122880 tgaaattgct acaatgactc ccacagtagc caaaagtagg tcatctcagt tacaatatat   122940
gcaatgtaat aatcatagat aaaatcataa tttcaatagt gggtataagt attgcttttg   123000
aaagctctgc cttcaggaag caggaaataa ctatggttag actgcactat atcccaggat   123060
agcccacatt atacaaacag ctcacatagg agaatattta ttagtagtca ctgagagaca   123120
agaacattag gctacattaa ggctattgtt ccatggaggt aatacttggg gaggccgcag   123180
tgagcagtta acatttcag acctggaggc agaattgtca agaacgtgt tgaaatgtcc    123240 tagttctatt ataggagt agggggtgggt cttaaagttc tatggcactc ttaatgacta    123300
ttgaatatta atgtttccaa gatctgctca aacttcagag ataaatcaag gccatcttct   123360
atagcatgca gtattttttc acattctaac caggctttct cttctggaag tgagtctcac   123420
cttccctgcc tccccctcct ccaaacagta ccttaggagt ggctagagaa cttaccatga   123480 gcccctaca ccagactaat tacaggtgag gagtggacaa ttgttccagg ttatcatcac    123540
gtcgcatgtt tccctgttcc ataatgtttg tgaggctaaa acctcccttc aaggttacct   123600
tcttacagtg ctcagcacaa ccacctagtg caatgtccta agtacatgtg ccaattttgc   123660
```

```
aaaatggtta aagaaagttt aggtaaggga caaagcatgt gcttactgaa tatctcacct    123720
caaccactgg gagggaggga aggagggagg gatggaggaa tgcaagagag caagtggaga    123780
gatgaaaaga gagttccagt gtccttgatc tctgctactt taatcaagac tttcaatctg    123840
tgctactcaa aaccattact taatatgaat caatcctttt gaaacagaag attgactcaa    123900
caagtatctt agcattaagg actcgtttgt gaaatcacat aagctgactg gtcacatttc    123960
cacatcagct ccttatagca gacggaggtc tctgatgaag cagaatgtgt aaacagtcat    124020
ttccaaaaca atagttgtgg tctctatcaa caacaatcat tctgtaattt caagattccc    124080
gagtgaccaa gctttgcaac ttgtttccca gataacagag actaagttca ataacccaga    124140
gaaaagaatt aaaagagca agcattgaag gctactctaa tatttattaa aagctaaaac    124200
tgccacgtac tgcccaaaga gactaccttc cattcaaata aatgattcta ctttacaaaa    124260
ttaatacaga tttcactttt aaatcataaa gatgttttga aatgtaaatg aaattacaga    124320
agaagatctg ttaagtctga gtgagcttcc tgatagtttc taggcacaag aaaggcatga    124380
aatatacaca attacattat agtatatttt agttctttta gtaaaacaaa ataatttat     124440 tcaattacac ccttcaagct aataatcact gatggtcaga cttgtttcag tcagcagtgt    124500
taagtccaat tctgtaaggt agaaatgttc cagcttatta agggaagact gtggggtggg    124560
gctgactcat ggaggggact aagatgttat caggaacgca gaattaatct ttattgaata    124620
gaaccattca caaatcaaat ctcactgtac ttcaatactt tcaagcagct ctaatcaatt    124680
acaacccttc tctagtgctt cagaactcat gtgctttcaa ttttacacac tggtggtcct    124740
gaagtactat atggggcaga gttaagacat tctgtatcac aactttaaaa aaaaaaacat    124800
ctagagagct ttatccctac ctctcaggag ctgtttgcat gcaaactgtg gtaatatttt    124860
tatactgtgc ttccttgtta aagcaaaagg tcagggggtta cccaaatacc tcaactgtat   124920
ttatatatta aaaagaaaa ggtaagtatt catatcaaaa ctccaatggg acaggcttct     124980
ttatttctac atttccaatg attaatgaag ccccacgcca cttggagact gacggcgaaa    125040
aaagggcaca tctcaaagtc gtctccacac ttaccccta ccatagccca gccccgtcaa      125100
tgagtcttgg gacgtgtgct attagacact agtatgtagc caggctaggg cagaagagct    125160
gtgcaagtcc ttcctgagca ctcagactgc agacgctatc aggcaagcct ttggagacat    125220
gtttggataa atggttcact gaaacggtaa acctctgcag cgtccttcca aaaatattac    125280
agatgtggcc aaataaatgc catcgattca aggtgaaaga aatcgtgtgg cagaagctaa    125340
aaccgtaatt cggacaatgc atgactattt tcacagctg gtcagacctg tcatttaatg     125400
tacactggcc aacccaatgc tagtttaggc agagacttcc taacaggtta cctaaatgaa    125460
ttattttttt tttcctctcc aacaccaatg aaacaaagtt gtataactct aactcaagat    125520
ttaacatagt taaaataaa actggcacta agcacctata ttaaagataa cagtaatctc      125580
caatacttga tattttctaa gtaaatatca gtaaaatatt ctgataaacct caagtgttta   125640 aaatgttcaa tggttttaaa tggatcttta taaggttttc tatacaatat acaccttaac    125700
aaaacctctt gtcatttcaa aacgacaaaa gtattcactg gatatgtatt ctgattaatg    125760
tgttacaatc caaataaaat gaggaaacac tatacccttat tcaagggag tttccataca    125820 attttagcca cagttaacca caaactttg ttcattcaac agaaaacaca aataaaacag      125880
accgtataac tttttaagac ttctatagca acctaaatga aatgttcctt tattatacta    125940
cttacacaat cttcagctta catggaattc tgaggaattt cctccccata tagtactatt    126000
aaggtcatag gattcaaggt ttgcaacact gttgaatgga tgtaagaaac accctataaa    126060
```

-continued

```
acatttcaag ctcctgctat tctaaaacag gagttaattc taaagcctat tttttcataa    126120
gcatgttttc ttcctttaag aaatagtatt gtaatctctc caaatgagat gaactataga    126180
gctcagactc ctttaaccgc tgcttgttat ggaagtactt aatatttcta tagaaagaaa    126240
aatgtgttaa atgtgttagt cattctcttc ctataagcat tccaaattgt tattaatact    126300
caaaaaccca gcatctagag gtgaggagtg gagctcagga gcagagtgtt tcccccacgt    126360
gtacatgccc acagttcagc cctcaaaaac acatttaaaa tgatagtaat ttttgaatct    126420
aatatacatc caaggaacaa aaaacataca aaatgtgaag actactgatg aaaataataa    126480
atgttatgta ccttgtttaa attttttcct ttaagtctat tgtttagaag aaagaattta    126540
ttgacataca gacataaaca caattttctg gaatgtttaa gggtgttaaa aattattgca    126600
tagatgttag aaaatttacc aagtcagtat tcgtgtcaag ctgtacttaa tttttgagaa    126660
ctactctaaa gactttgtga ctgctactga tcctactgcc atttctcctc agaaactaca    126720
catcagagtg acattacgct agtaacattc ttaataaggt agacctaaac attctagtca    126780
atacaattaa ttttgactgc aaagtcaaat aaattaattt tatcatgctt acttttcagt    126840
aacattaact tttctccatg aagaatgtct gttggatcat tatataacca actataaaca    126900
tatatctaca taaagattg agttaaaact cccaaaactt aaatacacat ttataggtcc    126960
ccttaaaact acatgagact tgagtgtgcc aaaacattat ttatgtattt cttatggtca    127020
gctatctcac gactaaattt attttgtggc tcaataaaag caaaaagaa agaaagaaaa    127080
aaatactagc caaaccaaa taacaattac caataaagtt ttaaaaacat atatatacat    127140
gatctttctt tgtaaaaatt acaataatag tgttgtggta ttctacaacc tttaatatag    127200
atattgacat ttttatactg aaactaaata cctgccacat atattgaact ttaattcctt    127260
tttgggtatc agtctgattt aaaatttta tacatggtac acacgtatgc atatgcacta    127320
gtgactatga agtttggaat aatgattata aatcaagaac aacaactata aattatataa    127380
ataaggaact gttagaatct cttggaaaag aattatttt ctatacttac aatattgcag    127440
taaaatgtca atctgtaaaa tcaaaataga gactaggcat ccatgaggaa ccatgctact    127500
aaaataataa atattatatt tataaaatcc aaagaccta ttttccaatt ataaatccaa    127560
atagtcactg acaccactca gtaaaacaag acattccagt ttacactagc aaatttgaac    127620
tttatcaatg cactaagaga tcccgattta tagccacctt agctgtccct aaacatacac    127680
atcttctata catctcctct ctgcccatct aacctaggta aggaagacac tatattttc    127740
attttgctg tttttttaat aataactgca attttctt taaatttct gtactgaact    127800
tctcaactta agactgaatt accaagtaaa aagtgatatt tttaacaaat acttaatgat    127860
attgtttcta ccacataatt tagaattatt tcaataaata taagtagcct gaatgtactt    127920
tgaagcagaa aacaggttat gacatcaatc ctactataca ttatatatca taattacata    127980
ttatatatca catattatat aataaagcac attatacagt taatggttca acctctgctc    128040
taccactgta actagctgct agaaaaaagt atcaaagggg aaaaggtat agactctctt    128100
gcaagatgtt ttatgtaggt acagttttta aagggtactg ttgttttgtt tgtttggtgt    128160
tgttttgttt tgatttgttt ttggagaaac aactcttact ttgttccta gacttctaac    128220
atactagacc tataacacag aaaaaaatct cctttagggt aacaatatac attatgtaaa    128280
tcagctttct atgaaccttg aaccaaacta taaatgtata tcagggttag ggctagagcc    128340
ctggccacat gctccaagtc ctgggatcct tccccagcac aagaaaaaaa gagagtaaaa    128400
```

```
tagatgtaag tacccatggg taaggccctg aacactcaga gggttaggaa aagactaaga    128460
gaagcctcca ctgaacactt gtgccttaac agtagacaac tggttacaaa agataagcta    128520
gtgaaattta tggttcactg tcatgaaatt tgtaagtctt ttatgtgatt cggcttttga    128580
aaaaaaaatc attaaagttt tgctactgct ctttcaaaat taatttcata catacacatg    128640
ctatttaaag aaacaatcag gcagataata cttttaaaa agaaactgta ttgcagtgca    128700
ttagtaaagc aatataaata ggaaattccg tgtattcaat tttcgatgat taatccacaa    128760
cagaaactac ttcttcatac tctcatgatc tccaggattc aaacagaatt ctctacaatc    128820
tcacacttag tgtaactaga tacatataca tatgcacacc agctttatat cactgtctgt    128880
ctctatcatt taggaagaaa atttatttt aaaaactttt actactcata tccacctcat    128940
tttaaaaact ttattatcta aagtagatat atatgagaag actcttgact gaccttgact    129000
cttgatgcaa tacaagtctt ttatggcata caaatgcaca ttacagaaga gccgagcact    129060
taagcagttg gaaagaagc acgcggagat gtattttaat tatcaatcac aaatacctag    129120
gaagttttaa agcatccact aacttcaagt cttatttta tttccatacg cattttcttt    129180
caaaacttaa gtaatttcaa atagagcaaa atattgtttt aaattgccaa attacttatt    129240
aaatctctca gaggtaataa atttcttatt gagatgaatc caacccattt tgtggctat    129300 aaaattaaat tgtgtatacc cacaaacaac gtagcacaaa attttgtccc aagtatttat    129360
ttatttacaa agtaagtata ttacatgtaa aaaaaaaaa aagataggaa gagatttct    129420 ctagtataat ctttctattt atttactttt atgcagatac atgatcatta atttttaata    129480
aaaaatactt aattaccatc catgctgctt cctttaaaga aaacattgag ggaaaatagt    129540
acccttattc attattataa gttaaagat aacttttaaa aagtagttat aaaaataatg    129600
tgatctgagg actcatattc aaaacatcaa aaataaacaa taaaaataca aactggaaca    129660
tataactact aaaaagaaa tataaagcca ctctgaacat aagaaatata catacacttt    129720
taaaacagac gtttacttga gcagttttta aaagcaagct ttaatttgag tacaataacc    129780
ctatgaatac agaattttct tctaaactgg taagactaaa agaagtgtct aacatctaaa    129840
ttcatcatct taatatgtga taattctctt aatcacacag ctaccacatt tccaaatcct    129900
gtaaaaggct tgaccattgc accttttcct gccattcctc ttccttattg attacagtgt    129960
ctcttcagca cttgaggctc caaaatccta actacattta gaattcataa ctgagtcacc    130020
attgcggcct gctctaaaag cacccgtttc tagaaggcaa ggaaaccctg gtctttaaag    130080
ctgatgcttc tacacaagca ggcaagttca gtgggctcct agctacacca gagccatccg    130140
ctccaggagc tcaagggtgc ccaaaacaac gggttacctg ttccagccag gctaaggaat    130200
gtggccaaat catttttatt gatttaacct ttacaggaat gctacatctc ctcgagcaa    130260 aacattttga atgtatttat aatatgatac acttctgaaa agccatgaaa aagaaagcta    130320
ggaacaaatc tagacagccc tccacccttg gttgttagga gttattttt atttaaaca    130380 ttatcagtgg acctaaatac agaataattc tacttgggga aacttacttt ggcacgattg    130440
tattagaaat aaaatttat ttcagagtag aaaaggtaca tttaagtaaa ttctaacttt    130500
aagaactaca actccaaact tgacaatgat tgacaaattt ttaacaaatt ctaaggctc    130560 ttttgacact ctgatgcgca tccaccatga aaacgacaaa catatcaaac taaaacttac    130620
agggcatagt ccccactgaa tagctaaaag ttatactcta gttacacttt ggcatgtac    130680 agagcaagtt ctgtggagtc tatctctctc gcttcctgca catggtactt tataaacggc    130740
tgcggcagct aatgcctaca ctaggtgcat ttgccaaata ataattcaca atattatgct    130800
```

```
tcctcacatt atgctccatc attagttaac ttgaacctca ctcctcaaaa agttctactt   130860
tcaccgcata ctgttctctt caaaatgcaa acaagttttg agcatttcca gatgtagcag   130920
accgcctctc tctctccctc tctctctctc tctcgctctc tctcgctcgc tcgctcgctc   130980
tcgctctctc tctcatataa acacactcaa agaactctaa ataacaacat aataaaggca   131040
gagacactgt tttccacctc aatatcgatg tatttgaaat gggagctgac tgacagggct   131100
gcgtctccaa tgaggtcgtg agtgctagct accagcacag gctgcaggta gctgacacta   131160
ggtaaaacag cagcatattt tggtagcagg caagattctg ccgacctggg ttttctgaaa   131220
ttctggcagc tactgagtta gcaagaataa aggcaatgct attcgctttt tcaaacttag   131280
cttgaatccc aggtaatata gctggaattc aactacatta ttttcatctt ctcatcaatt   131340
ttttacataa agcatcctag catgtatgag actatgctaa atgaaaatca aaatcatttg   131400
cacgcagcct acctctctga gtagggctg ggagccctgt gagacatggg aggtggcaag   131460
ggtgaaattt tcagaaagga ctcactcctc tacaaccctc aaaacaaggg ctttcctgat   131520
gctccctggg tactcgggag gagcacttca cccagggcct cgtgtcactc caagggcctc   131580
tcattacaga tcactgcctg aaacacgtgc ttagccaggt aacacaggta caacacagga   131640
aaagaccaat aggagagtga aaaggtaaag taagaatatg tataaccttc gggtgtgctt   131700
tatatttgat ttataaatgg gattttcttg agaaaagagc aataaggaaa tgtaatcagt   131760
ttagactcta accaattgtt attctgagaa agcacaaata gctcacaagt ttgctttcaa   131820
gttatttact ctaagaatca tgcaaagtaa acaaactgcc tttactactt ggtcatcaga   131880
cttttaaaaa acaattccag aatgtgctcc attaaatgtt cccagagcca cacgctgtcc   131940
tggtccaagc accatatctg gttgatcctc agctctgcct gaggcataga ccatgggaga   132000
ggaagggtga gacagggcca gccttaggtg ccttttgtaa acagacgcac acccctaggt   132060
aaatcaatga gagccattgg ctactgaatt tatgtcagaa ataaacaaaa gccaagataa   132120
acatgcaaaa cattcacggc aagctgtttc caaaaaaatt gcagtttgtt tttaataaaa   132180
cattacactt cctttcttct ctttggtcta gagctgtgac cataagtaat actaaaggga   132240
aaataaagac agagacaact ttgtaagatg aataaaccaa acagtcatta tttatttctc   132300
caatacgttt ttaagtacat atcaatctat accccaaata gttttatttt aaattaacac   132360
tgggaaaaca ccccaagtgt ctcctgctgc ctgtgattct aatggagtgc atgaacgtgt   132420
cagctgaaac tgcatgattt atttgttacc tgtccttggt tgagtctgtt tctctattag   132480
cttttctggc ttgagatttc ctgggccagg tgctgtgcta atccttttgaa aacactgctg   132540 ttgaattctc acaactccct tctatgaggg gttccctaat tcctcagata aggggaaaga   132600
atgaagtcat aaagcctgac cacacaactg actagctgac aagctaggca aagcctttat   132660
actctggaca ttcactttac agtattacac tggccttcat gaagtcattt cttgatcctt   132720
aatttcttct gtaaagttac tggttctcag aagcacaatc ctagtaatct ctgtgtctcc   132780
atctattcta gtccatcact ttacataaaa atcattaggg aactgaagca actaagaaaa   132840
ggtcaaaggc tatcaaggga aaaggttgtc taagtttgat cagaaaatga atttcaagaa   132900
acttgataat tcttagtcat tataatcagt agtcttttgc aatgtccatg gtaactctcc   132960
acatgattaa taatatcatt taggaatcaa aaactcagct tttataacac caataatttg   133020
caactatctt aatttaccac ctaaaatgat aacggtcaaa cacttggcct tccaacagtg   133080
gggaggtggg gaacaccctg ccaagatggc cataggggtt aaacagttca cattttcaga   133140
```

```
gacatgagaa ctgactgaga aagctatctg agatctcaaa agtctaacag cattcctgca  133200
cccacatttt acttgccatg gaataataac caggctagca actttaaacg tctaaagaag  133260
gttcacctgc taacataaat atgtagacaa atgtaaatca taggaacacc attttagaaa  133320
agaaaataat tttacatatt agttttaatt agaaacatcc aggggaaaaa aagttagagc  133380
ttggtttgtc atgatgcctt ccctagagtg tacaacccaa ggcactagag atcaacggaa  133440
tgggtaaaca acagtataca tataaaacta attttgaaat aatagagaaa gttcttctgt  133500
agttgcacta gtactgaggt tccgattctg ctgtcctgcc tatcaatgga tataagaagt  133560
tagaaaaaga taccatggga aagaaaagga gattggtttg ggtaaggcaa ttcactgcat  133620
ttaatttaat ccccacagta ttcccactta cattatcagg agccacaaaa atgacagaga  133680
caaaaatttc tgtatgtagc caaaacagtt aagaaacag agggtaaact ttaaaatgca   133740
aaatgtctca gcactaattg tgtgtgtgtg tgtgtgtgtg tgtgtgtgtg tgtgtgtgta  133800
aatgactagg cactagagat gtatatacct cagtgactga gtgtttgcct agcatggata  133860
gataggccct ggactgatcc cagcatccaa aaaaccaaaa ggttaaattg aaaatatccc  133920
aaataaacta gcagaaaaat ttggcaacag gaggactaag agaggggaga aatgggacta  133980
tagtccaggc ataattcctg aatgtactaa tgattatgag gagatggcaa gaggtggaca  134040
gattgctcaa gctatgttta tgagaaaaca ggatgctata ttacaggatg ccacaatctc  134100
agctctttaa attataagta tgtttttatg catactcaag gaatacaaac tagtaacaaa  134160
agctacgcat acacctaaaa gacaggaaca tatactacag tattacaatt tagttagcag  134220
ttgactctag tatttgacaa gttcactttc ctgagtcagt ataaaacctt cattttccca  134280
cattcaagtt gtaagaaata gagcaaagct ctccaaaata aatcatattc tcagaagaaa  134340
aaaacaaggc cctgacagac cagcgagaac ttaaattagt atctgaattt ccattatact  134400
cacataacct taagcaagga cacagtgtct gattccctca tctataaaca gcacctaccc  134460
caaagtttcc catgacaact aaataaaaag taaagtgctt acttatatcc tatctgcacag 134520
aactcataga gttagtaagt ataatcagct ttctaatcct ttggtttact gcagcacact  134580
tgactgttca cagtttcccc acagtgagca cacgagtact gcagcatcac catcagatca  134640
gcatcagcat cagcatcagc aacagcatca gcaacagcat cagcaggcct ggaaagcttg  134700
ttcagtgtag actctgagac tctccttaa agaagggcct gtgcctgagt aagagtggca   134760
ggaagtctca gtttgttagg cctgctccag acaacactaa gtaaggcaag ggtccagctg  134820
cccacttctc aaactaagca gagcatccag tagctttcta ctaatccctc attctcaggg  134880
actcaagagc ccaaggagaa aaggtgaacc taatttttact tccaaacaca actttcacat  134940
gcagagagca acttatgtcc cttactgctg agtttaccca caatgaccaa gcacttgcac  135000
aatgatctcc tgaaaagttc tgtctccttg ttacttgagg catcctgcaa atcatgacac  135060
tgcataatga tatcagctac tagctagtcc tcatgctatc aacaatttct catcagatag  135120
gttttccaga tgccttgaag gttttttgctt ttattttgca actgtgacta taatcatgac  135180
attcttgctc atgtatgtct ttccactctg tgcagatgag cacatacatc caatcttccc  135240
cttccctccc tctgctcaca ttgcctctaa gttcatagca ttgcatctac acagtatccc  135300
tgaagcagtg tccagtggtt gcgacccaga ctaagttggt gaaactgctg ctgttgggta  135360
aaatcatgtt gctcctagca tgtttgagat gctcacaaat cacttccaat cctcactcca  135420
aactcaccag cagagatctc aagcggatgg gtagactttt gcatctagtc ctcttctgat  135480
gttttatagc actttcttac tggtaaaata gtgtttgacc gtgattgcct gttttccccc  135540
```

```
tcttcccttg catggttact gattgaagaa aaatgttaat gtaggtagga tactgtcaag   135600
ccaaagagga aatcaagttc tgtttcctgg catgcacagt gatgtgcagt acagagctgc   135660
tgccatgatc agcagtggag ggagggctgc ttcaactgct ttccccagca ttttctagtc   135720
agcctgcact taccttacct gtgcttacat ctttaatttg gatctgtcct taattgcaaa   135780
tatgttctgc tgttcattca cacctgtatg aacttttttt tccccatata tgtcttgtga   135840
ctacaatatg tcctgtgccc tagatcctaa actttcaaca gagagctcag atctagagcc   135900
ttccctttga atggcatctg gtagagctgt gtaagcaatc aggtggttag taattttatg   135960
acgttctggt caatgccttg taagagacta caaggaaggg gatgtttacc acacatttaa   136020
caatcactga gaattaagag ttaattaatt aagtattaag caagttagta ctttgggcac   136080
agaaactgta tctaaaccag tacttgtttt tgactagaaa ggctcaagga gaaaagaaa    136140 gaaagaaaaa gaaaatactg actctgtaag gtgagcctaa gacaaaaaag aatacctgga   136200
aagagaaaat aggagcactt cagaaataag caatggcatg agcccacatg gagagccaac   136260
agggagacag tgagccaaac agaagatctg aaaccttaaa cctccctaca catgaggctg   136320
taacaggata gctcagctct caccatgtcc tattctctac tcaagcttta tccttacagg   136380
cttagacacc tctcccggaa gccctgagtc agaactcaac aaacctgata agtctgacaa   136440
aagaattaca tataaagatg cttctgagaa caggagacag agaaactacc catttacctg   136500
tgctgtaccc cacggacatt ttaaggtaaa aaggtgacac aagctgtcaa aactatcaga   136560
cattctcaaa gagtattaga tgtaaatata atcaagtact acagaaaat ccaaatgtac    136620 attcatgaga ctatatataa aagaacacgc ctggtatctt taaaaggcag ggtaggctat   136680
gaatggtcaa acttttacc aaagcacaaa actgtaaaat tggttagagg ccaacagttt    136740
tagaggctca acttatgaa attttgctca ttaaaaatca tttgaatgtt actgtattca     136800
tttttcaagc tcagtggaac attttgtcat gtcccttatc acaaaaaata agtaaacatt   136860
atacatagcc aatcatatat attttgatt taacatcatt tactttagac attactcata     136920
aaactagaaa taatcaatta taaaaataca ttcatagaag tctaaaaccc ttttcactt     136980 taggaatcag tagtttcaaa catttcctta tgagtctgtt caaacagcaa attttaagat   137040
gcacgtagca tctcaaacag acacggagaa gcagctctcg ctgccgagag aatgaaggaa   137100
aggacttctc catgttggtg atgaaattcc tatagctcca ctgagcacaa tttgaaagca   137160
ccaattttat gatcagactt gccaccaaca ccttaaaaa taaatgtttc tacttaatag    137220
tgctatttcc ccagttcaaa gtcagagatc ttactgattc aaccaaatat gtggatctta   137280
tatttactgt agacatatag ttaatgacac tggttgctga gtacataaca gggtcccata   137340
ggtttccatg gaaggaatgt tctcaggcct cacctccaaa acatgggaca atcctaacac   137400
ccaacccata gttcatggac taggtctgtt gtgctgaggc agtgcacagt gctgtgcttt   137460
cctgctgctg ttggaaggaa gaacagaaat gcatatttaa agtccctcac cagcgctgca   137520
ggcctggcta ctactttagg acttcacttt gatttccttc cctgccctat cctattgtgt   137580
tataatcttg ctgtaaacag ccctgacaga tgcctcaaat ctttttttgga attaagatac   137640 aaatgataaa actcattgct caatctaata ccattagctc tcattgggc tagaacactg     137700 gttctcaacc tatgggttga accccttc acaggggtc acctaagacc aacagaaaac       137760
agagatattt aaagttcata acagtagcaa aattacagtt atgaggcagc aacaaaaat    137820 aaatttgttt gggagtcacc gcatcatgca gaactgtatt aaagggtcac tacattaggg   137880
```

```
agattaagaa cactgctcta agataaagac cttgggcttt ctcctttaac tagtttgtaa   137940
aagtatcttt tattctgctg agttaattgt catctaggtg gcttactgcc tccctctgct   138000
aacctaggcc tagtcctaga agcttctagg ctctgagtaa tctattctag gcctagaatg   138060
ttctcagcct ctaagactta ctgctattca gcttatgcaa gctcaccttc tcttttgctt   138120
tctgaactct ggctagctga tcaactcagc tgttctggct caaaacccct ctccacgctg   138180
actgactcat gctggcttat cctgaattgc tcagcttgac ctcgaactga ctccagccat   138240
ctgttctaat cttctagcta cttcgaattc tcttgtttgt tttgtcttta tctgtatcaa   138300
gtttgttctc tctccaaact gtctctgtaa aactctccag gtaaaactgc ctccttcttt   138360
ttagcacagg agagttgggc acttcctatt ctgtcacacc tttctctgac cttgtctgcc   138420
actcagtcat cactttcaag aagggtgctt ccttctacaa actaacatta cctttgctgt   138480
ttgggattaa aggtgtgtac taaagggcct gtctgaattc cagccagaga gattaaaggt   138540
gggtgtgcta aggctgagcc acaccataac tagaaacagt ttttttcagt aaataacaca   138600
atcttgggc tcacagtgta atcaaatact ctgcaacact agttcactat tcccatgagc   138660
ctctaagacc taacaagcta acctgtgcaa tgtctgactg atttgttact ctccttcatt   138720
cctggtgcca ctgtctctcc cccagccaat ccaacttcca tggtgctact tacatattct   138780
cctcagtcaa ggtcaatgca catcaaacct gtcacttggc aaacaccta gaaaggtttc   138840
ctatgcccag acaaaagatt aaattcccta gtcatccatt cagtttgcca cattccaata   138900
ctgaccacca gtctgacagt attttctaca agcgcatttc cttcagctac attcaagcta   138960
cctgaagctc actcctagtg ctctccttca cttgtggtgc tccttccttg tgctgtcacc   139020
ctcccctagg tttctgaagg tttaaacagt acctatctaa agaaagatca aatggtatta   139080
ttttcataag attcctcctc gcagctgaaa accctctcag cctcctctgt cttaccgcgg   139140
gagaacatca gtaacctttc tttacatact tatgttctca atcgccggcc attctgcgtc   139200
cacctgtggg gaagaccta cttacacacg tgtgtttaat tactagttgg tgagtccaga   139260
actgaagctg cagaatccac ttgtctccta ctgtattcgg agaaagcctt ttaaaggagc   139320
tgactggcga ggaaaaagag ttgataatgt aataaaaacc tcaccctctc gagcagccac   139380
agatgccttg tgatgaggca gagcttagag tacactatgt ttcacactcc atgaagacag   139440
aaatatactt aatggtgtgc acctgcctcc cacataccaa gccaggattg tacaaattag   139500
agattgtgaa ttcaaattct acccaggcga cttaaaaccc atgttttctg tgtaaatctt   139560
taatgtctct gtacctaagt acatatctat aaagtaagaa aggcaaaaat tgcctcatgc   139620
aataatcaac gaccacaaga cacataaaac acatccgtac tgtatcagca acataagcac   139680
acaagaatcc ccatgcccct gcctcttaga tatcacctag cctcatgcct gcagaacacg   139740
ggaactcagc aaaatatatt gaatgtgggt ggctagacga ataacaatta cttaaataag   139800
aaaaaagact taaacaaat gtgataagtt acaggaaaac agaacatgct aaagaaatta   139860
tataagaaaa gaagaaaata cttttaaaag gacaactata gttgcaaaca aagaagagtg   139920
gtaggcacag tgtacaattt aaaaaaaaca aacaaacaca ttttcaattt aaaaaaactc   139980
acaaaatctg agtttatgat caagaagct aatattaaag aattaatcat tatattaggt   140040
agataatgtg ataacactca gtagtttagg gttaatacag ataaattaac ctacagtgaa   140100
caactgcgtt tttaaataaa gtctatttca ctgatttatt tacacttatg aaatgtctca   140160
gttttctttt aaagatatat atctccatgt tttctcacat tacaaacatg aagcttcaca   140220
accctagtta caatctttgg ataatctgtg cacaaaagaa atacctcaac atataacaca   140280
```

```
aggacagaaa atgaacccaa aaggaatggc catcatatgt aaaaacagtg cacttcaata  140340
actacaatca cctgaaacta aaacgccact cagattatac accatggccg ggcagtggtg  140400
gcacacgcct ttaatcccag tgcttggtag gcagagacag gcggatttct gagttcaagg  140460
ccagcctggt ctacagagtg agttccagga caaccagcga tacacagaga aaccctgtct  140520
cgaaaaaaca aaacaaaaaa taaataaata aaataaaaat tttttaaaaa gtaaagaaca  140580
ccaagacctt aaagaccttt aatactttaa ctgggttaat aaatataaat gcaacaggct  140640
atgcttttca tgtatattag aatactaaca tcctaggaaa atgcacatgg cagaaaaact  140700
tcagtaagaa aacatgatca taagtgactg ccttacatgg agaagggtgg tgattttttct 140760 gaacaaacca tcaaagcaag gtcaaagtag aactcatcaa gcttaactca taatgaggac  140820
tacactagaa tcttcattaa cttcattaaa aaaatgtgaa atctcaatac cccatgaaag  140880
ctaaaacaat acacaacaaa atggcactgc ttaaagatga aaataaaaaa gggattccaa  140940
aagcagacgt agacttatta agactgtaca tctgtcatta agtctcagtc actgttgtat  141000
tgctgtgagg agacaccaca attaaagcaa cgcttatgaa agcaagtatt gaattggggg  141060
ctcatacaat ctcagaggct tggtccatca tcatcatgac agggagcatg gtactagaac  141120
agtagatgag agctacgtcc tgagcagaga gacagaacag aagagcagcc tgggcctggc  141180
cctggcttct gaaactcaaa gcccaccttg agtgacacac ctactcagca cagtgtcact  141240
ccctgttgac taagcattca tatataagag cctatgaggg ccattcttat tcaaacctcc  141300
atattagcat acacacattt ttgaaaaact acattggatt tttaaagtca tgcctctttt  141360
atttattggg tttcattaat ttaatgagcc gatctttatt taaacattaa aatcatagtt  141420
tttcagtgta atctctaaaa tagtctaaaa ttagaaaaag ggttatctct gccagtgatg  141480
taaataagaa agcaaaaaat gattaatatt ctaggtccat gcaactcaca atcagttcac  141540
gttgctggta ttctctctta ttggaaatga atttcttctg atttgccttt taaacaaaga  141600
tccttgcttt aaactaattt taagtaaaac tagaaggtga ctcagataca ctccattttc  141660
aaaggtttca catgtcatag gaaaaacaag tcttgagcca aaactgcaat caaaagtaat  141720
gccacagcca taacacaaaa gtgtatataa ttaggtcaaa gactttaatg tacaatattg  141780
taaactccca agaacatggt cccacaaaag cagtagtaag tctaaaaact gagacatgaa  141840
gtgtttccaa cagagttgga atgtgaagtg cagccatcgg atgaggtacc ctgcatgctg  141900
tactcaccgc tagatataca gaaccatcct acagtaaaca ctcaattctg aatgaataaa  141960
caaaaagcat tagtaactag tatacaagaa tattctagaa caaatatggt ctaagaccca  142020
tttgttccac cataaggatt acccagaaca gtaaatcacc tgcatgagat gatccgagtg  142080
cacaccactg aattccactg tcatcatggg gaccctgctt acttcacaga gcaacagcaa  142140
acaaagctgg acgcccagag gtgctacggt ggactaaagg ttttaaatga aaggagaaa   142200 tgggagggag agctaactcc aaagtaaaga attactaatg aaaataatgg ctagcttctg  142260
aaaactgcta agtagatcac cgtgtctgtt aaagaaagct catggagcat gaaagcagca  142320
aagcttgcag ggtgaagggg tttctgtccg ctccattcag gtcccagttg tataaaattt  142380
aagacatacc agtaatgtct aaatgaatga agttttcaga gcgatctata caactgata   142440 acatgactta acatgacat  gcctgggatt aatgaaaatt cttcatcgtt ttaaatgata  142500
ttgtagtgcc atctcaaata taaggcaga  aggaaaaact aaataaatgc tgacagtttg  142560
aaaattaagg aaaaacacaa attggtcaaa tgaacactaa ttaatagcaa agacagttga  142620
```

```
aaggagtgga gagctgatat tcaaaagacc aggtattaag tcctaaacta actaaacagc   142680
taccctcgga caaatcggcc cttctctaca tcttcgcgaa tcaataatgg atggacctaa   142740
ccaatttcta agacactcag atttccagtc agtcaaaata accgacacta ttaaaaacag   142800
ttttctttgt ctctgaatac caaatcaatt gtccacattt taaaaagaaa aaaaagtgc    142860 caaaattctg ttctatccct ataatttaac agtcacttac ccagagttca gtgagcaggt   142920
tactatctat gcaaatggtt tatgcgcatt acctggctta tccgccttag agatgaatat   142980
tgttcctgca tattataaca ctgccagact ttactacgct gcctcctcct cccaccatcc   143040
acatggcgtc tgtaaatata gatctgccaa ggaagcaaca aagaggactt agctaaatca   143100
gaactctaaa tgcagaaagc cacacttaaa actactttca gcatataaga caaacccaa    143160 aagcaacata gtaagaggac aaaaaataaa aaataaaaaa acctcacaac tgaaatggag   143220
cagtcatttg agtttctaat atggaatcgt ggtctaagaa ctacccgggc tcctatttcc   143280
ttcctcttct acttggaaac ttttaagatt gcaactgtcg cctctcccct agaggctgtc   143340
ctcccaaaca cagtgtcggt atcaccgcaa cttcacatct acctaccaga cgcctacaag   143400
atgccagcta caagatgcac ctacaagatg ccagctagag cacatcagga aagggttaa    143460 agccctggaa agggactgga tgaagacaag cacagcactg tcggaaacta caccggggca   143520 agattttgc ccgggtggga agattaccag gcctctccta agaatagtac ctggtgtcag    143580
gcgcacagat cgggcagcac aggaagtcag agcagacctc aggagaatag ctcaggccaa   143640
caaccctcta agctccgagc actgctcaag cgctacataa atgtacagag cgctgaagtc   143700
tccaattctt tctcacatat tgtgtccaag ttgaccaact caattgcgtt ttagacctca   143760
tccctaggct ggatcttcca acatgtcaaa ttaataactt cctattacat ttgcccttca   143820
gattcccaca tcagcccagt gaccctgacc atccagtctt acgcccagca cagagtgagg   143880
ctataggaaa cgaacagcac ctgcctgcct ccgctgcgtg gcaggcagct tacgctctct   143940
ctgccacctc ctttactaca tgacaaccct tcaaaactct aagcaagctt cctatctccc   144000
agcattgcca gcagtctggt ctacacctgc tagggctaa gacagtgaaa tgtctcgaat    144060
tcgagaacaa taaatcagca tccaccaggg ggtgaaaacg attaaaactg caaatagaca   144120
tggtttacaa aagaaaacta gtacaattta ccatagaaca gacctaatgt gacgcctctg   144180
tatcacccta gagtgtcagc aggggaagcc caaagaactg tagtaaacta cacctggtgt   144240
tctatctgtg tgaactccat atccctgcag gctgttaacc tacagtagag acgtttactg   144300
aactggtcaa aagaagacac gttctattac ttttcttatg tttaaaaatg aatatattaa   144360
atatactcag cctcttaatt ccactgaatg gacactgata tatatttctc tattagtcag   144420
aatgcagtat tacagatcca ttttaaaaa ttgaactggc tgtttaaaac tgaccatttc     144480
tgccattcaa aaataaaatc tcttccatga tttaaaatta aggtgataaa ttgtctgggt   144540
tttgcatact gcagtcacag cacaattcta cactcaagca agaaaaacaa atagtaaaga   144600
agactgagaa gttttttcgct cggtctctaa tcatccactc gttaagcggc ccactcatta  144660
gtctggttgt ttttactgtt tctatcaggg gttgtttcaa ataaactctc aaaatgtaaa   144720
attacttcat taatcaactt taaaagtaaa atggattgca aagacccatg cctgaaatct   144780
gagaatacag caaaaagca taaaagaaa tgaaaaatga aagcccttaa aatttgcact     144840
tagaatttgt tttggagctc gttgaaatga ttcctaaaaa ttcatctgga agcataaaaa   144900
taagaagggg ccaaaaatat tttaaaaaga aaacttatgt ggacagactt gaactataac   144960
accaaatatt aaaacacatt aagaagctat aataactaca ataatgcagt gctggcaaag   145020
```

```
gaagagacca ctcggtggag gaaagcagag aggcaaagga gtcacttatt atctgataaa   145080
ggcagagttt cagctgtgag ggaaggaagg cttatggaat ttgtggtggt ggggacacta   145140
gcaaatggat ttaaagcaaa actgctttca cttagagccc tccctgacaa cagagaacaa   145200
tagcaaaatg gactaagtgt taaactgggg aaatcaaacc tgaatacaga aaagtgcata   145260
gggattgtgt gtagtgattg agaggacatc agggcaaaag cagaagcaag actgtgaaac   145320
tgactaagct aagttttac gaaagaaaaa ttaacacact tttaaatcac taaataatcc   145380
ttaaagaaac ttagtgctgg gtagaaggaa atgccaaatt ggatccacaa gacaggaaac   145440
ttttgaaata ttagaagtcc ctaataaact acaggaaaac aagaagatga taaaaatcta   145500
tgctaagaat aagaacatac aagcgtgcac acatgcacac acacatatac aatgtaagtg   145560
accaatatat tttgaaactc agtagccaag ctttcaacat cacaacacca tatctctact   145620
gttatcaatt ttttttggg gggggctct cagaatgaga caataacgta aagcagtcca   145680
gcttccttgg ggggaaactt aaaaatttgt accaaaggg gcattagact gaaaaagtat   145740
tcttctttaa ctttaaggta ataggtacca aatattttat ttcatatttt taataatact   145800
ggaaaacctg gaaataacaa taggggatta ataaagtcta agaacacaca cattgttcac   145860
catatactta ggagggaggc agacactaca aaagcacaat agtaactaaa tattgctaag   145920
aaccattaaa aagaaaaaaa gtagaaaagc tagagagatg gttcagcagt taggagcact   145980
ggctgctctt tcagaggacc caggttagat tttcagcacc tacgtggtag cccacaatgt   146040
ctgtaattcc agttacaggt gatctagcac ccccttctgg ctccctccag catcaggcaa   146100
gcaaatgtta cacagacata caggtaaata aaataccgta cacatgaaat aagaaggaat   146160
agctgccaca cagccacagc cctggtgtac aagttgccct tggccttggc acgggttata   146220
gcagactgtc tttgtttctc tgcctgtgtg accttgctgc ctccttgagc ttaggtaact   146280
tggcagctgt tcagtttctt taagggacgg agcacttgct tctgtttgtt agggcaacca   146340
cttggtagta acagaactgg gcaactttca ttgtaattgg caaccagata cttgtcagtg   146400
ataccaaccc ttgaaaagat tctcagtagt gttccctggt tagagagcct gcaatccaaa   146460
ggcaagaaac ttcccactag taagtgaata cagaaaatgg cagttgcagg actgaaaaca   146520
gcaaaacaaa caggaaacag catggggtaa ggattgggag tgaaatcctc ccagcaggca   146580
gggattaagt ctgcacttcc tcatatgaaa atgcacaca gccaagccct gcatgtccta   146640
tgcagatccc atttgtatac aatgtaaagc ctgaggtttt taaagtcata ggaagtatta   146700
gcaaacctaa aaggatcccc tcgtttggct ctagctccct ttctgaggtg aaattcataa   146760
ggggaaaaac ttagcctctc ggtgctgaat gtactattag gagcggcctc tccctcaggt   146820
ctgaagtgaa ggaaaagtgc atacttattc cagagtcaca gccaacaata acctttacat   146880
tctgaatcca gcttaggtag atcgcttgtg aagatgtgtg caaaagtatt taataaaaaa   146940
cgctgaattt agttttcctt ttcttttcc caactttctt aaatggtctt aggtctatta   147000
gatacaaata gtaggcacag ccattccaaa gtttctgttt tctttttata cagagctagt   147060
tttatagctc agaggttgac ttctgcataa gctagatggt aaacatttc agcttcatag   147120 tcacatggga tttgccacaa atatctagct ctgctatgta gcatgaagac agcagtgagc   147180
aatggctata aacaaggag catcactgag ggctagggca acatcattca ctgagacagt   147240
cccacagtgt gctgacccat gctgtggacc acctggcctg cacctactaa cttacatatt   147300
gttttcataa gttctatgag attagcttta aaatacttga ttttttaaa tgaatattgt   147360
```

```
gaaaaaaggt caaataaaac tgtgaaagaa taacttgtca aatttagata aaggatacat   147420
gagattcatt atgctatgat tttaagaatc ttaaaatatc caaattagca attaaaaaag   147480
attaagtaaa tcaatttagt gtcacagaaa aaatgatatt catcacttta tcataaagtg   147540
cacacttaat attttaaata taattaatat accataaaag tgataacaaa aagtccatta   147600
cactgtaatg aaaacttaaa gtatataaat atataaactc ttaaagtttt ccataattta   147660
aaatataggc aggctcacaa aattgagctt ctaaattagt gcttttcccc atcttagcaa   147720
tcacaaaatg ttaccagttt ttagttttag agcataattt tcataagaaa gagatcatat   147780
ttcatatgta agcttattaa ttttcaaatg aaggcctaaa ttttttatttc tcagttttaa   147840 actctaagaa ctcaatatct atagatgacc tatacaacca aggttctcaa agatgctcag   147900
taaataagac tataaagaga tgctgaacgc aaagtctgct gttaactatg acgctgatgc   147960
tttcctttgc ttccccagac tggttataat aatgtcctcc tcttaacacc gtgatgggag   148020
gagaggtggg aggagaaggc gcaatcagcc acaatcggga tgtaaagtta attaattagt   148080
tagttttaca aatgctttca atgtgaatag tttctttgaa gcaagtcccc tgagaaacta   148140
catgcaatca aatgtaacaa gactgtgctt tgaaggatca ttaccacaca gtatagaggt   148200
aacccggtaa aaaggctatc aatacacaca tggggaagac atttaaactt cccacagaaa   148260
tagtctttta taccgcctga tcaatcactg ggaaagaagt gctattgcct tgtcacctct   148320
tcctgtaaga tcccccttgtc ctgaagaact cactaaaaac tcagtccttc agggttccct   148380
gtctgccacc ccagccagtt aagaaggtag cttccctcac tgcaagctga caagcaccag   148440
catgaagtct taaacaaatg tgcaattcct caaagattca acacttgtga ttttttttta   148500
atgctttgca ttttttttaat ttattttttt attggatatt tcttcatttt acatttcaaa   148560
tgctatccca aaagtcccct attaccccca cacacaccct gctcccctac ccactcactc   148620
ccacttcttg gccctggctt tccctgtac tggggcatat aaagtttgct agttgcattt   148680
cttacaataa tctgaaatgc aatggttcaa atattatcaa aatttaaaac tactttgaat   148740
caggctcaca gaactaggaa aattaagaaa aactgcaaac ttctctgaaa acatttttgac  148800 tatccacaaa aaagagagcc aatagcactc aattttcaaa tacagtgcac caccggagca   148860
ctttacccag ttctgctggt cttccatgga gctatttaaa tgttagatta ttttacttct   148920
gtttaaatac aaaattacatt aagctaaggt ttatacattt tatttcaatt tcttcttcac   148980
cattaatcag tttaaaatag caacagtcat attgtgtaaa gacgtactca catcatactc   149040
tgcaactcgg ccgcaaagct tatagtcttc cctgcatttc ttccactact tgaagtggta   149100
gtagacatcg ggctagctgc agcattattc atctaaatta aaaggaaaaa aataaaactt   149160
acactcataa aaattacaca aaatagaggc aattttgaat tacttcaaaa agtatagaaa   149220 cttctcaaatt tctgattaat ttcagctatg tataagttca atttccttct actcaatgtc   149280
tttattcaaa tgagtagtgc tgtggagaaa ctgtttagtc agctcaggta tcaaactatg   149340
tgactaggac acatccagta actactctac agtaaataag agaactggaa cactctttaa   149400
actattctgg catagttcca tagttctgtc gttccccaga gtatggcact ccacccaaag   149460
tctcattagc aattcttcag ggagggtcca atagccccctt aacacgcttt ccccccacttc   149520 catccagatc catgaaaaca aaagtctctt agagagctgg agagttggct gtgggcacag   149580
tgctttgcaa gtacaaggac ccaagttcag atcccggcac acctatgaaa actggctcag   149640
cagcaactcc tgtaacccag cactggagaa gagaggggca agggtagatc ctggctgtcc   149700
tctggcaagt aagttaggct gaaacagaga acgctagcat ttgagatggc tttgaggaca   149760
```

```
acctatcctg cattactata aaatgataat agaactgttg ctgtagtcgg catgacacta 149820
catacgtaat cattgctgaa cactgtaagc acctgggaca agacgtagca cctactctgg 149880
atatttttca aacagaaata ctgttctgag taaaatgaat aatgtgcaga agtggctaaa 149940
gacaacctgg tatcaacctc tgccctccat gcacatgcat gcaccagata tgagtatgca 150000
tgttctctct ccctctctct ttgggaatac cagttgagag gccattgaaa gaagttctta 150060
tggccaggca gtggtggcgc acgcctttaa tcccagccct tgagaggcag aggcaggcag 150120
attttttgagt tcgaggccag cctggtctac agagtgagtt ccaggacagc cagggataca 150180
cagagaaacc ctgtctcgaa aaaccaaaaa aaaaaaaaaa aaaaaaaaaa gaagttttta 150240
taactataat atacaaaatg agaaaactac atcaaatcta gttctctttt gaatcaaagc 150300
ctacagtagc aattcaatca atagatcgga agtaggcatt atagtttata atcttatgag 150360
caaataactc attcaattta aaatacggta ttttccttat taaatcaggc tgacatttca 150420
tgagaaaact agccaatcct agcacatgcc ttttattta ctgtactagc caaagaacta 150480
gccaaaagaa cataaaactc attgaagtgg gtaaagtatc actaccatac aataaataca 150540
caatgaatgt tacttcctat gcttatgcaa actttggaat agcatcattt cccataagtt 150600
agaaattaga aatactttgt aaattctatg ttagagcatg caaacttaag aacattgata 150660
gagcatgtga cagagttttg ggcacagtct agttggtaaa caagttctag agttagtgct 150720
acataaaggg gtgggtcgtt caaaccactg cagaagacaa agcacaggca gagaacagaa 150780
ctttctatgg tgacacctga cctgaagatg ctggagaggc tgagttgagc atagcctgca 150840
ttaacaggag acaggagacc tcagcctggc actaccttcc caagtggaag catgcggctc 150900
actcctgtgc atggcctctt gtcgccctat ggaaaacact ctcccaccct gcacatctca 150960
aagacagctc ataacctcct ccggcatccg cctcactgat tagctttccc cacacagttc 151020
ctggcaaatc acacaatgtc tacccaggtg gctgtctcct gaggccctct ggctaactgc 151080
tagactctca gtaacaaaag aaaacaggtt tcacctgatt tctgtgaaag atatgagatg 151140
aagtaaaaag gaaagtctgg cataaagatc tgatttcaat atttggactc agaggccggg 151200
gttcaagtcc cagctctgcc tctttgtgag ggctttagag aggttacttc acttctcgtt 151260
gcttccatta tcctgtctat aacccgtgaa cagtggccct acttcttaaa aactattgtg 151320
gcaatttaga acaatcttga tacagtaagt atacaataat gttagctatt aaaataaaaa 151380
cctctaaaat acccctagag ctgacaaaag cttttatatc aatatggaat acctgtgtac 151440
tttaaaaatg caagtctgaa aatgggttct aaagagaccc ccagaattca tggaatatta 151500
tacatttat aaagtcctta gacaccaact gctaggcact ctacctatat acccatctca 151560
tctttaacac tccctgtact ccatgatgtg caagcagaca agaaattgac tttcttcccc 151620
tcccactcca ccactaccga cttctacgaa ctcatctctt tcacacctgg ctcatgctcc 151680
acacagacat aatgtgtcct tttaatctaa tcaaatgtgt ggaacatgac aaaagtcacc 151740
gagggaatct agatgatggt cacgcctcaa ggacagaaga ttacagaaaa agctactcaa 151800
ctacctgaga caggccattt ttgaaaaggt gatgacaaaa ttctacagca aacagcacct 151860
tgattatagc ataataagta ggtagacata cttatatgtg attatgtcta aaatacccca 151920
atactcctct gacttatgct gagtgcccta gggtccaggc tagaattaaa aagggcacag 151980
agcatttgtg ctctgaaaca caggaaaaaa agagaaagct tcattcaaac tgaacctaca 152040
gccaaacaca taaaaaacta atagtaagaa agactatcac tttcctttaa gcctgaattt 152100
```

```
attctggttt ttcacaaaga cttctgaaat aactactatt tttttatcaa caaaataaca    152160
aacaaaacga cctacagtcc catgttcttt tttgtttctg agactctcat gtattctgag    152220
atggcaatga atctggtagc agccgtcctg gtgctgagtg gctccacctc ctaggtgctg    152280
ggattctagg catgtgccat caaactccag cttgaaactt ggatccaaaa acaaaacaaa    152340
acaaaaaaaa ccatcacacc ctcccagccc atgactaggg gaaaacagga accacagatt    152400
cctacaatga gatcagcaaa cagaacagtt ctccttttc aaggaccttc cccagggttc     152460
tccaggttcc aacacaaagc ctggagaagg gttaacctca gcctcccaa aacagaattt     152520
gagttgaccc atttcacatt tgacatacgg gccattctgt ggccttctac tctggccaac    152580
cttttaagtg agactctgct gaaacagtgt gtcccttct tcagtttcaa atccagtcgc     152640
cttgttttta actctctcaa gaggacatat ttcataaagc caatttatac taagataggc    152700
ctgatggcca gctctttttc agttgtctcc ccattagaaa tgtttgctgt tgagattatt    152760
tattggaaag ggtctacatc caaatgtatt acaaacatga tcagcctttc acagacaagt    152820
gaattaattt ttaagacaaa caggtgaata acatttttct tgacataatg agctgatagc    152880
tcattagact ctccaaaata attctttcct gtacccacat tttgtttgat gatttagata    152940
attacttctt tagacattaa cttctttaca catcaaagtc ctatcatccc aacgcttat    153000
ttcctttctt ctagacatta aaaaaaaaaa aaagtctgtt aaaagcagaa gcactcaagt    153060
caattttcac taataaatac agttaacatg gaactgaaaa cctactgtaa tcttctcagt    153120
gggttaatgt cctgcagttg tttcggcttt cctaggagat gcagctgctt gccatatttt    153180
acaaaatgaa ttcagatgtg cagattgaaa gccagatcat ttcagcatgc cagtttatac    153240
gtggactcca ggaaaaagtt catttctgat gactactgta ttaactggat cactaaacca    153300
aaagccaatg ctgcgccaca tctggaaact cccattccag aaaataaaaa tttatgttta    153360
tttaatttaa acatatatgt atgtgtacgt atatacgcat tcatgcatgc aaaattcctt    153420
tcattataaa gtattgctac caaacacaaa aggtccccat tgtggtagag ggtaaagatg    153480
gacatcacga aagtaaatca agcaaaaggc tgctgaccat gtcactgggt gcccagtaaa    153540
gagcatattc ttgttgacaa catggccaaa gaagacagcc atgaaaaaca tcttccatca    153600
tatacctcac tctgagtagt ctctgtatcc tagaaggaat atcaaaattt gagatctaag    153660
tctaatggcc aagcagccac taagagacat aatggagatg accatttctt ccactatatc    153720
actggcgagt aacgttaagt cccatctaca gtctcaattc taagacatct cacataatat    153780
aaataagttt ttatgattaa taatgttttgt aaaacataaa ggcagaaaaa aaatcatagt    153840
taagtcaaca ttattgcata cgccattttt gttttattgt ttaaaaaaat gaagttacat    153900
cataatctaa atttctactg atatgaaaat taccaagtga tcaatcacta caagtgcagg    153960
aactcaaaag gtgaagaata tttataaaat gtctatagca tgcagaataa cacaagtttt    154020
ctagccagtg tctttgccag agtagagcac gggtggcagc gactagcgag gttcctgagc    154080
gaatgctcct tcccacaagg gtttctctag accaaaggtt caaacttcca agttccttct    154140
acaaagcagt ttcagaggcc tacaagtcac acacatggtc aggtagccca gcaaaaacct    154200
catttctcaa gtaccaattt cctctctttc tcaatactat gacaaaatgc ctagcaaaag    154260
caacttaagg aaagatatat tttggctcac agaggggata cagccagtca tgatgatgag    154320
gctgtaatag taaataatca tactgatccc ttgtcaggaa gctcaggtcc caggtttgtc    154380
ataataatag atagtcacac tgatccatgg tcaggaagca ggtacaaatg aatgctggtg    154440
tgccaggttt tttcctcttt gctttgtatt aagtttggga cgatatccta taggatggtg    154500
```

```
ctactcacat tcaggtgggt cgtccctcct cagttaaagt tctttgtaaa caccccttaga  154560 aacgtaccca gaatgtgtct tctaaattat tctaaatcca gtcccattgg caatgaaaat  154620
caaacatcac aactggatag gtaatactac cttagtgaat gtgagttatt ttattttcat  154680
tctaagcttc tgttccatac tgaatccctc ctcctacaac tggcaggcgc cacagtatct  154740
cttaaatgac atagaaacag aaactcacaa ttgacttatt tccctgctct ctatataaaa  154800
tataatatgc cttctattcc ctcttcttac cataaaggca ctggcaatgt cttttttaaa  154860
gtccaattta tattcataat tattgggcac ttactaaaag ccaaacattt ctatgtcctc  154920
ctcaggaagt tataatggct aaacaaaacc agagagagag agagaaagag ggtgggaggg  154980
agggaggatg ggagggaggg aaagaacggg agagcgagag ctggagagag agagggagag  155040
agagagagag agagagagag agagagagag agagatgcat cacaggtagg agtgacactc  155100
aacaacaatt tgaattagtg tttttgaaaag cagaagctac tgaaattgta tgtcaatggt  155160
tctgattaga caagagatgc agatactttt ggttattata gaaatggag ataagaacac  155220 attcggaatg cagagataac ttgcaggtgg aatagacagt gggtatgtga aagaggaaa  155280 atgactctga agctgggggt cctggaaact aactaaaaat actaccattg ctactaagca  155340
gaagggtggg aatgagggaa aaaaacgcct gacacagtga actttgttgg gaactatctg  155400 cttatacccca ctcacaatgg agcaggaaag ggctgagctc tggagttcaa gcagaggctg  155460
taaggtgtat cgtgaccttg ggcagctcat gtctcctctc ttcctcagct cctctaaagt  155520
agaaacttaa aatacttctc ttcatgaagt aatgactaag caagacctgg tgcacagaaa  155580
gagctcagtt cttgtgagac atgatagtga acataaagaa gacactgctc tttaaaaaca  155640
ttttagggtt ctcggtaagg gagctcaaaa aaggaggctt atgggtgcag ccgtctttc  155700 aaaactaagc tagcaggccc acaggagaca tacagggctc aacggcaaag ctgatgcat  155760 ttaaaatagc aaaaaaaaaaa acagttcatc ctcttcagtt aaaatgaatt cactcagcac  155820
aataacggaa tggctgaatt cttttctcata atgtaagtga attctaagca aaatcagtaa  155880
tattctaata cataaaaagc aagtttctga cctcaccaaa aacatttcaa caggaatact  155940
caatcttgtg gccttcctgt acttgcatat ttgtagcccc tcacaccaaa ggattttctt  156000
ttctttccca gagagaacca acaatcacac tacccatgat ttctatacaa cataaaaggt  156060
gaaattgaca gtggctaaag tcaccaagtc attctctagc ctgacttaca ccaggtatca  156120
cttaaataag ggcagcagca cggacttcgt cactgttttc aacaagtgga ttttggagac  156180
tgcaaaatag ctaatcattc caagattatg ttaagaattg acaagcctaa aaagtgtggc  156240
caggttagca ctgtccaacc tggtacacgt ttgattgtat gaaggagct ctagtagtaa  156300 gtatggaggg acatgactat cccagaaaaa ttaagatagc cagactactt atgtccagct  156360
cagtgtcatt tgcatgtcat gaactattct ctgcatatga tgcaactcat aagctttaag  156420
ctgccattcc agaaccaatg gttttcttca gccttgaggc caaggccaac attttacaaa  156480
tatcaggcgg gaactctgga tacaatccac catgatagtt ttgtttggc ttcttttccc  156540 ccatatgttt tattttcaag gcctgactgc atagcttagt tagtagagca tccacttagt  156600
atgtgggagg gcctggggttc aaccccagc acaaaaaagg ggaaggaa ggagagggag  156660 agacaggcaa ggaggggaaa gttttatttt caagatttac aaaacctcag ataaaatata  156720
gttgggtata tttcaaagaa agtggtctca tgacacatttt atcaccaaat ttcactttc  156780 tcttcagaag tttgactgtg aatactaaaa tgatttcaaa aattgctcaa aggttactat  156840
```

```
tataatttat taaactgctt tataacacaa aaacttaagg tggaattgcc acctcttaaa   156900 taggggggg gggaaccac aacaataaaa agtttaaact attctctaag aactaatcaa    156960
atggtaaaag acaatggaag ctatagataa ttaaagaaaa ctctagttag cactgttgtc   157020
tttccaacta aatctgccat tagctttaga accagagttc agagcatttt gctttagttt   157080
gccaagctgt aaataaatac tagcagatct acaatttgaa tgaaaggcat tatagagatt   157140
ctaattacga gtccttttaa aagcataaat agttcaaaag ctggcctgac ttaaaactca   157200
accaaataaa aaactgcaac tggctctcaa tctctcaact ttttcagacc tgtgggatcc   157260
catgcaataa gcaccatgcc tgtgtgtcta cttacttaca ttgtaattaa tttgctaacc   157320
aattaaaaaa tcaagctcat cagagccacc tgcacccggt ggttaccata ttggtagccc   157380
atagagtata gcatttccag cttggcataa agtccccttg ggcagtgcag ccggaaaagg   157440
gtgggaagct tgcaatagta tggttaaagt aaggtctggt tgtgcaaaac attatcttag   157500
tagtcatatt ccgcctcgct ggaacacgca gaaattctac cagttgtttc tttctttaag   157560
taaatctttt aacagtgaac taactcaaaa atactgagaa ctcaggtttt atcccagata   157620
aatatgtact ggtttcttcc tgagtctact aattccaagg acataaagct aatttttaatc   157680 cgggtgttca gtaacaacac tgctactggg atcctgtctg accgtcaaat atattccact   157740
atccctataa ctcttatcac ttgtcacatc aactagcctg acttccaata tagaaggcaa   157800
gatgacagac aatttccttg gagctcaaac gtaattaatc acagctggcg tgatacaagc   157860
ttttagcaca cagatcttct cccataaacc tgagttttga gctaggctgc gatgatcccc   157920
atctataccc cccgacacca ccggctaaat gatttatttc cccaggggtc ccagaggcga   157980
gctctgacag caacatctct gtgtcctctg tccctcagcc tgcatgcaca ctgcacttcc   158040
ttccactacc acttcctagc ttcctagctt gccttcttgg aggacttccc acccatttgg   158100
gtgacaagcc taaacggtgc ctctccgccc ggccccgagg gctcccctgc ctcacgccca   158160
ccgacaacgg ggaggagcca cggggcaccc cacgctcggc ggcctgcatc cggctgggcc   158220
cgcagccccg ggccaggcat ttggctgcca cgacgtccct caagttccca tgacctcgcc   158280
ccactccccg ccgcccccac gcgccccccac aacctctgct taagacacgt ggaggcacgt   158340
ctgcgcgtcc cgcgtggaga atgagagggg acagagatgg cgcggtgtct gcggcggcgg   158400
cggcccgggg acacgacggg cagggggcg gggagtgggg ggaaccagag attgtagaaa   158460
gggaaaaggt gactgagcta ggctggaggg ggtgggggta agatggcgag agcgccacta   158520
tgaggggcgg ggcgggggta gcggagcctg gggtgactag agggacgggc caagccgtgc   158580
ggcgagagcg catgcgcacc cggctggcca gcgcgcgcgg tcgcgggcct gcttcttcta   158640
cttccgccac actccggggg cggggcttcg cgctcccgcc tcggcgtacg gagcggcccg   158700
cagccacgcg gcggagcctc agagcgggag ttgtgatgag tcgagtgagc gatctggcag   158760
aggagctgga tttggcctgt ggtgactctg cagaccgtag gagtgagccc gaggagctag   158820
gattattgag agtcggtgat ctgcactggg agaaggtcta tgcaagcttc tcttcagggg   158880
ttggtcaggt gaccagaatt gtttccaatg acaaggggc gcagagttag gaaagactct   158940
ctcctcagag aagcactgtg tgaggactca gtccgttcta ggacctggga cacccacct    159000 acccaccct accggcccctt gcgcaaaatc gaaagcctgt gaaaactcat ctgcaaagtt   159060
accccacccc accccgttc ctttctacaa agttccatta cttttaaaag catgctttag   159120
ttaataactt tcactattgg ggaagcttta taaacaagca gtggtgattt ttccttgcac   159180
cacttatatt gaattgtatg tatgacctgt cttcccgtgt ttgatggttg caggtgtagt   159240
```

```
accttaatga actggagaca attgtgtgtg atgttttcac tcggctgttt agaaaagaaa  159300
atatccacta tcctaccatt tcaaatatta tttttattat attattttta ctattattat  159360
ttatattagt cactttttc gctagggttt tactgctgtg aatagatacc atgaccaaag   159420
caactcttaa aagaacattt aattgtggct agcttacagg ttcggaggtt cagtccatta  159480
tcaagacagg agcatggcag catccaggca ggaatggtgc aggaggagct gagagttata  159540
catcttcatc tgaaggatgg tagtagaaaa ctggcttcca tgcagcaagg atgagggtct  159600
taaagcccac acctacaatg acacacctac tccaacaggg ccataccttc taatagtgcc  159660
attccctgcg ccgagcatat acaaaccatc acattcacct ttaccaggtc ttttcaagca  159720
ctacttactt cattaatgtc ttgcctatga atgtatgagt tctgaaataa tcctatttgc  159780
tgagtgtctt taaaacagcc attcatctga tcatctcctc tctggattgc aattgtcttg  159840
tgcttagtcc tctgtaactg ccagacactt caatatttgc caaatacact tccaagagta  159900
gatttaggat gtggagggtc aacatgaagt gtaagatcca ggctcactct gcccaaagct  159960
gagtgcgagc tatatgggaa agtagccaaa aattgtcatt atttccttaa aaattaagac  160020
tagattatat acaaaaggtg aaaagacttt tttagtacat tgccaagaaa taggagattg  160080
ggctgggcgt gtaatcccag cattggagaa gtcaaggtca gccttgattt taagactga   160140
gctgtcttat aataaaaata aataaacaaa caaacaaaca aactgctgta aaaacagaag  160200
acagattatc caaagaaaaa aattccatgc agatcatttt aattaaaatt ctgctcaact  160260
aatatcatcg cacaggcatt tcacctccag ataaagacca gatttgactc aaaaacaaat  160320
tataatggtc aggtccaaaa aaaacttggg acaaatggct atctggttcc tattagctta  160380
aagcatgtgc tggcctccag gcttcctcag gaccacaaga acctgggact cttctcagct  160440
ctgctcatct tgccttttac cctaaacctt tccagctcat gggcttccct cacccagagt  160500
cttagtaacc ctactatttc agctacgcac actctttgcc ccctctctct tgcctctctc  160560
taggtctcat tgcacagact ctcttagtct tcctctcttg ctctcccag  ctctcctttc  160620
atggctagat ccagtctgct ggccaggttc agtccactgc tttctctccc tgctctgggc  160680
ccttccagat gcctctggct ctactctccc tcatacctac aataaaaacc ttcccttac   160740
ccataccttg cagcagccat gccctgcctt tattcaataa caaagctgaa acgaagctc   160800
ttgtgaagtt aaagctttgg agaccattag ctctcagaaa aagaaatgat ttccaaagtg  160860
ggtgggaaaa cacaacagga ggccaagtga catcacacca ccaaaagaag aaaaggagga  160920
ggaggaggag cagcagcagc ttggccattg tctatgtgcc cattttcaat gacaaaggaa  160980
gtcctcattc taaaaaggac agcagaagcc atagctaata ggaaccattt ctgtgaggaa  161040
gccacttctt cacttaagag tggttcactt caaataacct gcaaatcttg ctcttataat  161100
ccatgatttt aatttgttag gacaatcatg agagtctcgc tgtagaaata cagtgggcac  161160
tcttactgca tatgcatttg ctgctatagt caattgcttt tctgacgttg aaaactattt  161220
ttgtcttaca atctcaaaag caatcttatt ttaatttta gactaagtac ttcctggcaa   161280
gtttcttaac atcattgagc atcagttttc atatctatag gttgagacgt taaatctgtt  161340
gagctaaaac caagctgcct aaaagtctat gctcctttaa aataggaatt ccccaaaagt  161400
tgggtcctaa agttgtacag aaaaagttta acatgttcgc tttcaaaaca taggtgaatg  161460
aatataaaga gctcttactt tagatacatg aagatatcca actcacttta tacttgaa    161520
aagaaaaaac aatatgaata tgaaaaagta aatttgttgat acattagata ggaggtgata 161580
```

```
gtatttatgc ataatcaaac tggctactcc tactttccaa ttgcattcat atattgcaaa   161640
gcagaaaaag caacatattg ataagatatg ttcaaaattg caatacttgg tggcttttaa   161700
aactaaaatc atgggactgc agtgatggct cagtccctaa gagctcctgt ttggaaaggg   161760
tccaagtgca gttccacct ctcacatgct ggctcacaac catccatcca taactccaat   161820
gccagagtat ttgacaccct cttctgactt ccaagggcac caggcatata tatgtggtac   161880
acatatttcc atgcatctga aacactcata aaatagtatt aatctaaaaa caaaactaa    161940 tcataatcag cttcctagga cttttcgttc tacccaggtt taacaaacca gcatctttta   162000
aaactactgc ttggccactg agaaagcaat catgattttt gagagtcaaa ttaggaaggg   162060
aatcttaaaa catctggctt tcaaagtgct ctggaagtct ccaggcaaat gggaacttac   162120
tcccatggag tccagtgtct gatactctcc tagaagcaaa caactttcac tttgcaacaa   162180
atatttccca tgtgtctgcc atactctcga agctgctgaa ataacagtac acagagcaga   162240
tactcaggtc actgtccagc ttccatccca gtagaagaaa tccaataagc aacaaaataa   162300
atagctatgc tctatagtat atctgaaggg agtgggtgtt accagaaagg ggaaaaaatg   162360
gataggatga gggagttgtc actgaaaaat gtcaatttgg ggccagacag cctgagaaag   162420
tggtccagga atatggacat tcagaaggca aagcagattg ctactatgtt tgaagggcca   162480
ggctgagtca agtcactgag gctggatagg tctggtaagg tggaagatct gccaaaaggt   162540
tctgagctaa agaagagtta ctcagaaaga aaataatgtg ggttgaggac agaggagtac   162600
aagggaggtc caaaggagcg ctgacagcaa gcctttacta cagaagcctt cagaggatgc   162660
tgagtgtcaa gcacaccaaa ggtatgcttc actttgttta taaggtgagg aagtcgagtc   162720
tctttgtatt taaagtgaga acagagaagt gaagtaaagt atcaggaagg ggactttagt   162780
acctgaaagt aagatagaga attcaagttg agaccagtat acagaacatg cagttcttca   162840
atgtgttgga gcggaaacat tgagatgtga aattggatgt attttggtg aattattcaa    162900 ataactgctt tcctcttcta ttacatatga aaacagagcc aaaaattaat tggtgccatg   162960
tgcaataaac cacagtgtgg ctcatgcaac ctgcccttcc tgcttcacac cccaaagctg   163020
gatgcaataa gcctattttg actaagtaac actcagatca agtgttaagt aatgatcaaa   163080
gaatgtaaaa acaggcctaa tttctagcat tctatagaat gtgtgtgtgt gtacgagata   163140
tatatatata tatatatgtt ttcttttttt ttttcctag aatctttta aacaatctca     163200 ataactgagt caggtatagt gaaaacaga tgggtttggg tgccacattt tggccacagt    163260
aacttgctgt ggttcggcct ctctgaaagt aagcatcctc ctctgtatgt tgttacaggc   163320
tttagatgga agagttctga ccaattgaaa aagctcctta gtatgcagcg attattgtat   163380
tccagctttt aatgagctat ttgcaaattt tatcttctag tgcattgagt tgggaatata   163440
aagggaaact ttatctaaaa taccagggtt tgtttctgat aatataataa atctatatga   163500
acatgacagt tattttttg ttttccctcc ccctcccccct cttcctcccc cctcttttg    163560 aaatagttgt tagttcaggc tagcttcaaa ttcatgatcc tcctgacttg gactctgggc   163620
tagcctggaa ctcatgatcc tcctgcctca gaatcccag aatctgggat gcgagcata     163680 ctcctccatg tcctccatca atgaaacaat tactcttttt gacaaacatg tattgaggtt   163740
ccagtaggta caggaagcat agttaggcac tagacacata aagattggta acaaaggtcc   163800
tgtcttccaa aaggcttgtt gctattgacc taggaaagcc aaaggcagtg ccaatatata   163860
atgtctgctg agttctcctc aacttttggc gtgtaggtca ggatatctcg aaccaccact   163920
ccagccttac gcccaaccgg acagttcttc atatttcttt ggggctactg ttctcccctc   163980
```

```
tggcactgga ctccacttga tgctacatca ctgaagttta tggatgaact gctgtgtgtg   164040
tccctgttcc acaaacaacc actcaaatgg gaactgaacc gtgttccttg attttacctc   164100
agtgcatttt cttggaggtc tgtatggcca tagcaactga ctaaagtttc gagaggatgg   164160
aaggggtttt gccctcatac tgcattgcta tgttttggta ccatgcccct ttcaacatta   164220
tactcaaacc ttctctacct tctcaaacac ccatgcactg ctaatattga gtgttttggt   164280
catctctttc tctaacctga gattctagaa accccactct ttgaggctaa ctgaccaccc   164340
agctgcttgt actttcctaa ataatttgga gttcgtttcc tttgcaactg tcaactctaa   164400
tattaagtaa tccctattct gtgtataaat tgtagaagat agaaagttag ggagtagtca   164460
ctgagggcag tgaatgtgga ctgacacaca cacaagaaaa tgtgtcaagg tgggcagcct   164520
ctcttttctc aatagtttca tccttcaatt gagcataaca atagagactc ttaaaataat   164580
gctttatcac atgggaatga atgtagagtc ttacacattg ttaggactta attttcatta   164640
atgtgattct taccactgag acaatgagtc agaactcagt cttggaaagt gagtcatctt   164700
tgaacagaat ggggaaaggc gatttaagca gaggaggcag cactaggaaa gttatggtgt   164760
attaaagaga atcacaagtc cggcatgatg gagcacagag tctgggaaga aatttgtcag   164820
ggtcagatca aaggaagtct tagacatcat aattgggaat gtgagcttta tgtaattaga   164880 aattggggt gttgaaatta tttttaaggt gatatcatga ttacacagcc tgttttgaaa   164940
gatggaagtc atatgcaagt tagaaggaaa aatgggaaga cacaaacagt tcagtaaaga   165000
gataaaatag ggcagagctg agccaatagg taggaaacat gagaagatgc tgggagaaat   165060
ggaacgtgaa atgttagagg actcagttac caactggtaa tacgtgagga tcagaactgg   165120
agaaagggct tgatgggaaa agcacttgcc ttacaaactt aaggatctga gttcgaatcc   165180
ccagaaatcc tataaaaagc cagccatggg aatgccttcc tgtaatcttc atgctcccat   165240
gagaagatgg aaggtgaagg ctggataatc cattgaagct tctgtgcctc ccagcctgcc   165300
atatgtagtc tttaactaca gaggggaaaa aaaaataatt gtgaccctat ttcaatcaat   165360
atagaagtca aagtcaaaca ctcaaggtta tcttctagct tccacacaca gagaacatcc   165420
tacacatcac acatacacac acacacacac acacacacta taaactcaac   165480
agggaactcc caaatgattc caaggctcct tgaattgcca catagatggc aataccgttt   165540
ttcaagacaa ggaagactaa gagtgccagt ttcagatatg ttaagtttta agatgactgc   165600
acaaaatcgc aaatggctat aagcaatagt caattggaat aaccagtgtt aaaagcaaaa   165660
cctagcctaa agtctagaac caccggatta aatgcctgca ttacttttct agtgtcatga   165720
tagaatacca tggcaaagac aacagagaag agagagttat ttgggcttat ggttctaaag   165780
ggtcatagtc catgatggcc taacaaagtc atggtagcag aagcaggaag ctgagggctc   165840
acatattgaa ctacaggcac aaagcaggaa gagtgaacta gagatggatc aagttttaa   165900 attctcaaag cctacctcca gtgacatact tcctccagca agtccatgcc tcctacaacc   165960
ttctcaaata gcactgctaa ccagggaccc tgtattcaaa aaattgaagc ctactgggc   166020 ttattcttat tcacaccacc ataataaaca tgtagcttta ggaaccagat tcactatttt   166080
cactcattca aaaatatgat gctctgcccc attcctatat tcaatcaaaa aaaaaaaaa   166140 aaaaaaaaa cttctcacta gaatctctgt ggacacagag gaagccaaac aacaaaatgg   166200
tcaagacagc tcctagagta aggatgagtg actgggtcct caacacacgc aatgagtgag   166260
gtagacagtc tataaagacc attgagaaca tagtagtttc ctgatgtcag gaaaacggtg   166320
```

```
gcaaagaggc acattaatga tactaacaca gagttaatgt caactggact taactcaagg   166380
tgggctctgg caaaaccaag ttttatagag atgggaagag aaacttgatt attctgactt   166440
aagggaggaa tagataaagc aactccttat tctttccaag acctgcttgc cacgaggaaa   166500
cagggtggct ggaaacacat caagggacaa gggaaaaaag aattttatgt tcaaggcatt   166560
tgagcctgtt tatgggggtt tggagaagaa actggccaag agaataaggt cgaacactta   166620
agatagaaaa aagccaatga aaattgcact gggaagtttg tatagtattg attctggaaa   166680
agatagcaga aggctcagta aagagtccga gaaatggcta agacctaaaa tggaaaagaa   166740
gtttgactag gagaaagaaa tgaagaggaa gctctccata caagctgacc ctagttttc   166800 ctagtagaaa agaagctacg tgaagaaaat gggagatgac aaagtgaacc ttatataaga   166860
tgatataggg ttgctgggcc accatgagga gtgggagagc ctcaaaggct ggctgaattg   166920
aagttagtca gtacagagca gcgattctga catggaatta caacatctgc ttcttattag   166980
aaaggaatac gtggtcccca tcccacacct acagagtcag aaaccccaa gagcaggctc    167040 tgtggtctgc cttagcaaag ccctccaggc gattttgaag tacaacccct gggaaatgct   167100
tgcatagagt ttctacggaa tctgtggctt ccccaaccag caagcaatga cgaggtacaa   167160 acagtgcac ccaggcatat cctaggcagt tttttttaaa gtaatatttt ccatattgca     167220
ataaaaatac acttacttgg catgttagag attctgtaaa tttctatgtg gaatgagtg    167280 tcatacaagg ttttaaaaat ctgaacaaag agattccttt catctgaatt tcagaaagca   167340
aatactgttt ttaaaagggg ccttgctgct caagttttaa acttataata tagaaataat   167400
gaaattgcca ttcacttcct caaaaatatt ccatgaccca acactgtaat aatagctctc   167460
ggattttgct tgggcactgc tgtcatctca atctaagtga tgctgatcaa ctctcctggg   167520
ggaaatattt atgaatgaaa tgttctcaac tttaagtttc cctcccataa atttacctt    167580 gggtcttgat tctggctact gcctatctgg cagcaagtaa tgacatctgg caaaacaaga   167640
aacaagtgag caaacagtaa aaggttgtta atgaacctgg aggtggtcag tcaagcatag   167700
tccaatcgtg tcccccggaa ttaaatgcat gttcatgact gagacttta tatgccatac     167760 caatagtaag gtcattttct gctaccattg ttccaagaat gttgtcacag ttcaaatatt   167820
cagagcctag tttggaacca ttttcactta tctggggaat gttcctttga acacaccccc   167880
ccccccccaa ccaatggaaa agccaacaaa ctcacagcct cgaaggattt taagaattta   167940
tttacatgct gacttatcca ggtgtgtctt acataaagaa atatgggatc tgggaatcca   168000
tatttaaaaa ccagatgcaa gtatgcagag aacaatgagc cacaccccaa attactttta   168060
tagataagac tgagctctca aagtgaattt gtatagtgag caaatactga ctcatggtaa   168120
ggagagctag caagcctgaa tcatgacctg attaaaatac tatgtaaata aggagaaaca   168180
ttgtcatgga acaatgtaaa agcagattta aacacattag cttagcacat tccaacacag   168240 tggggggtata agcggaaaag atgaactagt caggctctct gggtcccaac actctgaaat   168300
tcaaattagg tagctaattc tccttaactt gattttactg tgaccaagca acctttactt   168360
ttttttttct tttctttttct taattccaag agtgatgggc tggtttctat gaataatatt   168420
ttactgccaa atatgacaat gagacacatt gaaaagtttc aattcatgta gcaattggat   168480
tgtctcactg cagatcagta actcagcagt gtgggttttg tttggatctc ttggaagctg   168540
aagtgtgttc gttctagagg aggaatgtgt ggcctggtaa gagtaaagga acaaattcca   168600
gacctgaatt tcactctgag tggtttcggc accccataat agcagcaatc caacccgac    168660 acctgctcta tcagtcagct ttccataacc atttaaaaaa atacagggac aattaatttg   168720
```

```
taaagagaaa gtatttattg tgaagcagag tttgcagggc ccagtccaag attaggcaag    168780
ttcattgatt taattctctg gtgggcatac cagatgctca tggcctggga gagcatgatg    168840
ggagaaaaaa taaaaaagat gctcacctct tcagcaagta gcaaagaaaa aaaagaaaat    168900
aagcttgggg gccccacgtt ttttttttttc aaggacatgt gtccacccag taacctaaaa   168960
acaccctctg atcagatcta ccctctaaag atctatagca ccaataacat caacttagat    169020
gtgccaggtc tttgacacat gcatcaacaa ctaggggaaa cagatgctta ttcacgtcat    169080
aaacgaacct ttcaccttac gaaagtcctt gcaaatacag agcacgtaaa gatgctgaga    169140
acctgagaag ggtgagaaac tgagttcagt tagaaatgcc gtgttgacct aacaagtgtt    169200
gatgacttct tcgggtgtac gtgcgagcaa gctaagcaga tcactcattt caagagtgta    169260
tcgagttaga agatgaaaag agcgattggt aaatggaaag agggctggtt gtaaggtttt    169320 cccccacga gaaggagagg aggtggggag ggggaggggg gccaatggaa acagagatat    169380
atgaggtaca gtgagggagg tagatttctg gcaatgcagg ttcctgagga tgttgggggg    169440
tggggcaagg agcacacatc ttttggagaa aacatctgaa atatattatt ctgaaatata    169500
atatttagtc acttcttcta cttatttctt tttattcggg gactccagac ccccaaatat    169560
tgctcatgca ggcaagcagt ctaccactgg tctacactgt aaatcctgat ctgcaaagca    169620
tgaattgcac catgcatcct aaaacatggg cttaaggaag cgaatgagaa gacatgcaag    169680
agcatttgga atagaaaaga gagtcacaaa attcagggaa gatgaccatc tctgattttc     169740
tttaccttac actacagcct atgaaaatga gcctcttgtc ttaggtaggg ttgctgttgc     169800
tgcaaggaaa cagcatggcc aaaatgtaag ctccacattg ctgtatatca ccaaaggaag    169860
tcagtacaag aattcaagca gggcaggaac ctcgaggcag gagctgatgc agaggccatg    169920
gaagggtttg gcttactggc tttcttctcc tggcttcctc agccagcttt ctttctttct    169980
ttctttcttt ctttctttct ttctttcttt tcttttcttt tctttcttt ttggttttgg      170040 tttttttttt gtttgtttgt tttcgagac agggtttctc tgtgtagccc tggctcacct     170100
ggaactcact ttgtagacca agctggcctc aaactcagaa atccgcctgt ctctgcctcc    170160
caagtgctgg gattaaaggt gtgcaccacc accgccagct tcagccagct ttcttataga    170220
accaaggacc accaatccag ggatggtatc atccacactg ggctgggccc ttccccattg    170280
atcactgtat tagtcagggt tctctagagt cacagaactt atggatagtc tctatatagt    170340
aaaagaattt aatgatgact tacagtcggt agcccaattc ccaacaatgg ttcagtcgca    170400
gctgtgaatg gaagtccaag gatctagcag ttagtcagtc tcacacagca agcaggcgaa    170460
ggagcaagag caagactccc ttcttctaat gtccttatat tgtctccagc agaaggtgta    170520
gcccagatta aggtgtgtt ccaccacacc tttaatccca gatgaaaggt gtagcccaga    170580
ttaaaggtgt gttccttaaa ctcggagatt taatcttctg gaatccatag ccactatggc    170640
tcaagatctc cataccaaga tccagatcag aaacttctat ctcccagcct ccagataagg    170700
gtcgctggtg agccttccaa ttctggattg tagttcattc caaatagagt caagttgaca    170760
accaggaata gtcactacaa tcactaactg agaaaattcc ctaaagctcc atctcatgga    170820
ggaggcattt cctcaactga ggctcctctt tttatgacca cgatagcttg tgttacgttg    170880
acacacaaaa cctgcagtat gcctttaaa taagttatat acaactgagc tcatatcagt    170940
ttaatgttag agaaatgtta attctattac tacaaaaga atcttgtttt attttaaaa     171000 aaaaaaacaa ctttttttct tgagggagga gtgtgtgtgc tgcttttgg cttttgaag     171060
```

```
cttctggttt ttcctagata gagtctcacc atatgattca agatggcctc aaactcacaa    171120
tccacctgct ccatcctccc cagggctgag attataagta cgtaacacta tggctagctg    171180
tgaaaagatt tcttaaagat gtaaaacctg agtagttatg atctcttggc aagcgcaaag    171240
gctttggaat aagaacctct tctaacatat tatggagcaa attttgttga accaaaatag    171300 tttcttaaa aaaaattgat tccatatgag ataagtaaaa atctaatttt cataattatg    171360
aataaaccat taagctatag ttattccata tgttcatcag tttggctgca caatttgctg    171420
gtttaatcca tttagtgagt tgggtgacca tcaccggaac ctagttttaa aacatcttca    171480
ctgcctcagt aagatcatgc atgcccatat atgattaccc ttcacccccc gattccagcc    171540
cttgataacc actagtctac tttgtctctc tctagttgac aattttgggc atctcataaa    171600
cagagtgggt tagttttca tctcgtggat agcatacttg gggaaacggg acgagggaga    171660
tagcagttgt ttggaatcat gatttcagag ctccaccttt ctccgtggtg gagaaggcat    171720
ggtggaacag aacagctccc ccctcacaga cttggaaagt gtatggttga gagagtgcag    171780
gtggtagtgg gcttccttca tctttctctt ttaggccctc caggtcatgg gacaattgga    171840
taatatcatg cacagccagg gtgggcatac aattgaatga tatcatgcac actcagggtg    171900
ggcatacaat tgcatgatac tatgcacacc aagggtggac ttttatctca ggttaattgg    171960
gttctaattg atacgttggg gccattttgt tgcagtaaat ctccaacccc aataaatcca    172020
tgcaaaaaac acacaactca gttacaatat ttataagttg cacgcccaga ttgggcagat    172080
ttgccactac actactctgt tccccggcta tgagatcctt gttacttgca gcttctctgg    172140
gccacatggt tctgttctat cttccttcca tctcttcttc ctccgtcttc ctctctctcc    172200
tctgtctcct cctctccctc tcctcctccc tctcttctcc ctctccaaaa cctccagccc    172260
cacctttctc ttccactgcc caatcacagg ctctagtctt tatttgacca tttaaaatgg    172320
ggagaacgtt cacaagaaat catctgagta cttcttgatc cactcctctt ctgggtagcc    172380 cttcttgag aaagcagaat tagcatcaaa atacaaacag cacttgggca acctacaaca    172440
cattccccaa actgcctcag atctagagga gtgttctatc ttctctctca actgtttctt    172500
aatccactaa tgttgacaat taagatcgcc catccctggg agacagaata caaggaactg    172560
aatatggtat cttcacttta gcataatgtc ctccatgttc atccattttg aaatatatca    172620
gtatttcact cacttttat gaccacatgg caagacctat tggctagata cagaacattt    172680 tatttacccca ttcactaact gatggacatt tgagcagtct ccactttttt ggtagcatga    172740
gtaatggtca tatgtgtgtc agacaagtgt gtggacgcat gttttttactt catgtagcaa    172800 acctagtggg tagaatgtct gattcatata gtagacctgt ttcacgtcta aagaaacaat    172860
tcaaatgtct cccaaagtca ctgcactgtt taacctccct ccccaccagc aatgtctgag    172920
gtttcccatt tttctactcc ttgtcaacgt tgttcttgt ctatttgatc ccaggaatct    172980
tagtggatgt gaaatggtat cgcccagtgg tttcatttgc attttgccaa tgactaatga    173040
tgccaggctt aggagacttt tgaatatatt aagaatccca ttgctttcc ttcaggaaca    173100 tgtctgttca aaccattttt atgaagctaa aatctaaaaa tgattgctaa gttatgtata    173160
ccgggttgct ttgggatagt ctagttttgt ttttgagata ggtctttggc atgttgcaaa    173220
agatgccctg aaacttccgt gatcaagtct ttttgcctca gcttcccaca tagcactctg    173280
cctttaatga tctcagcaga gactaaaatc tatctgacct tagtactctc tgcatctaat    173340
gttaacctag ccttgtgcct agcatgtctc cttttgccta gggtccttt gatagctagt    173400 ttacactcat gtctggaaat tcagactacg ggaactcatt tgaacttgac cagtggctcc    173460
```

```
actgatttgc cttccatgtg gcgctttgtg tagtcatttt ggggtgtctg ctgaagtcat   173520
gtgctcaaca ttactgtttt ctacctgtgt gcagatgaga aaaaggctcc acatttttta   173580
ttagactcta gtttccccac ttgctaacca aacatgtaaa gaattgtcac aagaagcagg   173640
ttaagagtag tcacacaaag ctcggagcag ttctcagatg taatcactgt tgactaaacg   173700
ggagctgtta tcacagtagc taagagtctg tgtggccagc tctatagctt tgattaatag   173760
agactgcttg gctactctgt ttcttcttaa agggttttac aagcagagtg agagagatgg   173820
ctcagtgtgt atagtgcttg ttgcacatat tgggacctgg gtttggatct ctagggttct   173880
ggtaaaagcc agatgcatca atgtgtgtct atgacatcca gcactacagg gcagaggtgg   173940
gtggatccca ggtttaccca gcccatctag ccaaaccagg agctccaaat tcactgtgag   174000
acactgtctc aagaaataaa gttgaaaagg atgaaggaag acattctgcc aacaacctct   174060
ggcttccaca cacatgggca aggacaccac atccatgcat atatgtttat agatgcacac   174120
atatacttca cacatacaca catacataca cacttgatgc atattcagca ttatgaatat   174180
gaaaaatatg tgaagatcaa gattttaaag aaactgtata cacagtgtgg catcttcatt   174240
acccactatc aaatgaatat tttcgaatga aaattttaag tccacccggc atatcttgac   174300
atattctagc tgtatccatt cccaaacata taaaggacaa ttttttataaa tcctacattc   174360 ctcttgtcaa tctgtcagtt ccccagatga actcttttaa tatgtacagg atttgtcacc   174420
tgttgcccca gcctagaacg tccttcctgg tgttattcag tgctctcttt tatcacacgc   174480
ttttatcaca tgcatatgct cttgtggaag tcttcaacat tctctcttac aatcgctttc   174540
cacccaagaa atctacacgt ctctccggac atagggttgt taccttcttg gctacaagat   174600
actagacaaa agacaaatta aggaagcatc tttagttagg gttttactgc tgtgaaggga   174660
catcatgatc aaggccactc ttacaaagga caacatttaa ttggtgctag cttacaattt   174720
cagaagtcca gtccattatc actgcaggaa gcatgcagtg tgcagacaga catagtgctg   174780
gaggagccta gagttctata tcttgatcca caagcaacag aaggagacta tgtgccacac   174840
taggtgtagc ttgaacaccg gagatctcaa ggcccacccc cttcccacaa cacccccccc   174900
ccagtgacac acttcttcca acaaggccac acctcctaat agtaccactc cctatggtac   174960
caccacagga agtgagagtt aatctggctg ccagtctcag ggcttggtcc accgtggtgg   175020
gatgccatgg tggcagaagc ttgaggctgg tagtcccatt ttggacagag atgaagactg   175080
gtgttcagct tgcttcctcc tcctattcag tctggaatcc atctgagtcc acactaagct   175140
aattaaccaa attaacctaa actaagcagt ctcaggcatg cccagagatt gtttccatgg   175200
tgatttaaaa gtctatcaag ttgacaagat taatcattac aatagatact tatgaaatta   175260
catacaatta aattaaataa taaatacaat aggtatttaa aataagtatg gaaaataaaa   175320
aatagggaca aaaaaatcaa atatttaatg ataataattc aaagaaattt accttaaagc   175380 acttttttgta tgcttacttt tgccattaat taaaatgaaa gcaaatttgc aaagtattaa   175440
gagaaataca gttatttatg tttggaaaca gaattagatc ttgtctgaat gtttgacatc   175500
ttgaccaata ttttgagtta gtagtcatca tcgtcaccgt caccaggcct gatggtgaat   175560
gtctataacc ctagcatttg ggaagctaag gcagaggcag ggggatcact gtattttgta   175620
agccagcttg ttctgcatag caaattccag tccctgtctc tcaaataaac gtaaccccaa   175680
aaagaaaaaa atatatagct aattcagggc acaccatttt gtataaatat gtagcatcaa   175740
agaaagaggt atattcaagc ccatttcaga aataattgaa aaattatccg taattccaag   175800
```

```
ccaaaattca ttgattttt ttttttttg agacagtgtc tcactatgta tctttgacta    175860
gcctgggcct cgatatgtag agcaggatac cctccaagtc acagatctct acgtgccttc    175920
tgcttcccaa gtgctgggat tatggtgtgt ggtgattccc agaacattta aaaataaaa    175980
taaaatacaa atcactaact caagcagaaa attttaaaat caagctttct aatgtatttc    176040
attccaaaaa aatatactaa attgatactt tacctaatga gaataatgg taggaaaata    176100
ttaaaagtaa ctgtagttaa atcattgttt ctgtaagaga agaaaagctt gtgtgcacag    176160
taagaacctg caaatcatag catacgatat aatatagcct tgaagttaag ccgaggttca    176220
gtggtagtgc atgctgtgag agcatgcgca gtgcacatgt tgcatgtcta taacgaggca    176280
gcagtagagc ggcgcgctgc aacatgcgtg agctctgaca gaagcaccta gggttataga    176340
tttgattttt gagttaactt ttggtcaaaa ctctctcact gttgacaaaa tctcacagcc    176400
accacattca gttttctgac ccctaaatag ggttacaaca cacagtttaa gaagctagac    176460
tccaagccgg gcgtggtggc gcatgccttt aagcccagca cttgggaggc agagccagac    176520
ggatttctga gttcaagccc agcctggtct acaaaagtga gttccaggac agccagggct    176580
acacagagaa accctgtctc gatcccccc cccccccaa aagaggctgg actccaaagc    176640
agctcatttt aatacatcca acaagttaag aaagttttg ttggttccag tttagattca    176700
agaaaatgga gacctggtgt ggttccatcg gtttcccgag tcaacaaaag tcaacaaaaa    176760
agcctctgct gaatctagtg tctggtgacc cctgcgggt atctcttagg gcagaagaac    176820
tgtaaaagtt tgtgtctaca aacgcaaact gaagaatcac cgcctgcctg gactgtgagg    176880
cggggttgct gagagggagt ttgagatttt gtggatagga aggacatctt gaaaagagg    176940
ttttctcttc tctcttatag cgccacttct tcctttgcct ccagttcatt tcctttctct    177000
ttcctccctg ttaatgaata gtcggcacag aaactgagtt aagactgcac tggaagccgg    177060
cagctcctcg gcccagttcc tggtttacct ctctcctctt cctcttgcta ctttctcatt    177120
ctatctccac tttgctcttc ctctcccat tcaaaggaag aagtaaggaa gaaggttagg    177180
ggtggggagg agggaagaaa ggaagcaaag gatagaggaa aggtggagga ggaggtggag    177240
aagagagagg agaactcctg tcaggaactg agcctctggc tcaaggcaag gtcttcttcc    177300
tctcctctgt gccctctgcc ccctcctcta cctcctcctc caccttcct ccacccctc    177360
ctccatcccc atcctttatc ttctcctcca cctcctcctc cacccctct ccacccactt    177420
ctccattccc tctcccaccc cctcctccat cccctcctcc atccctctac cagtactatc    177480
tatagttatg gaacacttct agctccagta aatggtaccc tcctctccag tggtaattgc    177540
ttatcagctg acatttagct gttccttaaa agatacaggt aaataagatg gacttagagc    177600
tctatttctg atgtatgcaa aatcctctgc ccttttaccag atgtcttta atccccatga    177660
cttaatggtc ctttggttgc ctctacgttt tgattcctaa ccccactaaa ctgggagtta    177720
tattgtacta tattatccct tataattata aaactagctc tccatatctg tgagctgggg    177780
tgtgttttaa ggaacatgtc tgtgcagaac atgtgtggac ttttgtcac tcattgttaa    177840
cacaatgaca gcaagccaca tagcatttac actgaggata cgtatcggtt gtaggcaaac    177900
acgaagccac gttccaggag agacttgaat atctgtaaac tttggtatcc aagggggcgg    177960
tcctgcaacc aatatgcaga catcgatgta gggatgtagg atacaagact gtgtatcttt    178020
ttgtgtgtag aatccacccc cccccctttt ataattttaa caaaccactt gcacacgggc    178080
ttgtgtgtgg taagctttat ttgcgggaag aaggaatgaa gaatttcaga gcatcatcac    178140
aaacctctca agatggaaca ctagtgcaaa cctgtgttcg ttcatgtaga gcttaggtgg    178200
```

-continued

```
tgaggacgtg gctgggcatg cgcagtcaaa agaagctccg gggctggaga gactgctcgg 178260
tgcttaagag agcttgttgc tcttgcaggg gaccctagtt tgattcatgc attcctatcc 178320
gtggctcaca acagcttgga actccaggtc caggagttca aacatccttt tatggcctcc 178380
acagacacta catatgtgtt cacatacaca caggcatgct catgtgcacg catgcgcgcg 178440
cgcacacaca cacacacaca cacacacaca cacacaaatg atgatgatga tgataattaa 178500
tgttcaactt tataatttgc ttgacatttt cctaataaga tactagaaaa aaaataggaa 178560
caaaaataaa tcccttgatc ctccgccaag catccaacat cctccccaca gtttcttcta 178620
ttctggatta tgttctggca caaaatctct gatacaattt cccttcattt atttctaagg 178680
gaaagtggtc tatgatgtgc tgtcttctaa tcacagcacc tttgggtcct cactcaagat 178740
gcttgaggcc ctgtcaacca gttaaaacct ccttaagttg caagaacaag aatcaccttt 178800
agttacattt atccggcctt tgctctcacg cgtttgcctt gatacagttg tctaggctgc 178860
ccttcacctt acagcgtagc caaggataaa gctgagctcc ccctcctcct gcctctgtct 178920
ctcaagtgct gggattccag gtgtgtgcca ccgtgcctgg ttccacaccc acacattctt 178980
taacacttca agtagcgccg tgtgtatact gactgtgtgg ccttataatt tctcagagac 179040
catttccaag atacctaata tgaaaagagg tacaatttt aaaccatgcc cactcactag 179100
atttctctaa gaattaaatt ggataatatg agctttaaaa aaaaaaaccc aacaacaacc 179160
aaacaaaccc tatcaccagt aattgaatag ctggataatg aaaagagaat ggaaccagtt 179220
tacatgactg gactgggact gactgctggg ggtccctgtg tttctgacta acaagcaaca 179280
gacactataa ggtgccttat gcggaagcac acaagttccc tctccccaag tccatgtgcc 179340
gtcctgatgt gcaaccttgt taaataagat acagtttaga tgactctggt gacttctccg 179400
aaacccatct gacacacagg aagctcccat ctcccaccca gtgatcctaa gaatgtccag 179460
gcttctgccg ccgttactgc tggcgtcagt gctgagtgtt ctagtgatca tttggggagc 179520
accaagcaat gtttcattca gcatcattat agcgcaggaa acaaacgtga cggttaatgg 179580
tgtctttaga gtctgcaggc atagttcttg ggaatgctct tcaagttttc tctgcccatg 179640
gaagttttgt tttgttttgg gttgggttgg tgtttggcca ttttctgaaa acattttaa 179700 atgtctctta tcctctctga cttgcctact tccttccttg atgctggtac aaacagacac 179760
gttaaaatta aaacattgtt gccaggcagt ggtggcgcat gcctttaatc ccagcacttg 179820
ggaggtagag gcaggcggat ttctgagttt gaggctagcc tggtctacaa agtgaattcc 179880
aggacagcca gggctacaca gagaaaccct gtctcaggaa aaacaataaa taataaata 179940 aataaataaa taaataaaaa cattgtcttg gctcctggca aattttgcaa acagcctcat 180000
accaatcttg aagttgcact tcaacacttt cgaaagatat gtcagtgtca gaatgcctcc 180060
cagagaaact catttgaagc tcatatttag aaaatgaagg cgagcgagag atcctcaaga 180120
caccattatt tccgtacata ttgaccagaa ccgcatgtgt ttcttaattg ctcttgtaga 180180
agtcttatag aacatgttat aaaatgccaa aacctcagtt ataaaaggct tttaaagtct 180240
aggctatgac aaatatttt aaaatagcta cttaataatt ccttttggg ggtaaacgct 180300 ggagaacgag acactttaaa agcaatagaa tttaaaggga taatccatat tcaccgcata 180360
tttttcttcc taaacttata agactaatat gtgtgctggg aatacagctt atcctagtac 180420
acataaggtc ctgggttcaa tccccagcac tctagcttag taaacaaacc acagggacat 180480
ggttagagta agtggacatg gttagatttt aatgagcact tttaccattt cattaagtct 180540
```

```
accattaaca caaaaacagg attggggatt tctatttagc ttcagcagct aatcaatttt    180600
aattaaccat agctgctttg tcattttgat ttattagtta gtagaggtct gtttaaccca    180660
gcattccagt ggtgagggtt catgccagta gctagaatgc cctcgctgtg tctgattatc    180720
ttatcacact gaagtcaagc tcatatttat cggatgccca ctgttctgaa cattaggtgg    180780
tcagggtaaa caaaacactc aggatctcac tcagctacgg cctccatgtg agaagaaaga    180840
ggaagggaga ggatagatta taaactaata aataacctca ggtaaataaa caacaaatgg    180900
tgtgtgccac gagggatata attacaacta actgacatag aaactcactg aagcagtgac    180960
tttttaaaat agtagggaga gagagccacg cgggtatcct gaaccaaagc aggatgtaca    181020
agcatgaaat ctcacttcct agaaattctt tccttgggct ggtgagatgg ctcagtgggt    181080
aagagcaccc gactgctctt ccgaaggtct ggagttcaaa tcccagcaac cacatggtgg    181140
ctcacaacca tctgtaacaa gatctgactc cctcttctgg agtgtctgaa gacagctaca    181200
gtgtacttac atataataaa taaataaatc ttaaaaaaaa aaaaaaaaaa gaaattctct    181260
cctcttctgg aatgtccctg ttttttggtt ttttgttttg gttttttgtt ttgttttttg    181320
tttttgtttt tgttttttgc tatgtctcta cattctctta aagaacacag agtttctcta    181380
gggaataacc gcataattaa agtgtccact caatgtttcc tatcaatttg gttataatta    181440
agatataatt tctataaaat agcattaaaa aatatgtata tgtgtgtgcc ttggcacaca    181500
cctgaggagg tcagaagaaa tcttttgggc cttagttcct tctctccttc cgctgtgtgg    181560
attctggagc ttgaaggcag accctcaggc tgggtggcaa gtgcctctac tcaccaagct    181620
atcttacagg gttcattggt ttaaaagccc acgattcaag ggctggagag atggttccgt    181680
gcccagcact cacaaggtaa atttcagttc taatggagct gataccttct tcgggcatcc    181740
acgggcactg cgtatgcaac agtgcacgtg acatgcatgc aggcactcat acatatatct    181800
aaaaaaactt caaatatctc gatttagaag cttcaaagaa gattggtggg gattactgcc    181860
gccaagggcc agacctcttc catttccttt agagaaaccc catactcaat aacagccatc    181920
cagcccctgg caaatagtaa tttacttcct gtctccatgg acatccctgt tataggctat    181980
gctggttttt tgctttggtg tttggttggt tgcttggttt gggttttggg gttcttttt    182040 ttttttttct ttcaaaatct aaatctatct aggaagaggg aatcttaatt gagaaaacgc    182100
tcacatttag attggcctat gggcatttcc ttgtttatgt ttgatgtgaa agggttccac    182160
tcactgtggg cagtgccatg cctgtgcaga aggtgccaga cggtataaga aagcagaatg    182220
agcaagcctc agggcgagcc actgagcaag ccactaagca gggttcctcc atggcctctg    182280
cttcagttcc tgcctccaga gttcctgccc tgacttcctt tgatgacagg ctgtgatgtg    182340
gaagtgtaag caaactaaac ccttcacttc tcaggatgcc tttggtcagg gtgtttatc    182400 acagcaatag aaggacatgg acattttatt attatgaatg aatacaaatg atatgtagtc    182460
atttctgtct ggctgctttt tttaaatata atgctttaaa agatttattt cattttaat    182520 tatctttgtg acttagtcaa tgttctattg ctgtgaaaag acaccatgac cacggcaact    182580
cttacaaaga aaagcatttc attggggctg gcttacagtt cagaggttta gtccattgtc    182640
atcaggcagg aagtctggca gcatccaggc agacaaagtg ctggagaagg agcttgaagc    182700
ttctacatct ggattcacag gcagcagaaa gtgcaaaaga cactgggctt ggcttgggct    182760
tctgagattc ccaaagccca ctggccagtg acacacccac tccatcaagg cctcacccac    182820
tctaagacca cacccactcc aacaaggcca cacctcctaa tctctttcaa ataataccac    182880
ttctcaatga ggaagaattc aactatttga gcctatggga gccattccta cttaaactac    182940
```

```
tacagtgtgt gtgtgtgtgt gtgtgtgtgt gtgtgtgtgt ctgagtgggt ataggcatgt  183000
gagagcaggt gcccatggag gccagaggtg ttggatcccc ttgaactgga gttgaagcta  183060
attagaaggc atactgtggg ttctgagagc aacacttgcg tcctcaacaa gagcagaaag  183120
cgctcttaac cactgataca atccttccca tcccaccatg ttttcaaaac tcaacagtgc  183180
cacagtattt atcaatagtt catgccttt tatgctgttg aattaatatt ctttggatga  183240
atataacagt tttaatttat tctctggttg agtgcttccc acattttgct tattatgagt  183300
atttacatac aaggtacaag gttttttaaaa atcttttgaa gtctgtcacg catatatatc  183360
tacataattt gcaccctccc tccctcccctt cttctaactc ctctcatgca ctcccaattc  183420
aattcttaa ttattattgc ttcatatatg tgtgtgcgta tatacattat ataacatgtg  183480
aatttgtatg tatatgaata tatatttata tatatcacag cagttagaag gacatggata  183540
tttattataa atggatacaa atgatgtagt cttttgtgtc tggcttcttt tattaataca  183600
atgtttaaaa aatatatttc attttaaatt atgtatatgt gtctacatat acaaattagt  183660
caaatacata tgatttatat atgtatatat acatacatat acacatatac atttaagtat  183720
gtacatatac acataggcac atttaaatac acaaaatata taatatatat gaatttgtat  183780
acatgcaggc acatgcctgt gtacataaag tttgctgagt tcatgcagta ctgtttatat  183840
gtgcacataa gctttctttt ctcttgggta tgcacataga cattgattag tgtgttgtat  183900
gtcgatttta tgtttaactt tttaagaagc taccaaactg tctgccatgg tggctgtact  183960
gttttatatt tccagtagaa atgtatgatg gttccagctt ctccatatct ttgccaattt  184020
tcttttttaac atccatcttc actgattaca ggcacttgtc cagaacagtt tgggatgtgg  184080
ggatatttgt agatatagtg aaataactta gaggtgggtc tcaactatat gtatgacact  184140
ccccatgcct tatatataaa tcatatacac acatatacac atacacacac acatacacac  184200
acatacacac atacacatac atacacatat acatacatac acatacatac acacatatac  184260
atacatacac acatacatac atacacatgc acatacatac acacacatac atacacataa  184320
acacacatac acacacacac atacactgaa tgtaaatagc tatgctactt ttagtgtgcc  184380
tgttttttgac tgttttattg tgagaggtca ggtgtaaaat tttctactca cagtattaga  184440
gtagtagttt cagattttag agcatttcag agttttttatt gttttattga aaatgctcag  184500
tttctgtgac caccataata atttgtaaag tgatatctca gattatctga tatgtatttg  184560
tctcatgaca aataataaaa aaaggtgag caccttttca tacactgatt ggccatctga  184620
gtttctcttt ggagaaatgc ctatattcag attctttgcc cagctttaaa ttggatagtc  184680
ttttgttgt tgagttggaa gaggtcttta tatattttg atactatgtt cttacaagac  184740
agatgatttg caaaccctat atctgctctc atttcatgag ttgtttttac atttttcttca  184800
tagtagcctt tgaatacaac tgttttttga aatctgattt attttcattt agttatttgt  184860
atttggatt tgaatccacc actgtctagt tcatagcgat acaaaattga ccctatttgc  184920
ttttgagatt tgtcgctcag tttttcatgc tttgacccttt gattcatttt gagttacttt  184980
ttgcatatga tgtaaagtag atttctgacg ttttccttc tcataggcta accccagttt  185040
gtgtcgacgc ctgcactgcc catttgccaa tcctctcttc ctgttctgct gtttcaggaa  185100
attacattcc tgagttcctt atcacatgac tcccatgtca gccttcggtt atggctttat  185160
tttattcttt taaactcttt tagttcattt ttctcagtct tcctttctttt ttccttcctt  185220
ctttccttcc ttcatttctt cctccctccc tctgtctgtc accactcctc ttcctctccc  185280
```

```
tccctccctc cctccctccc tccttccctc cctccctccc ccttctttcc tctctctctc    185340
tgtgtctctg tctgtctctc tttctgtctc tgtctctctc tctgtctccc ccccccccaa    185400
acctctctgt tcatatgatt ttaacagagg tttaaataca gaagctgtgg acacatccag    185460
tgctgaaatg aaggtttctg agtcacccag gcataggga gaagctgggg ctctggagaa    185520
gctggagttc tctgcctccc ctcagctgca gagtctataa ccagaagcac atgtgttgcc    185580
tcccggggtc catactgcac cagatatctg tatgtttcct ggtgtggtcc catcatgctc    185640
ctgcctccta gatggccttg cttttctgagg cgtagttaga acaccgcgtc ctgatgtttc    185700
tatagcccca gattgggagc aactgcactt gttgctagcc attgttgctt atggcccctg    185760
ttgactactc agttatgcaa cttgtgtttc attcattctg cttaaaaaga acctgctttc    185820
ccattagact tgagtgataa acatctaac atcttacatg tttaaatagc tgtaaagaat    185880
gttatttaca gtttattgta ataattgaca cttaaaacag atgtaccttg ccttcagatt    185940
tattgtgtac aaggtaaata ccacagtgag ccgagacctt gaagtcacct tcatccacta    186000
agaaagtgta tgaacaagat ctttgtcact cataaaattt gccttcctta tttttaatac    186060
cacttttatt aaatttttgt cataaactat attaatatat attttatgcc ttaaatattt    186120
aattaataat acctgactat ttctcagaag gaaaaaagg tacataaatt agaatcatac    186180
cttgttaact gtcttaggtt atataagttt tgattaaaat atttctgagg gttgggcata    186240
gaagcatgca cctttaattc caccactcag gagacagagg caggaggata tctgtgaatt    186300
caaggctaac ctgtttacag agagaattgt aggacagtca gggctacata gtgagtgaaa    186360
cttgtgacaa acaaaacaaa atgaactttg gggaccagag tgtgtgtgca tgcgtgtgca    186420
taagtatatg tgtgcatgtg tgtgtgtgtg tgtgtgtgtg tgtgtatgtg tgattgtgtg    186480
tgtgtgagat gtctgtgtga tctgtgggtt taacatgtgt aagagtttgt gtgtgtatgc    186540
acacatgcaa gtgtgtggtg acacatgtat gaatgtgtgt gtgactgtgt gcaagtgaag    186600
tgtgtgtgtg tatgtgtgat tgtgtgtgtg tgagatgtct gtgtgatctg tgggtttaac    186660
atgtgtaaga gtttgtgtgt gtatgcacac atgcaagtgt gtggtgacac atgtatgaat    186720
gtgtgtgtga ctgtgtgcaa gcgcagtgtg tgtgtgtgtg tctggggaag tgactatgga    186780
ggtttaatgt tgactttcaa gtatctttct ttgcggggct gtgggtgtag ggaaaagagg    186840
ggagtggaag agaacctgcg tctcaccaga gttccgttgc tctgggcatg ggaggactgc    186900
cagatacttt ccacgcggcc ccaggtgggc atctggctgt gttaggccgc tgaccccaca    186960
gggtgggtgg tggacaaggg gcagcctcag gtaccaggtt ctcagcctcc tgcattccat    187020
gtcagataag gtggaggatc tgaatagggg cccctgggc cgcacttggc tctggggagg    187080
aaggccctag agggcagggg gagaagaggg cgctgggtgg tttccacgaa gggaagagtc    187140
cttagtctgg tctgtggctg cagtgtagga aggccttctg gcgggaggtt agacatggct    187200
tgttaggcct atcccatcat ttaagcatgg cagaccttca tgatcagaga cagtctaagg    187260
ttttagagct ttgtggtaga aaggcaggga gaaaggagag aaggtagaaa gagagagacc    187320
agccatggct acgtggggg gggggggagg ctgagggaa gagaaagagg gctagagagt    187380
aagaaaggta aaagcttaaa gagagtgagg aggggccaag cagcccccct tatagagctg    187440
ggctgtcttg ctgtttccag gtaactgtgg ggttggagtc tagccagaat gccagaagct    187500
tgggacattg tctatgtgac tgatagccac atgcctctcc tgtgggggc tgtggggcg    187560
ggtaacttcg acaggagcca tgatcgaaca ccttccgtcc catgtaggca ggaattacca    187620
cccaccaggt cccaccagcg ttcaagacct aagttcaact ggagaccagg ctgtctgtgc    187680
```

```
atagcccatt gccccacatt tctttatcac tgttcatttt actttcttac acaggtctct   187740
tgctgaacct agagtttgac attagttagg ctagctggcc accaaagccc caggaccctc   187800
cctgagtact aggattataa atccctatgt tggtgactcg cttttatgtg ggtgctggaa   187860
tttatctcag gtcatgttgg catggagagc actttacctg cagagccatc tccctgccca   187920
ggagtcctta ggtggtcggg gtggggtgg ggtggatgct atgaaaccac gtaagagttt   187980
aaagctgtgc aatgtgatag cattcaacct cttaagggag agcacagatg cttatgccga   188040
gagtggattg tgattgaact gtgcataaat ggatatagca aggtacgttt cgtatctatg   188100
acaggtgaga ctcgagatga taaaggcctg atttagggta atggaggata tagacataag   188160
gaataataaa ggattaacag aatgaagaga caggccaatg tagaaagtgg tgattagtat   188220
agctcaggac ccaagtttct gcctacatag gcatgttcat aaatcaacta atacacatcg   188280
atcatatagt atctgctagg ctttctgctt cccaccaggg ctatctaggg ctagcccatt   188340
ccacgactcc tgtagacacc gcacactacc tgttcatggg atagagctag aacttctttc   188400
cctagacttc agtggtctag attacctatg tttgaaccaa aaggaaaaag catagcttct   188460
cttaccgtag aagtcccaat cctatataca ttgatggcaa agataagaac tgtgtcctaa   188520
gcttcaggaa cataaataaa tgtctctctt atcttttcc ccctaaaca gtgaagtgga   188580 catagtgggc atttttggtgt tgaggaactt acagaaactt cacttagaga cttctctgag   188640
gctgtagcat gtgttagtct agggttagtt cagggtttta cagtgagcca cccagctaga   188700
ttccccaagt tgtagctaca tccgttctcc taggagaccc tctatagaaa cagacccctc   188760
ccccgacccc agggatcttg ttgcctgtga ctttaaacag aagacaccaa ggatcctctc   188820
caacagtaac cttctgaaag tccattcttt ctcctctgtg acttccaatt ctatactctc   188880
cgaaggagaa ggtcagaaaa ccaagtagct cgtattaaat ttatcaaggc cacatatgtt   188940
actcatatga tagaatgatt tcaaggagga gtgaatgaga tgaatttatt tttctctcca   189000
tgcatgtgca atcagaatga ctgatagatt gtttctactg atacccttca tgtctttctt   189060
tccgtgacaa gtgcaaagca actctccaag gatttccttc cagtttcgcc attttaaact   189120
tgcatttgta actgctagca aagcaaagtt gaaaattgaa agccttttcca ttttccaagg   189180 ctgactgtac gctatgttct gctgctcacg ggtcctgctt ttgataactc tctcgttagt   189240
ctattttcca tggtccaatt ggatcggagc tgcctttgaa gagaattttt agtttcctgg   189300
gagaccagga ttaaactgtg aatgacatgt atgttaaaat ctaacaccct catcaagttt   189360
cataacgcag ttacaagcac agcataatca cattactaaa gataaacacc ggggcgggga   189420
tgggggtggg ggtggggtg gggtagggtg aggggtgagg taggtcagaa acaggagaag   189480
aaaaacacta gattcaatag aactagtaga tgcaacctat actttcagta gccatgaaaa   189540
taataaattt taagcagaat aagtcagctc aattctggaa aagttctttg aatctgacac   189600
gttgtgggaa gtctgacata aaaataatca taaggtcccc acatggaaat ttatatttgg   189660
aggcttgagt tgtgggtgac tgactcattg tgtgtgcggg tcccatgttc tgaaccactg   189720
gaaagcagtc ttgcctgctg agctatctct aataacccct aacccaatat tcttttcttt   189780
tttttttttt ctggttgttg ttgttgttgt tgttgttgtt gttttgagac agggtttctc   189840
tgtgtagccc tggctgtcct ggaactcact ttgtagacca ggctggcctc gaactcagaa   189900
atctgcctgc ctctgcctcc caagtgctgg gattaaaggc gtgtgccacc acgcctgact   189960
taacccagta ttcttaaaaa tcaattttga taccataaaa tcccacgatg aacaaagtat   190020
```

```
aaaaatttaa aaccaagtgg ggaatctcaa ccttaatctc acacttctcc ttcccctaaa    190080
accagcggta cctagagaac cactcctgcc ccaccccacc gaggaggctg ctgggatagg    190140
atgtgggcaa gggttggggc gtggcttctt gaggcagcct cgataagttt cctcccttga    190200
agaggtacac aagtgagaat catggtacca ggaccgagtg actgatgtaa acagcccaac    190260
caaatacgtc acagtagttt acagacaggg atggctgtct atttccataa tatcccttta    190320
cagacgcctc tttaatgttc taactcagcc cctcccactt tgctttagtt aagttagcat    190380
tcaaccaacc aaccaaccaa ccaaccaacc aaccaaccaa caattctgta tacttccaag    190440
gccttgagct ttctttggaa gcaatgatta aactcttaaa cattgctttt acgtttctct    190500
catggagatt gaaaatgtat gtggcatatt aagagcttgc agaaaattag caatattcaa    190560
cccgtttatt ttgtttaatc ccatattgcc tttgctttat tttcttttt tcataattca    190620 tttttaggt ttaggtatta atttattgta tatgagtaca ccatcgctgt cttcagacac    190680
tggaagagga catcggaccc attacatact gttgtgagcc accatgtggt tgctgggaat    190740
tgaactgagg acctctggaa gagcagtcag tgctcttaac cgctgagcca cctttccagt    190800
ccctagcttt attttttaat tgagttatag tcttgcccag tccttggctc agctgcaccc    190860
aggcattgta tacatgttgc tgctcctctt ttccttggaa cctaacattg tgcctttctg    190920
gtcccttgag atatccttct ctgccactgg ctcttgtcag atctgaacac aggtcaactt    190980
tggagttttt gcctgtgatt ttatttatgt attttttaaa caattttat tttattttac    191040 tttttgagag cttcatgcat gagtactgca acaccactac caccctttcct accctcctct    191100 gattcctctc atgtacaccc actcctaaat tcatgatctc tatatcttta atgtcacaca    191160
aatattcatc tacatttata tacacatatg catccaactg tctccattta ctattgtcca    191220
taattatata tcttttcatt atcacatgag ctgtaggatt ttatgaaata tagaaagaga    191280
actccagaag aaatgccaag tagtttcacc ttgtgtttta agacacccat cttttgcctc    191340
tgttggcatc ttcatctctt gaatatgtat atctcctaac tatgcttctc aataggtaaa    191400
aataaatcat ctagtagata tgatgtagtc cttagagtgc tcttcatatg acccaaaggg    191460
gtaatccaag tagaaaccag tgtggctgag acatgctgg gggctatcac gtgaaagcct    191520
tagcataacc aagtccagtg aagaaagacc acagaatgat ttgagcaggc aagtttaaat    191580
aattactgat aatatcaggg gattggagca aaaaggaatt gacctaacaa aggtaaatga    191640
agtctaaaga atacagaaag tagggacag aggaatgact taactgttaa gagtgttttc    191700
agagaaccaa cgtttgattt ccagcatgcc tgtaactcta gctccacggt gtctgatgcc    191760
gtctgctggc cactgtgggc attgctggca cctagagtac ttttatacat ataggcaaaa    191820
aaaatcacac acataacata atctttaaaa aaaacctaaa atgaacaaac aaacaatggc    191880
acagagaaag gggaggaagg aagggaggga gggaggggga gagggagaag gaaagggagg    191940
gagggagaca gggagggaga cagggaggga gggagaggga acaagtgctg agcctggtgg    192000
aaaaggccca ccattctagc ttctctggag gctgaggcag gagaacctca aattctgggc    192060
ctaatcgggt tacggagaga attcaaggtt agcctgggta acttagcaag accctgtttg    192120
ataaataagt aaataaaaat aaggaaaaag aactgagaat acagtccaat aaagtagtaa    192180
tgactagggg gtgggggaca aagttcaatc ctcaggactg aaagcgagca agaaagagga    192240
ataatagaaa atatctccta ttctcagggc aaccaaggaa gagtccttgc ctgtgtacat    192300
gcaaagctaa gatgcaaacc ttccatagct tagaatactg gaagacagaa aggttgtctg    192360
caggcacctg gactaagctg ttccttaaag gaatattgtt atgaacaatg cagatgggag    192420
```

```
ggtctatagt gtagggtggg gggctggctg ctaactgctt ttggttgata tgtgctgctt  192480
gcacccagca acactggaca agggagcttt gctgtagcac ttgggtctgg agtaattctt  192540
tccctctctc tttagtgtgt gtgtgtgtgt gtgtgtgtgt gtgtatgtgt gtgtgtgtgt  192600
gctgcatgtg ttagactgca gagacttgct gtagacacaa gagaactaga ccaaaaattc  192660
tttcttcccg aaatgtctct tccttatcct cttcggagtg aatatcatt gccagctagt  192720 aatgagaaat agttaatggg ccacagatac acaactggtg aaatgggaga actttgagct  192780
gagaggcaga aagttgataa ctgaaccttta caagggagaa caacggctct ggaagcagaa  192840
gctccgatag gaatgtgacc aggagaaaga cctgcccacc tttctaaaaa gtaaaattgc  192900
catattttaa ttaactcaca taggacagca ctgcagctgg cctatggaag ccattcagac  192960
actcgcccag tccgatctg gccattgaaa tgatgtgttg ggacagtcgc taaaggtagg  193020
aggagatgac tagaccattg tttatgggac ttgatcctag ctagatagga gaaaaatcca  193080
tttccagggg atcttaggtg gcaacgtgat aggcagtttc tgcgggtgag acctcacaac  193140
gcagaacacc actcatagta acggactgcc tgcgtacagt cagctggtag gacgatttgg  193200
attcttgaca cccggtttct ttttctactt ctttctattg taataggagt ttccgacatg  193260
gtgaaaatgg tgggttttgt actctgttat ttggagcaaa gatgtcatag tttccatttc  193320
tcccattgtt tgggcatgac atttggtcat ctctaggtct aaaatgaggc cttggtgcct  193380
tgagcagaga gattagaact gaacagcgcc atcttgggtg agtttagggt gagaggagag  193440
catttgataa gatgattgga ttcccacagg aaacctttaa ttttagggt tctcatatgt  193500 ttcatcacga aaccctgtaa acttttata tagatcattc cgccattgac cattgctgcc  193560
accacagacc aaaagccaac caacacctaa atgccagcgg gctaattaag gaaaattaat  193620
ttcacttctc tgaatggtgg aaaatgaagt aagactaatt tttagaatct tggtcttcag  193680
gtaaggagaa tattatttag gaagttggta ttttagtcaa ccaaaatgta agtccccttt  193740
aagggcataa agcttccaca ggagctccct cgatgcagct ctgagggatc acatggcaag  193800
catcaccgct ttacaacaac actgtacccct tatgagggtc tggaaatgcc cccacgggaa  193860
tgttaactag aacaatgagg agaggtttat gatgctaaac cctccgctgc gaacatttca  193920
tctcttttta cagccatgca aattgttaca ggtccactga caacaggaaa aatttactgg  193980
gcttaaaaca aatcaggcag catttaactg tctaaaatta aacaggaaaa gcatgtcaga  194040
aggcctcgga atcacgggag ttcttaagct gtcttaaaag tgtatgtaag acttgtgcac  194100
accagaaaat tctcggtatg tccatttgtg tgtgtgtatt ttgttgtttt cttttttgttg  194160 ctgtttttgt ttttttgaag tcagggtttc tctgtgtagc cctggctgtc ctggaactca  194220
ctttgtagac tagactggcc tcaaactcag aaatctgcct gcctctgcct cccaagtgct  194280
gggattaaag gcatgcacca ccactacctg gcaaaaattt attattatac ataattatac  194340
tgtagctgtc ttcaggcgca ccagaagagg gcatcagatc tcattatgga tggttgtgag  194400
ccaccatgtg gtttctggga tttgaactca ggaccttcgg aagaacaatc agtgctctta  194460
ccttctgagc catcccacca gccccatttg tgtttctttt ggagctatgg atggaaagtg  194520
agtaatgaac ctagtaaatc ctatctgtgc tgccaaggtg gcttagtggt tagaatgtgc  194580
ctagaaggat ggctcaacag ttaacagcac tggctgctct tccagaagac tttggtctaa  194640
tcccaagtat ccacatggca gcttaccacc atctgcaact tcagttgcca ggaagaccct  194700
cttctagctt ctgaaggtac caggcactca agcattgcaa gacacacatg cagacaaaat  194760
```

```
gcccaatcta catagaatga gtaagtaaaa atggttaaaa ggtcttgcca tgcaggagag   194820
gatgtgagtt cagattccaa agactgggga tccccggttc aaattggcta gtgggtttga   194880
gagcaatcca gggtgattcc ccaacatcaa ctgagggcct ctccatgcat atccacacac   194940
gtgtagccac gtggtttatg catgaatgta caaacacgca tacacattag catgaacatc   195000
atagcatata ggccagccaa aaagagactt taggccagat ttagtctatg ggctctgcta   195060
taactgttgg ttgggtgaca gcactgacct ctaggctagc ttcatacaat caaagcccaa   195120
agaaaactct ccaaagacct ttctgctttc aacacccatc ccatccccac tcccctccat   195180
acacacattc acacatgagc agaaagctca cagtggtcct aattttccag tagccatcct   195240
attttatcag ctggttcact gaaaggtatt taagatttta caggactttt caacatgaaa   195300
aaaaaaaaag gaaatcaca agtatataaa ataatgtgga aggagttagg acgggaaagc   195360
aaggagagag agacagagac agagacagag acagagagag acagagagac agagagacag   195420
agagacagag agagagagag agagagagag agagagaaga gactgtttta acatcacacc   195480
ttctttggag agtgaaagtt gccaggtgtt atcacaaaac agttatatta acattaagaa   195540
ggggctatgc ttgtatcttt cacagtagtc aaatcttcag aaaaaatgta tttattttag   195600
tgctgtaacc tacaactgaa aagaagaata tttgtacaga gaatctagt gggtgttttt   195660 ttttttttt agaagtgtgt gtatgtgttg cagggtgtat atataggatg tgtgtaaggt   195720
gtgtatgtgt gtataggggg tgtgtaggtt atgtgtatat atagggtgtg tattcgtagg   195780
gaatgtattt agggtgtgta ttcataggg atgtatatag ggggtttgtg tatgtgtagg   195840
gtgagtatag gtatgtttg gggtgtatgt gtataggatg tgtgtgtg tgtgtgtg     195900 tgtgtgtg tgtgtgtaga tgcatgcctg tagtggccaa aggtcaccct ctagcgtgat   195960
ccctcacatg taatccaccc tgtcctctaa ggcaggctct tactggcctg ggcccttga   196020 gtcagctagg ctgtctaggc agcaggtccc agggattagc ctagcttgcc ttcccagcac   196080
tagggttcaa acaccatctt attttgtatt ctgggtgagt ggggcttagg cactggcttc   196140
aggacctcct gtgcctgcag taagcacttt actgagtgag ctgtactctc agtcagccct   196200
tggttagaac atttttcacgt aggaaaaaaa aaatctaaga gacttagcat ttcatggcag   196260
cagtaaggac gcatacacaa aagccccccac gttttttttcc tatgctttta ctgctagggg   196320
aagtttgagg gaaggggctg tggaaatgtt tcctacttga agtttaatgt tcagagcaaa   196380
gaccacgcca gttccagctg agagcaagag cgctcttgaa agcagactga aatccagata   196440
cctgagccgt tggtagggca ttcagtggaa aatttcattt ccacattata aataactgta   196500
ggatatttta agggatccaa gactgggaac ttccaagagc tgcttacatt agttctactg   196560
aaatgtttaa tggagggagg atgcccagca aggctataaa gctgaattac cggatatgat   196620
taattaaaat aaataatctc accattgatt aaattgccct taaaatcccc aaccattgag   196680
gcctgcatgt ctcattatgc atcaagtaaa aaggggggag catggagtgg tggtaactaa   196740
acagcaatgg cgggaaagca aggtccccca agataggatt tcttatattc aaacgactgt   196800
agagtttctt gttggaaaaa gccccactct gggagcccct atttgaaaca tgggccgttt   196860
ctcagttctg tcagtttgtg gaagtcccctt gttctgtggg tttcctggga ggagaacaaa   196920
ataccctctc ccactatcga cactatcgat ttctggggac tctctgctct tctgcagttc   196980
ccaacactta aaatgagggg caatgaaagc aagccatctc tgtgggctgt gccactaaag   197040
aaagctgtcc cactaagggc aggaggggta ggtatgtaat tgagtcatga cgtcaggtta   197100
tgaatttgcg aggatacaag ttagtttggg tgcagtttct ctcttagatg ggttaggaag   197160
```

```
cctggcttcc ttttctaggc tggcgtctat ggctggggcg attagtgcaa gggagcgcac  197220
acacgcggtg aggcagtatt caggcttaga gctctcccct gtgatcaaaa agatatttaa  197280
agtagcaccc ttaggagaca gctcagtaac tcgctccacc tgtaatgtat atcgggagtg  197340
agcgctaggg acacagaggc caccagctac gaggaagtcg ggtgggagat gtgggcgcca  197400
caggtagtgg catagaggag cgggcagtgg aagaagaggg agactgagtg gctcagggag  197460
gtgactcaag tctgagggag gactggtgga agaatccgga aagagagcaa gagacaagga  197520
aagaccgaca tgggacgtgg gcggcggcgg cggcggcggg ggggggcggg gtttgcatag  197580
ttgtaagtgg tgcaagcaga aaggggaggc agaagcagtg actcaaaggg ggagggcaca  197640
ggagtgctcc ccagtatcat ccctagcctg tgagagagca agcagtcaca ctcaactctg  197700
tccactcctc aaccccccaga gcgcctctca ggcacaggag cacgggtccc cagaccatct  197760
gagcacagcg atccactttt tgtatttttct agtctcgagt tgcaaagagg cgcaaacaac  197820
ctcttttgcg cgctccgggt acctttttctg ggccctgctg ggcgcgcggg gagggaaggt  197880
cagagagtgg caactgcgct agggagggtc atgacaggtc ccttgctgaa tttggaaggc  197940
atttgcaccc cagcagtaaa agccccaaat taatggctac gtgaagagct ttaaataaga  198000
cggatggtga gaaatgttac ccagctagcc ctcttcttta gtcctcctag gggacgactc  198060 ccaattttttc attgatttca ccaaatcaca gttgcgtcaa ctaccttgtt acgaatcgcc  198120
ggggattttg gtaaaatgat tctatttgga agcgttggaa gttttaaaat aataggttag  198180
gcaagacata taacagaaca tcacgctgag aggtgagcca gcccgatatt gcttctgcct  198240
ggttcttggg gtgtatcagc ctccggcgga tttcccggct tctgtgggcg ccgccgcacg  198300
ttgtttgatt tgttttgaag gctcagaatt tgaggctggt cggagacacc cacgtgcttc  198360
tgattcccat cagtataatg atcgcctcag tttgagtcgt gtctatataa accacaaaaa  198420
cctaatcatt agaaatccca gcctccaaaa accacatttt aggtaaaaaa acaaacaaaa  198480
aaaaaaaaaa caaacaaaaa aaaaacaaaa ctgctgccgc tccccgcact ccttcatctc  198540
tcaaccacaa tcttttgggg attccaaaat cgcctccccc cataacgccg ggaaacaaaa  198600
acataaataa ataattactg aacttttttt taaacttttt atttttaacc ccccaaagtg  198660
gggagtggct agaaagacag ttagacacta gacttagtct gagacgaaga ctacacttaa  198720
taaaagattg gaaatgaat ggataaccgc tgtgtattcc cccttcccca gcaagcatttt  198780 tatcaactta caacttattt taattaccaa gctgtcattt tttagttctt tttattaaaa  198840
aagcaaccca tccttattct ccaataatga caagaaggaa tatataagaa aagtgtccag  198900
acatccgtta gagtttctaa aactattttg acaaacactc ctgtcaccca ttttggtgtc  198960
acctaagggg gggcactccc gaagcctgta aaaacctgcc ccccgcccca accaatgtgg  199020
ggtggggttg ggggcagggt gaagagtgct cagaagtcaa cgtggagact tgagaatttc  199080
ccttcctcct ctcctgaagt taacaacgaa aaattaacgc cagtcggagc agcctgaggc  199140
tctcccgctt ctcagcttta gcgtcgtcag accgagaagt ggttcccggt cctgagggtg  199200
aagtggggag ccgaggacgc aggcggcgat gtcctaggcg gggacctcct ccctacagct  199260
tcgggcgccg agcgagcgca gcggcgcttc tagcggccgg cgggcggcgg cagcggctgc  199320
gatccgcagg ctccagatct gtcgccccga gatccgctct cccccgccc ccacttacct  199380 cccggcacct tgaaacgcga gggggcccg ggcactttg caaagagcag gagagacgag  199440
gctgcgagct agacggcggc gaaggagagg gcgagaggag aagccgggga aaggaaggac  199500
```

```
tcggcggccg aggactcgg agcgcgctgc cggcgcgggg agcgcgcagc ggcctcggag    199560
gaggaggcgg aggaggcggc gcgggcaagc gacggcgccg cgagctgggc agccgcgctc    199620
tgcttggcgg tggcggacag cgaggagcca cacgcaccgc cgagatggac tgctgaacct    199680
gcggggctcc actaccgtac tggaacccgg agcggggcgc cagcgcaccc aggacacggt    199740
gccccaaggg gccctactg caagctgtta acttcaagtc ccttgcggcg gctgggccaa    199800
acacgccccc gcgtcccgct cgttgcagcc accgccaggg actcccaagc ctccggtgg     199860 agatccgcgc ctctcgggtg tccccacccg ctaccccgac tctgtccggt ctccagtcgc    199920 cggccccag cagactccgc ccggcacacg gcttcctcga acttgatttc tcacctcctc      199980
tgtcccgtca cctccatcct ctttccgccc ccgtctcgcc tccaccccct cgatttcctc    200040
ctcctcgccc cccatttcca ccctcctccc cctccccgg ccacttcgct aacttgtggc      200100
tgttgtgatg cgtattcctg tagatccgag caccagccgg cgcttcagcc ccccctccag    200160
cagcctgcag cccggcaaga tgagcgacgt gagcccggtg gtggctgc                 200208

<210> SEQ ID NO 3
<211> LENGTH: 344
<212> TYPE: DNA
<213> ORGANISM: Mus musculus

<400> SEQUENCE: 3
ttatcatgta attataatga tgatcattta caagtatcca aaatgactcc agcattttaa     60
agagctaagc agagttattt ttaaaatcaa acatatgtgc ttttctgtt tatgtctttg     120 gaaagaacat tctgcataat gaaaaacacg accaaatttt tcacagtaca tcactataaa    180
ccctgtaatt gacttttggg gttggtttac tctatatcta tttttgacca cgtagaaaac    240
agcaatgatg tggtgaaaag cccaaaatgc aagtcccatc gcaggctgag actccactct    300
gattagtaca aaagtatcat gtttgtgctg ggaagtgtgc ccat                     344

<210> SEQ ID NO 4
<211> LENGTH: 1273
<212> TYPE: DNA
<213> ORGANISM: Homo sapiens

<400> SEQUENCE: 4
ttagcatttg cttgttggga agagatgaga aaataagatg cgtttatcag atcttccaat     60
tgcgcaccag aaatactttc aaagtaccta tgttgtaatt tcattttaa aaaattcttt     120 tcaattgggg gggagggtga ataagtaatt acaaagaatg gctgccttta gatagaggtt    180
tatcatgtaa ttataataat gatcatttaa aaggatccaa aatgtctcca ctagttaaa    240 gggctaggca gagttatttt taaaatcaaa cgtatgtgct ttttctgttt atgtctttgg    300
aaagaacatt ctgtataatg aaaaacatga ccaaattttt cacagtacat cactataaaa    360
ccctgtaatt gacttttggg gttggtttac tctatatcta ttttgacct cgtagaaaac     420 agcaatgatg tggtgaaagg cccaaaattt aagtctcatt gcaggataag actccatcct    480
gattagtata aagtatcat atttgtgctg ggaaatgtgc ccattctagt agagaaaact     540
ttagtgcata ggaaccacct cttttctaat caagccatgt aaaaactagt aactctggtg    600
tctagtctgg gccttggatg gaatgtggat gttgtttaca ccgatcccct ccattaaagg    660
cagcataatg ttggtcttca aaactgatgt tggaaatgac aggttcattg cagttaatct    720
gatggaaagt aacaatgtat gtcacaggta aattataaat taaccttaa acatataaat     780 tatcattaga tagttctttt tctcttgtgt taacacagat taaataaaga acttaatctc    840
```

```
cttctaaaag ctttgaattc cgttactaag gaacaaacta atatgttatt cctaacaaaa      900
agcactgttc ttcatcgaag tctaaaatac ctctgaatgg gtactcctgc tttcaccagt      960
aaaatttaca tactaccaag taaaataaac ttatgttaca tggtatataaaa atcagccctg    1020 taacacctac cacagattta tctcctgtga gttgactcaa tcattccttc ttttcagtaa     1080
ataaactaca ttctacgcag ggaactgcag gaaagttttt cagaggccaa gtcaagaat      1140 atgtttcaca tggaaacttc caaattgaca gcctgcccat ttttggtagg tattaaaggg     1200
tcctcagcac tttatgaatt agttgtggtt tacctaaata atcatggcca aagctgccac    1260
cgtcactgca ttc                                                         1273

<210> SEQ ID NO 5
<211> LENGTH: 344
<212> TYPE: DNA
<213> ORGANISM: Homo sapiens

<400> SEQUENCE: 5
ttatcatgta attataataa tgatcattta aaaggatcca aaatgtctcc actagtttaa       60
agggctaggc agagttattt ttaaaatcaa acgtatgtgc tttttctgtt tatgtctttg      120
gaaagaacat tctgtataat gaaaaacatg accaaatttt tcacagtaca tcactataaa     180
accctgtaat tgactttggg gttggtttta ctctatatct attttgacc tcgtagaaaa      240 cagcaatgat gtggtgaaag gcccaaaatt taagtctcat tgcaggataa gactccatcc    300
tgattagtat agaagtatca tatttgtgct gggaaatgtg ccca                      344

<210> SEQ ID NO 6
<211> LENGTH: 1248
<212> TYPE: DNA
<213> ORGANISM: Artificial Sequence
<220> FEATURE:
<223> OTHER INFORMATION: Synthetic sequence

<400> SEQUENCE: 6
ttagcattgc cttctgcaga agacatgaga aaataagatg agtttagcag atcatccaat       60
tgcacaacag aaatacttcc agtacccatg ttgcaacctc atttaaaaaa aaatctttaa      120
aactgggaaa gaaagtgaat aaataattac aaacaaggcc tgccttaaga aaaaggctta    180
tcatgtaatt ataataatga tcatttaaaa ggatccaaaa tgactccacc agtttaaaga    240
gctaagcaga gttatttttta aaatcaaaca tatgtgcttt ttctgtttat gtctttggaa    300
agaacattct gcataatgaa aaacacgacc aaattttttca cagtacatca ctataaaccc   360
tgtaattgac ttttggggtt ggtttactct atatctattt ttgaccacgt agaaaacagc    420
aatgatgtgt tgaaaagccc aaaatgcaag tcccatcgca ggataagact ccaccctgat    480
tagtacaaaa gtatcatatt tgtgctggga atgtgcccaa tcctaagaga aaactctact    540
gcacaagaac cacccttttc aaaaaaaaca agcaaaaaaa gaagaacact ggtgcccagc    600
ctgggcctgg gagggaacct gcagatgttt acaccgatcc cctccatgaa aggcaccata    660
acactgatcc tcaaaactga ggttcactcc agttaatctg atggaaaaaa acaaggtata    720
caaagcaaaa atataaacta acctttaaac tataaattaa cattaaataa ttatcctcct    780
catgtcttaa cacagattaa ataaagaact taatctcctt ccaaaagctt tgaacgcagt    840
taacaaggaa aaaactaata tactattcct aacaaaaaca ctgttcttca tcaaagtcta    900
aaatacctct gaatgagcac tcctgccttc accagtaaaa tttacatact accaagtaaa    960
```

-continued

```
ataaacgaat gttacatggt ataaaaatca gccctgcaac acctaccaca gatttatctc    1020
ctgtgagttg actcaaccat tccttcttct cagtaaataa actaaattcc acgcagggaa    1080
ctgcagaaag tttttcagag gccaagtcaa agaatatgtt tcacatggaa acttccaaat    1140
tgacagcctg cccactctcg gtaggtatta aagggtccac agcactctat gaattagttg    1200
tggtttacct aaataatcat ggccaaaact accaacgtca ctgcacac                 1248
```